(12) United States Patent
Viguie et al.

(10) Patent No.: US 9,297,046 B2
(45) Date of Patent: Mar. 29, 2016

(54) TET2 AS A NEW DIAGNOSTIC AND PRONOSTIC MARKER IN HEMATOPOIETIC NEOPLASMS

(75) Inventors: Franck Viguie, Deuil la Barre (FR);
Olivier Bernard, Vanves (FR);
Michaela Fontenay, Paris (FR);
Christian Bastard, Ardouval (FR);
Francois Delhommeau, Antony (FR);
William Vainchenker, Paris (FR)

(73) Assignees: ASSISTANCE PUBLIQUE—HOPITAUX DE PARIS, Paris (FR); CENTRE HENRI BECQUEREL, Rouen (FR); INSTITUT NATIONAL DE LA SANTE ET DE LA RECHERCHE MEDICALE (INSERM), Paris (FR); INSTITUT GUSTAVE-ROUSSY, Villejuif (FR); UNIVERSITE PARIS DESCARTES, Paris (FR); UNIVERSITE PIERRE ET MARIE CURIE, Paris (FR); UNIVERSITE PARIS-SUD 11, Orsay (FR)

( * ) Notice: Subject to any disclaimer, the term of this patent is extended or adjusted under 35 U.S.C. 154(b) by 457 days.

(21) Appl. No.: 13/426,040

(22) Filed: Mar. 21, 2012

(65) Prior Publication Data
US 2012/0302517 A1 Nov. 29, 2012

Related U.S. Application Data

(63) Continuation-in-part of application No. 12/997,203, filed as application No. PCT/EP2009/057295 on Jun. 12, 2009.

(30) Foreign Application Priority Data

Jun. 12, 2008 (EP) ..................................... 08305255
Mar. 13, 2009 (EP) ..................................... 09155169

(51) Int. Cl.
C12Q 1/68 (2006.01)

(52) U.S. Cl.
CPC ........ *C12Q 1/6886* (2013.01); *C12Q 2600/106* (2013.01); *C12Q 2600/118* (2013.01); *C12Q 2600/156* (2013.01)

(58) Field of Classification Search
None
See application file for complete search history.

(56) References Cited

U.S. PATENT DOCUMENTS

| 4,683,202 A | 7/1987 | Mullis |
| 5,854,033 A | 12/1998 | Lizardi |
| 2011/0263523 A1* | 10/2011 | Viguie et al. .................... 514/43 |

OTHER PUBLICATIONS

Tao, Y. et al. Nucleic Acids Research 39(22):9508 (Dec. 2011; online Aug. 31, 2011).*

(Continued)

*Primary Examiner* — Diana B Johannsen
(74) *Attorney, Agent, or Firm* — Foley & Lardner LLP

(57) ABSTRACT

The present invention concerns an in vitro method for diagnosing a myeloid tumor or a lymphoid tumor in a subject, which comprises the step of analyzing a biological sample from said subject by (i) detecting the presence of a mutation in the Ten Eleven Translocation protein family member 2 gene (TET2) coding for the polypeptide having the sequence SEQ ID NO:2, and/or (ii) analyzing the expression of the TET2 gene; wherein the detection of such a TET2 mutation, of the absence of expression of TET2 or of the expression of a truncated TET2 is indicative of a subject developing or predisposed to develop a myeloid tumor or a lymphoid tumor.

7 Claims, 28 Drawing Sheets

(56) References Cited

OTHER PUBLICATIONS

Raza, A. et al. Cancer 113:1596 (Oct. 2008; online Aug. 20, 2008).*
Tefferi, A. et al. Leukemia 23:905 (May 2009; online Mar. 5, 2009).*
Thomas, X. et al. Expert Opin. Drug. Discov. 4(2):195 (Feb. 2009).*
Quivoron, C. et al. Cancer Cell 20:25-38 (Jul. 2011; online Jun. 30, 2011).*
Quivoron, C. et al. Cancer Cell 20 "Supplemental Information" (19 pages)(online Jun. 30, 2011).*
Weissmann, S. et al. Leukemia 26:934-942 (2012; online Nov. 25, 2011).*
Ahern, H. The Scientist 9(15):20 (1995)(6 pages).*
Kosmider, O. et al. Blood 114(15):3285 (Oct. 2009).*
Swerdlow, et al., WHO Classification of Tumors of Haematopoietc and Lymphoid Tissues (4th Ed), IARC: Lyon 2008 [online] <URL: http://apps.who.int/bookorders/anglais/detart1.jsp?sessian=1&codlan=1&codcol=70&codcch=4002, (1 page).
Fabre, C., "Treatment of AML with azacytidine (AZA): Current results of the French ATU program," Blood, Annual Meeting Abstracts, 2007, 110: Abstract 1849 (1 page).
Leone, et al., "DNA methylation and demethylating drugs in myelodysplastic syndromes and secondary leukemias," Haematologica, Dec. 2002, vol. 87, No. 12, pp. 1324-1341.
Garcia-Manero, et al., "Demethylating agents in myeloid malignancies," Curr Opin Oncol, Nov. 2008, vol. 20, No. 6, pp. 1-11.
Fenaux et al., "A multicenter phase 2 study of the farnesyltransferase inhibitor tipifarnib in intermediate- to high-risk myelodysplastic syndrome," Ecancer, 2008, vol. 2, No. 121, pp. 1-3.
National Comprehensive Cancer Network, "Acute Myeloid Leukemia", NCCN Clinical Practice Guidelines in Oncology™, Powerpoint presentation, www.nccn.org, 2008.
National Comprehensive Cancer Network, "Acute Myeloid Leukemia", NCCN Clinical Practice Guidelines in Oncology™, Powerpoint presentation, www.nccn.org, 2014.
National Comprehensive Cancer Network, "Myelodysplastic Syndromes", NCCN Clinical Practice Guidelines in Oncology™, Powerpoint presentation, www.nccn.org, 2014.
Buckstein, et al., "Myelodysplastic Syndromes (MDS)", May 2008 pp. 1-20.
Leukaemia Foundation, "Is Lymphoma on your radar?", www.leukaemia.org.au, 2014.
The Leukemia and Lymphoma Society (LLS), "Signs and Symptoms—AML", www.lls.org.(1 page), Jun. 2014.
The Leukemia and Lymphoma Society (LLS), "Diagnosis—AML", www.lls.org.(2 page), Jun. 2014.
The Leukemia and Lymphoma Society (LLS), "Signs and Symptoms—Myelodysplastic Syndromes (MDS)", www.lls.org.(1 page), Jun. 2014.
The Leukemia and Lymphoma Society (LLS), "Diagnosis—Myelodysplastic Syndromes (MDS)", www.lls.org.(1 page), Jun. 2014.
The Leukemia and Lymphoma Society (LLS), Signs and Symptoms—Non-Hodgkins Lymphoma (NHL), www.lls.org.(1 page), Jun. 2014.
International Search Report issued in application No. PCT/EP2009/057295 on Oct. 5, 2009.
Barany, Genetic disease detection and DNA amplification using cloned thermostable ligase, Proc. Natl. Acad. Sci. USA, Jan. 1991, vol. 88, pp. 189-193.
Baxter et al., "Acquired mutation of the tyrosine kinase JAK2 in human myeloproliferative disorders" Lancet, Mar. 2005, vol. 365, pp. 1054-1061.
Bellanné-Chantelot et al., "Genetic and clinical implications of the Val617Phe *JAK2* mutation in 72 families with myeloproliferative disorders," Blood, 2006, vol. 108, No. 1, pp. 346-352.
Braun et al., "NF-kB constitutes a potential therapeutic target in high-risk myelodysplastic syndrome," Blood, 2006, vol. 107(3), pp. 1156-1165.
Campbell et al., "The Myeloproliferactive Disorders," N. Engl. J. Med., 2006, vol. 355(23), pp. 2452-2466.

Chaligné et al., "New mutations of MPL in primitive myelofibrosis: only the MPL W515 mutations promote a $G_1$/S-phase transition," Leukemia, 2008, vol. 22, pp. 1557-1566.
Charbonnier et al., "Detection of Exon Deletions and Duplications of the Mismatch Repair Genes in Hereditary Nonpolyposis Colorectal Cancer Families Using Multiplex Polymerase Chain Reaction of Short Fluorescent Fragments," Cancer Res., Jun. 2000, vol. 60, pp. 2760-2763.
Claessens et al., "In vitro proliferation and differentiation of erythroid progenitors from patients with myelodysplastic syndromes: evidence for Fas-dependent apoptosis," Blood, Mar. 2002, vol. 99, No. 5, pp. 1594-1601.
Clasessens et al., "Rescue of early-stage myelodysplastic syndrome-deriving erythroid precursors by the ectopic expression of a dominant-negative form of FADD," *Blood*, May 2005, vol. 105, No. 10, pp. 4035-4042.
Cole et al., "The EBV-Hybridoma Technique and its Application to Human Lung Cancer," Monoclonal Antibodies and Cancer Therapy, Alan R. Liss, Inc., 1985, pp. 77-96.
Daser A, et al., "The versatile mixed lineage leukaemia gene *MLL* and its many associations in leukaemogenesis", Seminars Cancer Biol., 2005, vol. 15(3), pp. 175-188.
Database Genbank [Online], Apr. 2, 1996, XP002502623 (2 pages).
Database UniProt [online], Jun. 10, 2008, XP002502624, Database Accession No. Q6N021, http://www.uniprot.org:uniprot.q6n021.txt? (4 pages).
Database UniProt [online], Jun. 10, 2008, XP002502625, Database Accession No. Q8NFU7, http://www.uniprot.org:uniprot.q8nfu7.txt? (3 pages).
Database UniProt [Online], Jun. 10, 2008, XP002502625, Database Accession No. Q8NFU7 <URL: http://www.uniprot.org:uniprot.Q8NFU7.txt?> (3 pages).
Delhommeau et al., "LBA-3 TET2 is Novel Tumor Suppressor Gene Inactivated in Myeloproliferative Neoplasm: Identification of a Pre-JAK2 V617F event", Annu Meet Abstr, 2008 (2 pages).
Delhommeau et al., "Oncogenic mechanisms in myeloproliferative disorders," Cell Mol. Life Sci., 2006, vol. 63(24), pp. 2939-2953.
Dupont et al., "The *JAK2* 617V>F mutation triggers erythropoietin hypersensitivity and terminal erythroid amplification in primary cells from patients with polycythemia vera," Blood, Aug. 2007, vol. 110(3), pp. 1013-1021.
Ebert et al., "Identification of *RPS14* as a 5q⁻ syndrome gene by RNA interference screen," Nature, Jan. 2008, vol. 451, No. 17, pp. 335-339.
Fenaux et al., "A multicenter phase 2 study of the farnesyltransferase inhibitor tipifarnib in intermediate- to high-risk myelodysplastic syndrome," Blood, May 2007, vol. 109, No. 10, pp. 4158-4163.
Finazzi et al., "Essential Thrombocythemia," Semin. Hematol., 2005, vol. 42, pp. 230-238.
Gilbert H.S., "Familial Myeloproliferative disease," *Baillieres Clin. Haematol.*, Dec. 1998, vol. 11, No. 4, pp. 849-858.
Guatelli et al., "Isothermal, in vitro amplification of nucleic acids by a multienzyme reaction modeled after retroviral replication," Proc. Natl. Acad. Sci. USA, Mar. 1990, vol. 87, pp. 1874-1878.
Haase D., "Cytogenetic features in myelodysplastic syndromes," Annals of Hematology, 2008, vol. 87, No. 7, pp. 515-526.
Harper, et al., "Chromosomal Rearrangements Leading to MLL Gene Fusions: Clinical and Biological Aspects," Cancer Res, Dec. 2008, vol. 68(24), pp. 10024-10027.
Itzykson et al., "Optimal sequencing of treatments for patients with myelodysplastic syndromes," Current Opinion in Hematology, 2009, vol. 16, pp. 77-83.
Jabbour et al., "Evolution of Decitabine Development: Accomplishments, Ongoing Investigations, and Future Strategies," Cancer, Jun. 2008, vol. 112, No. 11, pp. 2341-2351.
James et al., "The hematopoietic stem cell compartment of JAK2V617F-positive myeloproliferative disorders is a reflection of disease heterogeneity," Blood, Sep. 2008, vol. 112, No. 6, pp. 2429-2438.
James et al., "A unique clonal *JAK2* mutation leading to constitutive signalling causes polycythaemia vera," Nature, Apr. 2005, vol. 434, pp. 1144-1148.

(56) References Cited

OTHER PUBLICATIONS

Kiladjian et al., "Pegylated interferon-alfa-2a induces complete hematologic and molecular responses with low toxicity in polycythemia vera," Blood, Oct. 2008, vol. 112, No. 8, pp. 3065-3072.
Köhler et al., "Continuous cultures of fused cells secreting antibody of predefined specificity," Nature, Aug. 1975, vol. 256, pp. 495-497.
Kojima et al., "*FLJ10849*, a septin family gene, fuses *MLL* in a novel leukemia cell line CNLBC1 derived from chronic neutrophilic leukemia in transformation with t(4;11)(q21;q23)," Leukemia, 2004, vol. 18, No. 5, pp. 998-1005.
Kozbor et al., "The production of monoclonal antibodies from human lymphocytes," Immunol. Today, 1983, vol. 4, No. 3, pp. 72-79.
Kralovics et al., "A Gain-of-Function Mutation of *JAK2* in Myeloproliferative Disorders," N. Engl. J. Med., Apr. 2005, vol. 352, pp. 1779-1790.
Kralovics et al., "Clonal hematopoiesis in familial polycythemia vera suggests the involvement of multiple mutational events in the early pathogenesis of the disease," Blood, Nov. 2003, vol. 102, No. 10, pp. 3793-3796.
Kuendgen et al., "Current status of epigenetic treatment in myelodysplastic syndromes," Ann. Hematol., vol. 87, pp. 601-611, 2008.
Kwoh et al., "Transcription-based amplification system and detection of amplified human immunodeficiency virus type 1 with a bead-based sandwich hybridization format," Proc. Natl. Acad. Sci. USA, Feb. 1989, vol. 86, pp. 1173-1177.
Levine et al., "The JAK2V617F activating mutation occurs in chronic myelomonocytic leukemia and acute myeloid leukemia, but not in acute lymphoblastic leukemia or chronic lymphocytic leukemia," Blood, Nov. 2005, vol. 106, No. 10, pp. 3377-3379.
Lizardi et al., "Exponential Amplification of Recombinant-RNA Hybridization Probes," Bio/Technology, Oct. 1988, vol. 6, pp. 1197-1202.
Lorsbach et al., "TET1, a Member of a Novel Protein Family, is Fused to MLL in Acute Myeloid Leukemia Containing the t(10;11)(q22;q23)," Leukemia, 2003, vol. 17(3), pp. 637-641.
Morgan et al., "A Role for JAK2 Mutations in Myeloproliferactive Diseases," Annu. Rev. Med., 2008, vol. 59, pp. 213-222.
Ono et al., "*LCX*, Leukemia-associated Protein with a CXXC Domain, is Fused to *MLL* in Acute Myeloid Leukemia with Trilineage Dysplasia Having t(10;11)(q22;q23)," Cancer Research, Jul. 2002, vol. 62(14), pp. 4075-4080.
Passamonti et al., "A dynamic prognostic model to predict survival in post-polycythemia vera myelofibrosis," Blood, Apr. 2008, vol. 111, No. 7, pp. 3383-3387.
Passamonti et al., "Prognostic factors for thrombosis, myelofibrosis, and leukemia in essential thrombocythemia: a study of 605 patients," Haematologica, 2008, vol. 93, No. 11, pp. 1645-1651.
Pikman et al., "*MPLW515L* is a Novel Somatic Activating Mutation in Myelofibrosis with Myeloid Metaplasia," PLoS Med, Jul. 2006, vol. 3, No. 7 (e270), pp. 1140-1151.
Robert-Richard et al., "Human cell engraftment after busulfan or irradiation conditioning of NOD/SCID mice," Haematologica, The Hematology Journal, 2006, vol. 91(10), pp. 1384-1387.
Rumi et al., "*JAK2* (V617F) as an Acquired Somatic Mutation and a Secondary Genetic Event Associated With Disease Progression in Familial Myeloproliferative Disorders," Cancer, Nov. 2006, vol. 107, No. 9, pp. 2206-2211.
Sheils et al., "Nucleic acid microarray: an overview," Current Diagnostic Pathology, 2003, vol. 9, pp. 155-158.
Tahiliani et al., "Conversion 5-Methylcytosine to 5-Hydroxymethylcytosine in Mammalian DNA by MLL Partner TET1," NIH Public Access Author Manuscript, Science, available in PMC Jul. 2009, pp. 1-11.
Tefferi et al., "Classification and diagnosis of myeloproliferative neoplasms: The 2008 World Health Organization criteria and point-of-care diagnostic algorithms," Leukemia, 2008, vol. 22, pp. 14-22.
Tiu et al., "Clonality of the stem cell compartment during evolution of myelodysplastic syndromes and other bone marrow failure syndromes," *Leukemia*, 2007, vol. 21, pp. 1648-1657.

* cited by examiner

MEQDETNHVEGNRLSPPLIPSPPTCQTEPLATKLQNGSPLPERAHPSVNGDTKNHSPKSYYGIPCM
KGSQNSRVSPDFTQESRGYSKCLQNGGIKRTVSEPSLSGLLQIKKLKQDQKANGERRNFGVSQERN
PGESSQPNVSDLSDKKESVSSVAQENAVKDPTSFSTHNCSGPENPELQILNEQEGKSANYHDKNIV
LLKNRAVLMPNGATVSASSVEHTHGELLEKTLSQYYPDCVSIAVQKTTSHINAINSQATNELSCEI
THPSHTSGQINSAQTSNSELPFKPAAVVSEACDADDADNASKLAAMLNTCSPQKPEQLQQQKSVPE
ICPSPAENNIQSTTKLASGEEPCSGSSSNLQAPGGSSERYLKQNENMNGAYFKQSSVPTKDSFSATT
TPPPPSQLLLSPPPPLPQVPQLPSEGKSTLNGGVLEEHHHYPNQSNTTLLREVKIEGKPRAPPSQS
PNPSTHVCSPSPNLSERPQNNCVNENDIQTAGTMTVPLCSEKTRPMSEHLKHNPPIFGSSGELQDN
CQQLMENKEQEILKGRDKEQTRDLVPPTQHYLKPGWIELKAPRFHQAESHLKRNEASLPSILQYQP
NLSNQMTSKQYTGNSNMPGGLPRQAYTQKTTQLEHKSQMYQVEMNQGQSQGTVDQHLQFQKPSHQV
HPSKTDHLPKAHVQSLCGTRFHFQQRADSQTEKLMSPVLKQHLNQQASRTEPFSNSHLLQHKPHKQ
AAQTQPSQSSHLPQNQQQQQKLQIKNKEEILQTFPHPQSNNDQQREGSPFGQTKVEECFHGENQYS
KSSEPETHNVQMGLEEVQNINRRESPYSQTMKSSACKIQVSCSNNTHLVSENKEQTTHPELFAGNK
TQNLHHMQYFPNNVIPKQDLLHRCFQEQEQKSQQASVLQGYKNRNQDMSGQQAAQLAQQRYLIHNH
ANVPPVPEQQGSHTQTPPQKDTQKHAALEWHLLQFQEQQQYTQQPQTESCHSQMHRPIKVEPQCKPH
ACMRTAPPENKTWKKVTKQENPPASCDNVQQKSIIETMEQHLKQFHAKSLFDHKALTLKSQEQVKV
EMSGPVTVLTRQTTAAELDSHTPALEQQTTSSEKTPTKRTAASVLNNPIESPSKLLDTPIKNLLDT
PVKTQYDFPSC**RCVEQIIEKDEGPFYTHLGAGPNVAAIRRINEERFGQKGKAIRIERVIYTGKEGK
SSQGCFIAKWVVRRSSSEEKLLCLVRERAGHTCEAAVIVILILVWEGIPLSLADKLYSELTETLRK
YGTLTNRRCALNEERTCACQGLDPETCGASPSPGCSWSNYYNGCKFARSKIPRKFKLLGDDPKEEE
KLESHLQNLSTLMAPTYKKLAPDAYNNQIEYEHRAPECRLGLKEGRPPSGVTACLDFCAHAHRDLR
NMQNGSTLVCTLTREDNREFGGKPEDEQLHVLFPLYKVSDVDEFGSVEAQEEKKRSGAI**QVLSSFRK
KVRMLAEPVKTCRQRKLEAKKAAAEKLESLENSSNKNEKEKSAPSRTRQTENASQAKQLAELLRLS
GPVMQQSQQPQPLQKQPPQPQQQQRPQQQQPHHPQTRSVNSYSASGSTNPYMRRPNPVSPYPNSSH
TSDIYGSTSPMNPYSTSSQAAGSYLNSSNPMNPYPGLLNQNTQYPSYQCNGNLSVIDNCSPYLGSYS
PQSQPMDLYRYPSQDPLSKLSLPPIHTLYQPRPQNSQSFTSKYLGYGNQNMQGDGPSSCTIRPNVH
HVGKLPPYPTHEMDGHPMGATSELPPNLSNPNMDYKNGEHHSPSHIIHNYSAAPGMPNSSLHALHL
QNKENDMLSHTANGLSKMLFALNHDRTACVQQGLHKLSDANGQEKQPLALVQGVASGAE**LNDEVWS
DSEQSFLDPDIGGVAVAPTHGSILIECAKRELHATTPLKNPNRNHPTRISLVFYQHKSKNEPKHGL
ALWEAKMA**EKASEKEEECEKYGPDYVPQKSHGEKVKREPAEPHETSEPTYLEPIKSLAERTMSVTT
DSTVTTSPYAFTRVTGPYNRYI-2002

Figure 1

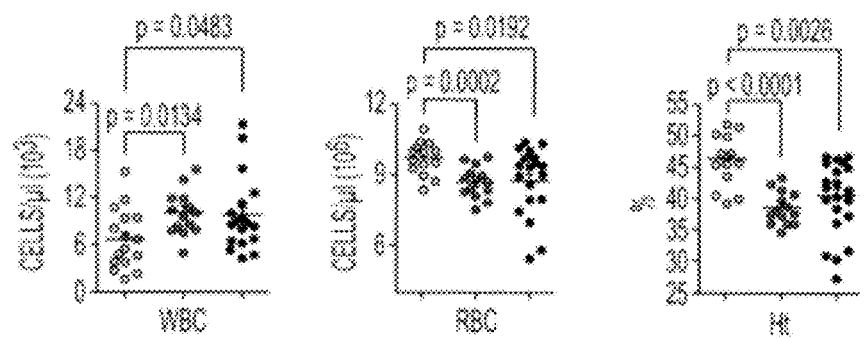
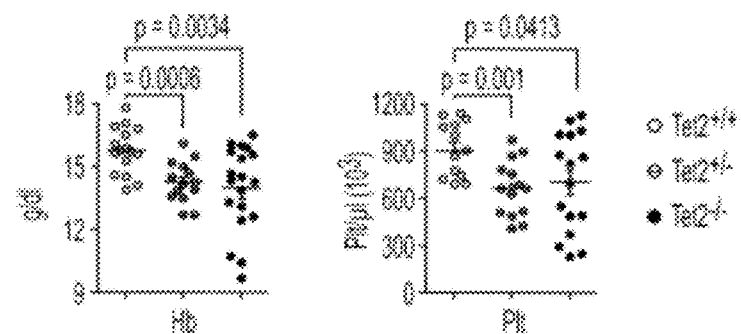
FIG. 13a
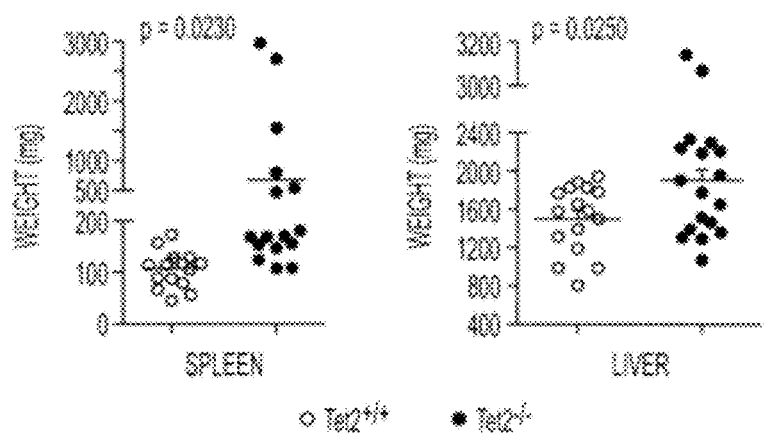
FIG. 13b

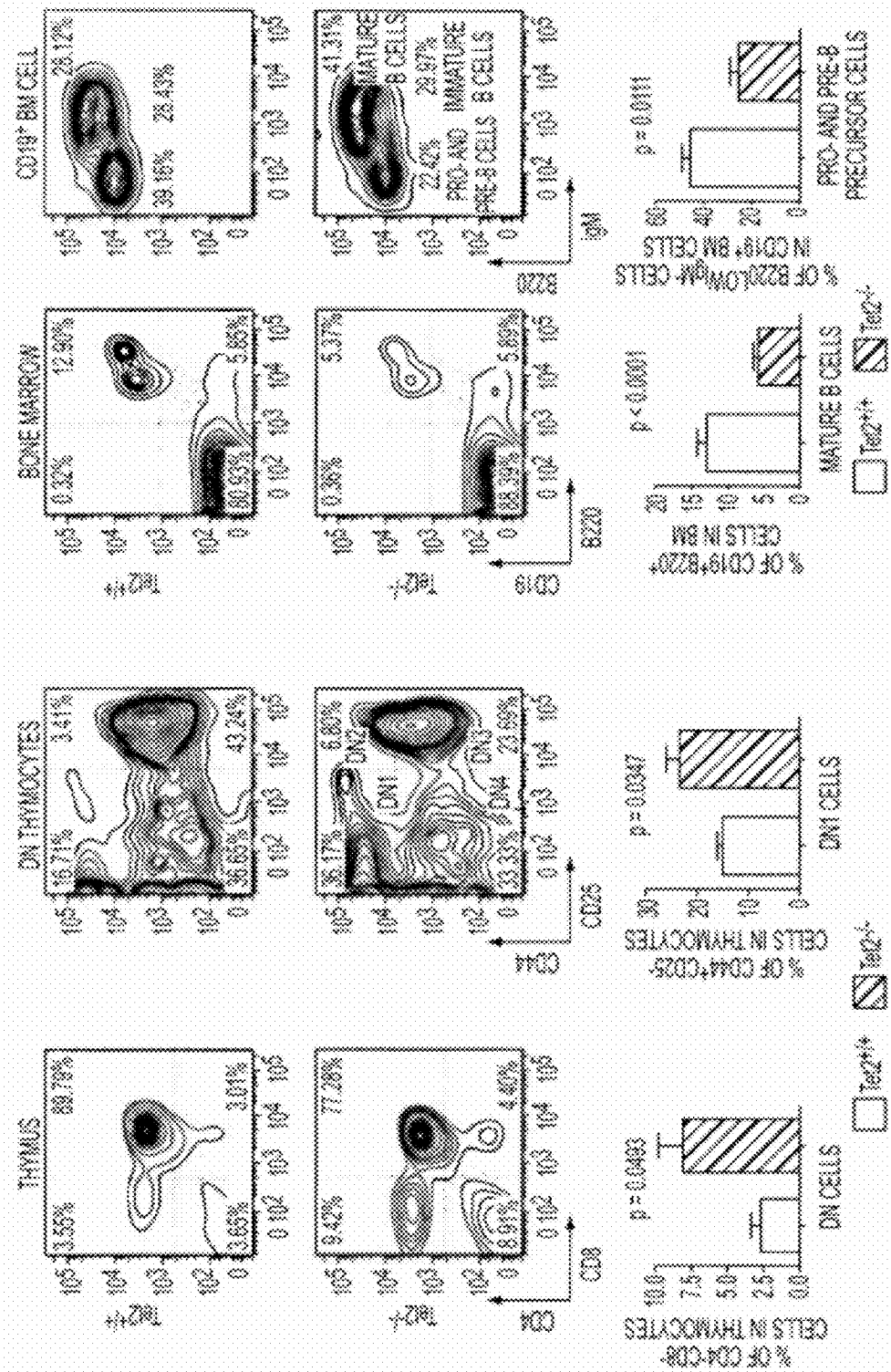

TET2 AS A NEW DIAGNOSTIC AND PRONOSTIC MARKER IN HEMATOPOIETIC NEOPLASMS

This application is a continuation-in-part of U.S. patent application Ser. No. 12/997,203, filed Dec. 9, 2010, which is a U.S. National Stage of PCT/EP2009/057295, filed Jun. 12, 2009, which claims the priority of European patent applications EP 08305255.5 and EP 09155169.7 filed on Jun. 12, 2008, and on Mar. 13, 2009, respectively, all of which are incorporated herein by reference in their entirety.

FIELD OF THE INVENTION

The present invention relates to genetic markers to diagnose myeloid neoplasms, more particularly to a new identified tumour suppressor gene, the Ten Eleven Translocation protein family member 2 gene (TET2). Genetic alterations of TET2 are useful to diagnose myeloid tumours, such as myelodysplastic/myeloproliferative syndromes, MDS, AML or MPD, and lymphoid tumours.

BACKGROUND OF THE INVENTION

Hematopoiesis is maintained by a hierarchical system where hematopoietic stem cells (HSCs) give rise to multipotent progenitors, which in turn differentiate into all types of mature blood cells. The molecular mechanisms controlling multipotentiality, self-renewal, quiescence and HSC commitment have been extensively studied. However, numerous issues remain to be addressed and important genes regulating these processes remain to be identified.

Myeloid malignancies include Acute Myeloid leukaemia (AML), Myeloproliferative disorders (MPDs), myelodysplastic syndromes (MDS) and myelodysplastic/myeloproliferative syndromes that are all clonal stem-cell (HSC) or progenitor malignant disorders (TIU et al., Leukemia, vol. 21(8), p: 1648-57, 2007).

Several genetic mutations have been correlated to AML, and four groups are recognized: (i) the AML with recurrent genetic abnormalities AML t(8; 21)(q22; q22) with RUNX1-ETO fusion gene; AML with abnormal bone marrow eosinophils and inv(16)(p13; q22) or t(16; 16)(p13; q22) with CBFB/MYH11 rearrangement; acute promyelocytic leukaemia APL with t(15; 17)(q22; q12) PML/RARA; AML with 11q23 (MLL) abnormalities); (ii) AML with multilineage dysplasia following MDS or MDS/MPD or without antecedent of MDS or MPD; (iii) AML or MDS therapy related and (iv) other unclassified AML among that comprises the group of AML with normal karyotype which prognosis is based on molecular analysis of oncogenes such as mutations of FLT3-ITD or NPM1.

Myelodysplastic/myeloproliferative syndromes include four myeloid diseases grouped in 1999 by the WHO: chronic myelomonocytic leukemia (CMML), juvenile myelomonocytic leukemia (JMML), atypical chronic myeloid leukemia (aCML) and unclassified myelodysplastic/myeloproliferative syndromes (U-MDS/MPS).

MDS include refractory anemia (RA), and refractory cytopenia with multilineage dysplasia (RCMD). MDS are characterized by ineffective hematopoiesis in one or more of the lineage of the bone marrow. Early MDS mostly demonstrate excessive apoptosis and hematopoietic cell dysplasia (CLAESSENS et al., Blood, vol. 99, p: 1594-601, 2002; CLASESSENS et al., Blood, vol. 105, p: 4035-42, 2005). In about a third of MDS patients, this ineffective hematopoiesis precedes progression to secondary AML (sAML). Although some molecular events associated with specific MDS subtypes (ELBERT et al., Nature, vol. 451(7176), p: 335-9, 2008) or disease transformation (BRAUN et al., Blood, vol. 107(3), p: 1156-65, 2006) have been identified, the underlying molecular defects are still poorly understood. No biological markers, except morphological features, are currently available for early diagnosis and prognosis.

MPDs, referred now as myeloproliferative neoplasms (MPN; TEFFERI & VARDIMAN, Leukemia, vol. 22, p: 14-22, 2008), are chronic myeloid diseases including chronic myelogenous leukaemia (CML), polycythemia vera (PV), essential thrombocythemia (ET), primary myelofibrosis (PMF) and idiopathic myelofibrosis (IMF). MPDs are characterized by an increased proliferation of one or several myeloid lineages. If most MPDs are sporadic diseases, familial cases of MPDs, for which the exact prevalence is unknown, have been reported (GILBERT, Baillieres Clin. Haematol., vol. 11, p: 849-858, 1998; KRALOVICS et al., Blood, vol. 102, p: 3793-3796, 2003; BELLANNE-CHANTELOT et al., Blood, vol. 108, p: 346-352, 2006). The clinical analysis of these familial cases has shown that they are phenotypically identical to sporadic cases. Nevertheless, MPD families are characterized by a clinical and genetic heterogeneity. First, MPD cases from a single family can either display the same subtype or different types of MPD (GILBERT, abovementioned, 1998; BELLANNE-CHANTELOT et al., abovementioned, 2006; RUMI et al., Cancer, vol. 107, p: 2206-2211, 2006). Second, about 6-15% of patients with PV and 3-5% of patients with ET are at risk of developing hematological complication after 15 years of evolution (FINAZZI & HARRISON, Semin. Hematol., vol. 42, p: 230-238, 2005; KILADJIAN et al., Blood, vol. 112, p: 1746, 2008; PASSAMONTI et al., Blood, vol. 111, p: 3383-3387, 2008; PASSAMONTI et al., Haematologica, vol. 93, p: 1645-1651, 2008).

MPDs, in both sporadic and familial cases, are commonly associated with an acquired constitutive kinase activity, as exemplified by the $JAK2^{V617F}$ mutation in Polycythemia Vera, in most PV cases and in half of ET and PMF cases (MORGAN & GILLIGAND, Annu. Rev. Med., vol. 59, p: 213-22, 2008; DELHOMMEAU et al., Cell Mol. Life. Sci., vol. 63(24), p: 2939-53, 2006, CAMPBELL & GREEN, N. Engl. J. Med., vol. 355(23), p: 2452-66, 2006; BELLANNE-CHANTELOT et al., above-mentioned, 2006; JAMES et al., Nature, vol. 434, p: 1144-1148, 2005; BAXTER et al., Lancet, vol. 365, p: 1054-1061, 2005; LEVINE et al., Blood, vol. 106, p: 3377-3379, 2005; KRALOVICS et al., N. Engl. J. Med., vol. 352, p: 1779-1790, 2005). MPDs frequently result from the expression of a constitutive tyrosine kinase protein:

Through a fusion like BCR-ABL in CML, FIP1L1-PDGFRA in HES, TEL-PDGFRB in CMML with hypereosinophilia, ZNF198-FGFR1 in rare MPD coupled to lymphoid proliferation and PCM1-JAK2 in rare MPDs, AML and T cell lymphomas A limited or single nucleotide mutation i.e. JAK2 V617F (1849G>T), which recent discovery of in PV (98%), ET (75%), IMF (50%) and a few percent of CMML, MDS/MPD and U-MPD allows for a new MPD classification and diagnosis criteria and perspectives for treatment. In addition, KIT mutations are recurrent in systemic mast cell proliferation.

Through activating mutations in the receptor for thrombopoietin receptor (MPL), especially of the tryptophan 515 ($MPLW515^{K/L/A}$) (PIKMAN et al., PLoS Med, vol. 3(e270), 2006; CHALIGNÉ et al., Leukemia, vol. 22, p 1557-66, 2008).

Marginal cases of CML presented with BCR/JAK2 rearrangement due to t(9; 22)(p24; q11).

The JAK2 gene on chromosome 9p encodes a tyrosine kinase that associates with type 1 cytokine receptors. The V617F mutation is predicted to disrupt the auto-inhibitory effect of the JH2 domain to constitutive activation of the kinase. Wild type JAK2 exerts a dominant negative effect on the activity of the mutated protein. Therefore the loss of WT JAK2 associated to the duplication of the mutated gene by mitotic recombination observed in most of MPD samples allows for a higher expression and activity of the mutated kinase.

However, several observations, such as the Polycythemia Vera co expressing the WT and mutated JAK2 and the characterization of secondary AML emerging from mutated MPD but lacking of JAK2 mutation in the blast phases indicate oncogenetic events earlier occurring before JAK2 mutation. Moreover, and as discussed previously, the MPD disease evolution is indeed highly variable within and between families. Thus, there is some evidence that there is at least one other mutation than JAK2 implicated in MPDs and, more specifically, their progression.

Lymphoid tumours consist of expansion of cells with lymphoid features. Acute lymphoblastic leukaemia/lymphoma are proliferation of cells blocked in lymphoid differentiation, from either T (T-cell acute lymphoblastic leukaemia; T-ALL) or B (B-cell precursor acute lymphoblastic leukaemia; BCP-ALL) origin. Some leukaemia lymphoma are from Natural Killer (NK) origin. Lymphoma involve expansion of more mature lymphoid cells (B or T). Some neoplasms are chronic, and can involve T cell (prolymphocytic leukaemia) or B cells (Chronic Lymphocytic Leukaemia). The classification of lymphoid neoplasm is based on anatomopathological analyses, differentiation markers and pathogenesis data (Swerdllow S. H., Campo E., Harris N. L., Jaffe E. S., Pileri S. A., Stein H., Thiele J. W., Vardiman J. W. (Eds): WHO classification of tumors of haematopoietc and lymphoid tissues. IARC: Lyon 2008). For example, Anaplasic large T-cell lymphoma are associated with NPM-ALK fusion oncogene (and variant thereof), follicular lymphoma are associated with BCL2 activation following t(14; 18)(q32; q21) chromosomal translocation, mantle cell lymphoma are associated with CCND1 activation following t(11; 14)(q13; q32) chromosomal translocation. Many lymphoma however lack any reliable molecular marker suggesting a pathophysiological mechanism. This is the case, in particular, for more than 50% of diffuse large B cell lymphomas (DLBCL), for most peripheral T-cell lymphomas (PTCL) and for a majority of non-follicular low grade lymphomas.

Therefore, there was an urgent need of a reliable diagnostic marker that allows to identify lymphoid and myeloid neoplasms, in particular MDS and MPD, and eventually to prognosticate their progression.

The Ten Eleven Translocation protein family contains three recently identified members, with unknown functions, characterized in that they share two highly conserved domains at their C-terminal end. As used herein, the expression "gene of the TET family" refers to members of the Ten Eleven Translocation family, TET1, TET2 or TET3, which have been recently identified (Lorsbach et al, Leukemia 2003).

Among them, TET1 is the only studied member, because it has been identified as a fusion partner with the protein mixed lineage leukemia (MLL) in two different and independent studies (ONO et al., Cancer Research, vol. 62(14), p: 4075-80, 2002 and LORSBACH et al., Leukemia, vol. 17(3), p: 637-41, 2003). This protein, also called LCX, or "leukemia associated protein with a CXXC domain in N-terminal region", contains an α-helical coiled-coil region in its C-terminal region, region which is retained in the fusion MLL-TET1. On the contrary, the N-terminus CXXC domain of TET1 is not present in this protein fusion (Ono R, Cancer Research 2002). The two highly conserved carboxy terminal regions are included in the MLL-TET1 fusion (Lorsbach et al, Leukemia 2003). One conserved region is disrupted by the translocation; the other one is fused to MLL. Despite its description as an MLL fusion partner 7 years ago, functional and sequence analysis of the TET1 gene have been reported recently, after the priority date of the present application.

The MLL gene is located at human chromosome 11q23 and is found to be rearranged in a heterogenous group of lymphoid, myeloid and mixed lineage human leukemias. More than 70 loci have been described to be rearranged with the 11q23 chromosomal band and at least 50 of these have been cloned and characterized on a molecular level. Most of the MLL rearrangements map to a 8.3 kb base of the genes. The partners genes are always fused in frame to the 5' part MLL and may include MLL itself. Amplifications of MLL have also been reported. The partner genes code for proteins with disparate functions. In the MLL fusion, they may provide transcriptional activation domains, chromatin modifier complex recruitment or dimerization/oligomerization motif. Indeed, the expression of an MLL-Beta-galactosidase (a bacterial protein able to tetramerize) or to dimerization domain is sufficient to induce leukemia in mouse models. Therefore, it is not possible to infer the function of a protein or its independent involvement in cellular transformation from its fusion to MLL (The versatile mixed lineage leukaemia gene MLL and its many associations in leukaemogenesis. Daser A, Rabbitts T H. Semin Cancer Biol. 2005 June; 15(3):175-88. Review. Chromosomal rearrangements leading to MLL gene fusions: clinical and biological aspects. Harper D P, Aplan P D. Cancer Res. 2008 Dec. 15; 68(24):10024-7.)

On the contrary, little is known about the TET2 protein, which is encoded by a gene located on the 4q24 chromosomal region, and the TET3 protein, which is encoded by a gene located on the 2p12 chromosomal region.

More specifically, the Ten Eleven Translocation oncogene number 2 (TET2) has been designated recently (Lorsbach et al, Leukemia 2003). The TET2 gene located on the chromosomal region 4q24, comprises 11 exons spread over >130 Kb and is normally widely expressed. This gene is referenced with the accession number ID 54790 (Locus ID NCBI) (SEQ ID NO:1), and its cDNA (Accession number NM_001127208, SEQ ID NO:39) is encoding a protein of 2002 amino acids (Accession number NP_001120680, SEQ ID NO:2).

The TET2 protein shares two highly conserved regions with a single orthologous Drosophila predicted protein. These regions are i) a 310 amino acid region located near the center of the protein TET2 (amino acids 1134 to amino acid 1444), and ii) a second 80 amino acid region located near the carboxyterminal end of the protein TET2 (corresponding to amino acid 1843 until amino acid 1922) (these regions are highlighted in FIG. 1). The predicted sequence of TET2 did not reveal any motif corresponding to an identified function.

Applicants report herein that one or both copies of the Ten Eleven Translocation 2 (TET2) gene are often inactivated/modified by acquired mutations in MPD, MDS and CMML but also in lymphoma. These events target the hematopoietic stem cell and indicate an important function for TET2 as a tumor suppressor gene in myeloid or lymphoid neoplasms.

SUMMARY OF THE INVENTION

In a first aspect, the present invention provides an in vitro method for diagnosing a myeloid tumour or a lymphoid tumour in a subject, which comprises the step of analyzing a biological sample from said subject by:
(i) detecting the presence of a mutation in the Ten Eleven Translocation protein family member 2 gene (TET2) coding for the polypeptide having the sequence SEQ ID NO:2, and/or
(ii) analyzing the expression of the TET 2 gene;
wherein the detection of such a TET2 mutation, of the absence of expression of TET2 or of the expression of a truncated TET2 is indicative of a subject developing or predisposed to develop a myeloid tumour or a lymphoid tumour.

In a preferred embodiment, said subject is a mammal, preferably a human.

In another preferred embodiment, said myeloid cancer is selected in the group consisting of myelodysplastic syndrome (MDS), acute myeloid leukemia (AML), myeloproliferative disease (MPD) and myelodysplatic/myeloproliferative syndrome.

In still another preferred embodiment, said lymphoid tumour is selected in the group consisting of lymphoma and more preferentially of T cell lymphoma Preferably, said mutation is detected on each copy of the TET2 gene coding for the polypeptide having the sequence SEQ ID NO:2 (encoded by the cDNA having the sequence SEQ ID NO:39) and is included in the group consisting of deletions, insertions and point mutations such as mutations affecting splice sites, missense mutation and nonsense mutations, preferably missense mutation and nonsense mutations.

In a more preferred aspect of the invention, the mutation is a deletion or an insertion which results in the absence of expression of the TET2 protein or in the expression of a truncated TET2 protein.

Even more preferably, this truncated TET2 protein does not comprise at least one of the two highly conserved regions shared by the other TET proteins and corresponding to i) the 310 amino acid region located near the center of the protein TET2 (amino acids 1134 to amino acid 1444, SEQ ID NO:3), or ii) the 80 amino acid region located near the carboxyterminal end of the protein TET2 (corresponding to amino acid 1843 until amino acid 1922, SEQ ID NO:4), preferably the 80 amino acid region located near the carboxyterminal end of the protein TET2 (corresponding to amino acid 1843 until amino acid 1922, SEQ ID NO:4).

For example, these deletions or insertions can be selected in the group comprising or consisting of those disclosed in Table I in reference to SEQ ID NO:39 for nucleic acid position and to SEQ ID NO:2 for amino acid position.

TABLE I

| Nucleotide Change | Consequence |
| --- | --- |
| del1264_1666 | p.Glu135 FS |
| delC 1642 | p.Ser261 FS |
| del1893_1896 | p.Lys345FS |
| delC 2448 | p.Gln530 FS |
| delA 2505 | p.Thr549 FS |
| delC 2524 | p. Pro555 FS |
| Ins 2540_2544 | p.Leu560FS |
| delT 2685 | p.Ser609 FS |
| delA 2815 | p.Gln652FS |
| del 2834_2835 | p.His658 FS |
| delA 2935 | p.Glu692 FS |
| delT 2944 | p.Leu699 STOP |
| delG 2994 | p.Glu711 FS |
| delC 3009 | p.His717 FS |
| insA 3009 | p.His717 FS |
| del 3131_3137 | p. Leu757 FS |
| insC 3151 | p.Gln764 FS |

TABLE I-continued

| Nucleotide Change | Consequence |
| --- | --- |
| delA 3166 | p.Gln769 FS |
| delT3215 | p.Phe785 FS |
| insA3350 | p.Gln831FS |
| insT3995 | p.Glu846 FS |
| delA3430 | p.Asn857FS |
| insT 3465 | p.Pro869 FS |
| insA 5757 | p.Gln891 STOP |
| insCT 3581 | pGly 908 FS |
| del CA 3756_3757 | p.Gln966 FS |
| dupT 3914 | p.Glu1026 STOP |
| delT 3998 | p.Leu1046FS |
| delA 4130 | p.Lys1090 FS |
| delG 4271 | p.Glu1137 FS |
| delA4327 | p.Asn1156 FS |
| delG 4527 | p.Ala1223 FS |
| — | p.del 1237-1239 |
| delG 4932 | p.Glu1357 FS |
| insG 5119 | p.Leu 1420 FS |
| delG 5133 | p.Asp 1425 FS |
| insA 5177 | p.Arg1440FS |
| dupA 5177 | p.Arg1440FS |
| delC 5222 | p.Leu1457 STOP |
| del5521_5524 | pThr1554 FS |
| insA 5540 | p.Tyr1560 FS |
| del 5583_5605 | p.Pro1575FS |
| delT 5570 | p.Leu1637 FS |
| del5828_5843 | p.Met1656 FS |
| del6049_6050 | p.Asp1830 FS |
| delC 6360 | p.Gln1834 FS |
| del6396_6531 | p.Val1846 FS |
| delA 6507 | p.Thr1883 FS |
| insC 6507 | p.Thr1883 FS |
| del6511_6512 | p.Pro1885FS |
| DelC 6555 | p.Leu1889FS |
| insC splice site | mutation of splice site exon 8 |

Del: deletion;
ins: insertion;
FS: frame shift

In another more preferred aspect of the invention, the mutation is a missense mutation. Said mutation in the TET2 protein, preferably resulting from a mutation in the open reading frame of the TET2 gene, is preferably located in at least one of the two highly conserved regions shared by the TET proteins and corresponding to i) the 310 amino acid region located near the center of the protein TET2 (amino acids 1134 to amino acid 1444, SEQ ID NO:3), and ii) the 80 amino acid region located near the carboxyterminal end of the protein TET2 (corresponding to amino acid 1843 until amino acid 1922, SEQ ID NO:4), and more preferably in the 80 amino acid region located near the carboxyterminal end of the protein TET2 (corresponding to amino acid 1843 until amino acid 1922, SEQ ID NO:4). For example, these missense mutations can be selected in the group comprising or consisting of I1175V, L1197N, H1219Y, E1235V, C1271W, K1299E, L1340P, R1302G, G1370E, A1344E, N1387S, L1398P, V1417F, P1419R, H1868R, G1869W, L1872P, I1873T, R1896M, and S1898F, preferably can be selected in the group comprising or consisting of L1197N, H1219Y, E1235V, C1271W, K1299E, L1340P, R1302G, G1370E, A1344E, N1387S, H1868R, G1869W, L1872P, I1873T, R1896M, and S1898F, and more preferably in the group comprising or consisting of: H1868R, G1869W, L1872P, I1873T, R1896M, and S1898F.

In another more preferred aspect of the invention, the mutation is a nonsense mutation. Said mutation resulting from a mutation in the open reading frame of the TET2 gene, is preferably located before or inside at least one of the two highly conserved regions shared by the TET proteins and corresponding to i) the 310 amino acid region located near the center of the protein TET2 (amino acids 1134 to amino acid 1444, SEQ ID NO:3), and ii) the 80 amino acid region located near the carboxyterminal end of the protein TET2 (corresponding to amino acid 1843 until amino acid 1922, SEQ ID NO:4), and more preferably before or inside the 80 amino acid region located near the carboxyterminal end of the protein TET2 (corresponding to amino acid 1843 until amino acid 1922, SEQ ID NO:4). For example, said nonsense mutations can be selected in the group comprising or consisting of Q232Stop, Q321Stop, S354Stop, Q417Stop, Q481Stop, R544Stop, R550Stop, Q557Stop, Q574Stop, Q593Stop, Q635Stop, Q642Stop, Q685Stop, L699Stop, Q743Stop, Q778Stop, S792Stop, Q886Stop, Q891Stop, Q916Stop, Q943Stop, Q963Stop, E1026Stop R1067Stop, R1216Stop, Y1225Stop, R1404Stop, Q1414Stop, Q1445Stop, L1457Stop, R1465Stop, K1491Stop, R1516Stop, Q1524Stop, Q1542Stop, N1624Stop, Y1724Stop, Y1751 Stop, L1819Stop, Q1834Stop and W1847Stop.

In another aspect of the invention, the mutation in the TET2 gene induces absence of expression or under-expression of the polypeptide having the sequence SEQ ID NO:2 and more preferably the absence of expression or under-expression of at least one of the two highly conserved regions shared by the TET proteins and corresponding to i) the 310 amino acid region located near the center of the protein TET2 (amino acids 1134 to amino acid 1444, SEQ ID NO:3), and ii) the 80 amino acid region located near the carboxyterminal end of the protein TET2 (corresponding to amino acid 1843 until amino acid 1922, SEQ ID NO:4), more preferably of the 80 amino acid region located near the carboxyterminal end of the protein TET2 (corresponding to amino acid 1843 until amino acid 1922, SEQ ID NO:4).

In a second aspect, the present invention provides a kit for diagnosing myeloid cancer in a subject comprising at least one nucleic acid probe or oligonucleotide or at least one antibody, which can be used in a method as defined previously for detecting the presence of a mutation in the TET2 gene and/or analysing the expression of the TET2 gene.

In a preferred embodiment of the invention, said oligonucleotide is at least one PCR primer, and preferably a set of PCR primers.

More preferably, said set of primers is selected in the group comprising SEQ ID NO: 5 to SEQ ID NO: 38 (see examples).

In a third aspect, the present invention provides the use of a hypomethylating agent for treating a patient suffering from a myeloid or a lymphoid tumour, for which tumour, a TET2 mutation, an absence of TET2 expression or an expression of a truncated TET2 has been detected.

In a final aspect, the present invention provides a method for treating a subject suffering a myeloid or a lymphoid tumour, for which tumour, a TET2 mutation, an absence of TET2 expression or an expression of a truncated TET2 has been detected, said method comprising the step of administrating to said subject a therapeutically efficient amount of a hypomethylating agent.

BRIEF DESCRIPTION OF THE DRAWINGS

The FIG. 1 shows the protein sequence of TET2 (SEQ ID NO:2), highlighting the conserved regions between species (bold).

The FIG. 2 shows the sequence traces obtained by sequencing the PCR products obtained for samples obtained from two patients A and E, showing that the mutation only occurs in the tumoral and not in non-tumoral samples (NT), and Peripheral Blood Lymphocytes (PBL). R corresponds to the sequence obtained with the Reverse primer, and F corresponds to the one obtained with the Forward primer. WT corresponds to the sequence obtained in healthy individuals.

Figure 3:
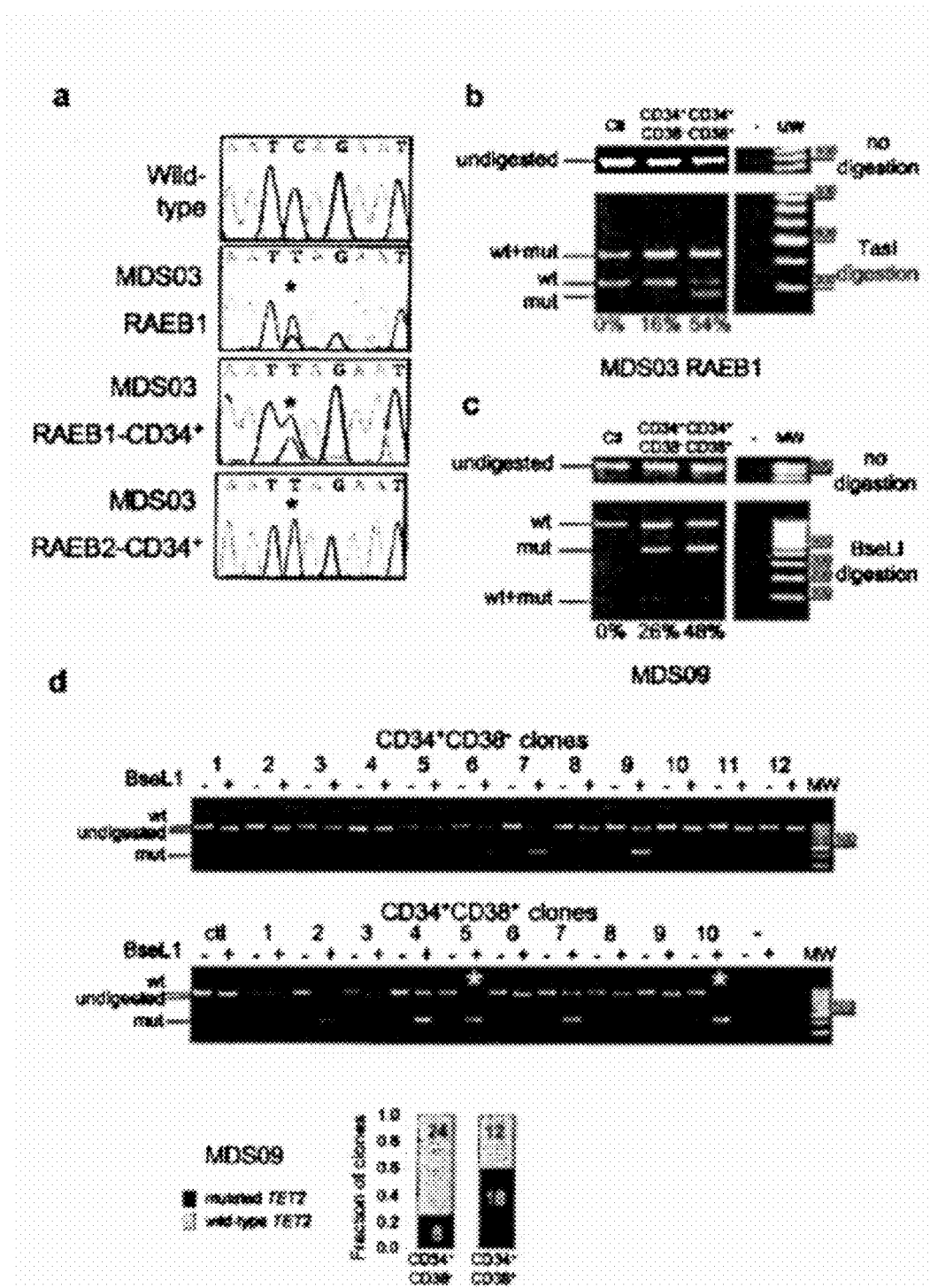

The FIG. 3 shows that in MDS samples, mutated TET2 is observed in immature CD34+ cells and is associated with in vivo expansion of the mutated clone. The FIG. 3a shows the sequencing histograms of sorted CD34+ cells. The FIG. 3b shows the PCR-RFLP analysis of DNA isolated from sorted MDS03 CD34+CD38− and CD34+CD38+ cells at RAEB1 phase. The FIG. 3c shows PCR-RFLP analysis of TET2. The FIG. 3d shows genotyping by PCR-RFLP.

Figure 4:
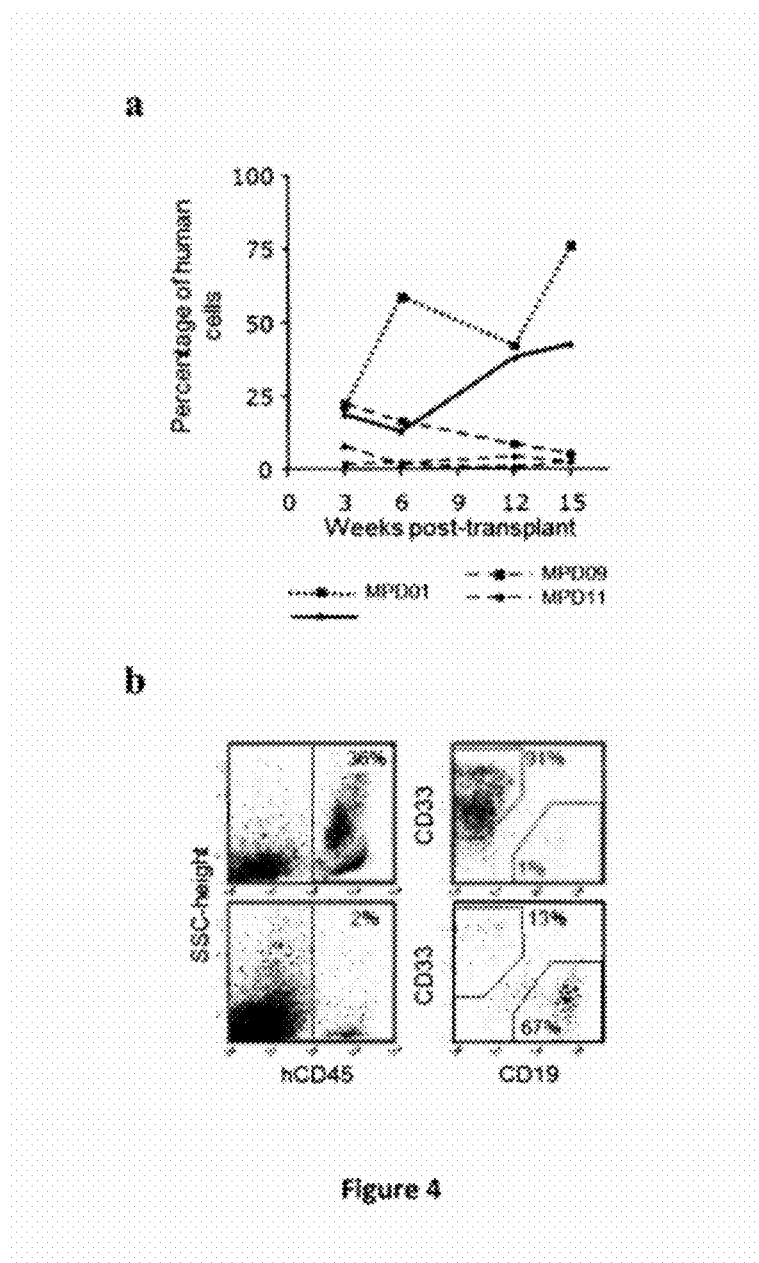

The FIG. 4 shows that $JAK2^{V617F}$-positive MPD hematopoietic stem cells with TET2 defects display enhanced NOD/SCID repopulating capacities. The FIG. 4a shows the percentage of human CD45-positive cells in mouse bone marrow. The FIG. 4b shows flow cytometric analysis of human cells present in NOD-SCID bone marrow.

Figure 5:
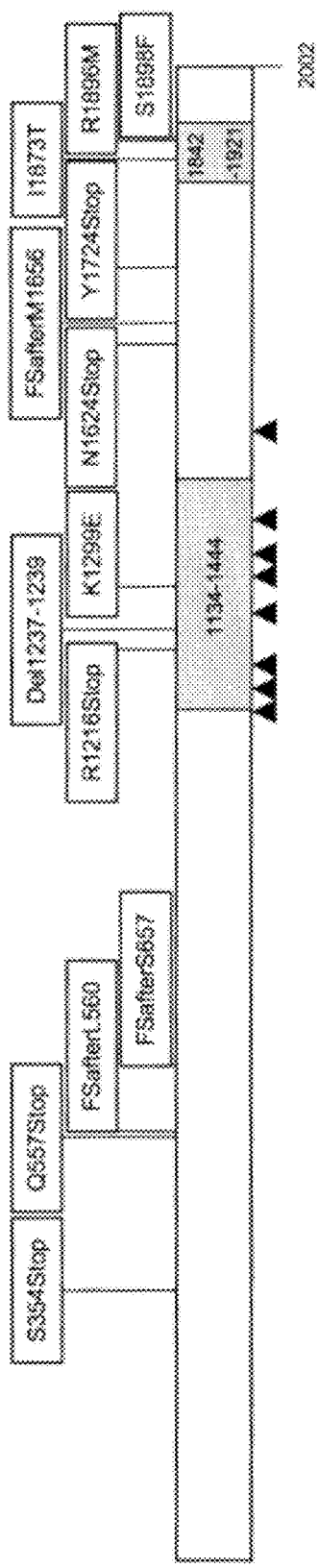

The FIG. 5 shows the locations of some of the identified mutations of the TET2 gene distributed along the protein sequence Conserved regions are marked with gray stripes. Arrowheads indicate the location of exon boundaries. FS: Frame shift.

Figure 6:
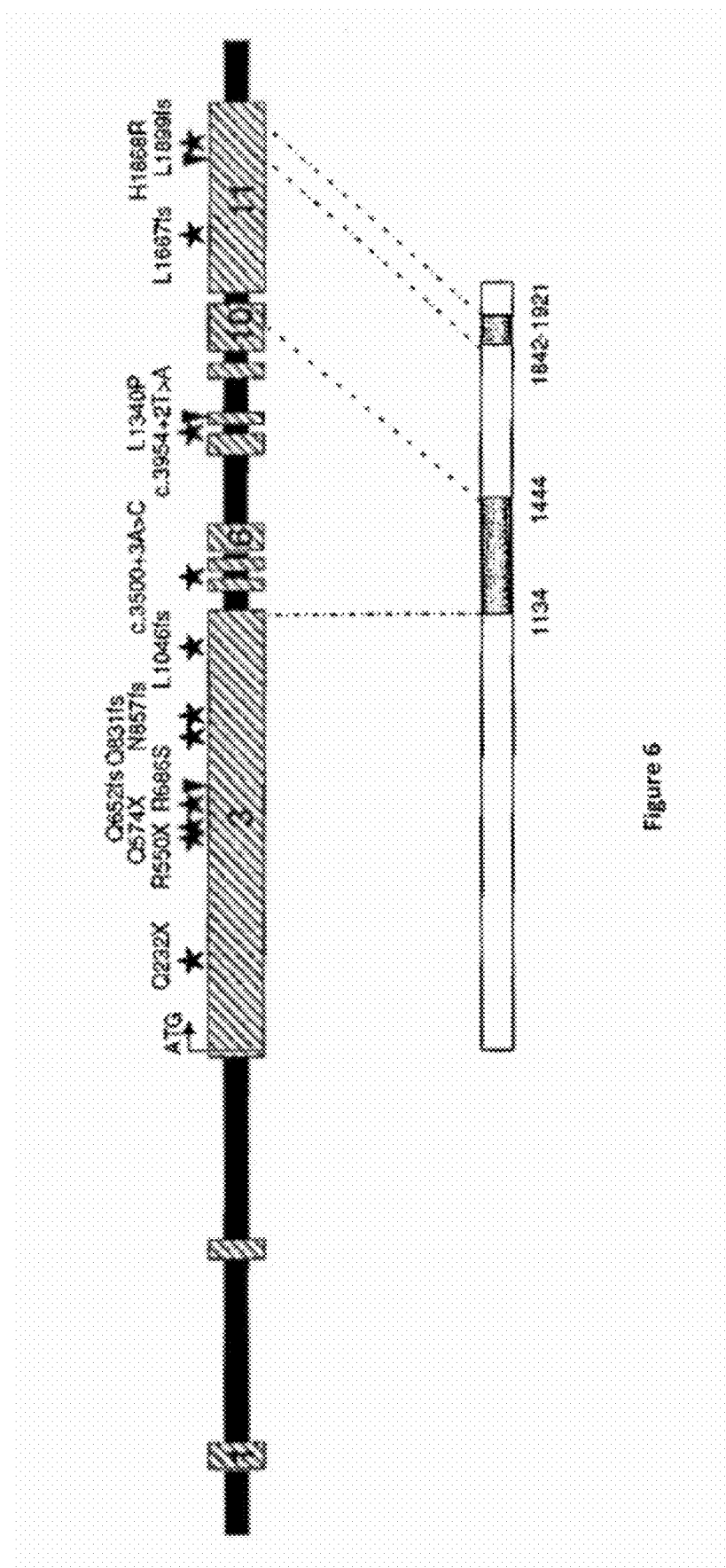

The FIG. 6 shows a schematic representation of the TET2 gene and protein showing the mutations identified in familial myeloproliferative neoplasms. Hatched boxes indicate exons. Truncating mutations are depicted as stars, missense mutations as inverted triangles. Conserved functional domains are depicted as boxes on the protein scheme. fs: frameshift.

Figure 7:
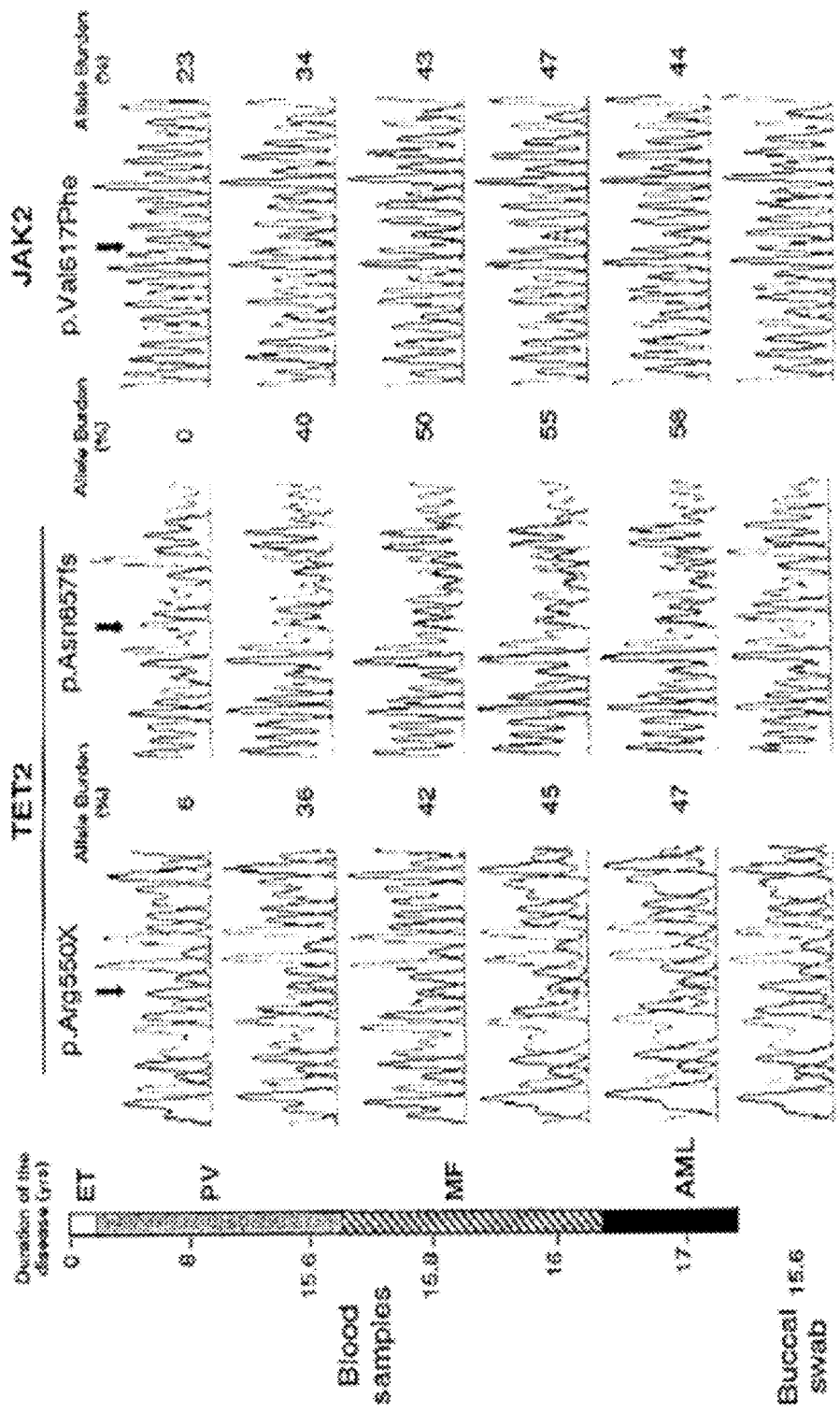

The FIG. 7 shows the sequential study of TET2 and JAK2 in patient P4 (F3). Sequence electrophoregrams are shown for each TET2 mutation and for JAKV617F. The diagram on the left indicates time lapse from diagnosis (in years) and corresponding phenotype for each sample (white: ET; grey: PV; hatched: post-ET MF; black: AML).

Figure 8:
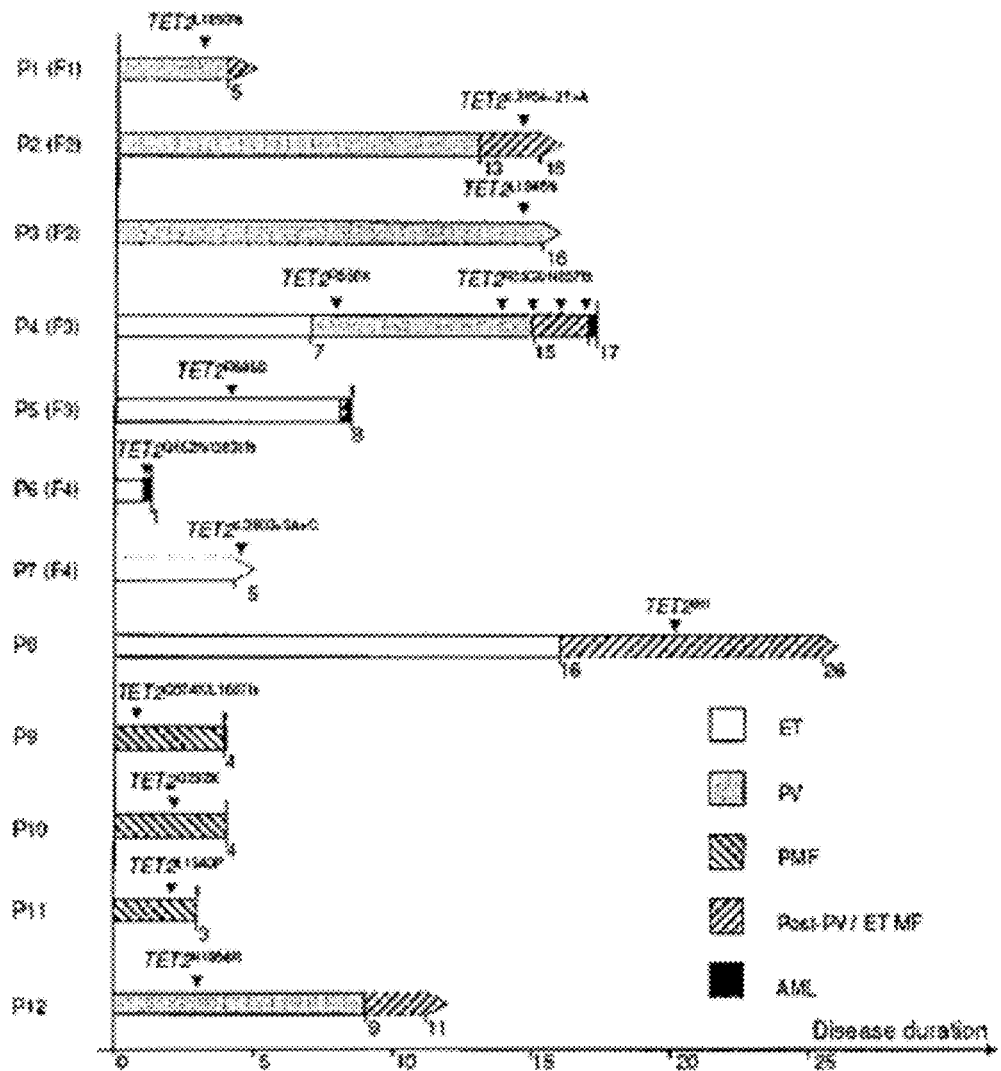

The FIG. 8 shows the schematic representation of the clinical status of the twelve patients with at least one TET2 mutation. White boxes depict ET stages, grey, PV, crosswised hatching indicates myelofibrosis, either primary (left-slanting) or post-PV/ET (right-slanting) and AML are symbolized as black boxes. Above each arrowhead indicating a molecular analysis is annotated the TET2 corresponding mutation. Disease duration (in years) is indicated below the bars, the "zero" point indicating time of diagnosis. Time of death is symbolized as a vertical line, when appropriate, at the right end.

Figure 9:
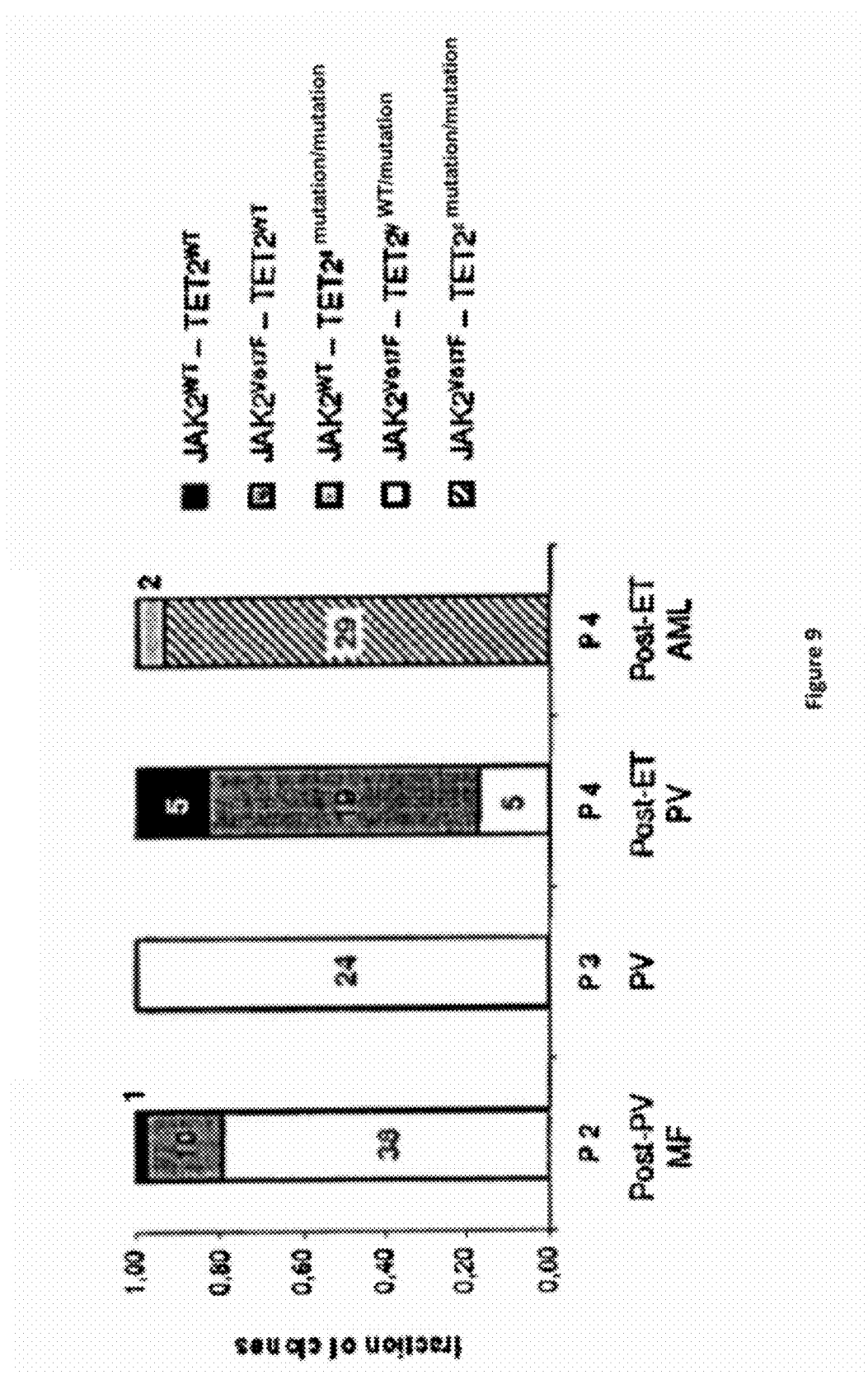

The FIG. 9 shows the TET2 and JAK2 genotypes in committed progenitors of patients P2, P3 and P4. Histograms show the fraction of clones harboring JAKV617F and two TET2 mutations (crosswised hatching), JAK2V617F and one TET2 mutation (white), wild type JAK2 and two TET2 mutations (light grey), JAK2V617F and wild type TET2 (grey) and no mutation in any of the two genes (black). Two samples were analyzed for patient P4, the corresponding stage is indicated below each bar. The numbers of analyzed clones are indicated.

Figure 10:
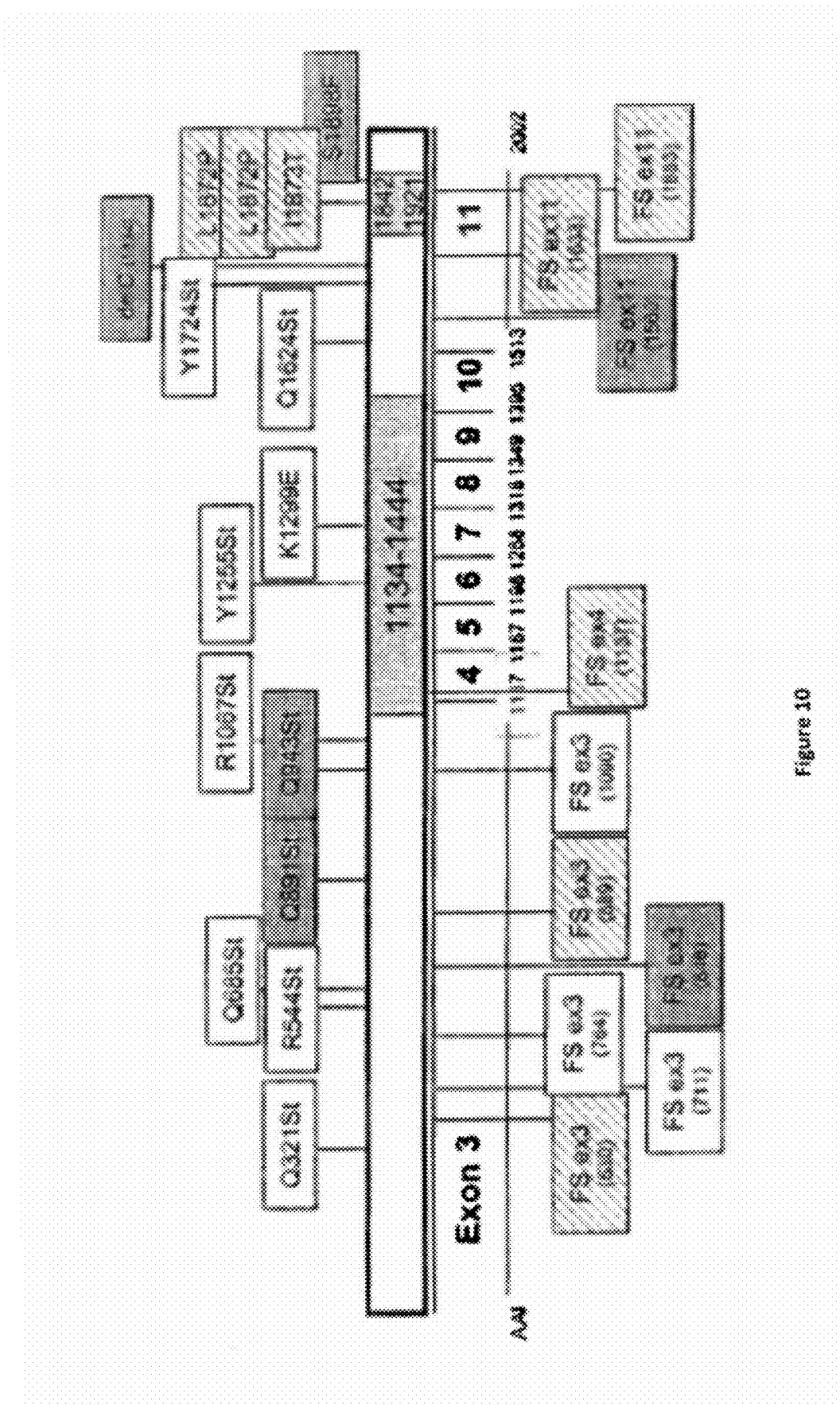

The FIG. 10 shows the clinical status and TET2 genotypes in MDS patients. Whites boxes represent low/int-1 grade MDS, hatched boxes represent int-2/high grade MDS and grey boxes represent secondary AML.

Figure 11:
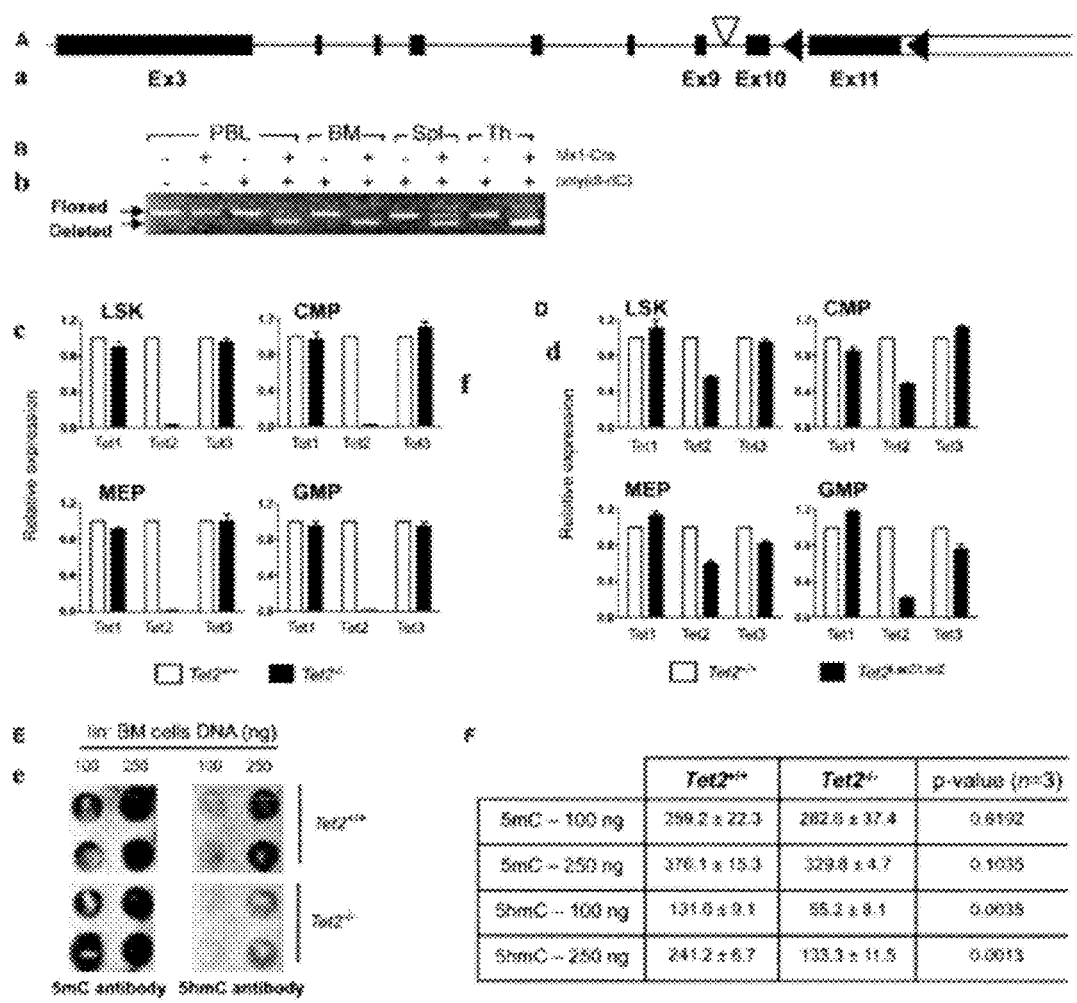

The FIG. 11a shows partial structure of the Tet2 gene. For the Tet2LacZ "LacZ" allele, the location of the gene-trap cassette containing a splice acceptor and a beta-galactosidaseneomycin fusion gene is indicated (empty triangle). For the Tet2Lox "foxed" allele, loxP sites (black triangles) have been introduced in intron 10 and in the 30 untranslated region of exon 11.

The FIG. 11b shows the PCR analyses of Mx1-Cre-mediated exon 11 deletion in peripheral blood leukocytes (PBL), bone marrow (BM), spleen (Spl) and thymus (Th) cells from Mx1-Cre-Tet2$^{Lox/Lox}$ (hereafter named Tet2$^{+/+}$) and Mx1-Cre+Tet2$^{Lox/Lox}$ (hereafter named Tet2$^{-/-}$) animals 2 months after poly(dI:dC) injections (floxed allele: 305 bp; deleted allele: 237 bp).

The FIG. 11c shows quantitative RT-PCR analysis of expression of the murine Tet1, Tet2 and Tet3 genes in flow-sorted hematopoietic progenitors from Tet2+/+ and Tet2$^{-/-}$ animals (n=3 per genotype). Results are normalized with respect to Abl1 expression and represented relatively to expression in control mice samples. Tet2 RT-PCR assay spans the exon 10-11 boundary. LSK: Lin-Sca-1+c-Kit+; CMP: common myeloid progenitor; MEP: megakaryocyte-erythrocyte progenitor; GMP: granulocyte-macrophage progenitor.

The FIG. 11d shows quantitative RT-PCR analysis in Tet2LacZ/LacZ versus wild-type controls as in C (n=3 per genotype).

The FIG. 11e shows drop in 5-hydroxymethyl-cytosine (5hmC) in immature populations of Tet2-inactivated mice. Immunoblot analyses of increased quantity of genomic DNA from BM lineage (lin)-negative cells of Tet2$^{+/+}$ and Tet2$^{-/-}$ mice 4 months after poly(dI:dC) induction using anti 5-methylcytosine-(5mC) antibody (left panel) and 5-hydroxymethyl-cytosine-(5hmC) antibody (right panel).

The FIG. 11f shows the quantification of the signal shown in FIG. 11e.

Figure 12A:
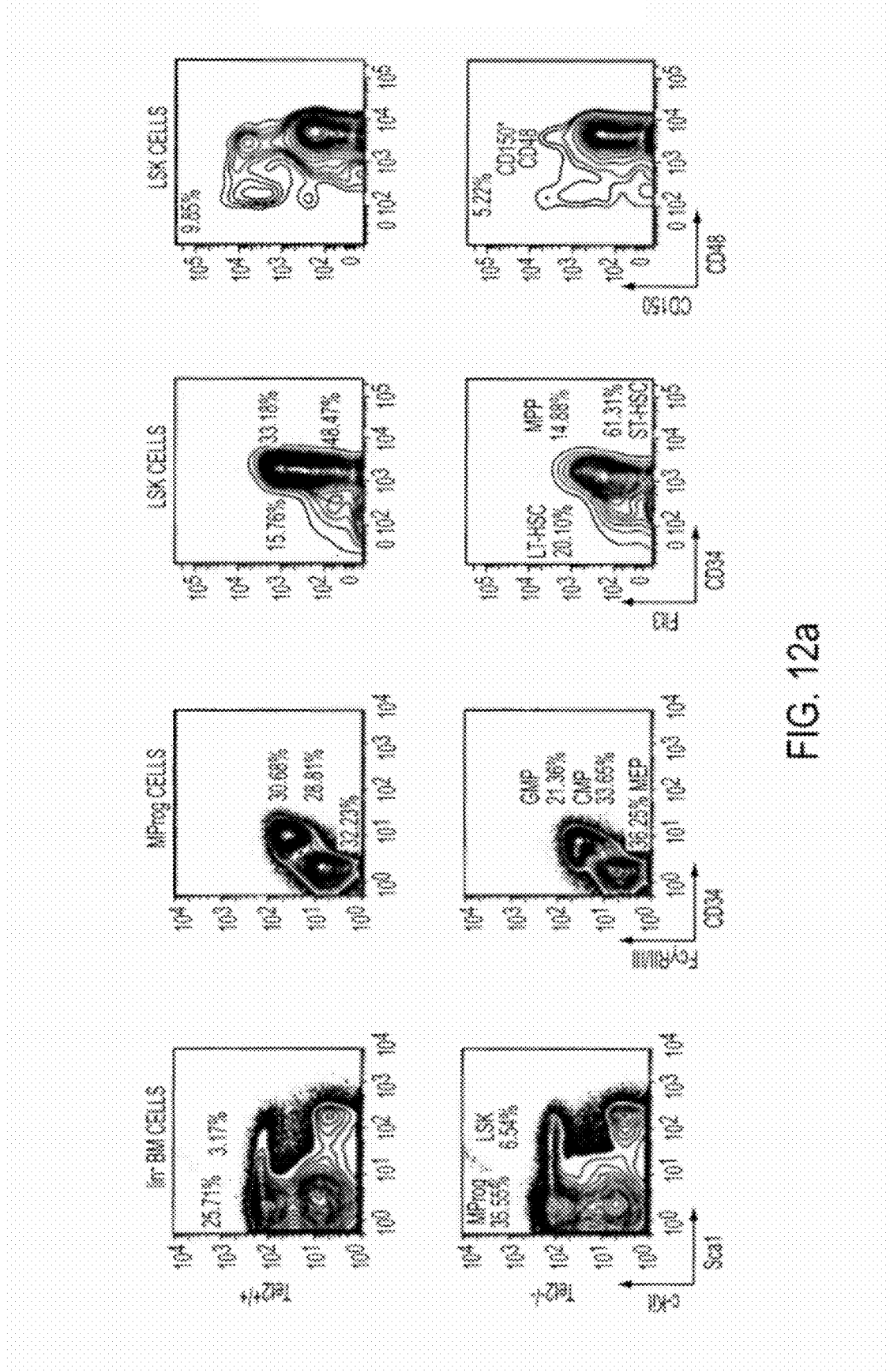

The FIG. 12a shows the flow cytometrical analysis of hematopoietic stem and progenitor cells in the bone marrow of Tet2$^{+/+}$ and Tet2$^{-/-}$ animals. Analysis was performed 4-6 months postinduction. Percentages within lineage—bone marrow cells (left panel), myeloid progenitor cells (MProg: lin-Sca-1-c-Kit+ cells; middle left panel), or within LSK cells (lin-Sca-1+c-Kit+ cells; middle right and right panel) are indicated.

Figure 12C:
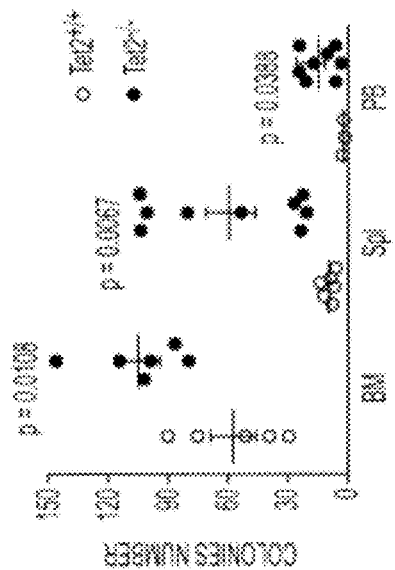
Figure 12B:
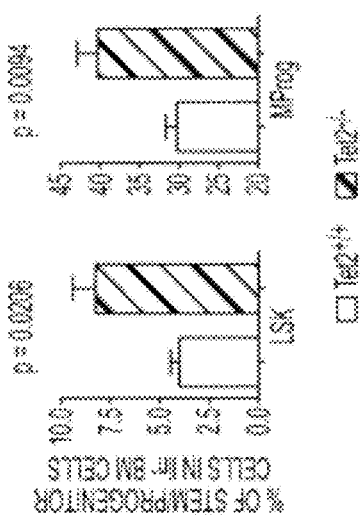

The FIG. 12b shows the representation of the results exemplified in FIG. 12a as a percentage of lineage-negative hematopoietic progenitors. Data are presented as mean±SEM Tet2$^{+/+}$ (n=6; white histogram) and Tet2$^{-/-}$ (n=6; black histogram) mice.

The FIG. 12c shows clonogenic activity of bone marrow (BM), spleen (Spl) and peripheral blood (PB) cells from Tet2$^{+/+}$ (n=6; white circles) and Tet2$^{-/-}$ (n=6; black circles) mice 4-8 months postinduction in methylcellulose M3434 medium. Colonies were scored after 7 days and results are represented as mean colony number±SEM.

Figure 12G:
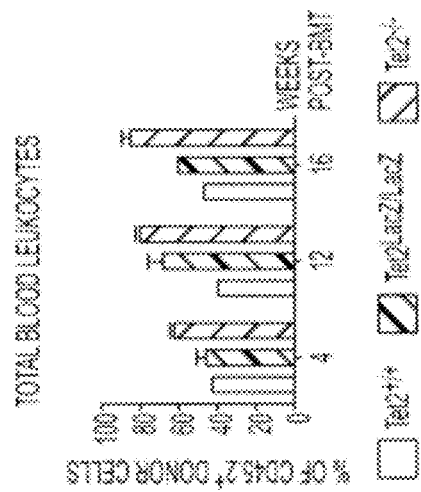
Figure 12E:
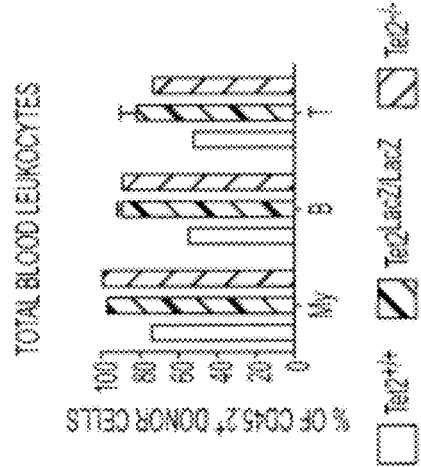
Figure 12D:
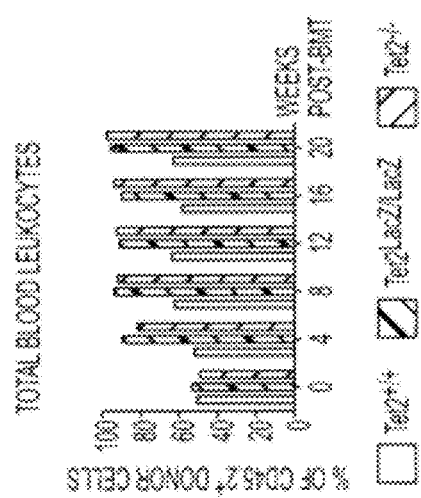

The FIG. 12d shows competitive bone marrow transplantation (BMT) assay. CD45.2+ donor BM cells isolated from Tet2$^{+/+}$, Tet2$^{LacZ/LacZ}$ and Tet2$^{-/-}$ mice were transplanted into lethally irradiated CD45.1+ recipients, in equivalent number to wild-type competitor CD45.1+CD45.2+ BM cells. The percentage of donor chimerism (CD45.2$^+$ cells) in the blood is given at the indicated time points post-BMT (n=2 mice per genotype).

The FIG. 12e shows the percentage of CD45.2$^+$ donor chimerism in blood cells 20 weeks post-BMT; myelomonocytic cells (My; CD11b$^+$Gr-1$^+$), B cells (CD19$^+$B220$^+$) and T cells (CD4$^+$ or CD8$^+$). Values shown are mean±SEM (n=2 mice per genotype).

Figure 12F:
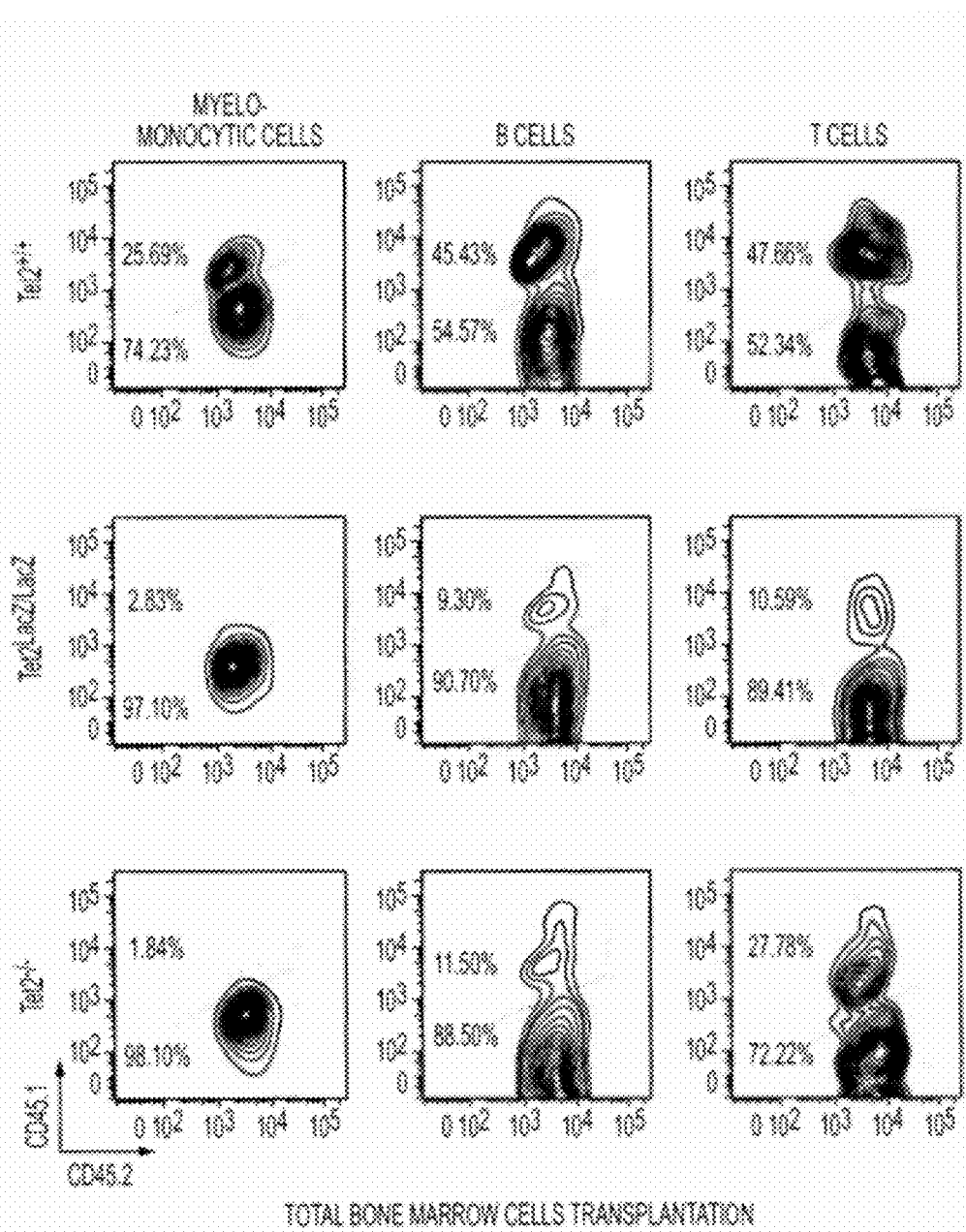

The FIG. 12f shows the representative flow cytometrical profiles of donor chimerism in blood subpopulations shown in (E) (host cells were electronically excluded with CD45.1).

The FIG. 12g shows LSK cells transplantation. CD45.2$^+$ sorted-LSK cells isolated from Tet2-deficient or wild-type mice were transplanted into lethally irradiated CD45.1+ congenic recipients. The percentage of donor chimerism in the blood is given at the indicated time points post-BMT. Values shown are mean±SEM (n=2 mice per genotype).

Figure 12H:
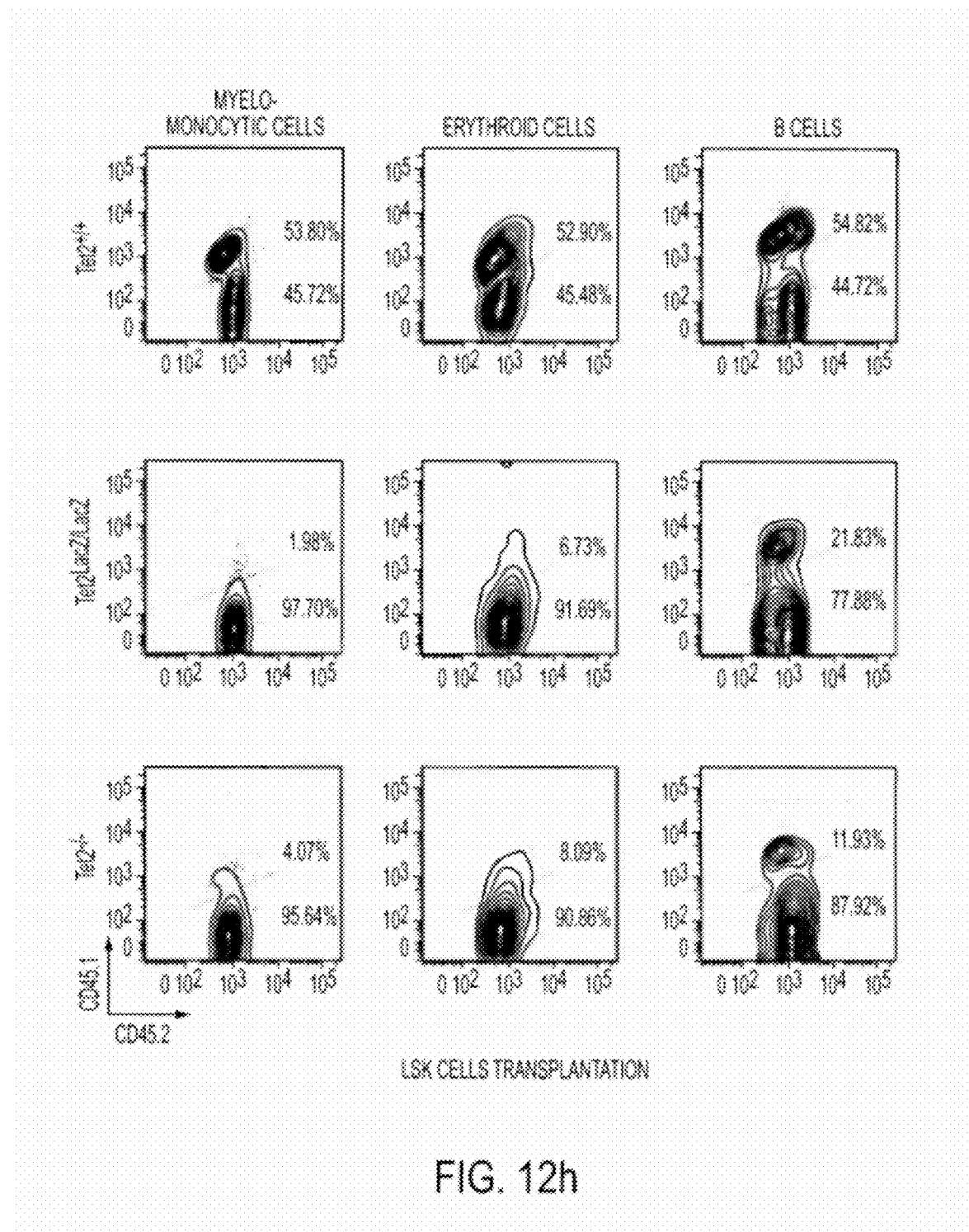

The FIG. 12h shows the representative flow cytometrical analysis of donor chimerism in bone marrow subpopulations 16 weeks post-BMT (CD11b$^+$Gr$^-$1$^+$ myelomonocytic cells; CD71+ erythroid cells; CD19+B220+ B cells).

The FIG. 13a White blood cell (WBC), red blood cell (RBC), hematocrit (Ht), hemoglobin (Hb), and platelet (Plt) counts in peripheral blood samples obtained from Tet2$^{+/+}$, Tet2$^{+/-}$, and Tet2$^{-/-}$ mice, performed 4-6 months post-induction.

The FIG. 13b shows spleen and liver weights of mutant and littermate control mice.

Figure 13C:
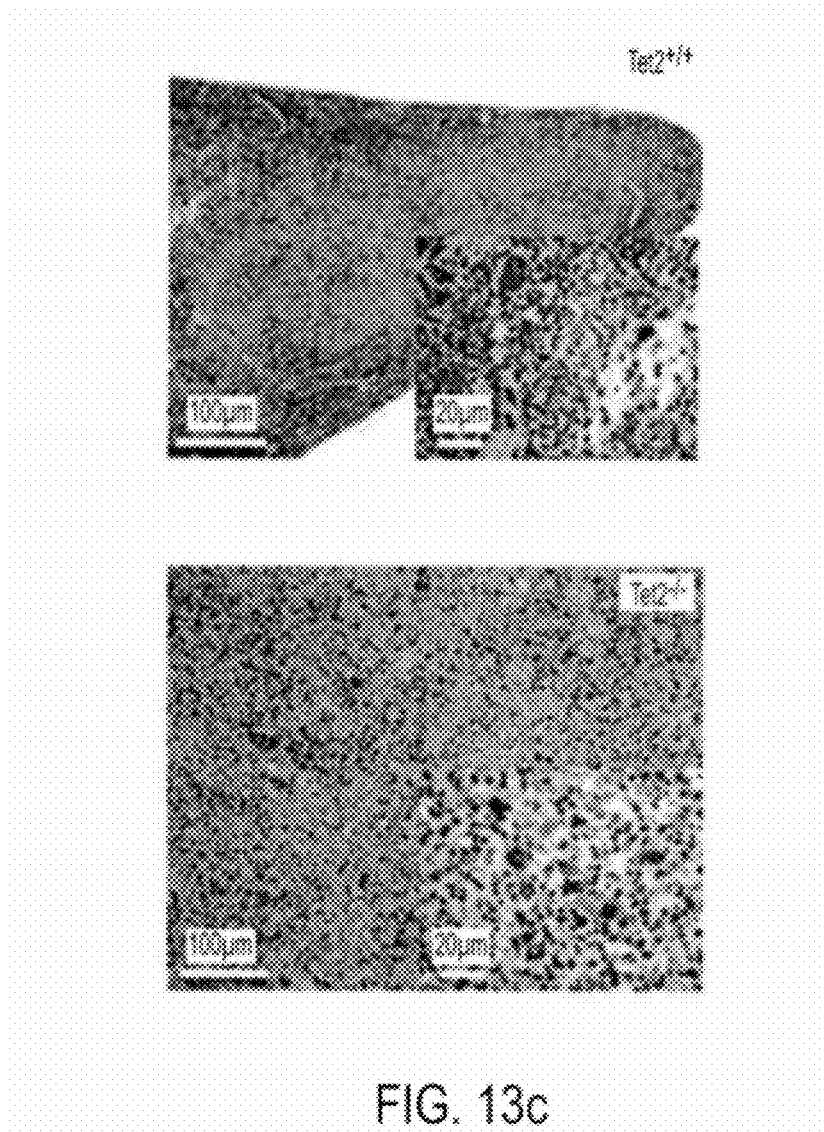

The FIG. 13c shows Von Willebrand staining on spleen sections from Tet2$^{+/+}$ and Tet2$^{-/-}$ animals highlights megakaryocytic hyperplasia in Tet2$^{-/-}$ animals 4 months postinduction.

Figure 13D:
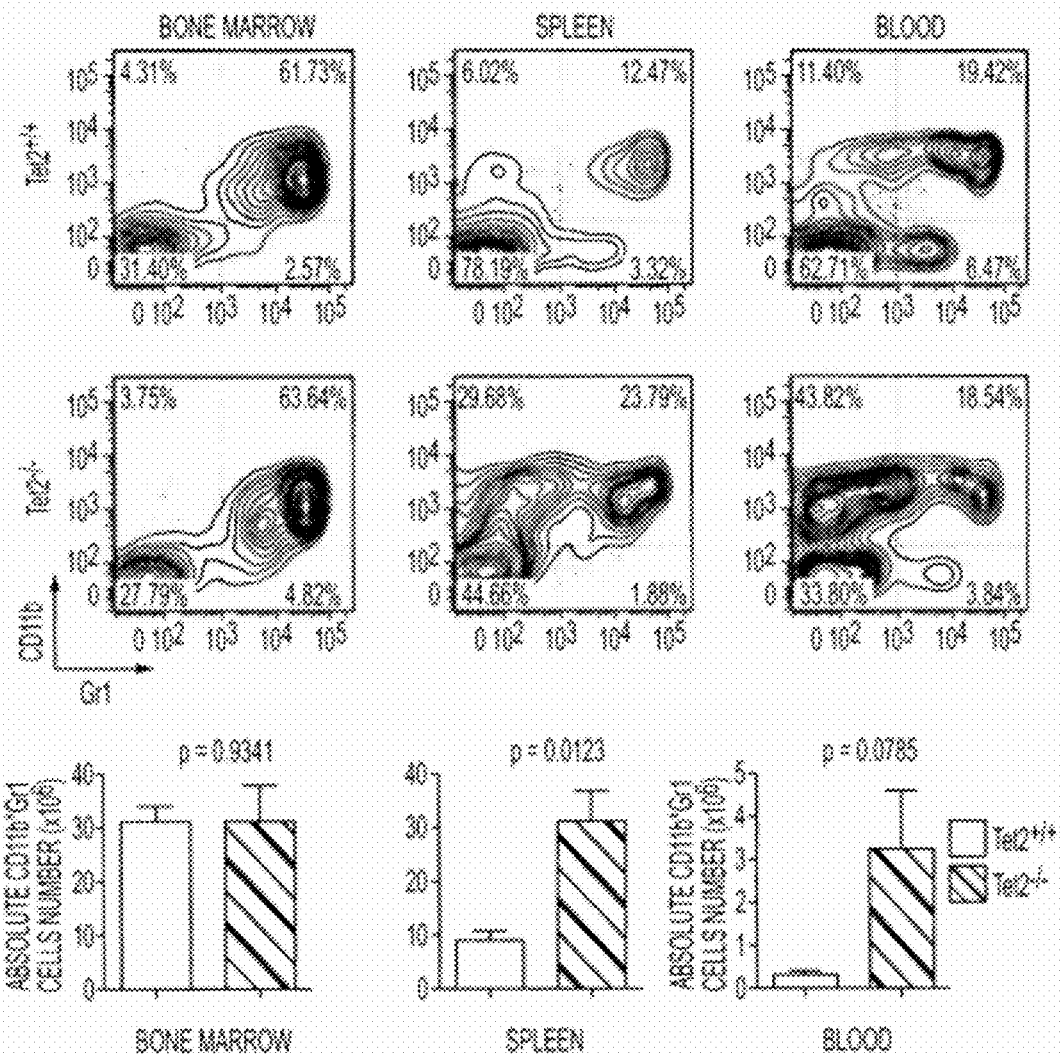

The FIG. 13d shows representative flow cytometrical analysis of the mature myeloid cells in the bone marrow, spleen, and blood of Tet2$^{+/+}$ and Tet2$^{-/-}$ animals. Percentages of total cells are indicated. Lower panel: absolute number of cells from analysis shown in FIG. 13c. Tet2$^{+/+}$ (n=10; white bars) and Tet2$^{-/-}$ (n=16; black bars) animals are represented as mean±SEM.

Figure 13E:
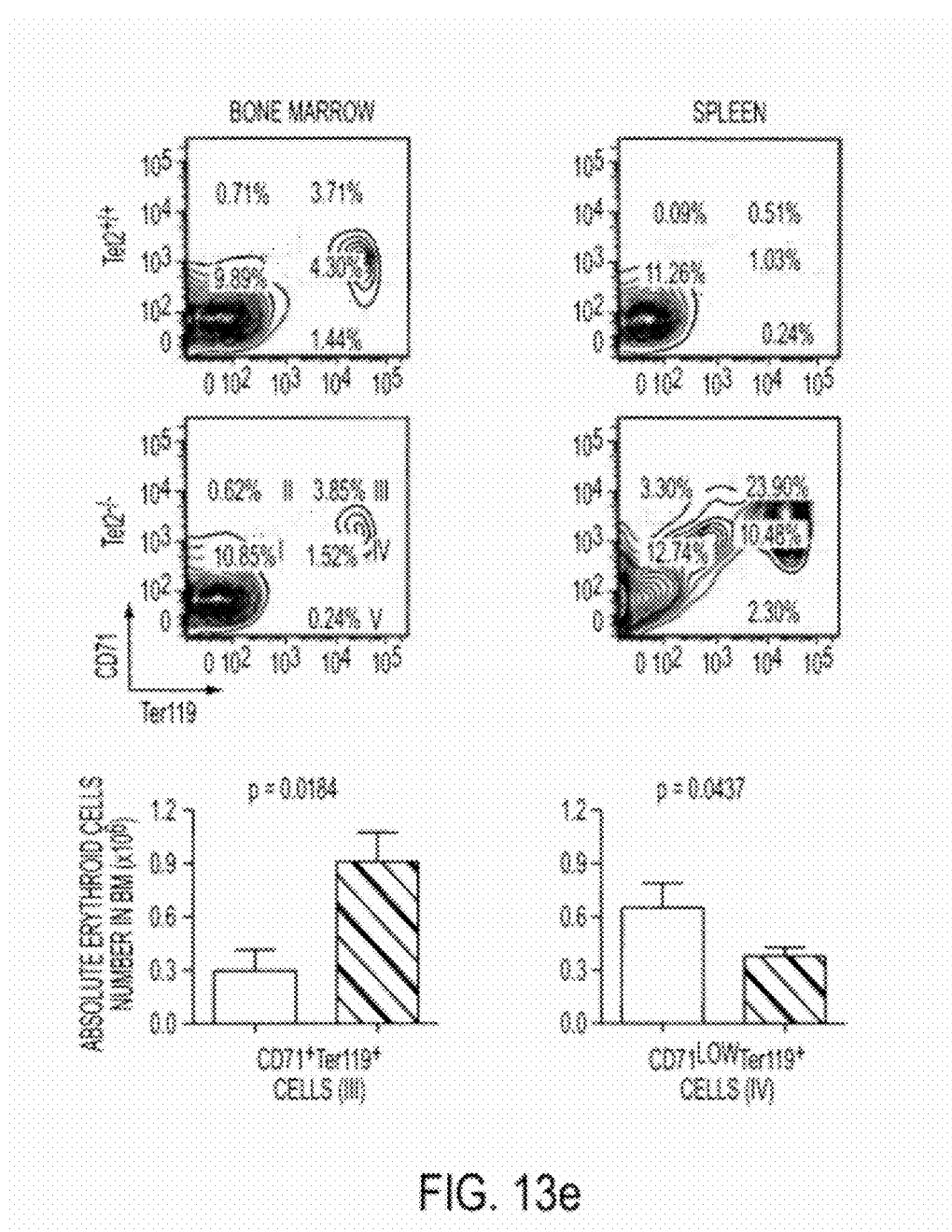

The FIG. 13e shows representative flow cytometrical analysis of the erythroid lineage in the bone marrow and spleen of Tet2$^{+/+}$ and Tet2$^{-/-}$ animals. Percentage of total cells is indicated. Lower panel: absolute number of cells from analysis shown in (D). Tet2$^{+/+}$ (n=10; white bars) and Tet2$^{-/-}$ (n=16; black bars) animals are represented as mean±SEM.

The FIG. 13f shows representative flow cytometry analysis of thymocytes in Tet2$^{+/+}$ and Tet2$^{-/-}$ mice performed 4 months post-induction. Upper left panels: the percentages of total thymocytes are indicated. Upper right panels: the percentages of thymocytes precursors in Lineage-CD4-CD8-double-negative (DN) cells are represented. Lineage antibodies included antibodies against CD19, CD3ε, CD8, TCR-beta, NK-1.1, Ly-6G, and CD11b murine markers. Lower panels: the percentages of CD4-CD8- DN in total thymocytes and CD44+CD25- DN1 cells in DN precursor thymocytes from Tet2$^{+/+}$ and Tet2$^{-/-}$ animals (n=3 per genotype) are represented as mean±SEM.

The FIG. 13g shows flow cytometrical analysis of B cells in the bone marrow of Tet2$^{+/+}$ and Tet2$^{-/-}$ animals 4 months postinduction. Left panel: whole bone marrow. Right panel: gated on CD19$^+$ cells (the frequencies are indicated as a percentage of CD19$^+$ cells). Gates include pro- and pre-B precursor cells (B220$^{low}$ IgM$^-$), immature B cells (B220$^{low}$ IgM$^{hi}$) and mature B cells (B220$^{low}$ IgM$^{hi}$). Lower panels indicate mean±SEM of eight animals per genotype.

Figure 13H:
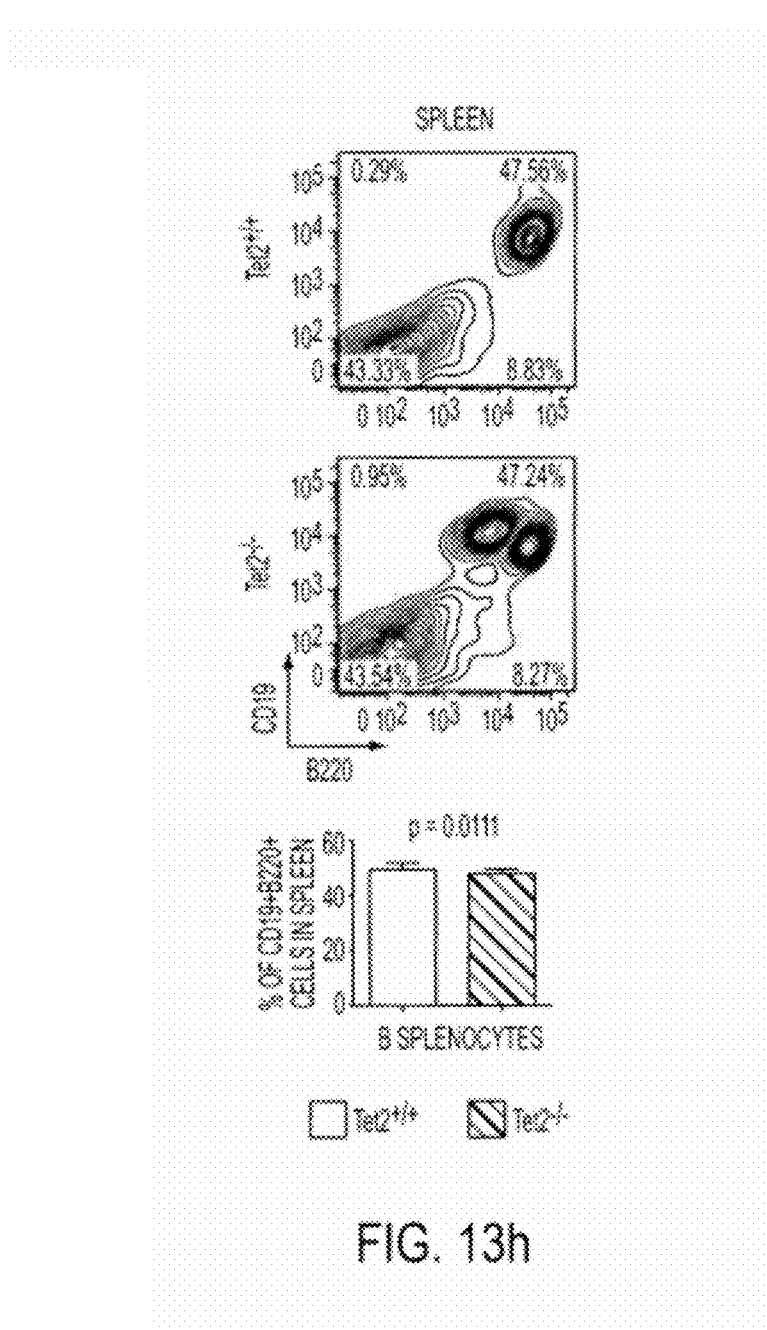

The FIG. 13h shows flow cytometrical analysis of splenic B cells in Tet2$^{+/+}$ and Tet2$^{-/-}$ animals. Lower panel indicate mean±SEM of ten animals per genotype.

Figure 14A:
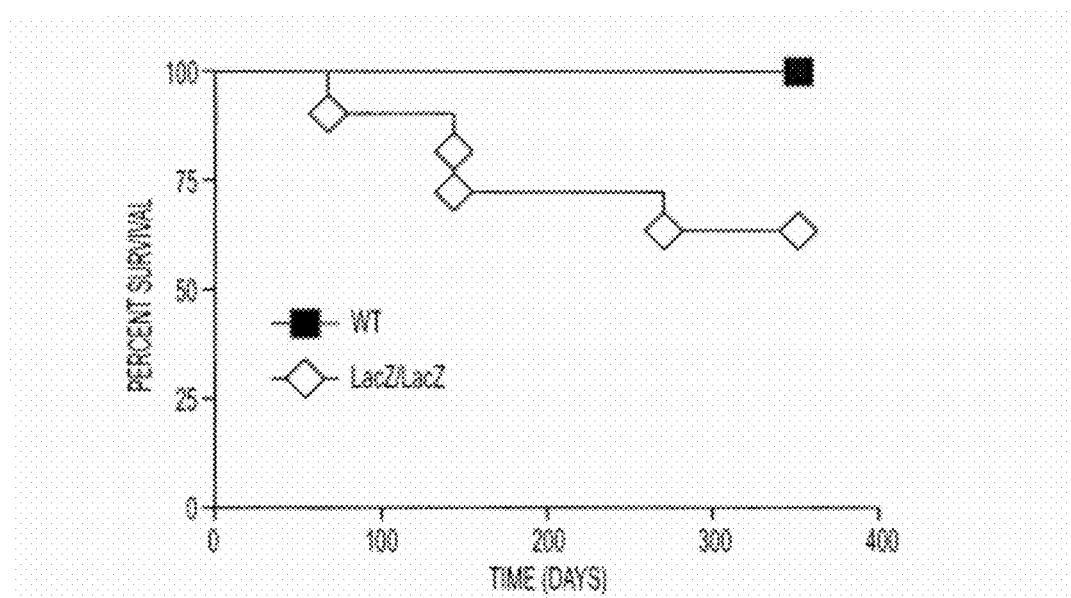

The FIG. 14a shows Kaplan-Meier survival curve of Tet2LacZ/LacZ animals and wild-type littermate controls. Only animals that reached moribund state were considered.

Figure 14B:
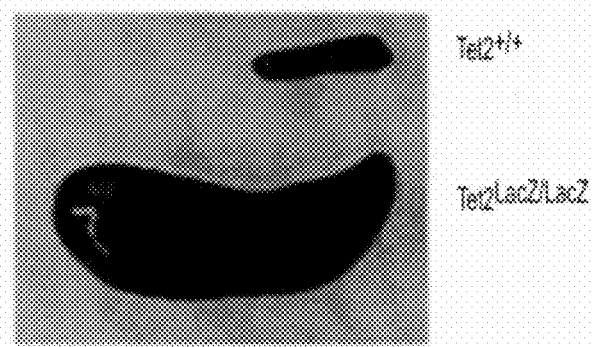

The FIG. 14b shows representative picture of spleens observed in mutant Tet2$^{LacZ/LacZ}$ mouse compared with spleens from wild-type littermates.

Figure 14C:
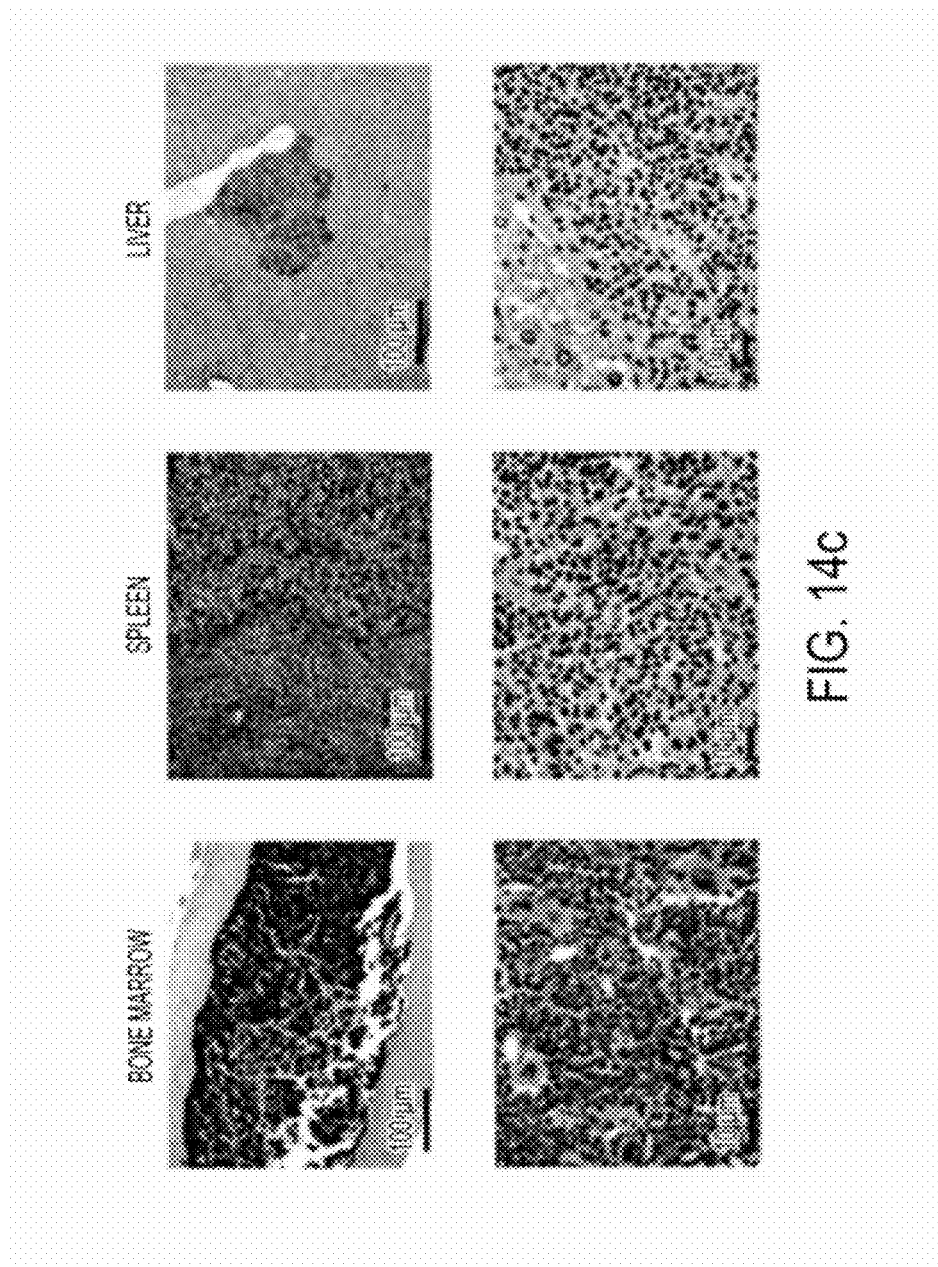

The FIG. 14c shows hematoxylin-Eosin-Safran (HES) staining of bone marrow, spleen and liver sections from a 14-month-old moribund Tet2$^{LacZ/LacZ}$ animal.

Figure 14D:
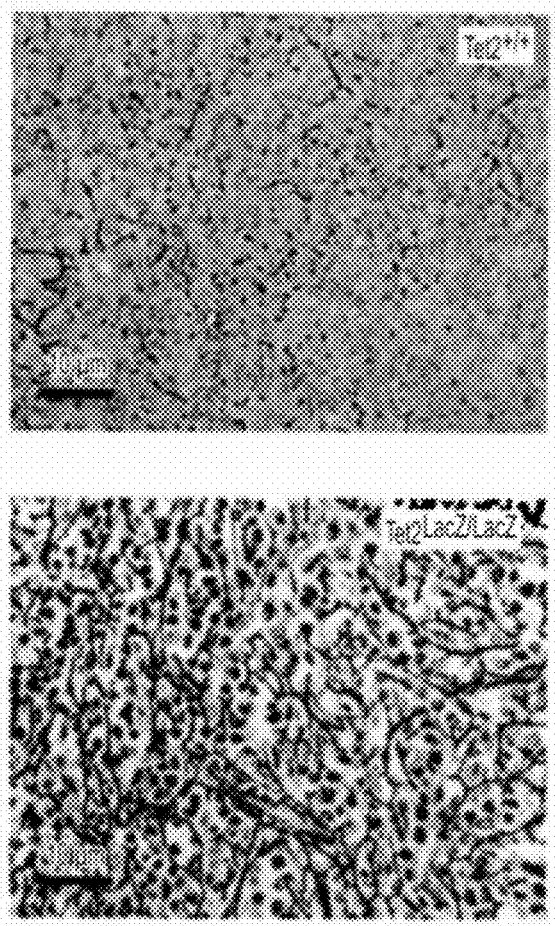

The FIG. 14d shows reticulin staining of spleen from animal in FIG. 14c.

Figure 14E:
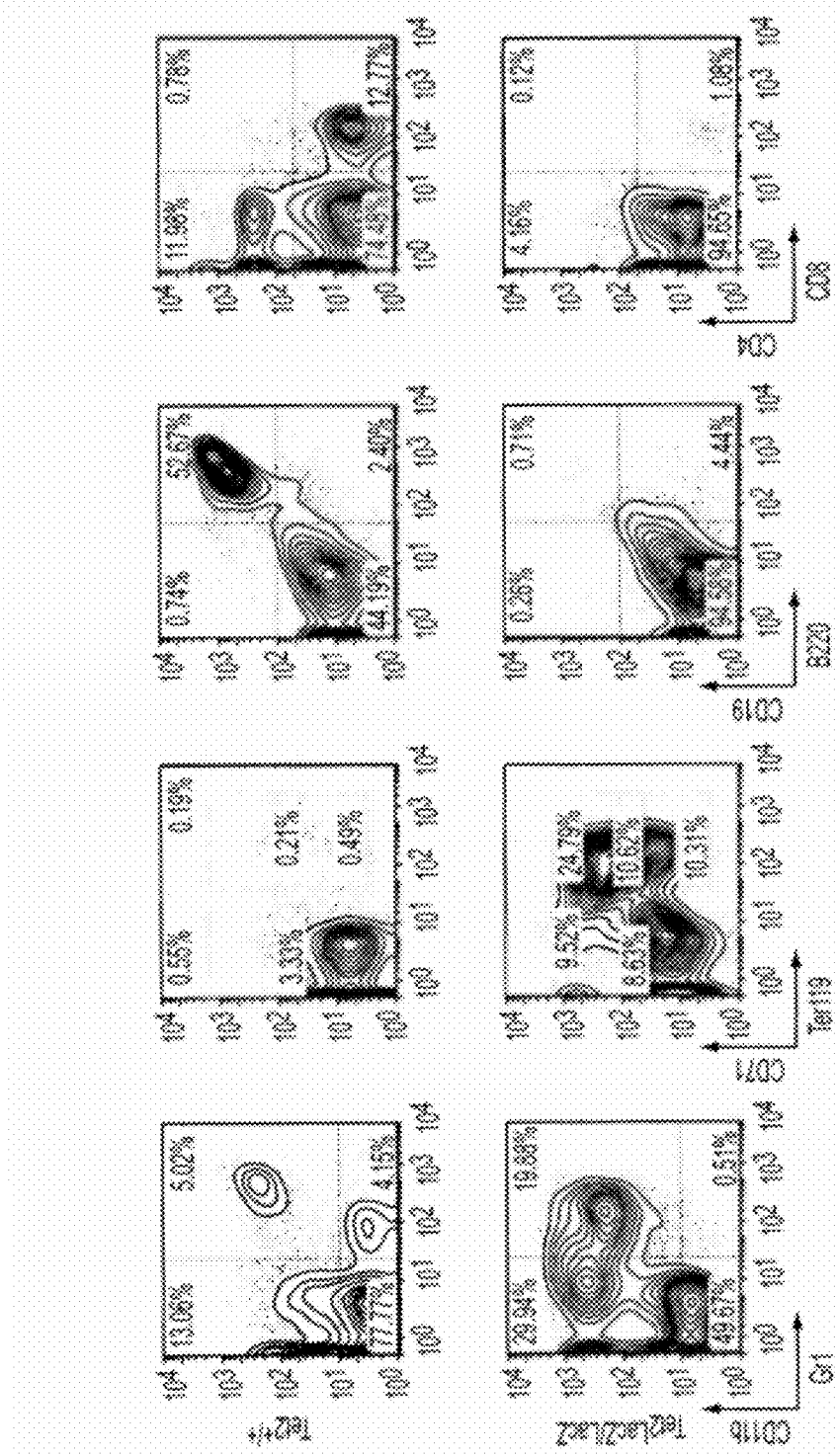

The FIG. 14e shows flow cytometrical analysis of myelomonocytic, erythroid, B and T lymphoid lineages in the spleen of a 14-month-old moribund mutant Tet2$^{LacZ/LacZ}$ mouse. Of note, this animal displayed leukocytosis (69.1×10$^6$ WBC/mm$^3$), anemia (1.76×10$^6$ RBC/mm$^3$, 12.6% hematocrit, and 4.7 g hemoglobin/dl), thrombocytopenia (189×10$^3$ platelets/mm$^3$) and hepatosplenomegaly (liver and spleen weights were 3960 and 2000 mg, respectively).

Figure 15:
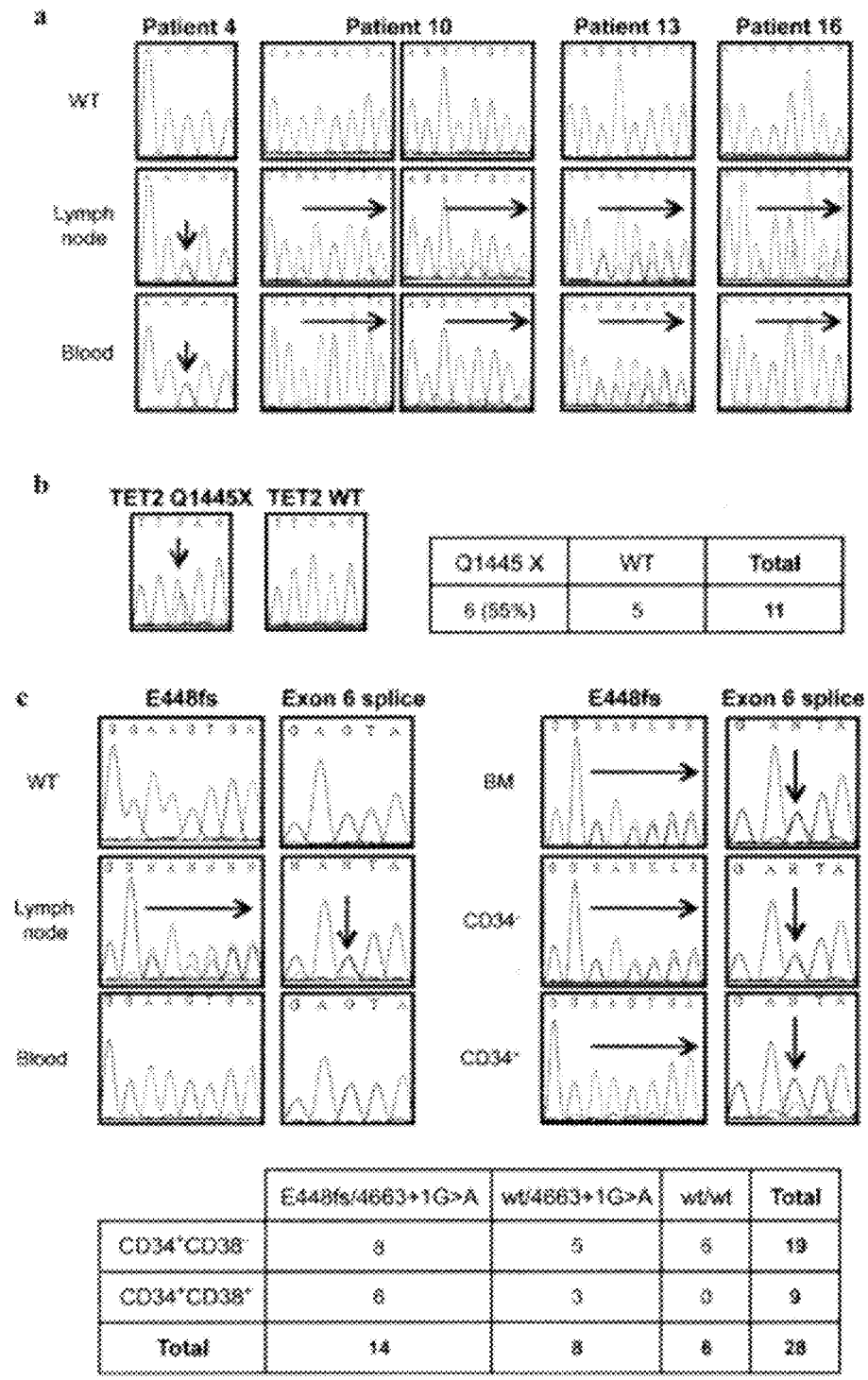

The FIG. 15a shows TET2 sequence in diagnostic and matched control samples. Vertical arrows indicate the sequence variations. Horizontal arrows hang over the frameshift mutations. The presence of the mutated TET2 sequences was confirmed by sub cloning the PCR product from patient 10. The [1893_1896 delAAGC] (on the left) was observed on 1/29 DNA molecules analyzed and the [4527 delG] (on the right) was observed on 2/18 DNA molecules analyzed.

The FIG. 15b shows genotype of CD34+ colonies from patient 8. Four erythroid lineage colonies were carrying the TET2 mutation.

The FIG. 15c shows genotyping of diagnostic and purified bone marrow fractions and CD34+ colonies from patient 2. Left panel: TET2 sequences at the lymphoma phase. Wild-type (WT) sequences are shown at the top. Node: nodal biopsy at diagnosis. Whole-blood sample was considered as normal matched DNA because it is devoid of IGH clonal marker. Right panel: TET2 sequences at the AML phase. BM: bone marrow nucleated cells. CD34−: negative fraction after CD34+ beads selection and CD34+: flow-sorted CD34+ population. Both mutations (frameshift [fs] and splice site mutation) are observed in all analyzed fractions. Bottom: Genotype of colonies obtained from single cells sorted on CD34 and CD38 expression. 4663+1G>A would have appeared first in the course of the disease. The cloning efficiency was extremely low (less than one colony out of 3000 seeded cells) and that colonies were small.

Figure 16:
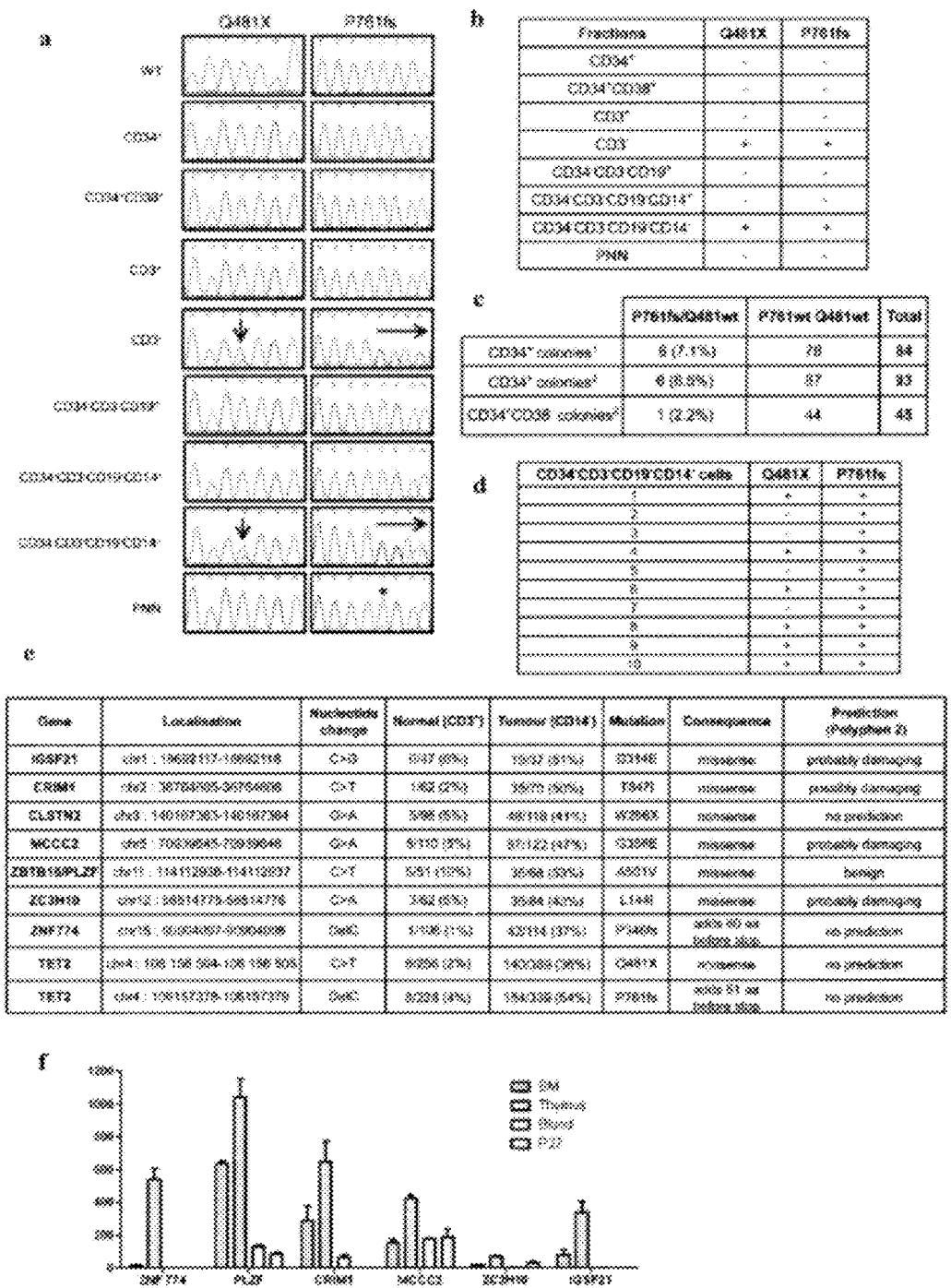

The FIG. 16a shows TET2 mutation status in flow-sorted subpopulations from blood samples from patient 27. The TET2 sequences in sorted subpopulations are shown on the right side of the picture. Both mutations are detected in the CD3− and CD34−CD3−CD19−CD14− populations, whereas only P761fs is observed as a trace (indicated by a star) in the other fractions.

The FIG. 16b shows a summary of results presented in FIG. 16a.

The FIG. 16c shows the genotype of colonies obtained from sorted single CD34+ cells. 1 and 2 correspond to two successive blood samples at a 4-month interval. Only the P761fs mutation is observed in CD34+ (about 7%) and CD34+CD38− (2.2%) colonies. No P761fs positive colony was observed out of 40 CD34+CD38+ single-cell-derived colonies (data not shown).

The FIG. 16d presents single-cell analyses which shows the presence of both TET2 mutations in the same cell.

The FIG. 16e shows somatic mutations identified through exome analyses of patient 27.

The FIG. 16f shows the expression level of the mutated genes in normal tissues and tumor sample. Expression levels were normalized with respect to GUSB expression.

DETAILED DESCRIPTION OF THE INVENTION

The present invention is based on the discovery by the present inventors that the TET2 alleles are often genetically targeted by mutations and/or deletions in tumoral cells in patients suffering from lymphoid tumour or from myeloid tumour such as MPD, AML or MDS and can be considered as a bona fide tumor suppressor gene of human myeloid malignancies.

In a first aspect, the inventors report that, for sporadic cancer, the frequencies of TET2 mutation in unselected patient series were 12% in MPD, 18.5% in MDS, 24% in AML until 50% in CMML patients. Also, applicants demonstrated that TET2 is a tumor suppressor gene in myeloid malignant disorders, because mutated hematopoietic stem cells are endowed with a growth advantage leading to enhanced proliferation.

In a second aspect, the inventors demonstrated by an analysis of 61 familial MPD cases (i.e. PV, ET, and PMF) that anomalies of TET2 gene are found in 20% of the three major MPD phenotypes (PV, ET and PMF) with a higher prevalence in PMF (42%).

Among the TET2-positive patients diagnosed with PV or ET, 77% developed myelofibrosis (MF) suggesting that the presence of acquired events of TET2 influence the evolution of the disease. In four patients (3 PV and 1 ET), we were able to show that the TET2 defect preceded from one to 7 years the hematological complication. The patients with a defect in TET2 are prone to progress to MF. This highly suggested a possible link between the TET2 acquired mutations and the severity of the disease, more specifically between TET2 and the development of MF.

In a third aspect, the inventors report that, for sporadic cancer, the frequencies of TET2 mutation in patients suffering from T-cell lymphoid tumour was ~20%. Finally, the TET2 rearrangements were observed in patients suffering from B-cell lymphoid tumour.

Thus, in a first aspect of the invention, there is provided an in vitro method for diagnosing a myeloid tumour or a lymphoid tumour in a subject, which comprises the step of analyzing a biological sample from said subject by:
  (i) detecting the presence of a mutation in the Ten Eleven Translocation protein family member 2 gene (TET2) coding for the polypeptide having the sequence SEQ ID NO:2, and/or
  (ii) analyzing the expression of the TET2 gene;
  wherein, the detection of a TET2 mutation, of the absence of expression of TET2 or of the expression of a truncated TET2 is indicative of a subject developing or predisposed to develop a myeloid tumour or a lymphoid tumour.

Recent evidence indicate that proteins of the TET family encode enzymes responsible for the conversion of 5-methylcytosine to 5-hydroxymethylcytosine (TAHILIANI et al., Sciencexpress, 2009), thus have potential roles in CpG demethylation and epigenetic regulation. Moreover, this reference established that the conserved TET domains, where most TET2 mutations are observed, are implicated in this activity.

Concomitantly, several works have established, in the last years, a role for hypomethylating agents in MDS (ITZYKSON & FENAUX, Current Opinion in Hematology, vol. 16, p: 77-83, 2009).

The results of the inventors now suggest that the observed efficiency of hypomethylating agent in some MDS potentially results from a demethylation defect in MDS with TET2 mutations.

Thus, the results of the inventors further suggest the use of hypomethylating agent on subjects suffering from lymphoid or myeloid tumour, such as MDS, for which tumour, a TET2 mutation, an absence of TET2 expression or an expression of a truncated TET2 has been detected.

Consequently and according to a preferred embodiment, the detection of a TET2 mutation, of the absence of expression of TET2 or of the expression of a truncated TET2 is indicative of a subject developing a myeloid tumour or a lymphoid tumour suffering from a demethylation defect, which subject can be advantageously treated with a hypomethylating agent, such as azacytidine (AZA).

Preferably, the method of the invention is dedicated to diagnose myeloid tumours.

In fact, the inventors have established that the frequency of TET2 mutations in patients suffering from myeloid tumor or from lymphoid tumour is greater than 10%.

The present invention furthermore provides a method for detection of the presence or absence of cells that have the potential to evolve to invasive myeloid neoplasms or to invasive lymphoid tumours, although those cells are not detectable as a lesion or precursor by conventional means.

As used herein, the term "subject" refers to a mammal, preferably a human.

Said subject may be a healthy, but the method of the invention is particularly useful for testing a subject thought to develop or to be predisposed to developing a myeloid cancer (i.e., myeloid tumour) or a lymphoid tumour. In that case, the method of the invention enables to confirm that said subject develops or is predisposed for developing a myeloid cancer (i.e., a myeloid tumour) or a lymphoid tumour.

More preferably, said lymphoid tumour is selected in the group consisting of lymphoma such as T- or B-cell lymphoma, and more preferentially of T cell lymphoma.

Still more preferably, said myeloid cancer (i.e., myeloid tumour) is selected in the group consisting of myelodysplastic syndrome (MDS), acute myeloid leukemia (AML), myeloproliferative disorders (MPD) and myelodysplatic/myeloproliferative syndrome. Advantageously, said myeloid cancer is a myelodysplatic/myeloproliferative syndrome, and preferably a chronic myelomonocytic leukemia (CMML).

According to a preferred embodiment, the method of the invention is for diagnosing a myelofibrosis (MF) in a subject, wherein said subject is suffering from polycythemia vera (PV) or from thrombocythemia (ET), and wherein the detection of a TET2 mutation or TET2 under-expression is indicative of a subject developing or predisposed to develop a myelofibrosis (MF).

According to still another preferred embodiment, the subject is suffering from myelodysplastic syndrome (MDS), and the detection of a TET2 mutation or TET2 under-expression is indicative of a subject with a good prognosis.

As used herein a good prognosis corresponds to a patient suffering from MDS and having a reduced risk of developing an AML.

In fact, the inventors have established that five-year survival was significantly increased in TET2 mutated patients suffering from MDS compared to unmutated patients (p<0.05).

As used herein, the expression "biological sample" refers to solid tissues such as, for example, a lung biopsy; buccal swab, fluids and excretions such as for example, sputum, induced sputum, blood, serum, plasma, urine. Preferably, said biological sample is a bone marrow sample.

In this aspect of the invention, the method comprises the step of detecting the presence of a mutation in the TET2 gene coding for the polypeptide having the sequence SEQ ID NO:2.

As used herein, the term "mutations" correspond to any modification in the sequence of the original nucleic acid sequence. These mutations comprise small-scale mutations, or large scale mutations. Small scale mutations are those affecting a gene in one or a few nucleotides, including point mutations, insertions or deletions of one or more extra nucleotides in the DNA. Point mutations can be silent, missense and nonsense mutation. Large scale mutation in the genomic structure, such as gene duplications, deletions, or mutations whose effect is to juxtapose previously separate pieces of DNA, potentially bringing together separate genes to form functionally distinct fusion genes. These last mutations include chromosomal translocations, interstitial deletions, chromosomal inversions and loss of heterezygosity.

Preferably, only a biological sample containing cells including genomic DNA (or optionally RNA) from the subject to be tested is required.

Preferably, this detecting step is realized on each allele of the TET2 gene. In fact, the diagnosis is more reliable when the mutation is detected on each allele of the TET2 coding for the polypeptide having the sequence SEQ ID NO:2.

In a particular embodiment, the in vitro method of the invention aims to detect mutation included in the group consisting of deletions, insertions and point mutations such as mutations affecting splice sites, missense mutation and nonsense mutations, preferably missense mutation and nonsense mutations.

The inventors have established that the existence of such mutations is associated with myeloid or lymphoid cancer. Moreover, the inventors observed that the polypeptidic C-terminal domain of the TET2 protein is preferentially targeted by the deleterious mutations in the studied patients (see examples).

For deletion or insertion, said deletion or insertion preferably results in the absence of expression of the TET2 protein or in the expression of a truncated TET2 protein, which truncated TET2 protein does not comprise at least one of the two highly conserved regions shared by the other TET proteins and corresponding to i) the 310 amino acid region located near the center of the protein TET2 (amino acids 1134 to amino acid 1444, SEQ ID NO:3), or ii) the 80 amino acid region located near the carboxyterminal end of the protein TET2 (corresponding to amino acid 1843 until amino acid 1922, SEQ ID NO:4). More preferably, said truncated TET2 protein does not comprise the 80 amino acid region located near the carboxyterminal end of the protein TET2 (corresponding to amino acid 1843 until amino acid 1922, SEQ ID NO:4).

For example, these deletions or insertions can be selected in those disclosed in table 1.

Other example of those mutations can be selected in those disclosed in table 1a below:

TABLE 1a

| Nucleotide change | Consequence |
|---|---|
| c.3087C > T | p.Gln743X |
| c.[2202delG(+)4663 + 1G > A] | p.Glu448fs |
| c.5406C > T | p.Arg1516X |
| c.3506C > T | p.Gln886X |
| c.4814 + 2T > G | — |
| c.5116C > G | p.Pro1419Arg |
| c.[3192C > T(+)3628_3629insCATA] | p.[Gln778X(+)Asn923fs] |
| c.5193C > T | p.Gln1445X |
| c.6564delT | p.Tyr1902fs |
| c.5523_5524insA | p.Glu1555fs |
| c.4815-2delA | — |
| c.[3747C > T] + [5331A > T] | [p.Gln963X] + [p.Lys1491X] |
| c.[1700_1701insT(+)3606C > T] | p.[Asn281fs(+)Gln916X] |
| c.6553C > T | p.Ser1898Phe |
| c.[1805delC(+)3602delT] | p.[Ser315fs(+)Leu914fs] |
| c.5100C > T | p.Gln1414X |
| c.[5053T > C(+)5253C > T] | p.[Leu1398Pro(+)Arg1465X] |
| c.2636C > T | p.Gln593X |
| c.1511delC | p.Ser217fs |
| c.[2301C > T(+)3142delC] | p.[Gln481X(+)Pro761fs] | and preferably said mutation is selected in the group consisting of: p.Glu448fs, p.Gln1445X and p.[Gln481X(+)Pro761fs].

In another more preferred aspect of the invention, the missense mutation, resulting from a mutation in the open reading frame of the TET2 gene, is preferably located in at least one of the two highly conserved regions shared by the TET proteins and corresponding to i) the 310 amino acid region located near the center of the protein TET2 (amino acids 1134 to amino acid 1444, SEQ ID NO:3), and ii) the 80 amino acid region located near the carboxyterminal end of the protein TET2 (corresponding to amino acid 1843 until amino acid 1922, SEQ ID NO:4).

As an example, said missense mutations are selected in the group comprising or consisting of I1175V, L1197N, H1219Y, E1235V, C1271W, K1299E, L1340P, R1302G, G1370E, A1344E, N1387S, L1398P, V1417F, P1419R, H1868R, G1869W, L1872P, I1873T, R1896M, and S1898F; preferably in the group comprising or consisting of I1175V, L1197N, H1219Y, E1235V, C1271W, K1299E, L1340P, R1302G, G1370E, A1344E, N1387S, H1868R, G1869W, L1872P, I1873T, R1896M, and S1898F.

More preferably, said missense mutation is located in the 80 amino acid region located near the carboxyterminal end of the protein TET2 (corresponding to amino acid 1843 until amino acid 1922, SEQ ID NO:4). Even more preferably, said missense mutations are selected in the group comprising or consisting of H1868R, G1869W, L1872P, I1873T, R1896M, and S1898F, as an example I1873T, R1896M, and S1898F.

For nonsense mutation, said nonsense mutation, preferably resulting from the introduction of a stop mutation in the open reading frame of the TET2 gene, is preferably located before at least one of the two highly conserved regions shared by the TET2 protein corresponding to i) the 310 amino acid region located near the center of the protein TET2 (amino acids 1134 to amino acid 1444, SEQ ID NO:3), or ii) the 80 amino acid region located near the carboxyterminal end of the protein TET2 (corresponding to amino acid 1843 until amino acid 1922, SEQ ID NO:4).

Also, said nonsense mutation can result in the introduction of a stop mutation inside at least one of the two highly conserved regions shared by the TET2 protein corresponding to i) the 310 amino acid region located near the center of the protein TET2 (amino acids 1134 to amino acid 1444, SEQ ID NO:3), or ii) the 80 amino acid region located near the carboxyterminal end of the protein TET2 (corresponding to amino acid 1843 until amino acid 1922, SEQ ID NO:4).

As an example, said nonsense mutations are selected in the group comprising or consisting of Q232Stop, Q321Stop, S354Stop, Q417Stop, Q481Stop, R544Stop, R550Stop, Q557Stop, Q574Stop, Q593Stop, Q635Stop, Q642Stop, Q685Stop, L699Stop, Q743Stop, Q778Stop, S792Stop, Q886Stop, Q891Stop, Q916Stop, Q943Stop, Q963Stop, E1026Stop R1067Stop, R1216Stop, Y1225Stop, R1404Stop, Q1414Stop, Q1445Stop, L1457Stop, R1465Stop, K1491Stop, R1516Stop, Q1524Stop, Q1542Stop, N1624Stop, Y1724Stop, Y1751Stop, L1819Stop, Q1834Stop and W1847Stop; preferably in the group comprising or consisting of Q321Stop, S354Stop, Q481Stop R544Stop, Q557Stop, R1216Stop, Q1445Stop and Y1724Stop.

More preferably, said nonsense mutation, resulting from the introduction of a stop mutation in the open reading frame of the TET2 gene, is located in the TET2 protein before the 80 amino acid region located near the carboxyterminal end of the protein TET2 (corresponding to amino acid 1843 until amino acid 1922, SEQ ID NO:4). As an example, said nonsense mutation is selected in the group comprising or consisting of Q232Stop, Q321Stop, S354Stop, Q417Stop, Q481Stop, R544Stop, R550Stop, Q557Stop, Q574Stop, Q593Stop, Q635Stop, Q642Stop, Q685Stop, L699Stop, Q743Stop, Q778Stop, S792Stop, Q886Stop, Q891Stop, Q916Stop, Q943Stop, Q963Stop, E1026Stop R1067Stop, R1216Stop, Y1225Stop, R1404Stop, Q1414Stop, Q1445Stop, L1457Stop, R1465Stop, K1491Stop, R1516Stop, Q1524Stop, Q1542Stop, N1624Stop, Y1724Stop, Y1751 Stop, L1819Stop, and Q1834Stop.

Also, said nonsense mutation, preferably resulting from the introduction of a stop mutation in the open reading frame of the TET2 gene, is preferably located in TET2 protein inside the 80 amino acid region located near the carboxyterminal end of the protein TET2 (corresponding to amino acid 1843 until amino acid 1922, SEQ ID NO:4). As an example, said nonsense mutation is W1847Stop.

Typical techniques for detecting the presence of a mutation may include restriction fragment length polymorphism, hybridization techniques, DNA sequencing, exonuclease resistance, microsequencing, solid phase extension using ddNTPs, extension in solution using ddNTPs, oligonucleotide ligation assays, methods for detecting single nucleotide polymorphisms such as dynamic allele-specific hybridization, ligation chain reaction, mini-sequencing, DNA "chips", allele-specific oligonucleotide hybridization with single or dual-labelled probes merged with PCR or with molecular beacons, and others.

Advantageously, the alteration is detected on the cDNA or DNA of the TET2 gene by either PCR and sequencing, SNP-array or CGH, all of them being well known for the skilled person.

In molecular biology and bioinformatics, a SNP array is a type of DNA microarray which is used to detect polymorphisms within a population. The basic principles of SNP array are the same as the DNA microarray. These are the convergence of DNA hybridization, fluorescence microscopy, and solid surface DNA capture. The three mandatory components of the SNP arrays are: i) the array that contains immobilized nucleic acid sequences or target; ii) one or more labeled Allele specific oligonucleotide (ASO) probes; and iii) a detection system that records and interprets the hybridization signal (see in Sheils, O., Finn, S, and O'Leary J. (2003) "Nucleic acid microarray: an overview." Current Diagnostic Pathology. 9:155-158).

Comparative genomic hybridization (CGH) is a molecular cytogenetic method of screening a tumor for genetic changes. The alterations are classified as DNA gains and losses and reveal a characteristic pattern that includes mutations at chromosomal and subchromosomal levels. The method is based on the hybridization of fluorescently labeled tumor DNA (frequently fluorescein (FITC)) and normal DNA (frequently rhodamine or Texas Red) to normal human metaphase preparations. Using epifluorescence microscopy and quantitative image analysis, regional differences in the fluorescence ratio of gains/losses vs. control DNA can be detected and used for identifying abnormal regions in the genome. CGH will detect only unbalanced chromosomes changes. Structural chromosome aberrations such as balanced reciprocal translocations or inversions can usually not be detected, as they do not systematically change the copy number (Emanuel B S, Saitta S C. From microscopes to microarrays: dissecting recurrent chromosomal rearrangements. *Nat Rev Genet.* 2007 November; 8(11):869-83. Review).

In another preferred embodiment of the invention, the method comprises the step of analyzing the expression of the TET family member 2 gene (TET2).

According to the results obtained by the inventors, the absence of expression or the under-expression of the TET2 gene or protein or the expression of a truncated TET2 protein as disclosed previously is associated with myeloid cancer.

Methods for analyzing the expression of a gene are well known for the man skilled in the art.

In a particular embodiment of the invention, the expression of the TET2 gene is assessed by analyzing the expression of mRNA transcript or mRNA precursors, such as nascent RNA, of said gene.

Such analysis can be assessed by preparing mRNA/cDNA from cells in a biological sample from a subject, and hybridizing the mRNA/cDNA with a reference polynucleotide. The prepared mRNA/cDNA can be used in hybridization or amplification assays that include, but are not limited to, Southern or Northern analyses, polymerase chain reaction analyses, such as quantitative PCR (TAQMAN), and probes arrays such as GENECHIP™ DNA Arrays (AFFYMETRIX).

Advantageously, the analysis of the expression level of mRNA transcribed from the TET2 gene involves the process of nucleic acid amplification, e.g., by RT-PCR (the experimental embodiment set forth in U.S. Pat. No. 4,683,202), ligase chain reaction (BARANY, *Proc. Natl. Acad. Sci. USA*, vol. 88, p: 189-193, 1991), self sustained sequence replication (GUATELLI et al., *Proc. Natl. Acad. Sci. USA*, vol. 87, p: 1874-1878, 1990), transcriptional amplification system (KWOH et al., 1989, *Proc. Natl. Acad. Sci. USA*, vol. 86, p: 1173-1177, 1989), Q-Beta Replicase (LIZARDI et al., *Biol. Technology*, vol. 6, p: 1197, 1988), rolling circle replication (U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

In another particular embodiment, the expression of the TET2 gene is assessed by analyzing the expression of the TET2 protein translated from said gene.

Such analysis can be assessed using an antibody (e.g., a radio-labeled, chromophore-labeled, fluorophore-labeled, or enzyme-labeled antibody), an antibody derivative (e.g., an antibody conjugate with a substrate or with the protein or ligand of a protein/ligand pair (e.g., biotin-streptavidin)), or an antibody fragment (e.g., a single-chain antibody, an isolated antibody hypervariable domain, etc.) which binds specifically to the TET2 protein. Said analysis can be assessed by a variety of techniques well known by one of skill in the art including, but not limited to, enzyme immunoassay (EIA), radioimmunoassay (RIA), Western blot analysis and enzyme linked immunoabsorbant assay (ELISA).

Polyclonal antibodies can be prepared by immunizing a suitable animal, such as mouse, rabbit or goat, with the TET2 protein (SEQ ID NO:2) or a fragment thereof (e.g., at least 10 or 15 amino acids). The antibody titer in the immunized animal can be monitored over time by standard techniques, such as with an ELISA using immobilized polypeptide. At an appropriate time after immunization, e.g., when the specific antibody titers are highest, antibody producing cells can be obtained from the animal and used to prepare monoclonal antibodies (mAb) by standard techniques, such as the hybridoma technique originally described by KOHLER and MILSTEIN (*Nature*, vol. 256, p: 495-497, 1975), the human B cell hybridoma technique (KOZBOR et al., *Immunol.*, vol. 4, p: 72, 1983), the EBV—hybridoma technique (COLE et al., *In Monoclonal Antibodies and Cancer Therapy*, Alan R. Liss, Inc., p: 77-96, 1985) or trioma techniques. The technology for producing hybridomas is well known (see generally Current Protocols in Immunology, COLIGAN et al. ed., John Wiley & Sons, New York, 1994). Hybridoma cells producing the desired monoclonal antibody are detected by screening the hybridoma culture supernatants for antibodies that bind the polypeptide of interest, e.g., using a standard ELISA.

As previously mentioned, mutations in the TET2 gene may trigger the absence of expression or the under-expression of the TET2 protein.

As used herein, the "under-expression" of a polypeptide occurs when the transcription and/or the translation of the gene is affected by the mutation, leading to an expression level in a biological sample that is lower than the standard error of the assay employed to assess expression, and is preferably at least 20% inferior to the normal level of expression of said gene, preferably at least 50% inferior to the normal level of expression of said gene, and most preferably at least 100% inferior to the normal level of expression of said gene.

Therefore, the method of the invention may comprise comparing the level of expression of the TET2 gene in a biological sample from a subject with its expression level in a control (i.e., normal expression level). A significantly lower level of expression of said gene in the biological sample of a subject as compared to the normal expression level is an indication that the patient may develop a myeloid neoplasm.

As used herein, a "control" corresponds preferably to a control sample comprising non-tumoral cells. Preferably, said control corresponds to peripheral blood leukocytes (PBL), and most preferably to a peripheral blood leukocyte immortalized with Epstein Barr Virus.

Thus, the "normal" level of expression of the TET2 gene is the level of expression of said gene in a biological sample of non-tumoral cell. Preferably, said normal level of expression is assessed in a control sample and preferably, the average expression level of said gene in several control samples.

Analyzing the normal expression of the TET2 gene may be assessed by any of a wide variety of well-known methods for detecting expression of a transcribed nucleic acid or translated protein as previously described.

In a preferred embodiment of the invention, said mutation in the TET2 gene induces absence of expression or under-expression of the two highly conserved regions shared by the TET proteins and corresponding to i) the 310 amino acid region located near the center of the protein TET2 (amino acids 1134 to amino acid 1444, SEQ ID NO:3), and ii) the 80 amino acid region located near the carboxy-terminal end of the protein TET2 (corresponding to amino acid 1843 until amino acid 1922, SEQ ID NO:4), and more preferably of the 80 amino acid region located near the carboxy-terminal end of the protein TET2 (corresponding to amino acid 1843 until amino acid 1922, SEQ ID NO:4).

In a second aspect, the present invention refers to a kit for diagnosing myeloid cancer or lymphoid cancer in a subject comprising at least one nucleic acid probe or oligonucleotide or at least one antibody, which can be used in a method as defined in the present in invention, for detecting the presence of a mutation in the TET2 gene and/or analysing the expression of the TET2 gene.

Preferably, the oligonucleotide is at least one PCR primer, preferably a set of PCR primers is provided, which allows to amplify the TET2 gene or a fragment thereof. The skilled person readily provides such an oligonucleotide or set of PCR primers which allows to amplify a region of the TET2 gene, provided that the nucleic acid sequence of TET2 is well known (Accession number NM_001127208, SEQ ID NO:39) (Current Protocols in Molecular Biology; edited by Fred M. Ausubel et al., supra).

In a preferred embodiment, the kit comprises at least one PCR primer selected in the group comprising SEQ ID NO:5 to SEQ ID NO: 38 (see examples and sequence listing) for detecting the presence of a mutation in the TET2 gene and/or analysing the expression of said gene.

As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. As used herein, the term "fragmented kit" refers to delivery systems comprising two or more separate containers that each contains a subportion of the total kit components. The containers may be delivered to the intended recipient together or separately. For example, a first container may contain an enzyme for use in an assay, while a second container contains oligonucleotides. The term "fragmented kit" is intended to encompass kits containing Analyte specific reagents (ASR's) regulated under section 520(e) of the Federal Food, Drug, and Cosmetic Act, but are not limited thereto. Indeed, any delivery system comprising two or more separate containers that each contains a subportion of the total kit components are included in the term "fragmented kit." In contrast, a "combined kit" refers to a delivery system containing all of the components of a reaction assay in a single container (e.g., in a single box housing each of the desired components). The term "kit" includes both fragmented and combined kits.

The present kits can also include one or more reagents, buffers, hybridization media, nucleic acids, primers, nucleotides, probes, molecular weight markers, enzymes, solid supports, databases, computer programs for calculating dispensation orders and/or disposable lab equipment, such as multi-well plates, in order to readily facilitate implementation of the present methods. Enzymes that can be included in the present kits include nucleotide polymerases and the like. Solid supports can include beads and the like whereas molecular weight markers can include conjugatable markers, for example biotin and streptavidin or the like.

In one embodiment, the kit is made up of instructions for carrying out the method described herein for diagnosing a myeloid cancer or a lymphoid cancer in a subject. The instructions can be provided in any intelligible form through a tangible medium, such as printed on paper, computer readable media, or the like.

Still a further aspect of the present invention refers to the use, for diagnosing myeloid or lymphoid cancer, of the above-mentioned kit comprising at least one nucleic acid probe or oligonucleotide or at least one antibody, which can be used in a method as defined for detecting the presence of a mutation in the TET2 gene and/or analysing the expression of the TET2 gene.

Advantageously, myeloid cancer is selected in the group consisting of myelodysplastic syndrome, acute myeloid leukemia, myeloproliferative disease and myelodysplatic/myeloproliferative syndrome.

Still advantageously, said lymphoid cancer is selected in the group consisting of lymphoma such as T- or B-cell lymphoma, and more preferentially of T-cell lymphoma.

In still another aspect, the invention relates to the use of a hypomethylating agent for treating a patient suffering from a myeloid or a lymphoid tumour, for which tumour, a TET2 mutation, an absence of TET2 expression or an expression of a truncated TET2 has been detected.

Preferably, said myeloid tumour is not a MDS.

Hypomethylating agent are well known from the skilled person and include, as an example, azacytidine.

In a final aspect, the invention relates to a method for treating a subject suffering a myeloid or a lymphoid tumour, for which tumour, a TET2 mutation, an absence of TET2 expression or an expression of a truncated TET2 has been detected, said method comprising the step of administrating to said subject a therapeutically efficient amount of hypomethylating agent.

Preferably, said myeloid tumour is not a MDS.
Preferably said hypomethylating agent is azacytidine.

A therapeutically efficient amount of hypomethylating agent can be simply determined by the skilled person. As an example of therapeutically efficient amount of azacytidine for treating lymphoid or myeloid tumour, one can cite the regimen which is disclosed in FENAUX et al. (*Blood*, vol. 110, 817, 2007) which is incorporated herein by reference.

In the following, the invention is described in more detail with reference to amino acid sequences, nucleic acid sequences and the examples. Yet, no limitation of the invention is intended by the details of the examples. Rather, the invention pertains to any embodiment which comprises details which are not explicitly mentioned in the examples herein, but which the skilled person finds without undue effort.

Examples

1. Identification of Tet2 Gene Mutation in MDS, MPD and in AML

We identified 6 patients suffering from myeloid cancer (AML (nAML1, nAML2, nAML3) or MDS (MDS01, MDS02, and MDS03)) and harboring an acquired chromosomal translocation associated with a genomic deletion in the vicinity of the chromosome 4 breakpoint at 4q24. These deletions were homozygous in one instance and heterozygous in the other cases and could indicate the location of a tumor suppressor gene in that region.

FISH analyses first permit to narrow the commonly deleted region in these patients to a ~500 kb interval (data not shown). Computer and RT-PCR assisted analyses uncovered the structure of a single gene, Ten Eleven Translocation (TET2) lying in this region (FIG. 1).

TET2 gene comprises 11 exons spread over 150 Kb. The predicted TET2 protein, encoded by exons 3 to 11, belongs to a three-member family (TET family) in human and mouse. Proteins of the TET family share two highly conserved regions with a single orthologous *Drosophila* protein in their central and carboxy-terminal part (FIG. 1).

The FIG. 1 shows the protein sequence of TET2 (SEQ ID NO:2), highlighting the conserved regions between species (bold).

For TET2, a translational initiation codon situated at the 5' end of exon 3 (Nucleotides 862-864 of the cDNA or 27-29 of Exon 3) was predicted to allow for the synthesis of a 2002 amino acids protein (FIG. 1). An alternative ATG situated in exon 2 (nucleotides 798-800 of the cDNA or 111-113 of Exon 2) will direct the synthesis of 21 more amino acids. Additional starts are not excluded.

TET2 transcript is widely expressed (ONO et al., abovementioned, 2002; LORSBACH et al., abovementioned, 2003), and as suggested by available data, the expression of TET2 was confirmed in human bone marrow and blood tissues by RT-PCR (data not shown). More specifically, TET2 transcripts were detected in umbilical cord blood CD34+ cells, in granulocytes from healthy controls, and in hematopoietic cell lines.

Finally, of these six patients, five harbored a deletion on one chromosome 4 whereas both copies were deleted in MDS01.

The involvement of the same 4q24 region was also found by using a different approach in MPD. Analysis of CD34+ CD38− multipotent progenitors, CD34+CD38+ committed progenitors, and mature cells, led us to identify two subsets of JAK2 V617F MPD at diagnosis with distinct kinetics of hematopoietic expansion (DUPONT et al., *Blood*, vol. 110 (3), p: 1013-21, 2007). The first subset is characterized by a late expansion of the malignant clone; i.e. downstream of the committed progenitor. In contrast, the second subset of patients had an early expansion of the clone, upstream of the committed progenitor. We hypothesized that the second subset of patients had a molecular defect able to promote the early expansion of the malignant clone. Five patients from this second subset (MPD01 to MPD05) were analyzed using high-resolution CGH and SNP arrays to compare presumed clonal cells (granulocytes) versus polyclonal cells (peripheral blood mononuclear cells or lymphocytes) DNA. One primary myelofibrosis (PMF) patient (MPD01) and one polycythemia vera (PV) patient (MPD04) exhibited a large acquired loss-of-heterozygosity (LOH) without copy number modification (uniparental disomy; UPD (20)) ranging from q22 to qter of chromosome 4. The third patient (MPD05) demonstrated an acquired deletion located in the 4q24 region. This 325 kb deletion in MPD05 was included in the 4q24 LOH region of patients MPD01 and MPD04 and contained TET2 as a single candidate gene. This region was normal in the two other studied MPD samples (MPD02 and MPD03).

As the 4q24 region is affected in patients suffering from myeloid neoplasms, and as TET2 localized in this region, the integrity of the TET2 gene might be affected in these patients. Moreover, loss of the two copies of TET2 in patient MDS01 and recurrent loss of one copy in 8 other patients with MDS, MPD or AML designated TET2 as a candidate tumor suppressor gene.

PCR on the TET2 gene was thus performed in order to detect alterations of the TET2 gene in these patients. Importantly, both alleles were analysed in order to detect bi-allelic modifications.

2. Experimental Procedure to Detect Alterations of the Tet2 Gene 2.1. Primers Used for the Identification of TET2 Mutations or Deletions (Table 2)

TABLE 2

| SEQ ID NO | Tm (° C.) | Sequences | Amplified region | Length of amplicon |
|---|---|---|---|---|
| 5 | 60.9 | TGAACTTCCCACATTAGCTGGT | 106374235- | 955 |
| 6 | 60.7 | GAAACTGTAGCACCATTAGGCATT | 106375189 | |
| 7 | 62.0 | CAAAAGGCTAATGGAGAAAGACGTA | 106374894- | 836 |
| 8 | 62.0 | GCAGAAAAGGAATCCTTAGTGAACA | 106375729 | |
| 9 | 63.0 | GCCAGTAAACTAGCTGCAATGCTAA | 106375458- | 843 |
| 10 | 62.3 | TGCCTCATTACGTTTTAGATGGG | 106376300 | |
| 11 | 60.0 | GACCAATGTCAGAACACCTCAA | 106376065- | 867 |
| 12 | 60.9 | TTGATTTTGAATACTGATTTTCACCA | 106376931 | |
| 13 | 60.5 | TTGCAACATAAGCCTCATAAACAG | 106376703- | 788 |
| 14 | 60.9 | ATTGGCCTGTGCATCTGACTAT | 106377490 | |
| 15 | 62.1 | GCAACTTGCTCAGCAAAGGTACT | 106377284- | 781 |
| 16 | 62.3 | TGCTGCCAGACTCAAGATTTAAAA | 106378064 | |
| 17 | 60.1 | ATACTACATATAATACATTCTAATTCCCTCACTG | 106381631- | 495 |
| 18 | 61.5 | TGTTTACTGCTTTGTGTGTGAAGG | 106382125 | |
| 19 | 61.7 | CATTTCTCAGGATGTGGTCATAGAAT | 106383324- | 286 |
| 20 | 61.5 | CCCAATTCTCAGGGTCAGATTTA | 106383609 | |
| 21 | 60.1 | AGACTTATGTATCTTTCATCTAGCTCTGG | 106383864- | 599 |
| 22 | 60.1 | ACTCTCTTCCTTTCAACCAAAGATT | 106384462 | |
| 23 | 60.0 | ATGCCACAGCTTAATACAGAGTTAGAT | 106400093- | 362 |
| 24 | 60.9 | TGTCATATTGTTCACTTCATCTAAGCTAAT | 106400454 | |
| 25 | 61.1 | GATGCTTTATTTAGTAATAAAGGCACCA | 106402226- | 354 |
| 26 | 61.5 | TTCAACAATTAAGAGGAAAAGTTAGAATAATATTT | 106402579 | |
| 27 | 61.7 | TGTCATTCCATTTTGTTTCTGGATA | 106410076- | 361 |
| 28 | 60.5 | AAATTACCCAGTCTTGCATATGTCTT | 106410436 | |

TABLE 2-continued

| SEQ ID NO | Tm (° C.) | Sequences | Amplified region | Length of amplicon |
|---|---|---|---|---|
| 29 | 63.0 | CTGGATCAACTAGGCCACCAAC | 106413052- | 774 |
| 30 | 63.0 | CCAAAATTAACAATGTTCATTTTACAATAAGAG | 106413825 | |
| 31 | 61.1 | GCTCTTATCTTTGCTTAATGGGTGT | 106415516- | 748 |
| 32 | 60.5 | TGTACATTTGGTCTAATGGTACAACTG | 106416263 | |
| 33 | 60.5 | AATGGAAACCTATCAGTGGACAAC | 106416016- | 1107 |
| 34 | 60.2 | TATATATCTGTTGTAAGGCCCTGTGA | 106417122 | |
| 35 | 62.0 | CAGAGCTTTCTGGATCCTGACAT | 106416670- | 535 |
| 36 | 60.3 | GCCCACGTCATGAGAACTATACTAC | 106417204 | |
| 37 | 66 | TCTAAGCTCAGTCTACCACCCATCCATA | 106416118- | 570 |
| 38 | 66.7 | TGCTCGCTGTCTGACCAGACCTCAT | 106416671 | |

2.2. PCR

PCR were performed in 20 μL starting from 25-50 ng of DNA on APPLIED BIOSYSTEM PCR 9700.

For each sample: 17 PCR were used to detect the mutations/deletions localized on the TET2 gene. The mix was prepared as below:

| | mix *1 |
|---|---|
| 10X | 2 |
| dNTP 25 mM | 0.15 |
| O1 100 pmol/μl | 0.1 |
| O2 100 pmol/μl | 0.1 |
| hot star (5 U/μl) | 0.2 |
| Water | 15.5-16.5 |
| DNA sample (25 ng/μl) | 1-2 |

We use the following PCR cycles conditions:

| 15' | 94° C. | 1 cycle |
|---|---|---|
| 20 s | 94° C. | 2 cycles |
| 20 s | 56° C. | |
| 30 s | 72° C. | |
| 20 s | 94° C. | 2 cycles |
| 20 s | 54° C. | |
| 30 s | 72° C. | |
| 20 s | 94° C. | 2 cycles |
| 20 s | 52° C. | |
| 30 s | 72° C. | |
| 20 s | 94° C. | 37 cycles |
| 20 s | 50° C. | |
| 30 s | 72° C. | |
| 10' | 72° C. | 1 cycle |

2.3. Sequencing of the PCR Products

Finally, the PCR products sequencing was realized by EUROFINS MWG Biotech (France, 9, rue de la Laponie, 91967 Les Ulis cedex) or by "Département des services commun de l'Institut Cochin" (Plate forme transcriptomique, Hôpital Cochin/Bat G. Roussy/3ème étage, 27 rue du Fg St Jacques, 75014 Paris) with the kit Big Dye terminator V1.1 and 3130 XL sequencing machines (both from APPLIED BIOSYSTEMS).

3. Mutations of the Tet2 Gene in Patients Suffering from MDS or AML with Heterozygous 4q24 Deletion 3.1. In Tumoral Cells TET2 gene integrity was checked on the 4q24 "intact" copy of the 8 above-mentioned patients harboring the heterozygous acquired chromosomal translocation associated with a genomic deletion in the vicinity of the chromosome 4 breakpoint at 4q24.

To identify potential mutations of the TET2 gene in these alleles, the sequence of the eight coding exons and of their splice sites in the DNA extracted from bone marrow samples of 8 patients having a 4q24 rearrangement was investigated by PCR as described previously.

Table 3 discloses the status of both alleles of the TET2 genes in patients suffering from MPD, MDS or AML and having a 4q24 deletion on one allele:

TABLE 3 discloses the status of both alleles of the TET2 genes in patients suffering from MPD, MDS or AML and having a 4q24 deletion on one allele:

| Patient | Copy 1 | Copy2 | Disease |
|---|---|---|---|
| nAML1 | R1896M | Deletion | AML |
| nAML2 | I1873T | Deletion | AML |
| nAML3 | Deletion | Unknown | AML |
| MDS01 | Deletion | Deletion | RA |
| MDS02 | FS after L560 (Exon 3) | Deletion | RA |
| MDS03 | N1624Stop (Exon 11) | Deletion | RA |
| MPD01 | Q557Stop | Q557Stop | PMF |
| MPD04 | Deletion (1237 to 1239) | Deletion (1237 to 1239) | PV |
| MPD05 | Deletion | Wild type | PV |

Comparison of the sequence obtained from the patients with the wild type counterpart identified nucleotide changes in 6 patients (Table 3). Changes were not attributable to identified polymorphisms. Patient nAML1 and nAML2 harbored single nucleotide changes, leading to an I1873T in patient nAML2 and to R1896M in patient nAML1. Patient MDS03 exhibited a CAG to TAG changes, introducing a stop codon instead of N1624. Patient MPD01 exhibited a single nucleotide change, introducing a stop codon instead of NQ557. Patient MDS02 had a 4 base pair insertion, leading to a stop codon 6 amino acids after L560. Patient MPD04 had an in frame 9-nucleotide deletion. No notable nucleotide changes were observed in DNA of patient nAML3. Patient MDS01 harbors a bi-allelic deletion of the TET2 gene.

3.2. In Non-Tumoral Cells of the Patients

To confirm that the observed changes were somatically acquired, we analyzed DNA from non-tumoral samples when available.

Figure 2:
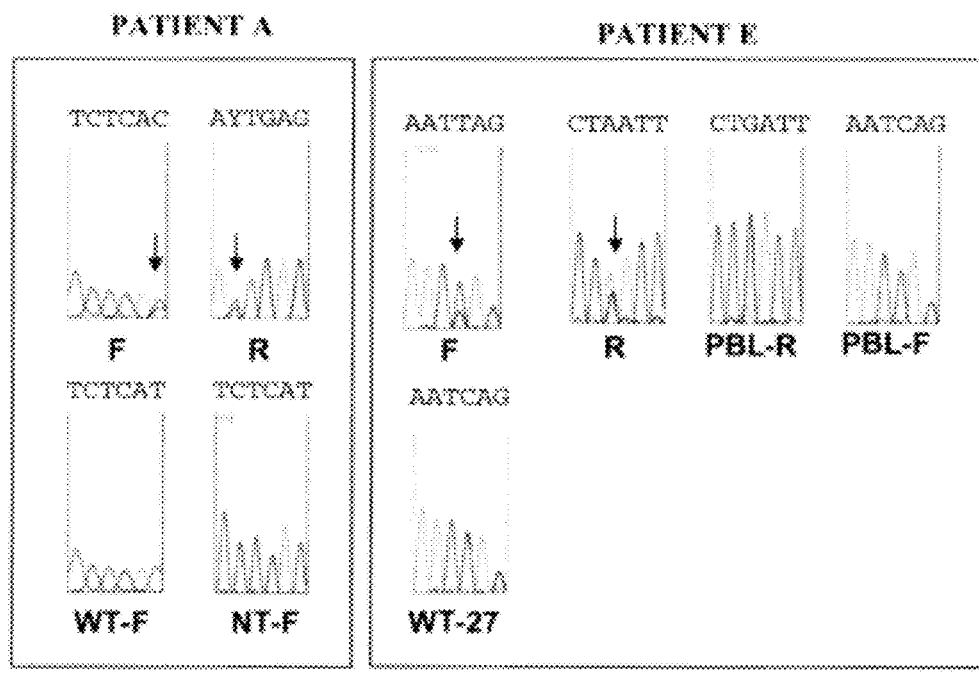

In patient nAML2, the T to C change was not observed in DNA from EBV-transformed B cell population (FIG. 2). In patient nAML1, the analyses of a sample obtained after autobone marrow transplantation demonstrated an inversed ratio between the wild type G and the mutated T, when compared to the diagnosis sample (data not shown). Similarly, the signal corresponding to the mutated T is almost absent in DNA extracted from stimulated PBL from patient MDS03 (FIG. 2). This analysis has also shown the absence of mutation for MPD04 or of deletion for MPD05 in non-tumoral cells (data not shown). This analysis has further shown that a small amount of residual wild-type sequence is detected in peripheral mononuclear cells from patient MPD01 (data not shown).

The FIG. 2 shows the sequence traces obtained by sequencing of PCR on samples obtained from the two patients nAML2 and MDS03, and showing that the mutation only occurs in the tumoral (R: reverse primer and F: forward primer) and in non-tumoral samples (NT or PBL).

Taken together, these results demonstrate that the two copies of the TET2 gene is targeted in patients suffering from diverse myeloid neoplasm, and this through two different events, a chromosomal translocation associated with a deletion and point mutations, establishing TET2 as a tumor suppressor gene.

4. Alteration of the Tet2 Gene in Patients Suffering from MDS or AML without Cytogentically Detectable 4q24 Deletion To establish whether mutation of TET2 could also occurs independently of a chromosomal abnormality, DNA from bone marrow samples of 309 additional patients with different subtypes of MDS (n=81), sAML (n=21), CMML (n=9), $JAK2^{V617F}$ positive MPD (n=181), and $JAK2^{V617F}$ negative MPD (n=17) without known 4q24 abnormality was analyzed by PCR as previously described.

Table 4 discloses the status of the identified TET2 defect in patients suffering from MDS or AML:

TABLE 4 discloses the status of the identified TET2 defect in patients suffering from MDS or AML:

| Patient | TET2 defect | Disease |
|---|---|---|
| sAML2 | S1898F | sAMLII |
| sAML4 | FS (Exon3) | sAMLII |
| sAML5 | FS (Exon11) | sAMLII |
| sAML6 | FS (Exon11)/Q891stop | sAMLII |
| sAML7 | Q943Stop | sAMLII |
| MDS04 | K1299E/R544Stop | RA |
| MDS07 | No amplification Ex11 | RA |
| MDS30 | FS (Exon3) | RA |
| MDS09 | FS (Exon3) | RARS |
| MDS35 | Y1225Stop Exon6 | RARS |
| MDS10 | Y1724Stop/Q321Stop | RCMD-RS |
| MDS28 | FS (Exon3) | RCMD-RS |
| MDS18 | FS (Exon11) | RAEB1 |
| MDS27 | FS (Exon3)/FS (Exon3) | RAEB1 |
| MDS33 | FS (Exon4) | RAEB1 |
| MDS39 | L1872P | RAEB1 |
| MDS40 | FS (Exon11) | RAEB1 |
| MDS42 | L1872P/I1873T Mutation of splice acceptor | RAEB1 |
| MDS34 | Site Exon5 | RAEB2 |
| MDS41 | FS (Exon11) | RAEB2 |

TABLE 4-continued discloses the status of the identified TET2 defect in patients suffering from MDS or AML:

| Patient | TET2 defect | Disease |
|---|---|---|
| CMML01 | Q685Stop | CMML |
| CMML02 | FS (Exon3)/R1067Stop | CMML |

RA, refractory anemia;
RARS, refractory anemia with ringed sideroblasts;
RARS-T, RARS with thrombocytosis;
RAEB, refractory anemia with excess blasts;
RAEB1: blasts 5-9%;
RAEB2: blasts 10-19%;
AML, acute myeloid leukemia;
FAB, French American British classification;
del, deletion;
FS, frame shift;
ND, not done.
All MDS/AML tested (22/27) were negative for $JAK2^{V617F}$.
MDS03 was studied at the RAEB1 and RAEB2 phases.
Two successive samples of patient MDS34 were analyzed.
Selected patients analyzed during the initial part of the study appear in bold.

TABLE 5 discloses the status of the identified TET2 defect in patients suffering from MPD:

| Patient | TET2 defect | Disease | JACK2 and MPL status |
|---|---|---|---|
| MPD18 | R1216stop | PV | $JAK2^{V617F}$ |
| MPD20 | FS Ex11 | PV | $JAK2^{V617F}$ |
| MPD35 | S354stop | ET | $JAK2^{V617F}$ |
| MPD43 | FS Ex3/R550stop | post ET MF | $JAK2^{V617F}$ |
| MPD45 | FS Ex3 | PV | $JAK2^{V617F}$ |
| MPD69 | FS Ex7/FS Ex11 | PV | $JAK2^{V617F}$ |
| MPD74 | FS Ex3 | PMF | WT |
| MPD81 | FS Ex6 | ET | $JAK2^{V617F}$ |
| MPD86 | FS Ex5/R1404stop | PV | $JAK2^{V617F}$ |
| MPD89 | FS Ex10 | PV | $JAK2^{V617F}$ |
| MPD92 | R1302G | PMF | $JAK2^{V617F}$ |
| MPD96 | W1847stop | ET | $JAK2^{V617F}$ |
| MPD99 | FS Ex3 | ET | $JAK2^{V617F}$ |
| MPD120 | FS Ex3 | PV | $JAK2^{V617F}$ |
| MPD130 | FS Ex3 | ET | $JAK2^{V617F}$ |
| MPD132 | FS Ex3 | PV | $JAK2^{V617F}$ |
| MPD133 | G1869W | ET | $JAK2^{V617F}$ |
| MPD142 | FS Ex3 | PV | $JAK2^{V617F}$ |
| MPD149 | FS Ex6 | ET | $JAK2^{V617F}$ |
| MPD158 | FS Ex3 | PV | $JAK2^{V617F}$ |
| MPD163 | Q1542stop | ET | $MPL^{W515L}$ |
| MPD164 | FS Ex3 | PMF | $JAK2^{V617F}$ |
| MPD183 | FS Ex7/Q635stop | PV | $JAK2^{V617F}$ |
| MPD200 | FS Ex3/FS Ex11 | ET | WT |

PMF, primary myelofibrosis,
PV, polycythemia vera,
ET, essential thrombocythemia.
WT: negative for $JAK2^{V617F}$ and $MPL^{515}$ mutations.
FS, frame shift.

Table 5 discloses the status of the identified TET2 defect in patients suffering from MPD:

Obvious abnormalities of TET2 coding sequence were observed in 45 patients, resulting in conserved amino acid substitution, generation of in frame stop codons, or frame shifts (Tables 4 and 5). In one additional patient (MDS07), amplification of the 5' part of exon 11 only resulted in trace amounts of PCR fragment despite the use of several conditions and primers pairs (data not shown), which was attributed to an uncharacterized structural genomic rearrangement affecting this region. Defects of TET2 were observed in all types of MDS (22/111) and BCR-ABL negative MPDs associated with JAK2 V617F (21/181), or MPL W515L/K (1/6) or devoid of these mutations (2/11).

The results demonstrate that TET2 defects can be identified in unselected diverse myeloid disorders with a high prevalence (46/309=17%). As an example, patient MDS04 showed two changes leading to K1299D and R544Stop. Patient MDS10 had two stop mutations, Y1724Stop and Q321Stop. Patient sAML2 had a point mutation leading to S1898F. These observed mutations may result in a partial or total loss of function of the TET2 protein. It can be anticipated that other defects such as deletions of the TET2 gene might have been missed and thus the estimated the frequency of TET2 defects in these malignancies would be underestimated.

Overall, in 19/55 of the patients with TET2 defects, two different mutations were detected, likely targeting both copies of TET2. This point was confirmed by sequencing individual molecules after subcloning of the PCR fragments obtained from patient MDS42. A single defect was observed in 35/55 samples suggesting that TET2 haploinsufficiency may play a role in these malignancies.

5. Tet2 Mutations Target Early Progenitors in MDS

MDS are myeloid malignancies originating from a HSC. If the mutations observed in TET2 are causative, they should also be observed in the HSC. To investigate this, we first analyzed the presence of the TET2 defects in CD34$^+$ cells, which include HSC and hematopoietic progenitors, from 4 MDS patients (MDS03, MDS09, MDS28, MDS35).

The FIG. 3a shows the sequencing histograms of sorted CD34$^+$ cells from patient MDS03 at RAEB1 and RAEB2 phases. Sequences observed in unsorted bone marrow sample and of wild-type control are shown for comparison purposes. Asterisks indicate the mutated nucleotide.

The FIG. 3b shows the PCR-RFLP analysis of DNA isolated from sorted MDS03 CD34$^+$CD38$^-$ and CD34$^+$CD38$^+$ cells at RAEB1 phase. Amplified fragments were digested using Tas1 and size-fractionated by agarose migration. The proportion of mutated TET2 mutated was evaluated by measuring the intensities of the mutated (mut) or wild-type (wt) signals relative to that of the signal generated by both alleles (wt+mut). Undigested (−) and digested (+). (ctl) correspond to PCR products from control DNA. MW: molecular weight.

The FIG. 3c shows the PCR-RFLP analysis of TET2 directly performed from sorted CD34$^+$CD38$^-$ and CD34$^+$CD38$^+$ cells from MDS09 patient using BseLI endonuclease.

The FIG. 3d shows the genotyping by PCR-RFLP using BseLI of sorted CD34$^+$CD38$^-$ and CD34$^+$CD38$^+$ cells from patient MDS09 grown at one cell per well. Annotations are as in b. The histograms represent the fraction of clones with wild-type (gray) or mutated (black) TET2. Note the absence of wild-type fragment in CD34$^+$CD38$^+$ clones indicated by asterisks.

In all cases, the mutated TET2 sequence could be detected (FIG. 3). In one of these patients (MDS03), CD34$^+$ cells could be analyzed at refractory anemia with excess of blasts 1 (RAEB1) and RAEB2 phases. Interestingly, the wild-type sequence was detected at the RAEB1 phase, but not at the RAEB2 phase (FIG. 3a), suggesting expansion of TET2 mutated progenitors with the disease progression.

We next fractionated the CD34$^+$ from these four patients into CD34$^+$CD38$^-$ (corresponding to HSC and multipotent progenitors) and CD34$^+$CD38$^+$ (corresponding to more mature progenitors) cell populations using CD34-PeCy5 and CD38-FITC antibodies (IMMUNOTECH) using a FACS-Diva cell sorter (BECTON DICKINSON). In two patients (MDS03 and MDS09), PCR-RFLP analysis was used to distinguish mutated and wild-type TET2 sequences. The mutated TET2 burden increased in both patients from CD34$^+$CD38$^-$ to CD34$^+$CD38$^+$ cells (16% to 54% in MDS03, and 26% to 48% in MDS09) (FIG. 3b, c). Further analysis was performed at the cellular level, by seeding single hematopoietic progenitors from MDS09.

Sorted CD34$^+$CD38$^-$ cells from MDS09 bone marrow were seeded at one cell per well on a confluent layer of the MS5 cell line in MEM alpha medium supplemented with 10% FBS (STEM CELL TECHNOLOGIES), and a cocktail of early cytokines (thrombopoietin (Tpo) interleukin-3 (IL3), FLT3-L, Stem Cell factor (SCF) and interleukin-6 (IL6)). CD34$^+$CD38$^+$ cells were also seeded at one cell per well using the same combination of "late" cytokines (SCF, IL3, erythropoietin (Epo) and granulocyte-colony stimulating factor (G-CSF)) as used in methylcellulose cultures (DUPONT et al., abovementioned, 2007). After three weeks (CD34$^+$CD38$^-$) or 10 days (CD34$^+$CD38$^+$), individual clones were collected for further genotyping.

The results show that TET2 mutation was identified in 8 out of 32 (25%) and 18 out of 30 (60%) clones derived from CD34$^+$CD38$^-$ and CD34$^+$CD38$^+$ cells, respectively (FIG. 3d). Interestingly, the wild-type copy of TET2 was not always amplified from clones bearing a mutated TET2, suggesting its loss in a minority of the cells.

For the two other patients (MDS28, MDS35), the increase in TET2 mutation burden from CD34$^+$CD38$^-$ to CD34$^+$CD38$^+$ samples was evaluated with the sequence graphs. To be more accurate, the amplified fragments from MDS28 samples were subcloned and individual bacterial clones were sequenced. The mutated copy was barely detectable in the CD34$^+$CD38$^+$ population of MDS28 whereas it represented 32% of TET2 sequences in the CD34$^+$CD38$^-$ population (data not shown). These data indicate that TET2 mutations target a CD34$^+$CD38$^-$ cell and that in MDS TET2 mutated burden increases from immature to mature progenitors, suggesting a selective advantage of the mutated cells during early phases of hematopoietic differentiation.

In three sAML samples (sAML2, sAML4, sAML5), TET2 mutations were also found in CD34$^+$ cells (data not shown). When analyzed, in sAML4, sAML5 sorted cells, no marked changes in the mutated TET2 burden were observed between CD34$^+$ C38$^-$ and CD34$^+$CD38$^+$ populations.

6. Prevalence and Prognosis Impact of Tet2 Mutations in MDS

So as to establish the prevalence and prognosis impact of TET2 mutations in MDS, we retrospectively analyzed TET 2 mutations and their prognosis value, in 204 MDS and AML post MDS enrolled in GFM multicenter trials (41 RA/RCMD/MDS-U/5q-, 18 RCMD, 28 RARS/RCMD-RS/RARS-T, 43 RAEB 1, 32 RAEB 2, 44 AML post MDS). TET2 mutations analysis was realized as described previously and the results are presented in table 6.

TABLE 6 discloses the status of the identified TET2 defect in patients suffering from MDS or AML:

| Disease | Nucleotide change | Consequence |
|---|---|---|
| MDS02 G04 | delA 3166 | p.Gln769 FS |
| MDS 04 | c.4755A > G + c.2490C > T | p.[Lys1299Glu] + [Arg544X] |
| MDS01 A08 | insT 3465 | p.Pro869 FS |
| MDS01 A11 | c.5071 C > T | p.Arg1404 STOP |
| MDS02 C01 | delT 2685 + insA 3009 | p.Ser609 FS + |

TABLE 6-continued discloses the status of the identified TET2 defect in patients suffering from MDS or AML:

| Disease | Nucleotide change | Consequence |
|---|---|---|
| MDS01 B03 | insA 5540 | p.His717 FS |
| MDS01 B11 | c.2913C > T | p.Tyr1560 FS |
| sAML1 | | p.Gln685 STOP |
| MDS 07 | | del/wt |
| | | No amplification of 5' Exon 11 |
| MDS01 C08 | delC 6360 | p.Gln1834 FS |
| MDS01 C09 | c.3532C > T + insA 5757 | p.Cys1633 FS + p.Gln891 STOP |
| MDS01 D01 | c.6475T > C | p.Leu1872Pro |
| MDS02 H02 sAML2 | c.4384A > G + c.4625C > G | p.Ile1175Val + p.Tyr1255 STOP Ser1898Phe |
| MDS01 D06 | del 2834_2835 | p.His658 FS |
| MDS 10 | | p.Gln530 FS + p.Tyr1724 STOP |
| MDS02 C12 | delT 2685 + c.6316T > G | p.Ser609 FS + p.Leu1819 STOP |
| MDS02 D01 | delC 3009 | p.His717 FS |
| MDS 01 | | del/del |
| MDS 02 | | del/p.Arg581 FS |
| MDS01 E02 | c.5730C > T | del/Gln1624 STOP |
| MDS02 D04 | delT 2944 | p.Leu699 STOP |
| MDS01 E06 | insC 3151 + p.5406C > T | p.Gln764 FS + Arg1516 STOP |
| MDS01 E07 | c.6475T > C + c.6478T > C | p.Leu1872Pro + p.Ile1873Thr |
| MDS01 E08 | delC 2448 + delA 4130 | p.Gln530 FS + p.Lys1090 FS |
| MDS01 F02 | p.6360C > T | p.Gln1834 STOP |
| MDS01 F04 | delG 2994 | p.Glu711 FS |
| MDS02 E01 | c.6114T > G + insT | p.Tyr1751 STOP + mutation of splice site exon 8 |
| MDS01 F06 | p.3688C > T + delA 6507 | p.Gln943 STOP + p.Thr1883 FS |
| MDS01 G01 | delG 4271 + c.6478T > C | p.Glu1137 FS + p.Ile1873Thr |
| MDS01 G03 | p.3688C > T | p.Gln943 STOP |
| nAML2 | c.6478T > C | del/p.Ile1873Thr |
| MDS01 G05 | delC 5222 | p.Leu1457 STOP |
| MDS02 F11 | dupT 3914 | p.Glu1026 STOP |
| MDS01 G06 | delA 2935 + del5828_5843 | p.Glu692 FS + p.Met1656 FS |
| MDS02 A12 | p.4969G > A + del6396_6531 | p.Gly 1370 Glu + p.Val1846 FS |
| MDS01 G7/8 | g.4366-1G > T | mutation of splice acceptor site exon5 |
| MDS02 E10 | insCT 3581 | pGly 908 FS |
| MDS02 H12 | delG 4932 + del5521_5524 | p.Glu1357 FS + pThr1554 FS |
| MDS02 G03 | insC 3151 + insC 6507 | p.Gln764 FS + p.Thr1883 FS |
| MDS02 G01 | delG 5133 + del6511_6512 | p.Asp 1425 FS + p.Pro1885FS |
| MDS02 G07 | p.5253C > T | p.Arg1465 STOP |
| MDS02 C07 | c.4561A > T | p.Glu1234Val |
| MDS02 B07 | c.2109C > T | p.Gln417 STOP |
| nAML1 | c.6547G > T | del/p.Arg1896Met |
| MDS02 E11 | c.2784C > T + p.5253C > T | p.Gln642 STOP + p.Arg1465 STOP |
| MDS01 H05 | c.4515C > T | p.His1219 Tyr |
| MDS02 H06 | del1264_1666 | p.Glu135 FS |
| MDS01 B08 | delA4327 + c.5020A > G | p.Asn1156 FS + Asn 1387Ser |
| MDS02 D10 | insC 3151 + c.4891C > A | p.Gln764 FS + p.Ala1344 Glu |
| MDS02 B02 | delT 5570 + insC | p.Leu1637 FS + mutation of splice site exon 8 |
| MDS01 F01 | insT3995 + c.4059A > T | p.Glu846 FS + p.Arg1067 STOP |
| MDS02 B11 | c.4673C > G + Del6049_6050 | p.Cys1271 Trp + p.Asp1830 FS |
| MDS01 E09 | insG 5119 | p.Leu 1420 FS |
| MDS | c.5430C > T | p.Gln1524STOP |
| MDS | c.5177dupA | p.Arg1440FS |
| MDS | c.5583_5605 del | p.Pro1575FS |
| MDS | c.5310A > G | p.Lys1197Arg |
| MDS | c.2375C > A | p.Ser792STOP |

We found 59 mutations of the TET2 gene by direct sequencing of exons 3 to 11 (27 frameshifts, 21 nonsense and 11 missense mutations in conserved domains) in 43/204 pts (Table 6). The frequencies according to the WHO subtypes were 21.8% in RA, 5.2% in RCMD, 21.4% in RARS/RARS-T/RCMD-RS, 34.9% in RAEB 1, 15.6% in RAEB 2, 19% in AML post MDS. Other anomalies of the 4q24 region were found including a deletion in 1/46 pts analyzed by CGH and 3 LOH in 3/22 patients analyzed by SNP arrays and 2 deletions in 5/23 pts analyzed SNP arrays. Thus, the overall prevalence of 4q24 anomalies was 21.6% patients (44/204). 20 patients had two anomalies of TET2 identified by direct sequencing (17 patients), or sequencing plus SNP array (3 patients), indicating that the two copies of the gene were targeted in 43.5% of mutated patients.

Then, univariate and multivariate survival analyses were conducted with Cox hazard proportional model so as to establish the prognosis impact of TET2 mutations. Comparison between the 43 patients with TET2 coding sequence mutations and unmutated patients found no significant differences in initial characteristics for sex, age, previous exposure to chemo or radiotherapy, Hb level, WBC count, ANC, plt count, % bone marrow blasts, multilineage dysplasia, WHO and FAB subtypes, karyotype and IPSS.

The analysis revealed that five-year survival (Kaplan-Meier curve) was significantly increased in TET2 mutated patients compared to unmutated patients (p<0.05).

7. Rearrangement of the Tet2 Gene in Patients Suffering from MPD with 4q24 Abnormality Detected by SNP or CGH Arrays Analyses Among 35 MPD samples, 4 patients had a LOH by SNP arrays and were analyzed for mutations within TET2 gene on both alleles. In 3 of the 4 samples a clear mutation or deletion was observed.

Table 7 discloses the status of both alleles of the TET2 genes in patients suffering from MPD:

TABLE 7 discloses the status of both alleles of the TET2 genes in patients suffering from MPD:

| Patient | Copy 1 | Copy2 | Disease |
|---|---|---|---|
| IGR-1 | Q557Stop | LOH | PMF |
| IGR-2 | Deletion 1237-1239 | LOH | PV |
| IGR-3 | whole gene deletion | No abnormality | PV |
| IGR-4 | unknown | LOH | ET |

In table 7, "PMF" stands for Primitive Myelofibrosis, "PV" for polycythemia Vera, "EV" for Essential Thrombocytosis. All these diseases are Class II MPDs.

Patient IGR-2 harbored a 9 base pair in frame deletion lead to the loss of three amino acids, P1237, L1238, S1239. As shown by SNP analyses and by the analyses of the sequence traces, patients IGR-1 and IGR-2 had lost the other TET2 copy. None of the mutations were observed in non-tumoral cells of the patients. These data establish that inactivation TET2 participates to the development of MPD.

Systematic sequencing of TET2 genes in 17 other patients revealed two patients with a stop codon on one allele (IGR17: S354Stop, IGR-18:R1216Stop) and one patient with one nucleotide deletion leading to a frameshift in exon 11.

8. Analysis of the Acquisition of the Tet2 Rearrangement

Recent evidence indicate that JAK2$^{V617F}$ may not be the initiating event in some MPDs. Therefore we used MPD samples to evaluate the relative roles of TET2 defects and JAK2$^{V617F}$ mutation in these diseases and to gain insight into the sequence of the acquisition of the mutations. We first analyzed hematopoietic progenitors from five MPD patients with mutations in both genes, like the patient IGR2.

For MPD samples, Immature CD34$^+$CD38$^-$ cells were seeded at one cell per well for four to six weeks in conditions permitting simultaneous B, NK and granulocytic differentiations (lympho-myeloid differentiation) as described (DU-PONT et al., abovementioned, 2007), whereas more mature CD34$^+$CD38$^+$ cells were grown in erythroid/granulocytic methylcellulose assays. Individual clones were collected for analysis of B, NK, and granulocytic differentiation by flow cytometry, and genotyping. CD34$^+$CD38$^+$ cells were seeded at 1,500 to 3,000 cells per culture dish in 2% standard methylcellulose supplemented with 37% FBS (STEM CELL TECHNOLOGIES), and a cocktail of cytokines as described (DUPONT et al., abovementioned, 2007)). Individual colonies grown from burst-forming units-erythroid (BFU-E) and colony-forming units-granulocyte/macrophage (CFU-GM) were picked on day 14. The obtained clones were analyzed for the presence of both molecular defects.

The results have shown that in all patients tested, sequence analyses revealed that both TET2 and JAK2 defects were present in clones derived from lympho-myeloid progenitors (data not shown). Interestingly the JAK2$^{V617F}$ mutation was not observed in the absence of TET2 defect whereas TET2 mutation could be observed in the absence of JAK2$^{V617F}$. These results demonstrate that, as in MDS, the TET2 mutation is present in immature progenitors of MPD patients and indicate that TET2 defects precede JAK2 mutation during the evolution of the disease.

To further define the role of the TET2 mutations in the amplification of the malignant clone, we compared the genotype of colonies derived from immature (CD34$^+$CD38$^-$) progenitors to that of erythroid and granulocytic colonies derived from committed (CD34$^+$CD38$^+$) progenitors.

The results shown that in three MPD patients (MPD01, MPD04, MPD35), almost all the colonies at different stages of hematopoietic differentiation harbored a TET2 mutation, suggesting that the TET2 mutated clone expanded at early steps of hematopoiesis (data not shown). In 2 other patients (MPD05, MPD20), most immature progenitors were wild-type whereas most committed progenitors were mutated for TET2. Within JAK2 wild-type progenitors from these two patients, we observed an increase in the proportion of clones with TET2 defects from the immature (2/37 and 0/34, respectively) to the committed (10/23 and 9/54, respectively) progenitor stage. Taken together, our results indicate that the selective advantage of the TET2 mutated clone at early differentiation steps is independent of the JAK2$^{V617F}$ mutation.

Overall, these data from MPD samples demonstrate that TET2 defects (i) occur at early steps of hematopoietic differentiation and that (ii) they may precede the occurrence of the JAK2$^{V617F}$ mutation and (iii) they give a selective advantage to the clone as it proceeds to myeloid differentiation.

9. Engraftment and Proliferation of Tet2 Mutated Cells In Vivo

We reasoned that loss of function of TET2 could confer a growth advantage to the hematopoietic stem cells. To demonstrate that the TET2 mutations occur in a HSCs with NOD-SCID repopulating capacity, we used a xenotransplantation assay by injecting, into NOD-SCID mice, CD34$^+$ cells isolated from JAK2$^{V617F}$ MPD patients with TET2 mutations.

CD34$^+$ cells (1 to 10×10$^5$ cells) from JAK2$^{V617F}$ MPD patients with TET2 mutations were injected intravenously into sub-lethally irradiated (3.5 Gy) NOD-SCID mice, previously treated with 200 µg of anti-CD122 antibody (JAMES et al., Blood, vol. 112(6), p: 2429-36, 2008). Bone marrow was obtained with heparinized syringue from the right femur at 3, 6 and 12 weeks after transplantation and mice were sacrificed at week 15. Human cell engraftment was evaluated by the sum of human leukocytes (CD45$^+$) and erythroid populations (CD45$^-$CD36$^+$ and CD45$^-$CD36$^-$GlycophorinA$^+$), as assessed by flow cytometry. Bone marrow cells were seeded in culture dish and 96-well plates for methylcellulose and long-term culture-initiating cell (LTC-IC) assays, respectively allowing the selective growth of human cells as described in JAMES et al. (abovementioned, 2008). Individual colonies were subsequently picked and genotyped.

We first compared the kinetics of chimerism after transplantation of CD34$^+$ cells from these JAK2$^{V617F}$ MPD patients with TET2 mutations and from three JAK2$^{V617F}$ MPD devoid of TET2 defects (MPD09, MPD11, MPD27).

The FIG. 4a shows the percentage of human CD45-positive cells in mouse bone marrow monitored at 3, 6, 12, and 15 weeks post-transplant. MPD01 and MPD04 are patients with TET2 defects whereas MPD09, MPD11, and MPD27 are control patients devoid of identified TET2 defect.

The FIG. 4b shows the flow cytometric analysis of human cells present in NOD-SCID bone marrow 15 weeks after transplantation with 3×10$^5$ CD34$^+$ cells from patients MPD04 and MPD09. The percentages of human CD45 (hCD45)-positive myeloid and lymphoid cells were determined using anti-CD45-PC7, anti-CD33-APC, and anti-CD19-PE antibodies.

The results show that human cells from the three patients devoid of TET2 mutation disappeared with time (FIG. 4a).

In contrast, the percentage of human cells in the bone marrow of mice engrafted with cells from the two TET2 mutated patients increased with time (FIG. 4a). In these mice, differentiation was skewed toward myeloid progenitor expansion, at the expense of lymphoid progenitors, as judged from CD33 and CD19 antigen flow cytometry analyses (FIG. 4b) unlike what is observed with normal HSCs wherein lymphoid differentiation is favored (ROBERT-RICHARD et al., Haematologica, vol. 17(3), p: 637-41, 2003).

Human cells present in the mouse bone marrow 15 weeks after transplantation (W15) were tested in in vitro progenitor and LTC-IC assays, and analyzed for the presence of TET2 and JAK2 mutations. The TET2 defects were found in pooled W15 CFU-derived colonies from both MPD01 and MPD04 samples, and in all individual human LTC-IC and progenitors present in the mice (data not shown). The results were compared with progenitor assays performed immediately before engraftment (D0). All colonies arising from patients' committed progenitor cells (D0 CFU) harbored TET2 mutation.

These results demonstrate that TET2 mutation occurs in a HSC. Interestingly, the results have further shown that the proportion of progenitor cells carrying only the TET2 mutation increased upon transplantation at the expense of cells carrying both TET2 and JAK2$^{V617F}$ mutations. These cells are thought to reflect the original HSC population. Therefore, these observations indicate that TET2 mutated HSCs with a wild-type JAK2 are more numerous than the TET2/JAK2 double mutant HSCs, further establishing the mutation of TET2 as a "pre-JAK2$^{V617F}$" event in these patients.

Therefore our data are compatible with the hypothesis that TET2 defects endow the HSC with a selective engraftment advantage independently of JAK2$^{V617F}$.

10. Positions of the Identified Mutations on the Tet2 Gene

We report that the inactivation of TET2 is a common early event in human MDS, MPD and sAML and that the frequencies of TET2 mutation in unselected patient series were 15/81=18.5% in MDS, 2/9=22% in CMML, 24/198=12% in MPD and 5/21=24% in sAML. It must be noticed that in these analyses we did not consider amino acid changes occurring outside of the conserved domains. Sequencing of the TET2 gene using the couples of primers identified in table 1 permits to identify a number of mutations in the TET2 gene (FIG. 5).

The FIG. 5 shows the locations of some of the identified mutations of the TET2 gene distributed along the protein sequence.

Mapping of the identified TET2 mutations on the TET2 sequence suggest an essential role for the carboxy terminal conserved region (amino acids in position 1860 to the position 1950) in the function of the protein.

Finally, the detection of acquired genetic defects targeting the two TET2 copies in 19 of the 55 patients with TET2 alteration establishes this gene as a bona fide tumor suppressor gene of human myeloid malignancies. TET2 defects are observed in both MDS and MPD, which are two distinct myeloid diseases. It is therefore likely that their characteristic clinical and biological phenotypes require at least another additional cooperating event. In MPD samples with both TET2 and JAK2 mutations, TET2 mutations likely occur first in the natural history of the disease, preceding the occurrence of JAK2$^{V617F}$ mutation.

11. Identification of Tet2 Gene Mutations in Familial MPD

Families with at least 2 affected patients with MPD were collected through a national network as previously described (BELANNE-CHANTELOT et al., abovementioned, 2006). The diagnoses of MPD were reviewed based on the 2008 World Health Organization criteria.1 All participants gave their written informed consent.

In a first step, we analyzed 15 probands of families compatible with an autosomal dominant inheritance, in search for a constitutional event that would account for these familial cases. Elected probands mostly suffered from PV or ET. In a second step, the analysis was extended to patients with hematological complications and to relatives of patients with TET2 variants.

Altogether, we analyzed 61 patients for mutations in the 6009 bp coding sequence of the TET2 gene from 42 MPD families (40 European, 2 African: families F3 and F4) including at least two available affected patients with MPDs. Thirty-four patients displayed a simple phenotype consisting of either PV (15), ET (12) or PMF (7) with no observed hematological evolution of the disease after a follow-up period of 12 years. Twenty-seven other patients had experienced an evolution in their MPD phenotype: PV evolving into myelofibrosis (post PV MF, 5) or into AML (12); ET evolving into MF (4) or AML (5), or PMF turning into AML (1).

The analysis was performed by polymerase chain reaction (PCR) on genomic DNA extracted from buccal swabs after heating at 95° C. for 10 minutes to release genomic DNA. Purified PCR products were sequenced using the BIGDYE TERMINATOR chemistry (APPLIED BIOSYSTEMS) and run on an APPLIED BIOSYSTEMS 3100 capillary sequencer.

The JAK2V617F mutational status was determined as previously reported in BELANNE-CHANTELOT et al. (abovementioned, 2006).

The whole coding region of the TET2 gene was sequenced as described previously. Two multiplex PCRs were set up to estimate the copy number of each TET2 exon using the quantitative multiplex PCR of short fluorescent fragments (QMPSF) method (CHARBONNIER et al., Cancer Res., vol. 60, p: 2760-2763, 2000). Two additional primer pairs amplifying short sequences of either the F9 or the DSCR1 gene were used as internal controls. PCR products were separated by capillary electrophoresis using a DNA genetic analyzer (ABI 3100). The analysis is based on the comparison of the peak heights generated from the tested DNA sample and the control DNA. The quantitative estimation of the height of peaks was determined using commercially available analysis software (GENEMAPPER VERSION 4.0, APPLIED BIOSYSTEMS).

Table 8 shows the TET2 mutations identified in 12 MPD patients.

TABLE 8 shows the TET2 mutations identified in 12 MPD patients.

| | | | | TET2 | | |
|---|---|---|---|---|---|---|
| Patients | Phenotype | Evolution | JAK2 | Location | Nucleotide change | Proteic change |
| P1 (F1) | PV | MF | 95 | Exon 11 | c.5695delC | p.Leu1899fs |
| P2 (F2) | PV | MF | 63 | Intron 7 | c.3954 + 2T > A | p.? |
| P3 (F2) | PV | | 49-82 | Exon 3 | c.3138delT | pLeu1046fs |
| P4 (F3) | ET | PV > MF > AML | 23-47 | Exon 3 | c.1648C > T | p.Arg550X |
| | | | | Exon 3 | c.2570delA | p.Asn857fs |
| P5 (F3) | ET | MF > AML | 0 | Exon 3 | C2058A > T | p.Arg686Ser |
| P6 (F4) | ET | AML | 0 | Exon 3 | C1955delA | p.Gln652fs |
| | | | | Exon 3 | c.2490dupA | p.Gln831fs |
| P7 (F4) | ET | | 39 | Intron 4 | c.3500 + 3A > C | p.? |
| P8 | ET | MF | 90 | All exons | c.1.4999_5014del16 | p.0 |

TABLE 8-continued shows the TET2 mutations identified in 12 MPD patients.

| | | | | TET2 | | |
|---|---|---|---|---|---|---|
| Patients | Phenotype | Evolution | JAK2 | Location | Nucleotide change | Proteic change |
| P9 | PMF | | 36 | Exon 3 | c.694C < T | p.Gln574X |
| | | | | Exon 11 | | p.Leu1667fs |
| P10 | PMF | | 33 | Exon 3 | c.4019T < C | p.Gln232X |
| P11 | PMF | | 66 | Exon 8 | c.5603A < G | p.Leu1340Pro |
| P12 | PV | MF | 78-96 | Exon 11 | | p.His1868Arg |

Patients were initially diagnosed with the phenotype indicated in the second column and subsequently had a hematological evolution shown in the third column. When measured in several samples, the JAK2V617F allele burden is indicated as a range.

The FIG. 6 is a schematic representation of the TET2 gene and protein showing the mutations identified in this study. Hatched boxes indicate exons. Truncating mutations are depicted as stars, missense mutations as inverted triangles. Conserved functional domains are depicted as boxes on the protein scheme. fs: frameshift.

Following this analysis, we identified a complete deletion of TET2 in one patient and a total of 39 point variants. Examination of these variants showed that 15 of them, identified in 12 patients, were deleterious heterozygous mutations. They were distributed as one deletion of the entire gene, 11 truncating (3 nonsense mutations, 6 out-of-frame insertions/deletions and 2 splice site mutations) and 3 missense mutations (FIG. 6, Table 8).

Furthermore, all three missense mutations were absent from 165 control individuals of ethnically matched populations, thus confirming their deleterious effect. Two, p.Leu1340Pro and p.His1868Arg, were located in the highly conserved TET2 functional domains (1134-1444 and 1842-1921). Truncating mutations seemed to be randomly distributed along the coding sequence (FIG. 6).

In patients P4, P6 and P9 two TET2 mutations were identified. For the former, multiple allele specific amplifications of the two mutations located in exon 3 showed that these two molecular events occurred on different alleles leading to the biallelic inactivation of TET2 (data not shown). The observation of such a biallelic inactivation of TET2 in these patients meets the criteria of the classical two-hit recessive model of carcinogenesis and supports the hypothesis that TET2 acts as a tumor suppressor gene.

Twenty-five other variants identified on the coding sequence of TET2 and the short nearby intronic regions were polymorphisms. Seven were substitutions in non-coding regions (intronic or 3'UTR), one was a variation in an intronic short tandem repeat, 4 were silent variations in the coding sequence and 13 were missense polymorphisms. They were all classified as polymorphisms on the basis of their presence in public databases, the fact that they were found in asymptomatic family members, or their identification in control populations. It is of interest to note that none of the missense polymorphisms were located in either one of the functional domains.

12. Tet2 Mutations were Sequentially Acquired in a Patient with Two Mutations Seven blood samples were available for patient P4 from family F3, throughout the last three steps of her evolution: PV, MF and AML. Sequencing these samples allowed us to determine the temporality of the clinical and molecular events.

The FIG. 7 shows the sequential study of TET2 and JAK2 in patient P4 (F3). Sequence electrophoregrams are shown for each TET2 mutation and for JAKV617F. The diagram on the left indicates time lapse from diagnosis (in years) and corresponding henotype for each sample (white: ET; grey: PV; hatched: post-ET MF; black: AML).

The results show that JAK2V617F and the TET2 p.Arg550X mutation were already present in the first sample, when the patient suffered from PV. The second mutation, p.Asn857fs was detectable in the second sample, 7 years later and 5 months before the diagnosis of MF. This sequential analysis has shown that the burden of each of these mutations grew in time, concomitantly with the development of the disease.

Finally, TET2 mutations were found in similar proportions in JAK2V617F positive and negative patients suggesting that molecular events in both genes may arise independently of each other.

13. Tet2 Molecular Events were Mainly Observed in Patients with PMF or Patients with PV or ET Who Secondarily Evolved Towards a Hematological Transformation Altogether, 12 patients were found carrying at least one TET2 mutation. They account for 20% of all MPD patients tested.

The FIG. 8 shows the schematic representation of the clinical status of these twelve patients with at least one TET2 mutation. White boxes depict ET stages, grey, PV, crosswised hatching indicates myelofibrosis, either primary (left-slanting) or post-PV/ET (right-slanting) and AML are symbolized as black boxes. Above each arrowhead indicating a molecular analysis is annotated the TET2 corresponding mutation. Disease duration (in years) is indicated below the bars, the "zero" point indicating time of diagnosis. Time of death is symbolized as a vertical line, when appropriate, at the right end.

This analysis shows that these TET2 defects were identified in patients diagnosed with the three main MPD phenotypes: PV (4/32), ET (5/21) and PMF (3/8). No TET2 mutation was observed in relatives with rare hematological phenotypes, including de novo AML and systemic mastocytosis (data not shown). All patients with a TET2 defect but two were positive for the JAK2V617F mutation. The allele burden varied from 33 to 95% (Table 6). The negative cases were ET patients who developed very active AML and died rapidly (P5 and P6, data not shown). We should note that the two patients, P3 and P7, who had not developed post-PV or post-ET MF at the time of examination, were characterized by a high level of JAK2V617F allele burden (82 and 39% respectively, Table 6).

Altogether, our results established that 20% of the JAK2V617F positive patients were found mutated for TET2 (10/49) vs. 17% among the JAK2V617F negative patients (2/12).

All patients carrying a TET2 mutation but two had either a myelofibrosis that occurred at onset or was acquired secondarily after PV or ET, or a secondary AML. Hence 29% (10/34) of patients with PMF or hematological complication after PV or ET were found mutated in TET2 compared to 7.4% (2/27) of patients without any diagnosed haematological complications after a mean time of disease duration of 12 years. Both patients with TET2 mutations and presenting PV or ET without hematological transformations had nevertheless an active course of the disease.

No correlation can be done between the clinical presentation, the hematological data or even the course of the disease in patients and the type and location of mutations or between patients with a single heterozygous TET2 mutation and patients with two. As shown on FIG. 8, TET2 mutations were found at different times in the evolution of the disease for each patient from the time of diagnosis (P9) to 20 years later (P8); the time to progression was also variable [1-16 years].

14. Tet2 Mutations were Present in Early Hematopoietic Progenitors and were Acquired Independently from JAK2V617F Three patients were available for analysis of their progenitor cells, patient P4 from family F3 and patients P2 and P3 from F2. Blood progenitor cells were available for the former at two different steps of her disease during the PV stage and the blast phase after MF.

The FIG. 9 disclosed TET2 and JAK2 genotypes in committed progenitors of patients P2, P3 and P4. Histograms show the fraction of clones harboring JAKV617F and two TET2 mutations (crosswised hatching), JAK2V617F and one TET2 mutation (white), wild type JAK2 and two TET2 mutations (light grey), JAK2V617F and wild type TET2 (grey) and no mutation in any of the two genes (black). Two samples were analyzed for patient P4, the corresponding stage is indicated below each bar. The numbers of analyzed clones are indicated.

The results show that eight years after diagnosis, during the PV stage, endogenous erythroid colonies already carried the p.Arg550X mutation (5/29) but p.Asn857fs was never observed (0/29, FIG. 9).

Nine years later, after leukemic transformation, all genotyped Burst forming unit-erythroid (BFU-E) and all colony forming unit-granulocyte macrophage (CFU-GM), but 2, carried JAK2V617F and both TET2 mutations (FIG. 9). The progenitor analysis therefore confirmed the temporality of these events: in patient P4, p.Arg550X was first acquired in the earliest stages of the disease; and the latest stages were characterized by the presence of both p.Arg550X and p.Asn857fs. Interestingly, two CFU-GM carried both TET2 mutations in the absence of JAK2V617F. For patient P2, colonies were found with either both JAK2 and TET2 mutations, the sole JAK2V617F or none (FIG. 9). This was an indication that for this patient the TET2 mutation occurred in clones already mutated for JAK2. All BFU-E and CFU-GM from patient P3 diagnosed with PV carried both JAK2 and TET2 mutations and did not allow concluding on the temporality of JAK2 and TET2 events.

15. Tet2 Molecular Events were Mainly Observed in Patients with CMML

The nature and frequency of somatic mutations in TET2 was also studied in bone-marrow or peripheral blood collected from 88 patients with CMML1 (n=70) or CMML2 (n=18) according to the WHO criteria and 14 acute blastic transformation of a previously identified CMML. Patients signed their informed consent according to current ethical regulations. Patients with CMML in chronic phase were newly diagnosed (n=43) or known for hematopoietic disease and followed up every 3 months for therapeutic abstention, supportive cares or cytotoxic treatment, in most cases with Hydroxyurea (n=45).

Blood and bone-marrow samples were collected on EDTA and mononuclear cells were selected by Fycoll Hypaque. DNA was extracted using commercial kits (QIAGEN). Polymerase chain reaction (PCR) and direct sequencing reaction were performed using standard conditions with gene-specific primers designed to amplify coding sequences spanning from exon 3 to exon 11 of TET2 gene as described previously. For each PCR reaction, 20 ng of genomic DNA was used for PCR amplification followed by magnetic bead purification and bidirectional sequencing using ABI 3300 capillary sequencers (AGENCOURT BIOSCIENCE). Mutation Surveyor (SOFTGENETICS) was used to detect nonsense and missense mutations located in conserved regions spanning from 1134-1444 and 1842-1921 and sequences were reviewed manually to detect frameshift mutations. TET2 abnormalities were numbered according to FM 992369 EMBL nucleotide sequence database.

The mutations identified in TET2 are listed in table 10.

TABLE 10

| Patient | WHO | Nucleotide change in TET2 | Exon | Consequence |
|---|---|---|---|---|
| 2 | CMML1 | c.4453G > A | 5 | W1198STOP |
| 4 | CMML1 | c.5214C > T; Ins 5537 (A) | 10 & 11 | R1452 STOP; Y1560FS |
| 5 | CMML1 | c.4942G > A | 9 | G1361S |
| 15 | CMML1 | c.4500C > A; Del 5118_21 (TTAT) | 6 & 10 | R1214W; L1420FS |
| 18 | CMML1 | delT 4172; c.5011A > T | 3 & 9 | F1104FS, D1384V |
| 19 | CMML1 | del 5362_5365; c.6441G > A | 10 & 11 | G1501FS; G1860R |
| 20 | CMML1 | c.2631C > T | 3 | Q591 STOP |
| 21 | CMML1 | Del 6507 (A) | 11 | T1883FS |
| 22 | CMML1 | c.2961C > T | 3 | Q701 STOP |
| 23 | CMML1 | c.1818G > T; c.4936G > A | 3 & 9 | E320 STOP; R1359H |
| 24 | CMML1 | c.4515C > T | 6 | H1219Y |
| 25 | CMML1 | c.4663n + 1 G > A; Del 6424_33 | 6 & 11 | Mutation splice donor site exon 6 + L1855FS |
| 26 | CMML1 | ins 2468_9 (AA) | 3 | K536FS |
| 28 | CMML1 | c.1272C > A; c.4814n-1 G > A | 3 & 8 | Q138 STOP, Mutation splice receptor site exon 8 |
| 31 | CMML1 | Ins 3151 (C); c.4390T > G | 3 & 5 | Q764FS; I1175S |
| 32 | CMML1 | c.3675C > T | 3 | Q939 STOP |
| 35 | CMML1 | delG 4754; dup 6569_6573 (GAGA) | 7 & 11 | K1298FS; M1570FS |
| 39 | CMML1 | delA 3874; del 4830_31 (TC) | 3 & 8 | K1008FS; S1324FS |
| 40 | CMML1 | c.2208A > T; del 4347 (A) | 3 & 4 | K450 STOP; I1163FS |
| 41 | CMML1 | c.6478T > C | 11 | I1873T |
| 42 | CMML1 | ins 1921 (A); ins 2703 (G) | 3 & 3 | S354FS; L615FS |
| 44 | CMML1 | ins 3995 (T); c.4059 A > T | 3 & 3 | E846FS; R1067 STOP |
| 17 | CMML2 | c.2814C > T | 3 | Q652 STOP |

TABLE 10-continued

| Patient | WHO | Nucleotide change in TET2 | Exon | Consequence |
|---|---|---|---|---|
| 30 | CMML2 | Ins 4293 (A); c.6510A > G | 4 & 11 | G1145FS; T1884A |
| 34 | CMML2 | delT 4277; c.6598G > T | 4 & 11 | I1139FS; G1913V |
| 38 | CMML2 | c.4936G > C | 9 | R1359S |
| 14 | TA | c.3235C > A | 3 | S792 STOP |
| 29 | TA | c.2490C > T; Del 5334 (G) | 3 & 10 | R544 STOP; E1492FS |
| 1 | CMML1 | c.5043n-1G > A; Dup 6575_6579 (GAGCA) | 10 & 11 | Mutation splice receptor site exon ex10; M1907FS |
| 7 | CMML1 | c.4439T > G | 5 | C1193W |
| 8 | CMML1 | c.4726G > T | 7 | C1289F |
| 9 | CMML1 | c.5100C > T | 10 | Q1414 STOP |
| 11 | CMML1 | Del 6023 (G) | 11 | L1721FS |
| 12 | CMML1 | Del 1921 (C) | 3 | S354 STOP |
| 16 | CMML1 | c.4827G > T; Ins 5178 (A) | 8 & 10 | E1323 STOP; R1440FS |
| 27 | CMML1 | insG 2703; ins 5125_26 (AA) | 3 & 10 | L615FS; K1422FS |
| 33 | CMML1 | Ins of 2950_85 (dup) | 3 | L718FS |
| 36 | CMML1 | c.4638G > A; c.4825T > C | 5 & 8 | C1193Y; L1322P |
| 37 | CMML1 | c.6414C > T; c.6496A > C | 11 & 11 | Q1852 STOP; E1879A |
| 43 | CMML1 | del 3859 (A) | 3 | N1000FS |
| 46 | CMML1 | del 1264_66 (AAA) | 3 | E135FS |
| 3 | CMML2 | c.4431C > T | 5 | Q1191 STOP |
| 6 | CMML2 | c.5070C > T | 10 | R1404 STOP |
| 10 | CMML2 | Del 2655_2658 (CAAA) | 5 | N598FS |
| 13 | CMML2 | Ins 5602_5606 (TCCAA) | 11 | S1582FS |
| 45 | CMML2 | c.2784 C > T; c.5253 C > T | 3 & 10 | Q642 STOP; R1465 STOP |

The results revealed that a mutated status of TET2 gene was detected in 44 out of the 88 (50%) patients. Among the 43 patients studied at diagnostic, a mutated status of TET2 gene was identified in 18 cases (42%). Such a mutated status was identified in 26 of the 45 patients (58%) studies along the course of the disease. These results thus suggest that TET2 mutation prevalence is higher in CMML than in any other studied myeloid disease.

Moreover, it must be noticed that two distinct mutations in TET2 sequence, suggesting a bi-allelic alteration of the gene, were identified in 18 out of the 44 (40%) mutated patients with a chronic phase CMML, including 5 out of the 18 (27%) patients whose mutations was identified at diagnosis, and 13 out of the 26 (50%) mutated patients studied along the course of the disease. Altogether, 69 mutations in TET2 were identified, including 33 frameshift mutations, 19 nonsense mutations, 14 missense mutations and 3 mutations in a splice site. These mutations most frequently involved exon 3 (22 events), exon 10 (9 events) and exon 11 (10 events).

An analysis of overall survival was performed in 40 of the 43 patients whose TET2 status was determined at diagnosis with an at least two months follow-up and indicated a lower 1-year overall survival in patients with the 16 patients of this cohort with TET2 mutation, but the difference did not reach significance. When overall survival analysis was limited to the 29 patients with a CMML1 according to the WHO classification and an at least two months follow-up, the difference was then significant (p<0.01). None of the other tested parameters includes age, sex and FAB classification did affect survival. Finally, the results established that TET2 mutation was associated in the 29 patients with CMML1 with a trend to significantly lower survival.

16. Alteration of the Tet2 Gene in Patients Suffering from Lymphoid Cancer

CGH analyses of 157 patients suffering from B-cell lymphoma showed the loss of a whole chromosome 4 in 2 cases, a partial deletion of chromosome 4q sequences deleting the TET2 gene in 4 cases and loss of the upstream side of TET2 associated with duplication of the downstream side of TET2 in one case. These rearrangements were found in diffuse large B-cell lymphomas (107 cases), whereas no rearrangement could be found in follicular lymphomas (50 cases).

We have analyzed 93 patients for variation within the coding sequence of TET2. They were 33 T cell lymphoma and 60 B cell lymphoma.

14 mutations were observed in 10 samples from T-cell lymphomas, including 10 frame shifts and 2 non-sense and 2 missense mutations.

Table 9 shows the TET2 mutations identified in 10 T-cell lymphomas patients. disease

TABLE 9 shows the TET2 mutations identified in 10 T-cell lymphomas patients.

| disease | Nucleotide changes | Amino acid consequences |
|---|---|---|
| T-lymphoma | c.3215delT | p.Phe785FS |
| T-lymphoma | c.[1893_1896delAAGC] + [4527delG] | p.[Lys345FS] + [Ala1223FS] |
| T-lymphoma | c.[2505delA] + [2524delC] | p.[Thr549FS] + [Pro555FS] |
| T-lymphoma | c.6564C > T | p.Tyr1902 |
| T-lymphoma | c.5523_5524insA | p.Glu1555fs |
| T-lymphoma | c.[3131_3137delCCAGACT] + [5109G > T] | p.[Leu757FS] + [Val1417Phe] |
| T-lymphoma | c.[3747C > T] + [5331A > T] | p.[Gln963STOP] + [Lys1491STOP] |
| T-lymphoma | c.3756_3757del CA | p.Gln966 FS |
| T-lymphoma (LAI) | c.1642delC | p.Ser261 FS |

Thus, these results established that the frequencies of TET2 mutation in patients suffering from T-cell lymphoid tumour is 30%.

17. Tet2 Inactivation Results in Pleiotropic Hematopoietic Abnormalities in Mouse and is a Recurrent Event During Human Lymphomagenesis To investigate the role of TET2 during hematopoiesis, two mouse models in which the 5-hydroxy-methylation function of Tet2 is impaired were engineered. In addition, the status of TET2 coding sequences in various human mature lymphoid malignancies was investigated.

17.1. Experimental Procedures

Generation of the Tet2LacZ and Tet2floxed Alleles and Animal Analyses

Gene-trap mouse embryonic stem cell clone (SIGTR ES cell line AN0709: Tet2Gt(AN0709)Wtsi, herein named Tet2LacZ) carrying a beta-galactosidase-neomycin (beta-geo) resistance fusion cassette in Tet2 gene were obtained from UC Davis Mutant Mouse Regional Resource Center (mmrrc.org) to generate gene-trap mouse line and the insertion of the beta-geo cassette in intron 9 of Tet2 was routinely genotyped on tail DNA by multiplexed polymerase chain reaction (PCR) using 5'-CAGCCAGGAAGACACTTACC-3' (SEQ ID NO:40) and 5'-GACACCGATCTTGCTGGTTG-3' (SEQ ID NO:41) primers into intron 9 to detect wild-type Tet2 allele and 5'-CGCCTTGCAGCACATCCC-3'(SEQ ID NO:42) and 5'GGCCTTCCTGTAGCCAGC-3'(SEQ ID NO:43) primers into the beta-galactosidase sequence (and after the splicing donor site) to detect gene-trap allele (Tet2LacZ/LacZ).

Mice harboring Tet2 allele with exon 11 flanked by two loxP sites introduced in intron 10 and in the 30 untranslated region of exon 11 (Tet2Lox/Lox; "floxed allele") were generated by the Clinique de la Souris (Strasbourg, France) and intercrossed with mice expressing Cre recombinase under the control of the type I interferon-inducible Mx1 murine promoter (transgene referred as Mx1–Cre). PCR on tail DNA using 5'-GGCAGAGGCATGTTGAATGA-3'(SEQ ID NO:44) and 5'-TAGACAAGCCCTGCAAGCAAA-3'(SEQ ID NO:45) primers allowed distinguishing between wild-type and foxed allele. The Tet2Lox allele was backcrossed into C57BL/6 background for at least six generations using speed-congenics (Harlan Laboratories) prior to analysis.

Acute inactivation of Tet2 in 6- to 10-week-old Mx1⁻Cre⁺ Tet2$^{Lox/Lox}$ was performed by intraperitoneal injections (three injections every other day) of 800 mg poly(I:C)-LMW (InvivoGen, San Diego). Induction of Cre recombinase and efficient excision of floxed allele was confirmed by multiplex PCR using 5'-GGCAGAGGCATGTTGAATGA-3'(SEQ ID NO:46), 5'-TAGACAAGCCCTGCAAGCAAA-3'(SEQ ID NO:47) and 5'-GTGTCCCACGGTTACACACG-3'(SEQ ID NO:48) primers that discriminated between floxed and deleted allele, respectively 305 and 237 bp. Therefore, the following nomenclature was used: Mx1–Cre+Tet2Lox/Lox=Tet2$^{-/-}$, Mx1–Cre-Tet2$^{Lox/Lox}$=Tet2$^{+/+}$.

Competitive transplantations were performed by transplanting equal numbers of total bone marrow cells from CD45.1–CD45.2+ Tet2-deficient and CD45.1⁺CD45.2⁺ wild-type animals into lethally irradiated CD45.1⁺CD45.2⁻ recipients. For LSK cells transplantation, LSK cells were purified by flow cytometry from Tet2-deficient animals and 4000 LSK cells supplemented with 1 3 106 total bone marrow cells from wild-type were injected to lethally irradiated recipients. Expression of CD45.1 and CD45.2 was followed by flow cytometry on blood cells every month and animals were analyzed at 4 months after transplantation.

Animal experiments were conducted according to the Institut Gustave Roussy Institutional guidelines and authorized by the Direction Départementale des Services Vétérinaires du Val de Marne.

Patient Samples Collection

Lymph node, peripheral blood, and bone marrow samples from the patients were obtained with their informed consent and the approval of the local Research Ethics Committees (Centre Henri Becquerel, Pitié-Salpétrière, and Cochin hospitals). Additional information on patient samples is available in Table 11.

Flow Cytometry, Cell Sorting, and Purification

Total white blood cells, obtained from peripheral blood after lysis of red blood cells, and single-cell suspensions from bone marrow, spleen and thymus were stained in toto in PBS supplemented with 2% fetal bovine serum (FBS) with fluorochrome-conjugated mouse antibodies raised against specific markers of hematopoietic lineages (BD Biosciences PharMingen, except otherwise mentioned). Additional information on antibody clones is available in Supplemental Methods. Viability of cells was confirmed by using the Sytox Blue (Invitrogen) viability marker. Flow cytometric analysis and cell sorting were performed using a FACSCantoII Flow Cytometer (BD Biosciences) and a MoFlow (Becton Dickinson) or a FACSAriaIII (BD Biosciences), respectively.

Immunophenotypic data were analyzed using the FlowJo Version 7.2.4 software (TreeStar).

For human samples, bone marrow or peripheral blood mononuclear cells, lymphocytes, and granulocytes were isolated and stored in liquid nitrogen as viable cells in FBS with 10% dimethyl-sulfoxide (DMSO, Sigma). Patients were selected on DNA availability. Their clinical and biological characteristics are summarized in Table 11. Diagnoses were made by standard International criteria. Cells were purified using Miltenyi beads according the manufacturer instructions. When mentioned, cells were sorted after labeling with PE-CD34 and APC-CD38 antibodies (Immunotech) using a FACSDiva cell sorter (Becton Dickinson).

In Vitro Clonogenic Assays

Sorted CD34+ cells were seeded at one cell per well on methylcellulose in MEM alpha medium supplemented with 10% FBS (Stem Cell Technologies), and a cocktail of early cytokines (thrombopoietin [TPO], interleukin [IL-3], Flt3-L, Stem Cell Factor [SCF], erythropoietin [EPO], granulocyte-colony stimulating factor [G-CSF], granulocyte/macrophage-colony stimulating factor [GMCSF] and IL-6). After 2 weeks, individual clones were collected for further genotyping.

For patient 2, total mononuclear cells were seeded in 2% standard methylcellulose supplemented with 25% FBS (Stem Cell Technologies), and a cocktail of cytokines as described.

Nucleic Acid Methods

DNA and RNA were extracted using commercial kits (QIAGEN or Roche). Polymerase chain reaction (PCR) and direct sequencing reaction were performed using standard conditions with primers available upon request. Nucleotide sequences were compared to wild-type human genomic sequence present in the databases (genome.ucsc.edu). All observed mutations were scored on both strands. Additional information on exome sequencing is available in Supplemental Experimental Procedures.

In Vitro Differentiation Assays

LSKs (5 3 102), total BM (5 3 104), and spleen cells (5 3 104) isolated from mutant or control mice were cultured in methylcellulose-based medium (MethoCult M3434; StemCell Technologies) and scored for CFUs (colony-forming units) using combined scoring for burst-forming unit erythroids (BFU-Es), CFUmegakaryocytes (CFU-Mks), CFU-granulocyte macrophages (CFU-GMs), and CFU-granulocyte erythroid macrophage megakaryocytes (CFU-GEMMs) after 7 days. All live colonies were counted for each of the two 35 mm dishes plated per sample.

Quantitative PCR cDNA was synthesized from total RNA purified (using the RNeasy microkit, QIAgen) from sorted LSK, common myeloid progenitor (CMP), megakaryocyte-erythrocyte progenitor (MEP), and granulocyte-macrophage progenitor (GMP) populations using the Superscript II reverse transcriptase (Invitrogen).

TaqMan probes were purchased from Applied Biosystems (Tet1: Mm01169089; Tet2 [exon 9-10]: Mm00524395_m1; Tet2 [exon 10-11]: Mm01312907; Tet3, Mm01184936; Abl1, Mm00802038). Tet2 (exon 3-4) transcript were detected using the following primers; Primer1: 5'-agaatcagatactcctg-gtgaacaaa-3'(SEQ ID NO:49), Primer2: 5'-cctagatggg-tataataaggagcttcat-3'(SEQ ID NO:50), Probe: 5' FAM-tctg-gattgcatccttcacatttgccat-3'TAM(SEQ ID NO:51). Tet2-LacZ fusion transcript was detected using the following primers and probe: Primer1 (Tet2 exon 9): 5'-cccacagagaccagca-gaaca-3'(SEQ ID NO:52), Primer2 (LacZ): 5'-tgcgttcttcttctttggttttc-3' (SEQ ID NO:53), Probe: 5'FAM-cctgggaccact-gtactgccatttgg-3'TAM (SEQ ID NO:54). The expression level of each gene was assessed by qRT-PCR with an ABI PRISM 7500 and calculated following the DDCt method; each sample was analyzed in triplicate and normalized with Abl1 and GusB expression (Applied Biosystems Mm00802038_g1 and Mm03003537_s1, respectively).

Statistical and Quantification Analyses

Results are expressed as mean values±SEM. Statistical significance of differences between the results was assessed using a 2-tailed unpaired Student's t test, performed using Prism (GraphPad software, version 5.03). p values <0.05 were considered statistically significant. Quantification of the 5mC and 5hmC signals was performed by dot-blotting DNA and using antibodies from Eurogentec (1/500 dilution) and Active Motif (1/10,000 dilution) respectively. Signal was quantified using GelEval (FrogDance software, version 1.32).

Accession Numbers

Microarray procedures and data have been deposited in the European Bioinformatics Institute (EBI) database with the following accession number: E-TABM-1161.

17.2. Murine Models of Tet2 Inactivation

To investigate the role of Tet2 during hematopoiesis, two Tet2-deficient mouse lines were generated. One was derived from a gene-trap ES clone (SIGTR ES cell line AN0709) in which a beta-galactosidase-neomycin cassette was inserted in Tet2 intron 9 (Tet2$^{LacZ}$ allele), thus leading to the expression of a Tet2-beta Gal fusion transcript (FIG. 11a). A conditional knockout allele of Tet2 in which the coding sequences of the last exon of Tet2 are surrounded by loxP sites were also generated (Tet2$^{Lox}$). After Cre recombination, this allele results in the loss of the last 490 carboxy-terminal (Ct) amino acids of Tet2. In both models, TET2 is predicted to lose the conserved Ct homology region of the double-stranded b-helix-2OG-Fe(II)-dependent dioxygenase domain. The two alleles were backcrossed for at least six generations into the C57BL/6 background, and then intercrossed to obtain homozygous animals.

Mice bearing the conditional Tet2 allele and the interferon inducible Cre transgene (Mx1–Cre) were intercrossed to obtain a cohort of Mx1–Cre$^+$Tet2$^{Lox/Lox}$ (hereafter named Tet2$^{-/-}$) and control Mx1–Cre$^-$Tet2$^{Lox/Lox}$ (hereafter named Tet2$^{+/+}$) animals that were injected with poly(dI-dC) to induce Cre expression and acute inactivation of Tet2 in adult animals. Full excision was observed in bone marrow and thymus (FIG. 11b) and correlated with loss of normal Tet2 mRNA expression in purified hematopoietic stem (Lineage$^-$ Sca-1+c-Kit+: LSK cells) and progenitor populations (FIG. 11c). Tet2$^{LacZ/LacZ}$ animals were obtained at a Mendelian ratio, were fertile and appeared normal (data not shown). Tet2$^{LacZ/LacZ}$ progenitors showed a 20%-50% residual expression of a normal Tet2 mRNA compared to wild-type progenitors, suggesting that the Tet2LacZ allele is an hypomorph allele (FIG. 11d). Importantly, Tet1 and Tet3 expression levels remained unchanged in progenitors from both models (FIGS. 11c and 11d). Quantification of mC and 5hmC in Tet2$^{-/-}$ lineage$^-$ cells revealed a marked reduction of 5hmC compared to Tet2$^{+/+}$ (FIGS. 11e and 11f). Using a similar approach, no significant change in 5hmC level was detected in Tet2$^{LacZ/LacZ}$ lineage-cells (data not shown). Together these data confirmed the inactivation of Tet2 in these models and indicate that loss of Tet2 during adult hematopoiesis is not compensated by increased transcription of Tet1 and Tet3.

17.3. Tet2 Controls Hematopoietic Stem and Progenitor Cells Homeostasis

Analysis of the hematopoietic compartments in these animals showed an amplification of the LSK compartment in 4- to 6-month-old animals in both Tet2 inactivation models (FIGS. 12a and 12b). Heterozygous animals also presented increased LSK in both models (data not shown).

Within this compartment, CD34+Flt3– short-term stem cells and to a lesser extent CD34–Flt3– long-term stem cells were amplified.

Notably, absolute numbers of CD150+CD48– LSK cells were slightly increased (FIG. 12a). The absolute number of common myeloid progenitors (CMP) and megakaryocyte-erythrocyte progenitors (MEP) was increased, whereas the granulocyte-macrophage progenitor (GMP) population remained stable in Tet2$^{-/-}$ animals compared with controls (data not shown). Bone marrow cells from Tet2$^{-/-}$ animals presented a functional increase in methylcellulose colony forming progenitors (FIG. 12c). Of note, the average number of cells per colony was higher in Tet2-deficient cell cultures compared with controls.

Culture of purified LSK cells from some Tet2$^{-/-}$ animals 12 months after induction also produced an increased number of cells presenting a decreased differentiation toward CD11b$^+$ Gr1$^+$ myeloid cells and a higher maintenance of the immature c-Kit$^+$Sca1$^+$ phenotype compared with controls (data not shown). The amplitude of this phenotype was variable among animals. Similar results were obtained from genetrap animals (data not shown).

To demonstrate the cell-autonomous nature of this property, total bone marrow or purified LSK cells were transplanted from both Tet2-deficient models (CD45.2$^+$CD45.1$^-$) in competition with wild-type cells (CD45.2$^+$CD45.1$^+$) into wild-type CD45.2$^-$CD45.1$^+$ recipients. Homozygous Tet2-deficient cells from both models efficiently reconstitute all hematopoietic lineages for over 16 weeks, indicating that amplified LSK cells are functional (FIGS. 12d-12h). In both myeloid and lymphoid lineages, the contribution of Tet2-deficient cells progressively increased over that of wild-type cells. An amplification of the LSK compartment was observed in some recipient animals (data not shown).

Together, these data showed that Tet2 inactivation resulted in a phenotypic and functional amplification and a competitive advantage of hematopoietic stem and progenitor cells indicating cell-autonomous control of their homeostasis by Tet2.

17.4. Tet2 Inactivation Induces Alteration of Several Mature Hematopoietic Lineages To further characterize the consequences of Tet2 inactivation on mature hematopoietic lineages, a cohort of Tet2$^{-/-}$, Tet2$^{LacZ/LacZ}$ animals and their respective controls for disease development were followed. Four-month-old Tet2$^{-/-}$ and Tet2$^{LacZ/LacZ}$ animals present a modest increase in white blood cell counts, a decrease in erythroid and platelets counts, and a significant hepatosplenomegaly compared with controls (FIGS. 13a and 13b). Histopathological analysis showed an alteration of the normal splenic architecture with significant expansion of the red pulp and infiltration of the lymphoid follicles with admixed maturing myeloid, immature erythroid, and maturing megakaryocytic elements (FIG. 13c). Interestingly, analysis of the liver showed that Tet2$^{-/-}$ animals presented a diffuse infiltration of the sinusoids with an admixture of lymphoid and trilineage myeloid elements with some focused perivascular infiltrations (data not shown).

Flow cytometrical analysis confirmed an amplification of myeloid cells in both models with a marked increase in a myelomonocytic CD11b$^+$Gr1$^-$ population in the peripheral blood and spleen (FIG. 13d). Alteration of the erythroid lineage was observed in the bone marrow with a significant increase in CD71$^+$Ter119$^-$ proerythroblasts and a decrease in the number of CD71$^{low}$Ter119$^+$ late erythroblasts (FIG. 13e). Splenic erythropoiesis was also visible with an increase in the number of CD71$^+$Ter119$^+$ erythroid cells (FIG. 13e). Tet2-deficient splenocytes could form multilineages colonies in methylcellulose colony-forming assays confirming extramedullar hematopoiesis (FIG. 12c and data not shown). Similar abnormalities were observed in the gene-trap model (data not shown).

Lymphoid lineages were also affected with a global increase in the number of immature double-negative (DN) CD4$^-$CD8$^-$ T cell progenitors in the thymus, more particularly, CD44$^+$CD25$^-$ DN1 cells (FIG. 13f). The B cell lineage was also altered with a decreased number of bone marrow B220$^+$IgM$^-$ pre- and pro-B cells and B220$^+$Ig$^{low}$M mature B cells (FIG. 13g) associated with an increase in the number of splenic B cells (FIG. 13h). Of note, heterozygous Tet2$^{LacZ/wt}$ animals present similar abnormalities of the myeloid, erythroid and B cell lineages (data not shown). Also, both lymphoid and myeloid lineage alterations were observed in recipients of Tet2-deficient cells (data not shown), indicating that differentiation abnormalities are cell autonomous.

With age, some Tet2$^{LacZ/wt}$ and Tet2$^{LacZ/LacZ}$ animals developed a lethal phenotype associated with important weight loss, high white blood cell counts, anemia, thrombocytopenia, and massive hepatosplenomegaly (FIGS. 14a and 14b; data not shown). Histopathological analysis of moribund animals showed complete effacement of the spleen architecture and massive perivascular as well as interstitial infiltration of the liver with myeloid elements (FIG. 14c). A Together, these results show that Tet2 inactivation in mice results in pleiotropic alterations of the immature and mature hematopoietic compartments including both lymphoid and myeloid lineages (data not shown). With time, Tet2 inactivation leads to bona fide myeloid malignancies with differentiation abnormalities reminiscent of human CMML.

17.5. TET2 is Mutated in Human Lymphoid Malignancies

Based on these results indicating that TET2 controls both self-renewal and/or proliferation of early progenitors and also late steps of both myeloid and lymphoid hematopoietic differentiation, it was investigated whether human lymphoid malignancies could also present TET2 mutations. Supporting this hypothesis, two of six patients presenting myeloid malignancies and initially investigated for TET2 alterations, concomitantly suffered from lymphomas (Delhommeau et al., 2009; Viguié et al., 2005). Therefore, the entire coding sequence of TET2 in a series of human lymphoid malignancies was resequenced. No nucleotide changes inducing truncation or aminoacid changes in the catalytic domain of TET2 were observed in chronic lymphocytic leukemias (CLLs) (n=75), plasma cell neoplasms (PCNs) (n=22), and leukemic or disseminated T cell neoplasms (n=45) [including T cell prolymphocytic leukemia (TPLL), T cell large granular lymphocytic leukemias (TGLLs), and adult T cell lymphoma/leukemia HTLV1+ (ATLL HLTV1)]. In a series of 301 B cell lymphoma and 177 T cell lymphoma samples, TET2 mutations were observed in 2.0% of B cell and 11.9% of T cell lymphomas and in up to a third of the angioimmunoblastic T cell lymphoma (AITL) samples. The mutations were mainly insertion/deletions, generating frameshifts and nonsense mutations, as seen for myeloid malignancies (Table 11). Of note, five of these patients had a known history of successive haematological malignancies, as shown in Table 12 below:

TABLE 12

Patients with multiple diseases

| Patient | Diagnosis | ge | Cytogenetics | tage | BM infiltration | Associated | Time of associated |
|---|---|---|---|---|---|---|---|
| 2 | GCB DLBCL | 7 | normal | V | no | RAEB then AMLFAB 5a | 5 months after B-cell lymphoma's |
| 14 | AITL | 2 | N.D. | V | yes | Myelofibrosis then RAEB | 4 years before T-cell lymphoma's |
| 15 | AITL | 6 | del (20)(q12) | V | yes | Sideroblastic anemia | 3 years before T-cell lymphoma's |
| 18 | PCTL, NOS | 6 | t(6; 15)(q21; q23) | II | no | Hodgkin lymphoma | 6 years before T-cell lymphoma's |
| 21 | PCTL, NOS | 3 | hyper ploidy with del (6q) | V | yes | Tcutaneous lymphoma then THRBCL | 8 years before T-cell lymphoma's |

GCB DLBCL: Germinal center B-cell like diffuse large B-cell lymphoma,
AITL: Angioimmunoblastic T-cell lymphoma,
PCTL-NOS: Peripheral T-cell lymphoma, not otherwise specified,
RAEB: Refractory anemia with excess blasts,
AML: Acute myeloid leukemia,
TCRBCL: T-cell-rich B-cell lymphoma.
BM: Bone marrow.

moderate fibrosis, assessed by increased reticulin fiber staining on tissue sections, was observed in the spleen and liver but not the bone marrow (FIG. 14d). Flow cytometrical analysis confirmed the myeloid and erythroid lineage hyperplasia with abnormal myelomonocytic differentiation revealed by a striking amplification of the CD11b$^+$Gr1$^-$ population visible in younger Tet2-deficient animals (FIG. 14e). Importantly, the disease was transplantable to secondary recipients, which succumbed with a shorter latency and a similar phenotype (data not shown). To date, Tet2$^{-/-}$ animals did not develop lethal disorders with a follow-up of over 15 months.

T-lymphoma samples by DNA micro-arrays, including nine TET2 wild-type and ten TET2 mutated samples were also analyzed.

The analysis revealed that one of the mutated samples also exhibited a small genomic deletion of chromosome 4q including the TET2 locus (data not shown). Therefore, as for myeloid malignancies, TET2 genomic abnormalities are less frequent than TET2 mutations but may occur in conjunction.

Matched nontumoral DNA samples were available for 13 patients with TET2 mutations (FIG. 15a, Table 11). The TET2 sequences were wild-type in two patients (patients 5 and 6). The mutated TET2 sequence detected in the lymphoma cells was clearly observed in the nontumoral DNA samples of five patients (patients 3, 4, 13, 15 and 26). In two of them (patients 3 and 15), this might be due to the presence of tumor cells, as judged by PCR analyses for TCR or IgH clonality or the presence of IGH-BCL2 fusion transcript (data not shown). Trace of the mutated TET2 sequence was suspected in six matched samples (patients 2, 10, 16, 17, 20, and 21) of which three (patients 2, 10, and 16) were devoid of tumor cells. Mutations observed in patients 17, 20, and 25 have been described as acquired in myeloid malignancies.

Together the mutated TET2 sequences were observed in the matched sample despite the absence of detectable circulating tumor cells in five samples (patients 2, 4, 10, 13, and 16). In two of these samples (patients 4 and 13), the estimated burden of mutated sequences was comparable to the wild-type sequence.

Two hypotheses could account for these observations: either the mutation was germline transmitted, or the mutation was acquired and had endowed the clone with a growth advantage over wild-type progenitors, leading to a skewed hematopoiesis.

17.6. TET2 Mutations are Detected in CD34+ Cells with Myeloid Potential

To test the hypothesis that TET2 mutations may arise in early hematopoietic progenitors in patients presenting lymphomas, three patients for which viable cells were available were analyzed.

Patient 8 was diagnosed with an AITL and carried a Q1445X mutation. Blood mononuclear cells were grown in a colony assay supporting myeloid differentiation. Of the 11 colonies that grew out, 5 showed only a wild-type TET2 allele and 6 showed both Q1445X and wild-type alleles (FIG. 15b). These results demonstrate the acquired nature of the TET2 mutation in this patient and also indicate its presence in progenitor cells with myeloid colony-forming potential.

Patient 2 was initially diagnosed with a B cell lymphoma carrying two TET2 mutations [(E448fs; 4663+1G>A: splice site mutation)] that were barely detectable in blood sample (FIG. 15c). Five months after treatment, the patient developed an MDS that rapidly evolved into AML. Viable bone marrow cells were available only at the AML phase. DNA was extracted from whole bone marrow cells, purified CD34− and CD34+ fractions.

In every DNA samples, both TET2 mutations were observed at seemingly variable ratios with respect to the wild-type sequence.

DNA was extracted from 28 colonies grown in myeloid conditions in vitro, from single CD34+ cells. Six colonies showed only wild type TET2 sequences, 14 colonies presented both TET2 mutations, and 8 colonies carried only the splice site mutation (FIG. 15c). These data demonstrate the presence of TET2 mutations in both the lymphoma and the AML cells, confirmed their acquired nature. Taken together, these observations suggest that the TET2 mutated clone had invaded the bone marrow and was at the origin of both the lymphoid and myeloid type malignancies.

Patient 27 was diagnosed with a T cell lymphoma. Bone marrow aspirate examination was cytologically normal. Two TET2 mutations (P761fs and Q481X) in the CD34−CD3−CD19−CD14− cell fraction (the remaining fraction after successive exclusion of the CD3+, CD19+ and CD14+ cell fractions from the blood sample) were observed, which were absent in the other fractions (FIGS. 16a and 16b). In vitro colonies assay of sorted CD34+ cells showed the presence of P761fs in 6 of 84 (about 7%) colonies, whereas the stop mutation was not observed (FIG. 16c). This fraction remained stable, since a similar analysis showed 6 out of 93 (about 6.5%) colonies with the P761 fs mutation 4 months later.

Of the 45 colonies obtained from cultures of Lineage-CD34+CD38− sorted cells, only one carried the P761fs (FIG. 16c).

These results show the acquired nature of the TET2 mutations in this patient and indicate the presence of a TET2 mutation on one copy in a small fraction of hematopoietic progenitors with myeloid differentiation potential.

Taken together, these results show the presence of TET2 mutations in B and T cell lymphomas. Detailed analysis of three patients indicated that lymphoma cells carried one somatic mutation originally acquired in an hematopoietic stem cell. During T cell maturation/differentiation, a second TET2 mutation may occur, leading to the total loss of TET2 function in lymphoma cells.

To investigate the sequence of events occurring during tumor development, the tumor cells from patient 27 were further analyzed. SNP microarray analyses showed several acquired abnormalities, including an LOH of the long arm of chromosome 7 and a duplication of the long arm of chromosome 4 (data not shown).

FISH analyses confirmed the presence of an additional copy of the TET2 locus in 20% of the nuclei in blood sample (data not shown). Sequencing of the PCR products obtained from single cells, sorted in individual wells from the fraction enriched in CD34−CD3−CD19−CD14− tumor cells, confirmed the simultaneous presence of both TET2 mutations in 6/10 assays (FIG. 16d). A fragment spanning the two mutations from the same tumor population was PCR-amplified, and the PCR products were subcloned using T/A vectors. Sequencing of individual bacterial colonies showed that a given mutation was always associated with a wild-type sequence at the other position. The P761fs/Q481 wt combination was observed 24/42 times (57%) and the P761 wt/Q481X combination 18/42 times (43%) (data not shown). No wild-type fragment was sequenced from these vectors, indicating that all three TET2 copies present in the tumor cells were mutated.

The observed ratio between both mutations indicated that the duplicated copy carried the P761fs mutation. In addition, these data indicate that the flow-sorted CD34−CD3−CD19−CD14− fraction contained essentially tumor cells.

17.7. Additional Genetic Alterations are Associated with TET2 Mutations

To identify additional genetic alterations in lymphomas, an exome sequencing approach was used to investigate DNA from the CD34−CD3−CD19−CD14− (tumor) and CD3+ (matched control) fractions. For each fraction, exonic DNA was captured using the SureSelect oligonucleotides (Agilent) and sequenced to generate 115600653 and 90633228 reads, from tumor and matched control libraries, respectively.

It was first confirmed the presence of both TET2 mutations in the tumor population at a ratio of 184/339 reads (54%) for P761fs and 140/389 reads (36%) for the Q481X, consistent with the duplication of the P761fs mutation (FIG. 16e). The two mutations were observed at very low frequencies in the CD3+ fraction (8/228 reads (4%) and 6/256 (2%) reads, respectively). It was next looked for sequence variations, with respect to the human reference sequence, that were present only in the tumor population.

Variations in seven genes (IGSF21, CRIM1, CLSTN2, MCCC2, PLZF, ZC3H10, and ZNF774) were validated by Sanger analysis (FIG. 16e).

Quantitative RT-PCR was then used to analyze the expression profile of the mutated genes in RNA from normal human brain, bone marrow, peripheral lymphocytes, and in flow-sorted tumor cells from patient 27 (FIG. 16f). CLSTN2 expression was observed in brain, but not in normal PBL, thymus, or bonemarrow nor inpatient's tumor samples (data not shown). The lack of detectable expression of CLSTN2 in the hematopoietic system suggests that the CLSTN2 mutation could be a passenger rather than a causal mutation. The transcription of ZNF774, CRIM1, and IGSF21 was not detected in normal blood cells and/or in the tumor sample, but was observed in the bone marrow and/or thymus, questioning their role in the transformation process. Finally, the presence of the mutations in the CD34+-derived colonies of the patient was investigated. Mutations in PLZF and CRIM1 were identified in eight of eight CD34+-derived colonies with the TET2 P761 fs mutation. The ZNF774 mutation was observed in six of eight TET2 mutated colonies tested, suggesting that it occurred later in the transformation process than the three others (i.e., TET2, PLZF, and CRIM1). ZNF774, PLZF, and CRIM1 mutations were not observed in 65 TET2 wild-type CD34+ colonies, suggesting that they did not occur independently of the TET2 P761fs mutation.

TABLE 11

| TET2 mutated patients | Sample | Diagnosis | Mutation Type | Nucleotide change | Consequence | TET2 mutation presence | Tumor presence[2] |
|---|---|---|---|---|---|---|---|
| 1 | node | DLBCL | Nonsense | c.3087C > T | p.Gln743X | ND | ND |
| 2* | node | DLBCL | Frameshift and splice | c.[2202delG(+)4663 + 1G > A] | p.Glu448fs | Trace | No |
| 3* | node | DLBCL | Nonsense | c.5406C > T | p.Arg1516X | Yes | Yes |
| 4* | node | DLBCL | Nonsense | c.3506C > T | p.Gln886X | Yes | No |
| 5* | node | DLBCL | Splice | c.4814 + 2T > G | — | No | No |
| 6* | node | FL | Missense | c.5116C > G | p.Pro1419Arg | No | No |
| 7 | node | AITL | Nonsense + Frameshift | c.[3192C > T(+)3628_3629insCATA] | p.[Gln778X(+)Asn923fs] | ND | ND |
| 8 | blood | AITL | Nonsense | c.5193C > T | p.Gln1445X | ND | ND |
| 9 | node | AITL | Frameshift | c.3215delT | p.Phe785fs | ND | ND |
| 10* | node | AITL | Frameshift × 2 | c.[1893_1896delAAGC] + [4527delG] | [p.Lys345fs] + [p.Ala1223fs] | Trace | No |
| 11 | node | AITL | Frameshift | c.6564delT | p.Tyr1902fs | ND | ND |
| 12 | node | AITL | Frameshift × 2 | c.[2505delA] + [2524delC] | [p.Thr549fs] + [p.Pro555fs] | ND | ND |
| 13* | node | AITL | Frameshift | c.5523_5524insA | p.Glu1555fs | Yes | No |
| 14 | node | AITL | Frameshift | c.3756_3757del CA | p.Gln966fs | ND | ND |
| 15* | node | AITL | Frameshift | c.1642delC | p.Ser261fs | Yes | Yes |
| 16* | node | AITL | Splice | c.4815-2delA | — | Trace | No |
| 17* | node | PCTL, NOS | Frameshift + missense | c.[3131_3137delCCAGACT] + [5109G > T] | [p.Leu757fs] + [p.Val1417Phe] | Trace | Yes |
| 18 | node | PCTL, NOS | Nonsense × 2 | c.[3747C > T] + [5331A > T] | [p.Gln963X] + [p.Lys1491X] | ND | ND |
| 19 | node | PCTL, NOS | Frameshift + nonsense | c.[1700_1701insT(+)3606C > T] | p.[Asn281fs(+)Gln916X] | ND | ND |
| 20* | node | PCTL, NOS | Missense | c.6553C > T | p.Ser1898Phe | Trace | Yes |
| 21* | node | PCTL, NOS | Frameshift × 2 | c.[1805delC(+)3602delT] | p.[Ser315fs(+)Leu914fs] | Trace | Yes |
| 22 | node | PCTL, NOS | Nonsense | c.5100C > T | p.Gln1414X | ND | ND |
| 23 | skin | Sezary | Missense + Nonsense | c.[5053T > C(+)5253C > T] | p.[Leu1398Pro(+)Arg1465X] | ND | ND |
| 24 | blood | Sezary | Nonsense | c.2636C > T | p.Gln593X | ND | ND |
| 25 | node | TLBL | missense | c.6745C > T | p.Pro1962Leu | ND | ND |
| 26* | node | Unspecified T-lymphoma | Frameshift | c.1511delC | p.Ser217fs | Yes | NA |
| 27 | blood | Unspecified T-lymphoma | Frameshift + nonsense | c.[2301C > T(+)3142delC] | p.[Gln481X(+)Pro761fs] | ND | ND |

*Matched DNA available
[1]Diagnosis and remission samples correspond respectively with whole blood and cytapheresis samples
[2]Clonality analysis (TCR/IgH rearrangement or BCL2-IGH transcript)
ND: Not Determined

The invention claimed is:

1. A method of treating a subject having a myeloid tumour or a lymphoid tumour, wherein the tumour comprises:
cells having a mutated TET2 gene encoding a frameshift at Leu757 or Glu448 in the resulting TET2 protein expressed by the tumour; or
cells having a mutated TET2 gene having
a nonsense mutation that encodes Gln963Stop, Gln593Stop, Gln778Stop, Gln886Stop, Gln1445Stop, Gln778Stop and a frameshift at Asn923, Gln916Stop and a frameshift at Asn281, or a frameshift at Ser315 and Leu914 in the resulting TET2 protein expressed by the tumour;

the method comprising:
detecting in a biological sample from the subject the presence of the mutated TET2 gene and/or the resulting TET2 protein expressed by the tumour; and
administering to the subject a therapeutically efficient amount of a hypomethylating agent.

2. The method according to claim 1, wherein said subject is in need of confirmation of having myelodysplastic syndrome (MDS), acute myeloid leukemia (AML), myeloproliferative disease (MPD) or myelodysplastic/myeloproliferative syndrome.

3. The method according to claim 1, wherein said subject is in need of confirmation of having myelodysplastic/myeloproliferative syndrome.

4. The method according to claim 1, wherein said subject is in need of confirmation of having lymphoma.

5. The method according to claim 1, wherein said subject is a mammal.

6. The method according to claim 1, wherein the frameshift and/or mutation is detected on one or both allele of the TET2 gene coding for the polypeptide having the sequence SEQ ID NO:2.

7. The method of claim 1, wherein the detecting comprises using a kit comprising at least one nucleic acid probe, oligonucleotide, or antibody.

\* \* \* \* \*

```
                          SEQUENCE LISTING

<160> NUMBER OF SEQ ID NOS: 54

<210> SEQ ID NO 1
<211> LENGTH: 132428
<212> TYPE: DNA
<213> ORGANISM: Homo sapiens
<220> FEATURE:
<221> NAME/KEY: Intron
<222> LOCATION: (1)..(100)
<220> FEATURE:
<221> NAME/KEY: exon
<222> LOCATION: (101)..(787)
<220> FEATURE:
<221> NAME/KEY: Intron
<222> LOCATION: (788)..(44167)
```

```
<220> FEATURE:
<221> NAME/KEY: exon
<222> LOCATION: (44168)..(44294)
<220> FEATURE:
<221> NAME/KEY: Intron
<222> LOCATION: (44295)..(87704)
<220> FEATURE:
<221> NAME/KEY: exon
<222> LOCATION: (87705)..(91159)
<220> FEATURE:
<221> NAME/KEY: Intron
<222> LOCATION: (91160)..(95146)
<220> FEATURE:
<221> NAME/KEY: exon
<222> LOCATION: (95147)..(95237)
<220> FEATURE:
<221> NAME/KEY: Intron
<222> LOCATION: (95238)..(96641)
<220> FEATURE:
<221> NAME/KEY: exon
<222> LOCATION: (96642)..(96735)
<220> FEATURE:
<221> NAME/KEY: Intron
<222> LOCATION: (96736)..(97377)
<220> FEATURE:
<221> NAME/KEY: exon
<222> LOCATION: (97378)..(97586)
<220> FEATURE:
<221> NAME/KEY: Intron
<222> LOCATION: (97587)..(113426)
<220> FEATURE:
<221> NAME/KEY: exon
<222> LOCATION: (113427)..(113577)
<220> FEATURE:
<221> NAME/KEY: Intron
<222> LOCATION: (113578)..(115566)
<220> FEATURE:
<221> NAME/KEY: exon
<222> LOCATION: (115567)..(115656)
<220> FEATURE:
<221> NAME/KEY: Intron
<222> LOCATION: (115657)..(123417)
<220> FEATURE:
<221> NAME/KEY: exon
<222> LOCATION: (123418)..(123555)
<220> FEATURE:
<221> NAME/KEY: Intron
<222> LOCATION: (123556)..(126371)
<220> FEATURE:
<221> NAME/KEY: exon
<222> LOCATION: (126372)..(126726)
<220> FEATURE:
<221> NAME/KEY: Intron
<222> LOCATION: (126727)..(128855)
<220> FEATURE:
<221> NAME/KEY: exon
<222> LOCATION: (128856)..(132328)
<220> FEATURE:
<221> NAME/KEY: Intron
<222> LOCATION: (132329)..(132428)

<400> SEQUENCE: 1
gcgcgggggc gtgtgcgcgg gacctcgaag tggtggtgga gtgcagacca gcaaaaagtt      60
tcaaagggaa atcttagatg tcacgtctttt gtccaggcac ccg tgc cat ccc aac      115
                                                Pro Cys His Pro Asn
                                                 1               5 ctc cca cct cgc ccc caa cct tcg cgc ttg ctc tgc ttc ttc tcc cag      163
Leu Pro Pro Arg Pro Gln Pro Ser Arg Leu Leu Cys Phe Phe Ser Gln
               10                  15                  20 ggg tgg aga ccc gcc gag gtc ccc ggg gtt ccc gag ggc tgc acc ctt      211
Gly Trp Arg Pro Ala Glu Val Pro Gly Val Pro Glu Gly Cys Thr Leu
           25                  30                  35
```

-continued

| | |
|---|---|
| ccc cgc gct cgc cag ccc tgg ccc cta ctc cgc gct ggt ccg ggc gca<br>Pro Arg Ala Arg Gln Pro Trp Pro Leu Leu Arg Ala Gly Pro Gly Ala<br>     40                  45                      50 | 259 |
| cca ctc ccc ccg cgc cac tgc acg gcg tga ggg cag ccc agg tct cca<br>Pro Leu Pro Pro Arg His Cys Thr Ala     Gly Gln Pro Arg Ser Pro<br>  55                     60                        65 | 307 |
| ctg cgc gcc ccg ctg tac ggc ccc agg tgc cgc cgg cct ttg tgc tgg<br>Leu Arg Ala Pro Leu Tyr Gly Pro Arg Cys Arg Arg Pro Leu Cys Trp<br>  70                     75                        80 | 355 |
| acg ccc ggt gcg ggg ggc taa ttc cct ggg agc cgg ggc tga ggg ccc<br>Thr Pro Gly Ala Gly Gly     Phe Pro Gly Ser Arg Gly     Gly Pro<br>85                90                            95 | 403 |
| cag ggc ggc ggc gca ggc cgg ggc gga gcg gga gga ggc cgg ggc gga<br>Gln Gly Gly Gly Ala Gly Arg Gly Gly Ala Gly Gly Arg Gly Gly<br>    100                 105               110 | 451 |
| gca gga gga ggc ccg ggc gga gga gga gag ccg gcg gta gcg gca gtg<br>Ala Gly Gly Gly Pro Gly Gly Gly Glu Pro Ala Val Ala Ala Val<br>115                 120               125               130 | 499 |
| gca gcg gcg aga gct tgg gcg gcc gcc gcc tcg tcg cga gcg ccg<br>Ala Ala Ala Arg Ala Trp Ala Ala Ala Ala Ser Ser Arg Ala Pro<br>             135               140                     145 | 547 |
| cgc gcc cgg gtc ccg ctc gca tgc aag tca cgt ccg ccc cct cgg cgc<br>Arg Ala Arg Val Pro Leu Ala Cys Lys Ser Arg Pro Pro Arg Arg<br>          150               155                     160 | 595 |
| ggc cgc ccc gag acg ccg gcc ccg ctg agt gat gag aac aga cgt caa<br>Gly Arg Pro Glu Thr Pro Ala Pro Leu Ser Asp Glu Asn Arg Arg Gln<br>          165               170                     175 | 643 |
| act gcc tta tga ata ttg atg cgg agg cta ggc tgc ttt cgt aga gaa<br>Thr Ala Leu     Ile Leu Met Arg Arg Leu Gly Cys Phe Arg Arg Glu<br>     180                 185                     190 | 691 |
| gca gaa gga agc aag atg gct gcc ctt tag gat ttg tta gaa agg aga<br>Ala Glu Gly Ser Lys Met Ala Ala Leu     Asp Leu Leu Glu Arg Arg<br>     195                200                    205 | 739 |
| ccc gac tgc aac tgc tgg att gct gca agg ctg agg gac gag aac gag<br>Pro Asp Cys Asn Cys Trp Ile Ala Ala Arg Leu Arg Asp Glu Asn Glu<br>    210                 215               220 | 787 |
| gtcagagcgc ttctcttatg ccgcgaaact ctcccttct tctccccttc gcttttctc | 847 |
| gggcttccag ggactgggga gcaaaccctg tagtgtcacc cacaaatacc aagagggaag | 907 |
| agggaagctt cacaaattac tggagcctct tcaacatggc tgacaaatat agttttaatt | 967 |
| ccctctaccc cttttaaacc tgtagttctg tgttctcttc tcctcctca atgctcgtcc | 1027 |
| cctcatctcc cagaaaactt acctttgtgc ctccgacgag ccggtttccc ggcctttttt | 1087 |
| aatcctcaga aaagtgattt ttaaatttgc tttcctttct aaaatagttc agctttgggg | 1147 |
| gcactacttt tcccttaat cctcttcccc tgtttcttc gtgtaagtga acgagtctc | 1207 |
| ccgtttatcc tgaacaacct cagagagaac actgataggg tgttttcga cccttttatc | 1267 |
| agctgtaggg tctgggtctg ggtttgtgtc tgcctcctcc taccttctta tccccttta | 1327 |
| gggggctgta cgaagtgaat gtcacaggga gtggaattgg agtacactga gtgggtttt | 1387 |
| tttttcctta agtccgcgcg ttttgttagc ggcgctgagt gaaagaggaa agaatagttt | 1447 |
| ctctggttcc ccaaacaaga ccagaactca cttttctcaa ggtacataag tcagcgctgg | 1507 |
| gctgagcctt ccagcctggg gaatgtatgt aagagaattt atggacaaat ctgtgtcccg | 1567 |
| gctttgtgct ctcccgaat cagcttcgtt tggttccttg gtaagtgaca ggcagacaca | 1627 |
| aaggcaggcg caggcccggg gaggggggcgg gaggggtgg ggagcgcagc gttggagttg | 1687 |
| caagactgca aggtcagggg cgcctaaaga aatgaaaccc aatcccagca aagaagtgaa | 1747 |

```
gagcagattt ataacagtcc catccaaatt tctctttggc ttctctcttt ggtctttcat    1807
ctctctgcct ttctctctgt gtctcctctc tactctttct tctctctctc tcatacacat    1867
acacacacac acacacacac acacctcact cgcatcttgc tgaatctttt cactgggact    1927
gcttgtctag ttttattaag ctaatagggt ttgtatggag agttttctac ctatgacata    1987
atgaagtgtg gcctggatag actcctggaa aggccgaaaa tgaaatataa gtgttatttg    2047
ctggttattc ccctcatgat atacttttaa ttacattgag ggagttctcc cttcttcatc    2107
taatgtttaa gaattgagaa aaggcttatt ttccagcggt aaaatttagt gcataaaatt    2167
tagtgaaata tttatatatt tacgtgtcta gggagtggaa tacattcatg aatttaatat    2227
ctcaaatcac acattgtgct ttttccccctt cagtcaggga ttataatggg aaacccaaat    2287
tcaaagatat tcatcaacaa atgatccatc ataggaataa gattgtatct taagggaagt    2347
tgggattcac agagaaaaga cattggtttg gtttggtgtg atactgtggg tattgttgcc    2407
tggctaatga aatcattaca tttgcatttt aatggaaagt tgaaatacta gggggagtta    2467
tgttctttta catgtttgta tgtgtgctta ataatgtttg gaatagaata taaatttaaa    2527
cacaataaat attgattttt ttaaatgtta ataagcagag aacggttaat gaagtgttgg    2587
ataatcaaac tgaagtttag aagacaattt ataggattaa aaaatggata gaaggaaaaa    2647
cacaataata gatatttctc cataagtcga atttccaaaa ctatttgtcc tcgatagttc    2707
actttgtaac tttctatttt gatctttgtt aatttaatgt agtttgcttt aatcattgat    2767
acgtggggtt ctttcacatg attacaaggg agaagcatta ctcatctctg tggaatagaa    2827
acggttcatt ggttagttct tatttgccct aaaattaaaa caaaaattag gattttacca    2887
ttaatgctgt tcatggtaaa ctatcgagaa aactatggtt aattattcca gcaattcaga    2947
attaaaaaca attcctttttg ctaacaaact aatatttact ttttggggac aacttttcaa    3007
atgttgtggt atatactgtc ttcaggctac tcaactaata atagatacaa cattttccac    3067
tcaataaata agaataacta cattggttaa taattttgaa tacaactatg aaggcttgtt    3127
ttttcctgtc atcaaattta gattcttgtt attttgtgca tcctactttt atactgaaaa    3187
tagctgctaa ttaatactgt ataaagtatt tcagtgatta taaggaagag atgtgtatgt    3247
tagtcacttt atcccttgtt ggaaaagaga aattatttta ataagtatgg ggtagtttac    3307
aataaaagac ataacctcag ttctttcttt accatatatg tgatcatact acctaggtgc    3367
tccaaaaatt ccataggact gtcttgggtt attgaatttt aggaacatga taatggacaa    3427
taacaagata gatagctttt cttaactatg acattgtttt gcttattttc ttattgaact    3487
aatcatcaat gagaaattaa gttgcagtga gagaaatccc ttgctttgtt taaattgtca    3547
tatttgccaa actcttctta aggctttaat taggtctgat gtgccagttt atgccagaag    3607
ccggaggaat tgatatgatt ttgaggcagt ggcacatggt cctactagac attggcaagt    3667
gaatatcact tccagaacaa gtgaagtgca cctgccaagg agttgttatg aaagaattcc    3727
aaagtcctta ttgggcactg gtcttgtatt aggtaacaac aactggagtt aatgtttag    3787 tttcacttgt tgaagttaaa agttcccctat caattcttct aagactccac ccccaaacaa    3847
tgttgtaagt caaatgtcac tattgaaatg tatttcctta attactgacc tcattaagaa    3907
gcccttctta tgattcatag gcacacctca cagaaactct attttccatc ctgcccaaag    3967
tctgagtagg taaattctta tgaattctta tgaaattacc ttgaaataaa atatcttcaa    4027
aagttacgga tgctagacat tgtataatgt caatatttta gaatatctaa tatttagaaa    4087
```

```
atcttagatc tactttttat gctttaattg cttctaatgc aagttaaatt gttttttgttg    4147
ttattgtttt aatagaattt catagtctta tctagcaatt tcaaatcgct ggaaagagtc    4207
atctttgtta tataaataac catgtagact gttttaatgt tattgtttcc taccttggga    4267
acaggctaaa actttggacc agctgtcagt atttgttcat cagaataaca ctttgtcaat    4327
gattattcta ccattgcaca gtagttctta aggatagtaa tggtaccaaa gccagcagca    4387
atagaatatc tcccaagcca actttacaat tggagccttc actgtgggaa agaccagttg    4447
ccaagtagag ctggtggtta tctgggaaac tgtgctgaag aacacaacca caaatgattt    4507
tgccaaatat acagtattta cttggtctag atctccaatt tctatttcta ctcactgcca    4567
aaactgagtg aatactgtga cattattgaa ggaggttatg cagtacatct gttggtttgg    4627
tatatagtag gagagaaggg ttccaggagg gaaaggggaa agtcagagca tgtgaatcac    4687
tgtgactaca atccaaaaag aattatgtat gtctgctatt tccagcatta ttttgtcct    4747
atattgtaca ttgcagagac ttgctgactt aaaatagata tataatcttt ttctcaaaag    4807
aatagatatt tggttgtcca ttccaaataa caaattttgg atgggcgtgg tgactcatgc    4867
ctgtaatcct agcactttgg gaggccaagg tgagagatca cttgaggcca ggagtttgaa    4927
accaccctgg gcaacacagt caggccccag tctctacaaa aaatttaaaa agttagtggg    4987
gcatggtggt acattcctgt agtcccagct actcaggaga ctgagatagg aggatggatt    5047
gagctcaagt gttctaactt atagtgagct ctgatcacac cactgcgctc cagcccaggc    5107
aagagggaga gaccctatct caaacagcga caacaacaaa accaaacaaa caaaaaagca    5167
cattctatca gctttgattt atgttttctt catttgtaat gacatgtagt taaatgtgtc    5227
atacttcaaa aagaagaaac agatagtagg tggattttca atataatata tattagatat    5287
agataatata tattttcaat atataatata tgtaaaaata aattcagtga taatatcatc    5347
ctacctgcag ttttaagaat tcagaactca ggccaggtgt ggtggctcat tctgggaggg    5407
gaaggcagga ggatcacttg aggccagaag ttctagacca gcctgggcaa catagtgaga    5467
tacctgtctc tattcaataa aaataaaaat aaaaataatt cagaactcaa tgctttatac    5527
tcactgaaag ttgttcctct aaactgactt gaaatcatgt tccaaataaa ctgagaatta    5587
aagtaagaga cgaggccggt gtggtggct catgcctgta atcccagcac tttgggacga    5647
caaggcaggt ggatgacctg aggtcaggag tttgagacca gcctggccaa catggtgaaa    5707
ccctgtctct actaaaaata caaaaattag ccgggcatgg tggcacacac cagtaatccc    5767
agctactcag gaggctgagg cccgagaatc acttgagcct gggcatggtg gctcatacct    5827
ataatcccag cactttggga ggccgaggca ggtggatcac ctgacgtcag gaattcgaga    5887
ccagtctggc caacatggtg aaaccccatc tccactaaac atacaaaatt agctgggtgt    5947
ggtggcacat gcctgtagtc tcagctattc tggaggctga tacaggagaa ttgcttgaac    6007
cctcccggga ggcagaggct gcggtgagcc gagatggctc tgctgcactc cagcctgggc    6067
gaggcagaga gactctgcct caaaaaaaga aaaataataa taataaatag gagatgaata    6127
aattgggata aagtgttttt gaaggacagt ctaggatata aaatgaactg gttgtttgac    6187
taaaaatact acaaatgttt cttttcaaatt acatttcttt tttgtctatt ggaaggtagg    6247
cactgatttc tatgtctttc tattccctaa tagaacctac tgttgacctc tcagtcaata    6307
tttaatggat gatatagaac tagtgaaaaa ccatgcaatt taactagaaa aaaaagtat    6367
aatctatttt cttttcctttt tcttctctt cttctttct tttttttttt tttttgaga    6427
cggtatcttg ctctgtcacc taggctggag tgcagtggtg tgatctcggc tcactgcaac    6487
```

-continued

```
ctctgccttc caggttcaag tgattctctt tctcagcccc cagagtagct gggactagga      6547
gcgtgcccca ccacacctgg ctaattttc tattttatt agagacaggg tttcaccatg        6607
ttggccaggc tgatctcgta ctcctggtct caggtgatct gcctgcccgg gtctcccaaa      6667
gtgctgggat tacaggcatg agccactgca cctggtctaa tctattttca atgtataaga     6727
gaaaaatagt gttaagtgtc ttggtgatgg tgatgatggt aggagtaatg gtgtgttttc      6787
cttacattta atttctacag gctatggcaa ttgccctata aaagccaccc attttaagca      6847
caaaagtgaa tggttttag taaacttata tgggatcata tatttttaat tgaaatattt       6907
tttgagttaa ttatagattc atatgccatt gtatgaaata atacagagag attccacgta     6967
tacttgctca atttcccca gtggcaacac tttgcaaaac tataatatca tatcacatca       7027
catgcaaaac tataatatca tatcacaacc atgatactga cattgatgtg gcctactaat     7087
cttattcaga tgtcctcagt ttaacttgta ctcatttgtg tgtgttttgt tttataccat     7147
ttagtcacat gatcacatat ttttaaacct ttttttctca aaacagagaa gtttagcaca     7207
aaagtttagc aatttatcaa tcttgtgatt gtgctgttat gccatattaa aatgtgtgtc     7267
agaatgtaag ttttgtttt cttaaaagtc ctttttttga tagaatggcc tttatgttaa      7327
aaatatttta agttgttttg tgacagtgta agtcgatgtc atttaattct catcacaacc     7387
ctagagatag gtattattct tatccctatt tatgagtgag gaaactgaag cccagtgagg     7447 ttaataact tccttaagtt catacagcct atacatggct taggcttagc cagcatttga      7507
gttaagcagt ctgtctctag tgccaaatct tttaatcact atattatact tcatcattat     7567
cattgatagc tgtaaaagtg tataatgtgg actatgtaga gaaagtcata aaggagatt      7627 taaaatgcat acagttgttc acatgaaaac ttgtagccaa atgttcatta cagcattatt     7687
aataatggta aaaatggaa acaacccaga tgtctatcat gtcatgagtg aataaacaaa      7747
ttgtggtata tccatacagt gaaatattat taagtagtat aaaggaatgg attattgata     7807
aatgctgtca cataggtgaa tctgagaggc acaagaaagg ccacatatga tatgctttca    7867
attttaagta acgtccagaa taggcaaatc taaggagaca gaaagttggc tagttattac    7927
taggggctag ggatgggagg gaggtgactc ctaataagta tgagatttct tttggtgatg    7987
atgaaaatgt tctataatta gatagtaatg attgcccaac tctttgaata tgctgaaacc    8047
cactgaatta tatgctttaa aaggatgaat ttattgtatg tgaattatat ttcaaaaagc   8107
tgttgttata aaaatgaatg tagttgagtt atttggttta ttttatgtca gaaaatgtct    8167
tacatctcat gcaaaagaaa tgcaggaact atttggattg aatgaggcta agcatatctt    8227
tctaggaaga tggcatcaag gagttttatt atgcctgtaa tcctggcact ttgggaggcc    8287
aaggcgggag accagaagtt tgagattagt ctgggcaaca tcctcttata gatgagaagg   8347
atacttaatc actcaaaagt tggcattgtg ttttgtgata acaatagcct ttagagctca    8407
tatgggaaga ttcaatagat agtgataggt tatatgactt ggtaaagagg gcttaatgta    8467
taggtgcaag aaactttctc agatgtcttt agttacctag ccattcagtt caggagatgt    8527
aacccaagtg ttaaaaggaa tgtgactggg tgcggtggct cacacctgta atcccagcac    8587
tttgcgaggc ggaagtgggt gggtctcttg agctcaggag ttgagacaa gcctgggcaa    8647 catggcaaaa ccccatccct acaaaaatg cacaaattag ctgggtgtgg tggcacatcc    8707
ctgtagttcc aggtacttgt ggggctgagg cggaggatg gctcgagcct gggaagttga     8767
ggctgcagtg agccatgttg gtgccccac acttcagcct gggtgacaaa atgagaccct    8827
```

```
ctctctcaaa aaaaaactat aaaaattgct gttcttgttt aaattactac aaagtgcagt    8887
ttaatctaga aataataaca aattactaga tttgggggt tattaatgtc ttatctatgt    8947
gaaaacagaa gggcaatgca gggcagagaa taaacttcaa aactttgagt tgttaactg    9007
tttatatctc cacttgtcat gtttcagatt ttaaagttaa aatgacaaag tatctcatag    9067
ggtttaaaca agtgactctt ttcctgttaa ctgatactgt ggcatgttga agatgtaaaa    9127
taaggttgaa aaggaaattg cttttgcagca gtcttcataa tgccaggaca aagtgagaaa    9187
cagggtcaga atgatgatgg ctctccatct ttgctacaca tggctgcaag tatttacaaa    9247
taccagcaga acttctacaa accacttaca ggtaaaatga gtgcagattt ttaacactag    9307
tccctatgga actatgactt gtagttttgg acacacaggg tgaattactt ggggttgatt    9367
gtatttgaat ttctaacctt atgtaattct agataccaga cattcttgtt gtgcaatgct    9427
tctctcccctt tttattctca tgagaatgct gggttgcagc cggttggatc ccataccttg    9487
ggaccatgac tgataactgg agtggagaaa attcactgat ctggaaaggt tgagctttag    9547
ggttcagaga cttatttaag gtacacatgt gattgtaccc aataaggaag tatattggct    9607
ttatataatt gttatgatca cttgttcaat gagtaactat agaattttac ttttttaagag    9667
tatgatcata gcatctactt gtaggtttgt tgagtatgtt tgacaagccc aagatagatg    9727
ctcatgttag acccattaag aagttggtgt agtgatggtt atggaaagca gtaagataga    9787
atttaggttc tgttctcctt actggagaaa tgactagctt acttgtcttc actctctctt    9847
gtttctctca aaactttgtg aaccacctca gctgactata aattttttgta ctagtatctc    9907
cataatttta aaaagttgt tcacaagttt gagtgtagta cttcatcttt gcttttaat    9967
gcacttccaa aaaatgtaaa tctgttctcg catattagga acattttgat ttgttgttta    10027
tttttagctt tgcttttttat aagtaattta tacagaaggt acaccatatt caaaagaaga    10087
aaaatgggct gtgaatttt gctgatgtac tactctcttc aaagggaatt gcctatgttc    10147
aggcatagaa atgcaggcag tctgacattt aggtatgcca tacagagtat tgatattttt    10207
aatttgctac ttttaacatt ttgagatttg tcacagtttg ttctgtgggt gggtaaaagt    10267
aatggtaatt ttaattacag ttgtcgtgcc tcattagcca ttgctaaaac ctgccttacc    10327
aaatcactta ttttcttgat gcagtgttaa atctagcttc tatgtccagg ttatacatta    10387
atgagaacat tcacccatct ctcaaatggg ttattatagt attttctcct gaaatagatg    10447
atgcataaaa aaaagtaaaa aagcttcaat agggataatg aaagccagat aacatagcat    10507
ggtatatgag ttattcctcc cgttttcctt acctgtctgc actaagaagg gcacccatta    10567
aataccataa ttattagttg tgctgcctct gaagtagagc accagaatgt gagagtaata    10627
caatgagacc acaccagat tctatccata acatactgtc ctggtcttat taattttttt    10687
aacctgtttg ttcttttagc acttttcctg cttttgtttg aagtctcttg ctttgaagtt    10747
atagaattt tatatttgcc attggctgta aagttatctc agctcttta taacttttca    10807
ttatatttgc attaaaagga tcactttgag caccctgtaa ttaattcaga tgattattag    10867
ctttttttgtt tgttctactg tgcactctcc tatatacatt ataacagaag aaaaaaccat    10927
ttctacaaat acagtgtctg atagttcatc aaatcagaat gagcatctta aaaagtgaat    10987
tattaaaata ttaattcatt tacattccta tttttaatgta ccaaatgtaa ctgatgaaaa    11047
gaagaatacc ataaatgggt acctttcaaa aatgaaggaa aaaaaatct cacaactaaa    11107
gattcttacc atataaatta tttattttag taaataatta ttttagtaca aacagataca    11167
ttttagcagg aaaaaacaca ctttaaacct tgttttatag attttatctt tcttccaatc    11227
```

```
tagccactga aatggttttt tctccagtga agttatatta tctacataag ttgaatttaa    11287
aacaaggttg tattttaatt ttgcagttgt ctgccacatt acgcttgtgg aaaaacactg    11347
gcagaaagca aagctaatag acattttgct gttggctcac cttattaatg gctaagattt    11407
aattatgtat ttctactgaa aagcaaactt gaaaaagacg tttggttact aactgtggga    11467
actaaaaatt tttatttatt tttatttttt attttttggt agagtctcac tctcttgccc    11527
aggctggagt gcagtggcat gatcttggct cactgcagcc tcctccttct gggttcaagc    11587
gattctcctg tctcagcctc ccgagtagct gggattatag gcaccagcca ccatgcctgg    11647
ctaatttttg catttttagt agaaacagcg tttcgccatg taggctaggc tggtctcgaa    11707
ctcctgacct ctagtgatcc accccttct gcttcctaaa gtgctgggat acaggcatg     11767 agccatcggc ctggccaact tatttactgt tacaacttac ttactttgaa acaacttatt    11827
tactgttaaa aaatgtggtt cttatttcaa ataagatttt atggacatca actaattttt    11887
taaacatata ttgtaatttt aaaacatttt taccaacatt tttcaagagc atgggaaatc    11947
tagggtatgg cattttaaag tgactttaaa gacacttctt gggttttgtt gaagtcagaa    12007
tatttttaaa aatacaatga gtttaattta ctactgacag attttcttta attttttttg    12067
cattgttata attagtcatg ccttaatcct cggggttttt gggaaactat atttaggggt    12127
taaaaactta gttattgaca ttgtaatttt tctcagtatt ggtaagaatt caggtgttta    12187
aggaatggag tttacttgtt ttctgttcac aaacccattg taaaagatat aatgaatgta    12247
gatgaaggtg aaatccgaga taggaagaga ggtaaaatgc tacttttttt tccttcaccc    12307
aaggaaagcc attgaatact gaatgggtca tgttgtaatt taattgggtg taaattataa    12367
ctttgtaaat catttgccta cttagtgtat atctctggtt tttatgtaat tcatctccca    12427
taatatctca gtttacactg aagtaaataa gcaagcagga ataagtcctg caaatagagg    12487
aagtagaaag tgcattcaga atgcattgct gaaattgtaa aactgatcct aaattgaatt    12547
aggtagagca gttaatttag attacaagaa atgcaacagg aaaaaaatat tacagttctt    12607
cctctttttt ggaaaaaaaa aaagaaagaa aagacaaata aatcacccct agttagtgat    12667
aattccttga catctgtatg ctcatttttta gggccaaaaa atagtaggct tctctttgga    12727
aattgtagac gctttctctc cttccagtta cacgcggtca catcaacatt tgacacgtgg    12787
gtaccgtgca cgtggcagca gtatttacaa acaccatcct aggattccag agactcttat    12847
gtaacagtgg agagagtaag ctttgagtgt ctgtgggcgg aggaatcaac acagtttaat    12907
tcattgtccg ggagcccttg tctggctctg atagggtcat gaaccaaaga tcaaggtgtt    12967
taggtcagga tattccctaa cgcatggttt tcctaccaaa gcctcaaaag ctgtgcctaa    13027
atacaagatt aatctttttc tttctttctt tctttttttt ttttttttt gagacggagt    13087 ttcgctcttg ctgccaaggt tggagtgcag tggcgccgcg atctcggctc actgcaacct    13147
ccgcctcacc ggttcaagcg attctccagc ctcagacacc caagtagctg ggattatagg    13207
catgcgccac cacgcccggc taattttgta tttttagtac agacggggtt tctccatgtt    13267
ggtcagcctg gtgttgaact cccgacttaa ggtgatccgc ttgcttcggc ccccaaagt    13327 gctgggatta caggcttgag ccaccgcgcc cagctaagat taatcttttt atgccctgca    13387
gcaaacaact agtcatgcca aaccattttt gtgatttggg gaaacatgag cagatgatgc    13447
tttggatctg attataattc acagtgctct tgtaatttac gtgagatttg catacctgcc    13507
tcccagcctc acaaaatgcc tttaaaaaat tacatcttgg ccaggatggc tcacgcctgt    13567
```

```
aatcccggca ttttgggagg ccaaggcggg tggcaagaga tcgagatcat cctggccaac   13627
acggtgaaaa cccgtctctg ctaaaaatac aaaaattagc tgggcgtggt ggcgggcgcc   13687
tgtaatccca gctacttggg agactgtggc aggagaatcg cttgaccccg ggaggcggag   13747
gttgcagtga gccgagatcg cgccactgca ctccagcctg gcgacagaac gagactccgt   13807
ctcagaaaaa aaaaaaatct tgatatttgt atgcatctta aaaagcaaga gaattcatga   13867
ttgacttccc aaactaaacg gtctgaccag aaaacactca agaaaactct tggttaatca   13927
tgctccttag tataccatta tacctgcctc tccccttttcc ccatcctctg taaattctct   13987
caaccttctc tcatttttaa tttcatacca agacctagag ctaaacaac aacaacaaag    14047
ctttaagtct ctatatttag ggaatgtgcc tcctatccca aattgatttt tagagctttt   14107
catttatttt tatcaataca aagcaagttg aaataaaaaa aaaggcatca aaaatttaaa   14167
tgtctaacca cgtatatttg gtatatgtat actggtgcta tgtattagct gtaagcagac   14227
tggtttgaat atttaaaata tgaacagaat ttgagttctt tttgtattgc atctaaggat   14287
catttgagat ggatgtcatc atttatcatc caaaatagaa gccttcttgc ctaacaaga   14347
attgtaatta gatcatcaaa gatgaaattt atagtaattg aaagttagc tcatttgact    14407
gcttctttca tagactgtgt ttttgtaatt acactacctt tctaaagata ggaaaaatca   14467
gagtctctga aatgtaatac tataagtgaa atatgtattt tttaaaataa aggatctttt   14527
cccaagagct aaaccaagca ccaaatctgt tttttggggg ttttttggtt tgttggtttg   14587
tttgtttgtt tgttttttgac agagtctccc tctgtcgccc aggctggagt gaagcggagc   14647
gatctgggct caccgcaacc tccgcctcct gggttccagc aattctctgc ctcaggcttc   14707
ggagtagctg ggattacagg cactcgccac cacgcccggc taattttttgt atttttagta   14767
gaggcggggt tttaccatct tggtcaggct ggttttgaac tcctgacctg gtgatccact   14827
cgcctcagcc tcccaaagtg ctgggattac aggtgttttt ctttaagtaa tacttggtat   14887
aagagaactt tatatctgga ataatttaaa tattatctga ccgaatctat tattcacata   14947
tagaaactca ggttttagcc atttaacatc taaagctgtt ctcatttaga ggaaattacc    15007
aaaagagtga cttatttaac taacaataaa atctaaggat agatattttt tcattctgtt   15067
gcagagcaaa agcagccttc tggatatgaa aagatattac ttctttagtg tttattactt    15127
ataatttatt gtacatttct gatacactga attaagatgc gatgagagta ggttgtagat    15187
ttttaaaagt tcttatttgc gtgatttatc tacttgcttt tttagtgtcg gactataaat   15247
gatgtatttc tctcaattat cctcggccta aatagtaaaa gcttgggtga aattacttat   15307
gagtatactt ttcctgcaca gagcagagcc attactgaac actctcgagc tttaacaaaa   15367
atcatcctat cttatattag aatattaata ttttccctct ttctcggacc tttgtttcac   15427
agtaaatcat atatggatat aagctgcaag tgctcagaat ttgattaagg ctataagtta   15487
atttctacta aaaagggat tcaaatagaa ctttcatttg gctgtactgt agtttcactt    15547
gaagggcaa gcatgcaata aacattgact tattcaatgc ataggctgtc ttcataaaga    15607
tgagactgag tgacagttgt ctgtgtatta taaaatatca gaatggtaga ttgaatctga   15667
tgcataccaa ggagcaatgt ggaaatttta ggctgttcgt cttttttcag ttactactaa   15727
gtgtgtgtat gtggtgtgta tgtgttttga acttttcata tttaagctga atcctctttg   15787
gtagaaatgg ttaaatagac tatagtaaaa gtttctgtct ataaatataa aatgaaaaaa   15847
tactgatatc ttgcattttc cctaaatatgt tgaaagtgca cagaatcctt ggggtctttt   15907
gtataaactg ttttttatatg gttcctgtag aagacagctg aggcaccaaa cacacacaca   15967
```

```
aaacaaacag cttgcttggt gatgataaca ttcgtgcaag ggagttctct cttgcatagg   16027
agtcccaggt taccctaatg ccttcccaca tggtcaaaca catggagctt tcatatttac   16087
acacagctcc agaattctga agcctgcagt tgtttatcag tgggatacag ggagaaagag   16147
tggtgtctat cttactaact gtttaatgac ctggatcatg aatactgata cagaataaga   16207
aagcactggc ctgactgcag gggaaacatg gtagatgcct aaaggaggct tttccctgcc   16267
ccacactgtt tattttaaac tatcattatc acctgaaagg agcttttcac tttgaactta   16327
aaatagtagc ttttaacccct gacaagcaag taggcacttt agtattcaag aactgaaggt   16387
gacaagccct gaggagtgtt actctctttc ataaccaagc tgactcaaac tcttttagaa   16447
gctagtgtag taacttaacc atctctaata atgttgctgc atgccttcat agaaacagtt   16507
ggagcaagag ctgcattttc ttttttttaa gtgtttatta tttacatttt attttgaaa   16567
acatgccatt cctattacat atagaaatac ttcccaaaat cactgtttgt atagaactat   16627
tttgcttaac attaggattc tattgaagag cctatatctg caataatacg gggagaaaat   16687
ccccttttgt gtgatagatt aatgataaag agaagaaaa ggtgagaagt aatttttggga   16747
aatatgcaat gataaactag tggtatttat tgaactaaac accagcagct gtgcttagca   16807
tggataattg cctaaaagga tgagaaaaaa aagtaaaaat caggagacta taaatttttc   16867
agtgaagaat aaattttctg tcacaaatta tgaacatttt aaatatgtat tttaaacttt   16927
ttcctacttg taacaaatta tcagactttt taatctacct tttttgagct tttcatcttt   16987
ttccctgaat tatagattta attctgtgta tgtatgtgtg tgtttgaata tatttttata   17047
ttttagatct agatttgtaa actagagctg tttctaactg cttataagac attgccacct   17107
ggattgccac cactttcact ccagtatttc aataaacact tcatcaaaaa catagtttat   17167
tttcaaacat agaatcatgg attgctacaa gctgaaagga ctttagagac tcagtaaccc   17227
cattccttgc atttacagat gagaaaatgg aggcatggga aagtaaagtc agttgcctca   17287
aatagcgtaa caagctatgt atatttctaa taatagctac tattgattaa gttcttatgt   17347
tgggttaagt accatgctaa gcactttcca aagattatct aattcttatg tcatctatat   17407
ttttgttggt gctattactc tcctcacttt actaaggaag aaaccaagac atggggttaa   17467
ataacttccc tataaatttt gaattatctt tggcatcatc tccctatttg caaatctcca   17527
ttgtctcttt gttcgtaatc aatgtaaatc aactcttaaa cagttggatg ccaacaagca   17587
gtctggtgtt tggagctcga agtttcgag agagagagag agagagagag agagagagag   17647
agagagagag agagagtgtg tgtgtgtgtg tgtgtgtgtg tgtgtgtgtt ccagctttgt   17707
tgaggtataa ttgacaagta aacagtccac aaaactgtac acatttaaga gatacagtgt   17767
gatgttttaa tatacattgt gaagtgatta ttactatcag gctaattcac atgtccatca   17827
cctctcagtc attttttgtg tttacggtga gaacacttaa gagctactca aatgtagtca   17887
aggataccat acagtactaa ctgtagtcac catgctgtac attagatctc cagaatgtat   17947
taaatattca tctggcataa ctgaaactgt gtatcctttg acaaacctat ttcccctact   18007
acccagccca tggcaaccac catgttactc tctgcgttta tgagttcgac ttctttagat   18067
tccacatata agtgagatca tgcaatagga agatctaatt tagcatcctg actttccttt   18127
ttattagctg tgtatgtcat attcaggttg ccttagcatt tgtgaatctg cttctctacc   18187
tgtaaaatga gaacaactaa taattcttat ctcatggatt actgagagga tcagatgaag   18247
taacataaat aaaacatcca gcatgttact tggcaaaatt gtagtgattg aataaatatt   18307
```

```
tgtttattct tcaagcatgt gttgagcatc tatgtatcag gcaagaagag agccatcatc    18367
tttacccttc tggaatatac aggctcatag gaaataatca atgctttgat ctttttttaa    18427
agcataatga gatgaaaatt ataggactca tagactggtc agttgaggaa tttcccagga    18487
tgcttccagc ctctgctcaa aaggtgtgaa ttcccagttg cctgaatagg cgccagagtt    18547
ggcatagctt tctcagtatt gggacctgac agggagattg cacaagtgta acagcacagc    18607
ctctgaaagt tggctcaagg gggaagagat gaaggattac ttccatccct tttattgttt    18667
caatcaagat atatattatg agctcatagt accatccttt catgatcatc ctttattgtc    18727
tttattagat acaatgaaaa gatacaaatt tgtccataga aatattaaat gatagcaggc    18787
atgatttaaa aagtactaag gactatagat attactgttt ttcctctatt ttgtatcata    18847
ttttcaggaa gaagagacaa cattttggca taccttgctt aaagatagat gatagccggg    18907
tgtggtggct cagacctgta attccagcac tttgggaggc cgaggcgggc agatcacctg    18967
aggtcaggag tttgaaacca acctggccaa cgtagagaaa ccccgtctgt accaaaaaat    19027
acaaaaatta gccaggcgtg gtggtgggcg cctgtaattc cagccactca ggagactgag    19087
gcacgagaat cacttgaacc caggaggcag aggttgcagt gagctgagat cgtgccattg    19147
cactccagcc tgggtgacag agggagactt cgtctcccaa aaaataaaaa taaaaataa    19207 ttgtcttggt gtgctaatca ggagcttcct gtgagagtgg aaattcctta catggcagtg    19267
tcatgaaatt ttaggcccat gtgaaagatg tttttgagtg tctcaaaata gttaacggtt    19327
taaaaataca ttatttatgt gtcagaaact gctttcattg aaattgaagt ttctttgaga    19387
actaggatca tatcatgtat atctattgaa tttcccacaa caattatcac gcaagcaaat    19447
gaatagcaga ccctcaataa cacttactga tgattattgc catgtataag ttgggatact    19507
cttgagtacc tttctaagtc tgcatttagg gaaatacaga acacaaaatg aaatgtttga    19567
ttggttgctt agtttccaca gtgacttttc aaaatgtata ggagcatggt aacaaaacta    19627
ttttaaatac tacaatctta agtatgcctt tattattctt acccacaata atgcattgct    19687
ttaaaaaatt gtttatcagt gtcagaccat acctttctga gtctctacta tgtaagatgt    19747
gaaagttaat attcttcaat tccagctact ttttcttttcc tgccttctgt caactcctgt    19807
attccatatc attacttctt attgctaaat ttataatatt tatattctgg tttgcatcta    19867
tagttaattc tcttgtgctt catttctcag tgctaattga aaagaaaac acatcactta    19927 caatgccatg attgtaataa ataaaattca ctgtaacacc tagcagtatg gttgaacatg    19987
tagaaaagga aaagtgatc ctgtgacact aaaatttagc ttgttctaag gatgctactt    20047
taagcattag ggtaaaatgg attccctttt gctaaattct ttcagttcct caaaattatg    20107
ccacattttt gtttctttca catttggact tagattttcc tgtaagcatt caatttttct    20167
tgaaaatttt aattgcattt ttttattctt gttgacagaa gaaacatttt catcatatca    20227
caattttttt tcagatttct taattatacc atttgatgaa tgaaatacac tttcttcttg    20287
aagtctgatt tttctgttct aatttagagt ttcttctcat ttttctcctg gctatgtcta    20347
ttattgcttt agtctcatgt ctttgtattt gattattatt tttctttttta ctactgtttt    20407 tcttcttaca gaaaaaaaaa gaaaaaaaaa caggggtttt tacaaatatt gtgctgagtc    20467
tttacatgtc caaaatgcct tatatttttc cttatagtac attcataaat tattgtgatt    20527
agaaccataa attcaaagta attttctctc agagctggg aaacattggt acgttgttac    20587
ccttcatcta ggattgctta tgagatagat atctgatgcc agtctgattc tgtcttttt     20647 agataacttt tttccctatt catatgttta ttaggatctt tatctttttca cttctgaaat    20707
```

```
tcctccagat atggctctgt taaaatgtat tcttctcagc acttgatgat tctgtacaat    20767
ctggaaacaa ctgcctttat ttagcttaag gtacttttct tccattgtac ctttgattat    20827
ttcttccttc tttttttcac cctatcttta tgaaactcat gttaatggtg cattagaact    20887
tgtgaactga ttttcttat ttattaaatt ccatcacata tttttcatct gtttatctct    20947
gtatatttta ttttctcaac ttttgatatt tttgttaatt gaaatttaat ttccaagaag    21007
tccattttct attctctgat tgattctttt taatggtagc ctatttcgtg gctcaaatca    21067
tataaaatgt attaaatttt gtgggaaaat taggcaaaca aagaaaatta aattttacct    21127
aactatatct aaaaacaata caactaaact taagaaaagt gcgtatatgt gtacacatat    21187
acatatgcgt gtatatgtgt acacatatgc tacatataca tgtatatgta gtatatgtac    21247
atgtagtata tgtgtgtatg tatgtatata cacatgtagt atatctatat acatgtatat    21307
gtacaaagaa aaaatatgta tataatagtt tcactgtact ttatttgctc cccttttaaa    21367
aataacagtg ctagagttca tgactgacta attttcagaa cttggtgtgt atggttgttt    21427
attaagccct caataataat gctttagtat tacagtgccc aggcatagtc agtgactgtg    21487
ctaatagtcc tagcagtagc agttcatcct gtacagatct aaggtgtaac tattttcatt    21547
tctgggccct tggagattct ttggttgtct tcatatcttt tacctatctt gctgttcaat    21607
aacaggtaat agaaaggag ataaaactta aatgtcatca tttcccactg cttaacagtc    21667
tttaaaaata aatgtgaaac ccgtaaggac gtaatcttgc ctagctttaa ggaatgaagg    21727
aaacactaga aacaacagag agaaaaggaa taactgatcc tccaacatgt tctgttgact    21787
ctacctgtaa agtatattca ggatctgact acttcacacc atttcaccaa tttccatctc    21847
cattcaaacc accttcatgt gttactttga aaagtgcagt ttccctgtca tgggtttccc    21907
tgtttctagc tttgctcccc cttcttacct caccgtgggt ttttacccaa acaaaaattc    21967
aagtgatcat ttaaaaatta agtcaggtca tgcctctcct ctgcttaaaa ccattaatgg    22027
gtctctgttt cactcagaat ataagccaaa gcccttttca tgacccacca gtcctcaagt    22087
gaattggctg ctatttgtgt ttctgattcc atttcttgcc actattctcc ctcattctat    22147
tctaatttcc ttggttttct tgctgtcctg gcaacaagaa gagcatcctt tttcctccag    22207
gcctttgcac ttgctgttcc ctcttcctgg agcacccttc cttcagagag ccacaggtat    22267
tgtttctatc tttccttcta atctctcctt gagtgttact ttttcagaga taaattccct    22327
aaccattcta tctaacagaa ctctgactat tgaccttgct ttatttctc tctttttttt    22387
taaaatttta tttttttatt cccataggtt attggggaac aggtggtatt tggttacatg    22447
ggtaagttct ttagtggtga tttgtgagat cttggtgcac ctatcacccg agcagtatac    22507
acttcaccct attcgtagtc ttttattcct caccccttc ccacccttt cccctgagtc    22567
cctagagtcc attgtgtcat tcttatgcct ttgcatcctc atagcgtagc tcccacttat    22627
gagtgagaac atatgatgtt tggttttcca tccctgagtt acttcactta gaataatagt    22687
ctccagtctt atccaggtca ctgcaaatgc cattaattca ttccttttta tggctgagta    22747
gtattccatc ttataaatat accacagttt ctttaactac tcaccgattg acgagcattt    22807
gggttggttc cacattttg caattgcaaa ttgtgctgct ataaatgtgt gtgcaagtat    22867
cttttttcata taatgacttt tttcctctgg gtagataccc agtagtggga ttgctggatc    22927
aaatggtagt tgtactttta gttatttaag gaatctccac actgtttcc atagtggctg    22987
tactagttta cattcccacc agcagtgtag aagtgttctc tgttcaccat atccatgcca    23047
```

-continued

```
acgtctacta ttttttgatt ttttattgcc gttcttgcag gagtaaagta ttgcattgtg    23107
gttttgattt gcatttccct gatcattagt gatattgaac attttctcat atgtttgttg    23167
gtcatttgta tatcttcttt ttaaaattgt ctattcatgt ccttagccca cttttttgata   23227
ggattgtttg ttttttttcct tgctaatttg ttggagttcc ttgtagattc tagatattag   23287
tcctttgccg gatgcataga ttgtgaagat tttctcccac tctgtgggtt gtctgtttac    23347
gctgctgact gttcctattg ctgtgcagag gctcttttgt ttaattaagt ctcacctatt    23407
tatctttgtt tttgttgcat ttgcttttgg gttcttggtc atgaagtctt tacctaagcc    23467
aatgtctaga agggttttttc tgatgttatc ttctagaatt tttatagttt cagcacgtag   23527
atttaagttt ttgatccatc ttgagttgat ttttatataa ggtgagagat gaggatctag    23587
tttcattctt ctatatgtgg cttaccagct atcccagcac catttgttga atagggtgtc    23647
ctttacctac taatttatgt ttttgtttgc tttgtcaaag gtcagttggc tgtaagtatg    23707
tgggtttctt tcttggttct ctatcccccc attggtctct gtacctattt ttataccagt    23767
accatgctgt tttggtgtct atggccttct agtataaagt caggtaatgt gattctgccc    23827
aatttgttct ttgtgcttag ttttgctttg gctctgtggg ttcttttttg ttttcatatg    23887
aattttaaaa ttgttttttcc taattctgtg aagaatgatg gtggtatttt gatgggaatt   23947
gcatagttta tcaacccttg gcaaagtgtt tctgcttttc ttaaacaatt tttattgtct    24007
gctttctcca gtagatgtga gttctatgag atgaggaaca ttgtttgggt cactgacatg    24067
tattgtcagc ataccaaaca gtggctagca catggtgagc actcaataaa tatttggtga    24127
aagttgcagt gaatgaaaat ggtttctaaa atggcaatga ctatagtccc agctactctg    24187
aaggctgagg caggaagatt gcctgagtct caaaagtttg gggttgtagt gcactatgat    24247
tgtgcctgtg aatagctgct gcattgtagc ctggtcaaca cagtgagaac ccatctcttt    24307
aaaaaaatgg caatgaaata atcttatttt tactgctttt ctctttaagg ctgccagtgt    24367
tgtcttttct ctgctgattt atcctcattg gaaattgaag atagataaaa tatccattga    24427
ttatttatag gtgaaattag gcttttggat ccatgaggaa tagctgagac aatcttccag    24487
gagcttctgg agccgaggaa acattggtca ctaaaatacc atttatattg gcaactgtac    24547
tcttttccga tgctagtgtt tcaattacat tgtgcattta aaaggctgtt gcggctacct    24607
caaaatataa acatgatgtg cgacactact tgttagtttt gaacaactga tttataaata    24667
gacttagggt gctcaagcct cctgcaagat gagcactgcc tgtgttcttc cttctgcttc    24727
ctttatttca gctgtgtgtc taccaacttc ctcctccttc tacactagga gaaattgcac    24787
tgtttccaat atctttaaca tctgctatca tgatgagaaa atatcttttc tggatttgaa    24847
ataccttctt cattctttttt ttttaaatgg cggaaataaa ttcatagtgt tttgagtgca    24907
gttttcttcc tgctgttatt gctggctcaa aatccaggag catttcagtg ttatttctga    24967
gctccatgat gggagttcca tttctgtttt attcaaagtg ttatctccag tgtctagcac    25027
agtgcctggc acattataag cctataatgt ttatctagtg gatgtagacc aatactatta    25087
aagaattatc attgcaaaga tttagtggca tgaaaaaatg ataatgatta atgctctact    25147
ccatgctaag gaaatgaagt gcaaatcgtt ctttattttt cttccaagta tagagaactt    25207
tctgaaatta aagaagcatt gattaataag ttttaatata tgttattgat cataataata    25267
tgtaatcata taaccaaata agataacaca ggccatcttt tgttctttaa aaaatgacag    25327
gaagattaga ataagagaaa aaattagagg tcaaaacagt tttcttcaaa ccagtagtgt    25387
aacttactga gatatcttct gtaatcctta aattctgtat tgatgctacc aagatgcaac    25447
```

```
tcttgagcta caactgcctc ttgataaagg atgctggtcc ctgctgccag tgtaatgttt    25507
gctcatttac agtggaatgt acaatatagt acctgggatg gtgaagaagg tgaagcaaca    25567
aatttaaaat agctgtgggt aaacctacag aaacagacta ttctctttct tccagattgc    25627
attattcatt ttcatatgcc tgcctttatc tgctttggaa gcctatttcc taatcttcca    25687
agatttatca tcaccttcat atgtccatag catgcatttc tcagacaggt aagatagaat    25747
tggtatatat ttggtatagc aaaaagtcaa ggttgtcttt agattatatc cttggttttt    25807
catgtggtac tggggagaaa gcctactgtt tcttcatcta taaaatgaag gacctgggca    25867
agataacatt ctgtgaaatt tcactgaact ttgagctcag caaagtaggg atgcgtgtgt    25927
gtgtgtctat ttgcaatgca tcacagacct taaataaata cagttgaccc ttgaataaca    25987
tggaggttaa gagcaccaac cccctgcact gtcaaaaatc cacatgtaat ttttgactcc    26047
ccaaaaactt aactactaat agcctgctgt tgtctggagg ccctgctgat aacacacaca    26107
gttgactaac acatattttc tatgatatgt attgtgtact atattcttac aataaactaa    26167
gctagagaaa agaaactgtt attaagaaaa tcgtaaggta agaaaatat atttactatt    26227 tattaaatgg aagtagatca tcataaagat cttcatcctt tgttgtcttc accttgagta    26287
tgctgaagaa gaggaggaaa aggatgggtt ggtcttgctg ttccaggggt ggcagaagtg    26347
gaagaaaatt cacatataag cagtccatgc agttcaaacc tgtattttaa ggtcaacggt    26407
atttgttaca ttgcattttg taagtgacct tgttaatttt tttcaatgaa aaaaatagtg    26467
ttccattcaa atgcctgtat gtttatgaga aacatttcag aactatgaaa gttgaattca    26527
aggtttcttg cagattgttt gtatactttc tgtaatgttt gtcatataat gagaatacta    26587
atggtcttac aacttgaaac tgattaactg attaactctt taagcaactt aaaaagaaaa    26647
tctttcagtg aggaaagagt attcatcaga agtattctag tagatgacat attttttggta    26707 atgaaattga tatgggcaat taacagcttt ttccaagttg gctatgctgc tactctctta    26767
ttatacaatg atactatttt tcagagcaga aagcaaatta gttttatttt tataaaccaa    26827
attttaaata tccctttaga gaatagaaaa tatgaaaaag tatttgcttc tcagacctct    26887
caacaatata aattttcttc ttaagaggaa atttattctt gcatgccaac acaaggata    26947 aaaagtttac ctatccttag tttctaagag gaaaatgtgc ataaaatttc catctgctgt    27007
gtgccagtta ccaaaacgat aagttccaac tcaatcttgg ttgggtgtgg tggctcacgc    27067
ctgtgatccc ggcactttgg gaggccgagg tgggcagatc acgagctcag gagtttgaga    27127
ccagcctggc caatatggtg aaaacccgtc tctactaaaa atacaaaaaa aaaaaaaaac    27187
aaaactagcc cggcatggtg gtgtgctccc gtagtcccag ctacttggga ggctgaggca    27247
ggagaatcga ttgaacccag gaggtggagg ttgcagtgag ccaagattgc accactgcac    27307
tccagcctgg gcaaaagagg gagactctct ctcaaacaaa caaaaaagac tcaatcttac    27367
taaaaaactg cagagaagaa tgagtcattt tagtcaataa aggaaataaa gaattctag    27427 ttttgaaaat gacataattt gctacaagaa tgcaaaggtg atgacatgag gaaaaagggg    27487
gtttgctgat ttgttttctc tactactcag caaatgcagg ccaggaaccc atttattcaa    27547
atatttatta catggtaaat taaaacattt ataaaattag gctcatattc ttagaattcc    27607
tgttaacaaa gtgacatata aacaagatta taatctaatg gagattaata ttggttgaga    27667
aaaatcttga gacttcttta agacttcagt ttaataaaat attgacttag gtagatatat    27727
gtgaggaaat atatatttta cccatgcatg caaaaatgat gtatgtattt cttaaaagag    27787
```

```
taggtagcaa tgacttcaaa ggaccatagc tgtccctatc aacatatata ttaacaaaac   27847
aattagaaac atgagcttag tatgctaatt atatttctac ccaaagcctc aatttgttct   27907
atagctatac tgttcatata taagtaaaat tttaggggta tcagagagag ttagaaaaga   27967
gcaaatacat gtatgaattt gataagccta tcccttaatt tgatagatct taaaagatat   28027
tttatcactg cattcttcta aagaaatgta tttgtacatt gcaaacaac cctttttgag    28087 aagtagacta tgatcacaga ttttcttgcc actagtattt cctaagattt atttggaata   28147
gaagatcgat atttttctgg gatgacatat ggttaaaaag taaaaaacaa aacaaaacaa   28207
aaaactcttt aaaaacacaa caagtaaaaa gctgaatgaa ttggaaaatt aacgaatctt   28267
cttagatctg tcagaaaaat gagattatag ggcaaaccac tgcatcaaat attagagaag   28327
cagacaggta gatagaaaga atcacaactt agtgggcaa aaacctacaa ggaaaatttt    28387
tgtgggaacc ggtgccaggt aggaaaacat gaactgtaat tgaaaaattg ttcagtgtgg   28447
gcggttgttc agtgtggcaa gtctgagggt taaaaactcc aggaggactc acttacggaa   28507
gggcctgtac ttttgtgagt ttaacctcca ggagtgttca cagtgactac tggagaaaat   28567
tccctaaggg gagaagaaaa ggaaccatct tgaaatatgt cagagcattt tgttggactc   28627
aagcctgctc tcaagtgaaa ctattttacc agagcctaaa cttttgggat tttataagag   28687
tgtaacctcc caagggaag ggaaatacct aagttcagcc ccctttagc tttccacata     28747 gggaaaggaa aatatataac tctggacaac tcaaaccatc ctgtccacgt taggggcct    28807 aggggaactg agaaaactgg tgaagttcat agtccatggg tacagtttca ccaaagaggg   28867
agaccaaatt ataaggctac agaatgcttc cctttcccac accttttact atcatattac   28927
taaaagccta tttgcagcag tttctttac tgagtatatc atgtctgtca ttcaaccaaa    28987
aaattataag gcatgctaaa aggcaggaaa tgcagtttga agacactgaa taagcatcag   29047
aagcagagtc aaatatggca gtgacattgg aattatcaga ccagaaactt tataaaaaac   29107
tatggttaat atggtgaggg attaaaaaaa tgacatacaa gaacagatgg ataatgtaaa   29167
tatagagacg gaaattttag gaaagaacca agagaaatg ccaagtatca agcatagtgt    29227
acagaaatga ttaaaatgtc tttgataggc tcataagtag attgaacata gccgaggaaa   29287
aaatctttga agttaaggat atgataatag gaacttcaaa actaaaatgc aaagagaaaa   29347
aagactgtga aaaaacaga agagattatt caagaactgc aggagaacta caaaaggtat    29407
aatgtacgtg caatgggcat actagaaaaa gaaagaaagg attagatgca atatttgaag   29467
aaatagtgtg tgaaaatctc ccccaattaa tgtcagacac caaactactt ctccagagag   29527
ctcaaagaac accaagcagg ataaatgtcc caaaactact catgggcata ttatattcaa   29587
acttcagaaa atcaaagatt aaaaaaatat cgaaagaatc cagaaggaaa aaacacctat   29647
agaggagcaa aaataataaa ttttatctga catatcctca taaaccatac aaataagaga   29707
gtagagtgag acatttaaga tgttgaaaga aaaatccggc agtgtacgat tctgacctt    29767 gcaaaattgt ccttcagaag ttaagaaata aagtctgtct taaagaaaca aaaatttcag   29827
gaatttgttg ccagtggacc acccttgcaa aaaatgttta agttctttta gagagaggta   29887
aaatgataca ggttagaaac tcagatccac ataaggaaaa taaaattagg gatatagtag   29947
tattcctcaa cttgataaag aaaatacaca aaaaacctac agtttacatc atacttaatt   30007
tttagaaact caaagctttc ctgctaagat caagaacaag acaaaggtgt ctcctcttac   30067
cactttgttt cctactggaa gtgctaccta atgcaataag acaaaggaaa gaaaatgaaa   30127
agcatacaga ttccggagga agaaatcaaa ctgtctttgt tcacggatga cagttgttta   30187
```

```
tatgaatat ccaaaggatc agaaaaaaga aaactggaac taataaatga ttattgtaag    30247
gttacagaat acaaacttaa tataaagaaa gccaatcact ttcctgtata ccagcaataa    30307
acaagtgtaa tttgaattaa aaacacatta ccatttacat tagcaccca agaaatgaaa    30367 tacttttgta taaatctaac agaatatgta catgatctat atgaagaaaa ctacaaaagt    30427
gtaatgaaaa ataccagtga actaaataat gaagagatgt tacatgttca ttgtcaagat    30487
gtcagttctt cccaacttga tctatagatt cagtgcaatg ccattaaaaa acacagcacg    30547
atattttatg gatatcaaca aaaggattct aaagtttata tggagaggca aaagagcaga    30607
atagccaact cagtatttga ggagaacaac aaagtcagag gactgacact acctggcttt    30667
aaagcttact ataaagctca gataatcaat gtagtgggta ctggtgaaag aatattcaaa    30727
tagaccaatg gaatagaata aagagcccaa acaaacccat gtaaatataa tcaaatgatc    30787
tttgacaagg gagcaaaggc aatacaatgg agcaaagatg gtcttttcaa caaataatgc    30847
tggaaaaact acacattaac atacaacaac aaaaattttt taaatccaaa ttgagtgtaa    30907
acacagatct tatacccttt gcaaaaatta acttgaatca tagacctaaa tgtaaaatgc    30967
agaactataa aactcccaga agataacaca ggaaaaatcc tagatgactt tggtatggca    31027
gtggcatttt ttagatacag ctccaaaggc acgatacatg aaggaaatga ttgacaagct    31087
ggacttaact aaaatttaaa acttctgctc tgtgaaagac aatattaaga gaatgagaag    31147
acaagccaca gatggaaaaa ttatttgcaa aagatacttc tcataaagga ctattgttca    31207
caatgtgcaa acaactctta caactcaaca gtttgaaaat gaacaactca acttaaaaaa    31267
tgagcaaaaa acctgaacag acaactcacc aaagaagata cacaagtgtc aagaaagcat    31327
aggaaaagat gttaaacatc atagtcatta gggtattgaa aattaaaaca acaatgagat    31387
accgctacat acctgttaga atggctgaag tcagaacact gatgaaacca agtgctggtg    31447
agaatgtgga gcaacaggaa ccttcattca ttgctggtaa gaattcaaaa tggcatagtc    31507
actttggaag acagtttggc agtttcttac aaaataaaca tactcttccc atatgattca    31567
gcaatagcgc tccttggtat ggacttgaaa acttatgtcc tggccgggca cagtagctca    31627
cgcctgtaat tgcagcactt tgggaggccc aggcaggtgg atcatttgag gtcaggagtt    31687
caagaccagc ctggtgaaat cccatggtga accccagct ctactaaaga tacaaaaaag    31747
tagctgggtg tggcagtgtg cgcctgtaat ctcagctact agggaggctg aggcaggaga    31807
atcacttgag cccaggaggc ggaggttgca gtgagctgag atcatgccat tgcactccag    31867
cctgagtgac agagcaaaac tccatctcaa aaaaaaagc aaaacaaaa acaaacaaac    31927 aaaacttatc tccacataaa aacctgcaca cattgtttaa cagctttaca taattgccaa    31987
aacttgggtg caatcaagat atccttaat atttgagtgg ataaactgtg gtacatccag    32047
atgtaagaat attattcagc actaagaaat gagctatcac atcataaaac gacatggatg    32107
aaacttaaat gcatattata aagtgaaaga agctaatccg aaaaggctaa atactgtatg    32167
attccaacta tatgacattc cggaaaagcc aaaattatgg agacagtaaa aagagcagtg    32227
ttttccagag ggaggaatgt ataggcaaat tttagtgca gtgaaatgaa tctatgtaat    32287
actatagtgg tggatccatg tcattataca tttgtccaaa cacgtaggat gtaaccacca    32347
atagtgaacc ctaatgtaaa ctatggggtt tgggtatcaa aatgcatcaa tgtaggttta    32407
tcagttgtaa caaatatacc actctggtat gggatgttga taatggggaa ggttgtgggt    32467
ctgtggggac agggtatat gggaactttc tactgtttta ctgtgaatca attttactgt    32527
```

```
aaagtttatt aatgttaaaa aatttaatgc acatgtaccc taaaacttaa agtataataa    32587
taataaaata aatttaggca atctgaaaaa atgttaataa aaaagaaaat aaactagttg    32647
aatgtatcag ttcattttca tactgctata aagtactgcc tgagactgag taatttataa    32707
aggaaagaga tttaattgac tcacagttta gcatggctgg ggaggtctca ggaaacttaa    32767
cagtcatggc aggtgacttc acaaagtggc aggaaggaga aatgaacgca gaagcaacta    32827
ccaaacactt ataaaaccat cagatctcat gagaactcac tccctatgat gagaacagca    32887
tgggggcaac tgcccccatg atccaattac ttccacctgg tctctgcctt gacacatggg    32947
tattatggag attatgggga ttataattca agatgagatt tgggtgggga cacaaagcct    33007
aaccatatca gtgataaaac tatgtctttt cttttatggg gtgctatagt gtttcatttc    33067
aagttgtctt tttgacctcc attttccaat ttctggttag gaaaaataac tttgtctcct    33127
ccttaattga cccacaacct tgtttgcaat gaagaatcaa cacaaatctt tcattaaaag    33187
aaatagggga ggtgatgggg gatatccatg agtgtccatg ggcataattc agttgccttc    33247
attcaatgcc aatgatactg caaagcctac aaggcaaatt catgtaccta cagacagact    33307
ccatcctttt tctcaaacta ttcaagataa aaaatcttgt ttcattttat gtgaggattt    33367
ttttcaccat ctatcctcaa aaaatgaaaa atatcctctt catttgggaa atgagtgctt    33427
ataatagaaa gtaatttgta gtcagctgtt acacttagat gatttgtgtc acctctgacc    33487
tgctttctga taatgcatga cttcattcat ggctctctag gtgacctgtg taccctgacc    33547
tggcataaac cactagagta ttaagtcatt tcagtggcac atgtttgagg gaagattgac    33607
atcccactgg aagactatct acagtgagat cctctaaagc agctgcattc ctagtgaggc    33667
atgattaagt ttatcccact attaggttct ggagtattac ttgtcatgcc caagaggaaa    33727 gttttttctag catgcagagt atctggtttt taatggctac tgagctgaaa taaaatgtgc    33787
ctactaaggg ttgttcattt gtctgtctcc cttctttcac tgttttttt cttggaggtt    33847 acagtagtta tgcctttctg gtcagctggc tgttgaccta tcatagaaat gacactttca    33907
catcttcaag tgtaaggaat tagatgttcc agccttcact ttgtttctca tccaaaatca    33967
atgacaaaac tttcagtatt gatttctcat ggcctatgaa cctgagtcaa cttggcataa    34027
aggacttttc agacaagctt ctctaaatgc agagtcagtg gcttcttttt gccaaactcc    34087
actttgctca gtgataacat taaaatggtg atttgattca ttcctagtct aaaaatactt    34147
cctcatattc caaaatctca gtcattaata catggaggaa aatacaaatt attacatgcc    34207
tgtgcttctc ggctgttgta gatagataaa atatatacaa ttgtgttcta taattattga    34267
gttcttttaa gttttatctt tttttgtttt accaggaagc aaaattatgt ttatttcaga    34327
gcttatttac tgcatttaga atctcatgac acttaaaaaa cctttctaaa acgtaaaatat    34387 tctccatgat ctccatggtc acaaacagta tttcacgttc taattgatat tgccatttta    34447 tcatttttt ttttttcttg gagacagtct cactctgttg cccaggctgg gatgcagaag    34507
cacgatcttg cctcactgca acctccacct cctgagttca agcgattctc ctgcctcagc    34567
ctgccgggta gctagaatta caggcatgtg ccaccacacc tggctaattc tgtatttta    34627 gtagagacag ggtttcacga tgttggccag actggtcttg aactcctgac tcaggtgat    34687 ccacccaccg cagcctccca aagtgctgga attacaggcg tgaggcactg catctggccc    34747
ttttatcttt cttttaactc aaatcctcaa atatatccct ccatgtgaag ttgccttccc    34807
taattatgta ctgtcctagt ttaatcttca ttccttgttt gcctctataa aaccaagttt    34867
aaaaatagtc tctgattctg taaatcatca ctcttatgct catttatatt tctatctaga    34927
```

```
atattttaaa tcctttgtaa caaagtttct actatgcagt ctacctttct cagctacgat   34987
ctatatactc cttggccatg tcttttgtta ttgtgtgtgt ttgtctttgt gtgtgtctgt   35047
atagtagtgg tttgtaaatt ctccatttag tcacaatatg cttttgagg attttccttt    35107
tcctgggaat ttcttgatga tttttatttt gtcatgtgat gaagaatgta tgtcaaagca   35167
ccactgcaga aatagtgctt ttctatttac ttgcactctt ccatcttaga agagctggtg   35227
atagacaacc gactcttctt ttatcttggt ttctacaaca cagaggttgc taagcgactt   35287
taatcccttt taacacagga caatcaacaa caaattcctt cttctcttag attcagatat   35347
ttcacttaga aaatctagca aataaaaaat ggtttaaaac ttcttaaaaa tgtgtaattc   35407
tgtacaatct cctacatctg taaccctgc cccaaatatt ttttacttat gctatttctt    35467
gagcattatg atatgcttat tcataggcaa tcaacttgta agtagcaata gtgtagcccc   35527
ttctaggaaa tcgaagatgt gaaaatccag tttaatgtga taatgagtta ctttgatgaa   35587
aaatactatg tcacaatttg ttataaaaat actcatttgg atttctgatt cacttatatt   35647
accctccaac cttaagtatg attgaattta tagcttttta tactactttc tttatttagg   35707
gaggagtgta tttaaattct gttatctcgg ttattacttg aaagttcaac ctcatacttt   35767
cattttata taatttttaat attatgaaaa tatttatgt aattttatgt ataattcgaa    35827
aacatttta aatattgcat ctttaaattt ttatttcttt tatcaaattt tccctatcat    35887
ttgttctctg gctacaacca aagttaatag ttacattttt ttccagtgac aaatggtaat   35947
ttgcaaagac ttgtaacagt tgcttaatac ttttttatcc cttatttaag aatcatgcaa   36007
acaaccagag ctgataggca gcaggtgcac atgagtgtgg ctgtgctgat ggttactgaa   36067
agatttccaa ggtagctagt aattctgcta ccctaagcca ctatagctcc ttccccatta   36127
ctccctgggt ctacccacca tcctgcagct agaataataa atggcatgta ggttcctcta   36187
ggatcctcct ccagcactat gtctcatgcc tggacatatg agctgttaaa tatttgatt    36247
atcactcctg tgtggtaagg gagacgtcta cttgtcgtaa cttgatgttt actaaactac   36307
ttttaagatt accttatgat aaagtagac acttgcaatt ttgcagaatg catagtttgt    36367
ttttaacaaa ccaggtaaac ataactgcag agttttccta tacgttttga aatctttaaa   36427
aaagtatttt ttatttgcct ttctattaga aatagattag ataaaaattt ccttgtttca   36487
atttttagaa tgaacattag agaatattgt tactgaagga atttttttaa aaatagtgac   36547
tgatcaaatg tcagcagctt tatactatag tgtaaaattt tattttgtag tttgccatcc   36607
cattaagcat tagaattttt ataattgatc ctttgatgtt tatattcatg atattaatgt   36667
aatgtcttta aaccttagct catataggtc atatgactta aagcatcctt agatgaagat   36727
atttgggcta taaataattt atgacataag tgatttaaaa attcattctt tccatccatt   36787
ttgaagaaat tgtaaggtag ggttcatgta tacctaatac ttatcccccc aaaatacgaa   36847
aaataaaatc attttttaaaa tatctgggtt aatgctatag attggaagca gttttttaaaa 36907
agcacttaaa gtctaccagt ttattgatcc tcaatctgtg gctgttttaa atggatgcaa   36967
ttagcagttc agtctaagag aaccatggta gtagactcat tactccccag aaaccattac   37027
atcattttgt aatattaaat tactaaatat aaggaataga atatatattg taaaaattgc   37087
tttggaatca ataataagta ttgtggctat caattatagt tatatattac aatgtaaggg   37147
atatcctttt ataaacttaa tatcacacaa gtagacttag aataattcca ttaatataat   37207
tttgcttgtg tttttatacc tattcatttc aataactctt tttcctatat atatttttta   37267
```

```
tctcaaattc gatagtatct aaatcatgga atcataaaac cttaaagctg ggttggaaca    37327
gaaataatac aatttaacat cttataggct ctctagtcct cagtttccct aagtgatcgg    37387
ctcaagatca tgaatttatg gaggattaga gtcagaatta gacccaaga ttaatttata    37447 cttttgttatc tcttctacag cctacccct tagtttgcct gtgggttat ggaagttaca    37507 ggagagacat tctgagattc agctaaaaac ctagctccca atagaattat tgccctgtag    37567
tcagccgcgc aaatacaatc acaaatacct gaagttcctt gtgtgaagaa aaagaaaatg    37627
actattaaag catcaaaatc aatgcaagtt acctttcttt gcccctttct tcccctttca    37687
ctcctttctt ctcctatact acttgaaatt tctagcgggg atctctaaaa tgcctggatg    37747
ttaggaatgg taagtctatt gtagagaatt atattttcta ttttagtgga tgaaaaataa    37807 accatacct taagaggctt ttcaaagtta agattttgag cacatccttc attggcccag    37867
tctctgacca gtgaggtcaa gtattagcca gtgtcagaat gtcgtgaaaa gtttgtgttt    37927
cagatgcaga attttttttt gcattttctg tgtgatgttt atagggtatt ttcttctgaa    37987
atgttttcca tcttggtttt taaaaatatc tattatttta aaaatattc cctcataact    38047 tctttttatt ttcggaaact atataaattg atctgataat ctatacacaa tgccttgtga    38107
atttatacct gtacctctca tgttccagtg tttggttctt aaataatcac tttgtataat    38167
ggaaatacta tgttaaattg tttataactg gtggttgata tttcagcctt gtttggctat    38227
cgtagttata taaagactgt taattagaaa caacctcata tggtgtatgc ttgttttat    38287 cttcatggaa tttgttctgc aaacactgag ttctttactg ggagtcacca ctttgtctat    38347
gttaggagga gcaggaagtg aatacattta aggtctttaa ttttcttctt aaaactttga    38407
ctactgtagt ggttttttaa agcattaaca ggagaatagc catcactgcc aagtagctga    38467
cattctgaaa tagcacttcc ctttaggcac tgtacagttg gaatcattta cttgcagaga    38527
ggtgtgtgtg tgtgtgtgtg tatttatgtg tgtactcatg tgtataagaa taggagaaac    38587
actttgtggg catatcctgc tgaggtgagt aacgtgctga ttagtgaact ccagtctcat    38647
cccatttaaa cctggaggag aaccacatca agcacagaag cagccaaagc agcatttcaa    38707
caggaaggaa acatctatta ctggggcttt gaagaaacat gccatgaagg tgtactaata    38767
tcacaaaggg aagggaagga ctaaattcag catgataaac aaagtcccctt ttttgtaacg    38827 gaagtgtttg atgatgttttg atcaatggtg gatctatctc ttgaaaggaa aatgcattta    38887
aaccccaaat ggaggattct tatataaggt gcctagcttg taatgatata ttcatgttta    38947
taggtagagt gactggtttt tagagaagag gttttttttt ttccttcatt tttgaacgaa    39007
aacttgtctg tctctaggct ttgaaatgta gaattattta cctttcccca aaatgaaatg    39067
tttcactgaa tctcctacaa gcttgtggag gccatgaagc atgttgaata agagcacagg    39127
ctctggaggc cctgccaccc acaaagggtg tgctaaggta acaactgat agtatttga    39187 aaattagatg acttagaatc cattcaataa attttagcta ttttttattgt cttttttttc    39247 taaatctatt tggaaaatat tgcagataaa gtagataata cctttctaaa acacagtgag    39307
accaggcgca gtggctcatg cctgtaatcc cagcactttc ggaggccgag gtatgcggat    39367
cacgaggtca ggagatcgag accatcctgg ctaacacggt gaaatcccgt ctctactaaa    39427
aatacaaaaa ttagccaggc gtgggggcat gcgcctgtaa tcccagctac tcaggaggct    39487
gaggcaggag aatggcgtga accgggagg cggagcttgc agtgagccaa gatcgcacca    39547
ctgcactcca gcctgggcta cagagcaaga ctctgtctct aaaaataaa aataaaaat    39607 agaacagtga atagtttata aagataaaat agaataggct tcaatttagg gaacaaagga    39667
```

```
aaatatgttt aggaatgata ttatgctcaa aatgattgca actttgatgg tgaagtgtat    39727
tttattcaat taaaaatgta gatatggctg ggcgtggtgg ctcacacctg taatcccagc    39787
actttggaag gttgacgcag gtggatcact tgaggttagg agtttgagac ctgcctgggc    39847
aacatagtga gacctcatct ctacaaaaaa taaacaaaaa atgtgctggg tgtggtggta    39907
catgcctgta gtcctagcca cttgggagac tgagatggaa ggatagcttg agtctgggag    39967
gtcagtgctg cagtgagccg agatcgtgcc actgcacttg agcctgggtg acagagcaag    40027
accctgtctc aagaaaacaa acaaaaaaac aaaaacaaca gtagatatgt gtgtgggaat    40087
gagaacattt aaatgtgctc atcggcttag attttctttt aaccccttc atggccctta    40147 tcttaacctc tgtcttcagc actacccttc atatgtttgt tccgttttat cttctaagtg    40207 attttttat aactctcaat gtatcatggc agaaggaaaa ctcagtgtat aagctgactg    40267
tattttgcat tttctttttt tttttttttt ttttgagatg gagtctcact ctgtcaccca    40327
ggctggagtg cagtggtgcg atctcagctt attgcaacct ccgcctcctg gaggcgattc    40387
tcccgcctca gcctccccag tagctgggac tacaggcttg caccaccatg cctggataat    40447
ttttatattt ttagtagaga cggggtttca tcatgttgtc taggcaggtc tcaaactcct    40507
gacctcaagt gatccaccca ccttggcctc ccaaagtgct gggattgcag gcatgagcca    40567
ccgcggcctg gcttcatgat ccaaaatagc atcattaagc ttctcttca aaacatgtat    40627 ataagcctgt gagtcatcac tgtatttatc agaatattat catattggag actttgcaaa    40687
gctgaacaaa gccagaatta ttggctactg aggaactata ttctagcaag agactattct    40747
atttgttggg gatcacctct ttttactaaa ggggactgtt ttgggcatat aaaactagaa    40807
ttcatggttt ctccttgata gtttgccagc ttgattccca gtcaaccaga taactgctgg    40867
tagtgacact catgtcctcc aggactccca atcttgtgcc agtcagaga gggaaatccc    40927 cctagaactg ctcacaccat tccaagaacc acaagcacca ccttggtata gttaaaaatg    40987
tgataccaac tcaaattctg ataaaaacaa gttctataaa gcttaataaa gttatatttt    41047 ttactttta agttttgttt tactatttta aacagaaaac agaaggtaaa aactcctctg    41107
ccttcctcag tatttggttt gtcagttgct gaactcagat ttaagagtct aatcatatac    41167
aggcaataac cctcttctaa tcttaataat gtttctttga tcatttcttt aaaaagaaaa    41227
atgaaatagc ctattgactc caaccctgac ctcctgtact tcacctgcct gatgaatatt    41287
tatttggaat acataagttt tttcaaatgc atcatgtcaa gaatttgtca tttcagattc    41347 cttttctagaa ttatctatt atctcattag tagcatcatt ctttcagaca accaaactca    41407
aaagctttat cactataatt gaatttcttt tttcttctta catttaaaat gttactaaat    41467
gccattcatt tctttatcag taatatttct gtttgatcat tttatttcat ttattctgcc    41527
accctctcat tccaactatt gcttatactt gagtactgca ataagccaat atcttgcata    41587
tgattattta taacacctaa atcttctacc acttcacact cactgggatg gatataaattt    41647 ttaaaacata caataacagg tgttagtgcg gatatggaaa aattggaacc ctgacacatt    41707
gctagtggaa tgtaaaaagg tgcagccact ttgcaaaaca gtttggcagt tcatcaaaag    41767
attaagcatg gaactaccat aagacccagt agtttcgctc ttagggattc cactctcaag    41827
agaattgaaa acatatgccc atacaaaaac ttataaacat tgtatatcca tgtttgttgc    41887
agcattattc acaatagcct aaaggtagaa gcaacccaaa tgcctacaga tggatgaatg    41947
gataaacaga atgtggtata gacatacaat ggactattat tcaaccttaa agaggaagaa    42007
```

```
aattctgaca catgctagaa aataaatgga tcttgtatac attctactaa gtggaataag   42067
ccaatcacac aaagaaaaat attatgattc cacttacatg aggtacttag aatagtcaaa   42127
ttaatagagg catacagtag aataatgatt gccaggggct gggaggagga gcaaatggga   42187
agttattgtt taatgagtat agaatttctg tttaggaaga tgaaaaagtt ctggagatgg   42247
gtggcagtga tggttgcaca gcaatgtgaa tgtacttaat gccacagaat agtatactta   42307
aatatggttt gaatggcaaa cttttgttaca tacattttat cacaattaaa agtttgaaa   42367 tgaatatcca aagaagcatt atttatgagg ctaaaagtgg aagtaaccca aaagttcatc   42427
attgatagct aaaggaaaca tggcatatca aaacagtaga atattagtca tacaaaggaa   42487
taaagtacag acacatgctg caatacagat gcaccttaaa aacattacac taagtgaaag   42547
aaaccagacg taaaaggcca aattttgtat ggttttatat atataaagtc gttcaaaata   42607
ggaaaaccca taaagactga aagttgatta gtggtcacca aggcccgggg gaggaatgaa   42667
tgaaaactgg ctcctaatgg gtactgggtt ttttggggcg aggggacag agtgatgaaa   42727 atattgtaga atttgatagt aatgataggg gagagtggca taattttttt taatatacta   42787
aaacccactg actcatatac tttacaagga tgtatttat ggtatgtgaa ttatatctca   42847
aaacacccct taaattttaa cgtatggctt ttatgatgcc atgtttctaa gaagcaacg   42907 tgtcccagtc tcagcttact atttctaggc atgtgacttt gagaaaaaat taagagacct   42967
cccttcttac tctgtaaaat gggaataata ataatgatga taatgataat aataatgatc   43027
ttaccagatt tttttgagtg ttaaatgagg taacatatgt agtgcatcta gcatagtgtc   43087
tggcatttac caagaacccc gggaacctga gcttcaactg cttctgatac tattccagat   43147
actatttcag gatattccaa tactgtttcc atatattcag acaatggac caactccttt   43207 agccatttta tcaaaactct ttagattctg tttcaaatcg gtctttccaa agtcttcttg   43267
tgctcctttg tagacactct tcagtcagag agagcttttt aatctcctcc aatttgctgc   43327
agctgtatct gtgcctcaaa acaacgcttt ctccccattc ctctttttctc tctgcccttg   43387 gaactctgtg gacttctctc atgttttaa cctactccct tttatcagtg catgtcatct   43447
ccacttattt gtagcaccca atatttttac tacatctttg accaattaag tcttacttgg   43507
gttatgtttt taaagtaggt atcttattag gtggtccttt taaagtatat gtccagtctc   43567
tccagctaaa ttaaaccct tgagcacaga gaccacatgt tataatgttt tacctttcc   43627 atagcactta gcatgttacc ttgacatggc atatactgaa tgaatgcttg ctatttatga   43687
gtttagttag tgccacatct catgaagtac agggacttaa tgattctcaa tcctgacttc   43747
atcttacagt cacctggaga ataaagtttc ctcttagctc aacaagtcag aatctctgag   43807
caaaatcctc aacttcttac ctaggtgata ctccttgtaag ccacactgtg aaccactgga   43867
ttcaacagat gaagtaatat aagccactgg ctcttaagcc tcattgatta ttgcggtgaa   43927
gatgtgaaga ctaaagatgc tttgggcatg gcaaagtgtt ctacagatat tagaattgtt   43987
attatggtac atttgagagt gtcattgctt tgagaaagat tctctaagtt ttttaacagc   44047
cacactgtaa tggaaatatc caattatagg tatccaaaac cttttaaact ctttatatca   44107
ggtgtatata ccctgttcct ttttgctaac ttaaaaatgt tcaaactctg tcttctctag   44167 gct ggc aaa cat tca gca gca cac cct ctc aag att gtt tac ttg cct   44215
Ala Gly Lys His Ser Ala Ala His Pro Leu Lys Ile Val Tyr Leu Pro
225                 230                 235                 240 ttg ctc ctg ttg agt tac aac gct tgg aag cag gag atg ggc tca gca   44263
Leu Leu Leu Leu Ser Tyr Asn Ala Trp Lys Gln Glu Met Gly Ser Ala
            245                 250                 255
```

```
gca gcc aat agg aca tga tcc agg aag agc a gtaagggact gagctgctgg      44314
Ala Ala Asn Arg Thr     Ser Arg Lys Ser
            260                 265 taagacagtg gagacagttg acacttgttt gtcaagtatg aatttattcc taatgtaatg    44374
gtaatctctc tcccaaactt caacttcaag ttaccctgca ccctctcaaa tacttttctt    44434
tattgtctat gcttaggaca catggattag attgttaaga tttgtgaatt tactaaagtt    44494
gtgtactgac ttatgtatag ctgtattttt ctggagaaag atagatttt atcaattctc     44554
aatgtctatg gagtttttaa aagaggtaa ggattattca aatgtaacta taaacataag     44614
aaaatgtgat atctataacc agttgttaga gtatttatcg cctccatttt gcttcacttg    44674
tagccacttc gtctcaatct tgttaaggac caaataaatg gtatttgtgg ttacttgctg    44734
atctgaaaag tgagtacctc ctgcacctgg ctagtcagtc ttgtgacaat tggtgccat     44794
agaactagca gagaactaaa ttatggaatg gcagatctca ggagcagcta tgtgatttta    44854
catacggttt gttttaatg gatagagaca gagtctggct atgttcccca ggctgctctg     44914
aaactcctgg gttcaagcca tcatcctgcc ttagcctctt aaggagctgg gattacaggt    44974
gcatgccccc aggcccagtt catatgattt tctgaaaata caaagaaag agggagatac     45034
aaaatacttt tttaatcatg ttcttataat tatcttaata aaaatcaatt tgctctgaat    45094
gccatgacct gctgagtgtc ccaacctaag ggttgtcaga ccattttctc atatatgcat    45154
gtatagaagt agggaactaa tatattttg tctaaaatgt ttaagatgaa gatgagaatg     45214
aattctacaa tatataattt tgcctgaact atataagaca gttaaaatta tagagacatt    45274
gcaggagaga ctctggatta gatagaaaaa aggaagaatt aggctttttt tttgtctata    45334
atccttttag taggtaattc agcttcagtt tcactaaatc ttgtttatgc attcagcata    45394
acaaatcttc taataagcct gtatagctct aatctctgcc ttactgcaga cacctgagga    45454
tataagtatc cactctgcca cttgatactt ctcagagact gttctggtgc tgagaaatcc    45514
tttccagtgt gtcctcagtt gaactcccat gattcctgga tgttgccatt ttcaagacac    45574
agggcaagcg catctgtcta gattacctct ctaccttggg aattttaagt cactctgtga    45634
gggaaagaga actcagtata gtagtaactc tcagaatgaa aattttcccc ttgcatgtta    45694
atatttttag agtaatcatt gtcactgaaa atagacttcc tctttcccct ctcatgctgg    45754
aaaatcttag gtaattatga ataaagcatt ctttactttt cccctcctcc cttgatgatt    45814
gctttacctc actctgtgag aactgtgact actcattctg ctcttgtctt ttacatgaga    45874
actgagagcg cattttaag atggaatttt cctccttaat gaagtcataa cattagtcag     45934
aagattttct cttcttgaac gttaagcctg ggtaaggaat aaagtgcaga agtttatgga    45994
aaattataag ataacttaaa aaaaaaacga agacaacaaa ttaaaatatt agccattgag    46054
ggaaaaggtt ttacaggtag ctctctgagg agttcttccc tcatatctcc tcaaaaatct    46114
tgttttgcat ttaattttt acagttggat aagctcagcc cttgacatat tttcaatagc     46174
aaataagcct agagtttatt tttagtacat ttattaggaa tgtgttcttg ggaaaattat    46234
ttaacctctg taagccctgc tttaaatggc aaagaagaaa gtaggtaata atagataata    46294
acaggattat tttatgcatt acctgtacat tgcccaacat atagtaagtt ctcaatttta    46354
tattggtatt tgttttatta ttaaccactt ttattaatgt tgcttttagt ttttgaaata    46414
tgaattcatt caaaaatatt tcttgagcac ctgccaaata ccaggcactc ttctaggaac    46474
tagagtggca ttaatgagta agaggcaaaa atctcttccc ttgttgagct tagaatccat    46534
```

```
tagagtaaga gacagacaca tacaaaataa aatgtataat atagtaaata ccaagaagtg   46594
ctaagttttta aaaatgtaaa gcagaaaaag gaaattgagt ggcagggtta ggtagtaatt   46654
gaagatatag tagtcaagta aggcagcttc aagagaagat tatgtcttaa ataaaaatct   46714
gataaagata taaaaacaag ccatgaagtt atctgaagga attgcaggta gtggagaaca   46774
gccaaaagac ctggagtagt aaaaggtttt atgcagagtg atttaaaaag aatcacagta   46834
tcttatacat cagtaaatat ttacacatac acttaagtaa gtgatatgga caagaacttt   46894
ggaagttgaa tagcaaggtc catctggact ataacagagg aggcttcaca aaggaaggtg   46954
acagggcatg gcctggatcc tgaaggacag gaagaattgg gatcgataac aaagaatgac   47014
atcccagtgg agagaagtgg aggggaaaca gcatgaaatg gagtgaaata agaatgttgg   47074
cctttagggc aggaatgggc caggcagagg gcaagtggga agcaggaaaa aggcgacctt   47134
gtataaagtt catgttggca aatagagaga agatgggaaa gcagggtaag gccaaattta   47194
gtaaaatcct aaagtcaagc taaagattat tgcatgctat cctgaaaata ttggggaata   47254
attagagcag atgagtagaa aggtgaattc ttgtatttag ctatatcatt atttttacaa   47314
atttaaacaa ataaggaaat ggaggcagta gttggagtaa tttaggagat aaattgaaaa   47374
tggattttgt taagagagaa gggaagatag attttatata ttttaaggaa aaatcatgag   47434
gatttatttg ctgactgcac gtaagagata aagagagga gtcaaagatt tctctaaaat   47494
tttcaaaatg attaattacg tgttggtatt aaaagaaata gggaagttgg acatatgag   47554
tttgaattca gcatgagtca gttaagacaa tcagatgcag atattcttaa ggcaactaaa   47614
gttcatttga tatttgtcat ataggctgaa ttaagtttct aagagctgtt tttactatgc   47674
attaaatccg tgtaatacta acatagtaca aaagttgttt gctatccaaa ttttgtattt   47734
ttataataag ttggagagac agagaatcaa aaaattattg atttggaacc attagacatc   47794
agctagtcca attagttcat tttgtggaag gaaaaaggat acccagagat gttacatgac   47854
tttatagcca tgcctctagc tagtatctaa cttggtctag cccaggtctc catactgaga   47914
ctctcctcct gctaataaaa aaataataaa aaagtattag tggtttgtat tttgctggct   47974
tgcttgtgga gaataggatt agaaggtttg acttgcctgt tagcactctc ttgtagccat   48034
ttttctaatt aacatacaca ttttaccctt tctcatgaaa cagatctaac ttgtttagaa   48094
gcttcagtct tcttgattta attaatcact ttctcccacc tttagtcatt gttgaagtttt  48154
cctgatttac aatgttatct ttttatcttt tcagtagtat aaggaggaat gatatttcta   48214
ctgttgtact atttttctgt ttatctttca gaagaaaaat agcttttctt attggcccaa   48274
aaaaccatca ccctacagga aataaatcac actctttgct tgattttcct gatctggcta   48334
ctgatttctc ttcaaattta agccaatact tagactttaa gacttcattg ttacttcctt   48394
acaggtcatt cttatgaact aaaatccata gtcattgttc tagcaagcct gagcagttta   48454
ttctttgagt cacaggatta taaaagaaaa aatagacctt agagatcata atacagtgct   48514
cttcaaactg tactcttcaa ttttttctact acttatcagt tgtttttttat tctaataaaa   48574
tataattacc tagcaagtga gcagacatgt atttacagta gctttacaat tctttataca   48634
cttctttact ctctccatta cacatgccac atggtatgat acaagtcata actcaactat   48694
gtgaaagcaa aaccactctt atacatggtg tcttgcatat atattaaggc ccagagtggt   48754
atcagtagtc tctgtgtccc aagagactga attaaacaag actgttgacc ttcttgtggc   48814
atttatctga caaccttggc aatccctaaa ttcacaaata gctgtatagc attttttgca   48874
tttaatgcat atccacatat gatgtgtcct ttgattttag aacaagtaaa gcatgctaaa   48934
```

```
atagactgca ccttatgaaa gtcattttca ctattcttgt gtttcagttt cctcatcaaa   48994
aggtgaaata tcagctgcct ctgttgatct caggatcttt aagtagaaa tggaagagtc    49054 ttagtgaaaa cagtttgtat tctgaaagaa aattgcaatg taaatacagg cactaaaaac   49114
gtttattcat ctttacagat gttaatctga ccagacattt ttctcaaaat gtgaaaatag   49174
tatggatttt cttagctcat ttaatattga aagactagaa aaacaagtaa tgatgttcta   49234
gaagaatcta tgatcatata attacagttg tccttcagta tctgtgggag attggttcca   49294 ggaccccca tggatatcaa atctgtgga tcctcaagtc tcttatataa aatagtgcag     49354
tatttgcaca tgatttacat ataccctccc atatacttcg aatcatctct cgattattta   49414
taatactaca atgtccatgc tatgtaagta gttattacac tgtattgttt agggaatagt   49474
gacaagaaaa ttaatctgta catgttcatt acaaacacag caatccattt ttttctgag    49534 tattttgatc tgtgattgat tgaatccaca gatgctggaa tccatgaata cccatggggg   49594
gctgactata atgttgtcta tgtgcgtagc aattttgtaa ttctcaacca aggacacgta   49654
tagtccttga atcttggtag gagtcttggg gacttttctt aaaatatttt gaccatcttc   49714
tcaagatctt gactcctacc cccacttgta cacgtgcaca tacttgtgca cactcacaca   49774
caatacccct cctttaagtcc tgctcaccag cttgcttcct attgcattga gagcattcaa   49834
cctgtagacc aagaacttct accatatttt tccacctcta ccccaaaaca cagtttagac   49894
atatccattc ttttcattct tcagagtcat ctcaccactt ccataaatta tttcctaatt   49954
gttccctctg cctctgttct ttttttttt tctgatgatc agttcaaagt acctctgtat    50014
gcccattctt aagtgcaaat ctgaccatct ataccccttc ttaatatcct ttcttttatg   50074
gatacccatt tcagacttta ttaaaggagt ggaagcttcc ccctccccac ctcaccactt   50134 gaagttttg caattagaat ggagtttatt tggttaatgc aaaaatagat gtgatgtaga    50194
attcttgggg acacctactt atcccctttt cagagtggcc ctgaatagct ctgtgaaccc   50254
aggaatctga agaactcagt acagaaaacc atcagcctac agaaagtaga tcaaactcta   50314
tgcttgatat tcctgatctg gctcctggtt actcttcaaa ttcctcctta ctatattgtc   50374
ccttcagatt tgtaaatctt taccgtgaca tcgtatttta cacactgaac ctttgtaccg   50434
ctgttcctct cctgatgaac ttcccttttc tcttaactac acagctcaga tttctcataa   50494
gggaagcttc atatttgttg tggcactgtt gttcctcaaa catcctactt actgtagtca   50554
tttgtttatg cttgtctcct ttgcagattc tgaaattcct agggcaaagg ctgcatcttg   50614
tcttcttatt actaatattt tacacagtat ctggttacat agtaggcatt caatcataca   50674
atttaaaaga agaggttgac tttgtgatct ttttcatatg tttttatttcc ctctcccct    50734 actggcaact tcttcctact tcttaaaata gatacagcac ttgcccacta agtggaggga   50794
agaggtgtgg gagtcgagta gttggaactt caagtgtcaa acatgataa tctcatttgc    50854 aaagttacat tatatcggag cttgaacctc agagatactt aattataagc aacacttgtg   50914
gaacatttga tacctacatt tttttcacta aagtatccta tcaaaattaa atgtgttgca   50974
gttgagattt gtgaggtttt agctatttag agacttaagg gatatgttta gtgttctaat   51034
tctaatagta ttgatgaata taaatgtttc actgtagaaa gagaagtttg agagctgttg   51094
tgaatgatat ttgatgtcta ttaggtgata atttctgatg actaaacatg ctcaagacct   51154
tagtgagaaa tacatgaata cagaaaatat tttgaaaatt atgagaagtt tatcattgat   51214
tatagatttt cttatccagc agttttggt tgtgttctgt ttttcactgt cagagaagca    51274
```

```
gaaagtggtc agtggacttt agaatgtagg ctcttgtagg aggccatatg tttgagagtg    51334
ctgtccaggt gctttgtgat gtggctgaga atggatgcag gcttgcaggg aaaaactaat    51394
actgtagatc tctagagagc attttaggaa agacttctaa gctttaggtt ccctgaccaa    51454
agagtaaaaa gtgattctta atatccatag ctatagagga aagtaaatac acttcccaca    51514
tcaaatgtag aattaaatat ttaggcattt caagtgtatt tcatttagaa caaaataaaa    51574
tcatatattc actaatgaaa tataaaacca gatggtctct gaaaggtttt tcccttttact   51634 cactttcaga gtaaggcaag gaagagtagt tttgtttttt aatttatatt ttaattgtcc    51694
ctttctgttt ttccaaaagt tttatttttt gaaagtgagt caccttttag acatttgaaa    51754
aattagaatt actatgatgt ttatttttatt agtaagtctt cctagagtag caacgtagaa   51814
aagcatctct gaatgcctac atagtaagta tttaataaat gttttttggg ccaggtgagg    51874
tagctcactc ctgtaatccc agcaatttgg gaggccgagg cgggtggatc acctgaggtc    51934
aagagtttga gaccagcctg accagtatgg tgaaacccca tctctactaa aaatgcaaaa    51994
ttagctgggg gtggtggtgc atgcctataa taccagctac tcgggaggct gaggcagggg    52054
aatcgcttga actcaggagg tggaggttgc agtgagccga gatcgtgccg ttgcactcca    52114
gcctgagcaa caagagtgaa actctgtctc aataaataaa taaataaata aaatacataa    52174
ataaatgctt tttgatttaa cgaaggtgtc attgtcctat gaaaaggaaa actatcaaaa    52234 tatattttt aaaacttagc ttttgataat gatatgaag atatttctct taattaacct     52294
aagtcagaaa ctaaaatatg ttataaaatg ctaacatcaa atatttgaga ccagttaaag    52354
gagacagaag gaagttatgg agaaagaagc agtagccaga aaataagggc aagaaaatgt    52414
tttctaaatt tatgagaatc agaatgttta caaaattgct attattatca tctggaaaaa    52474
atatgccttg taggctgaaa aaatgaacat tcccttttcca taccatgcag gaaccttctt   52534
tactgcattc ctaagaggac tagtctagca cctaattgga tacttgtggt aatatttggg    52594
aactcactga tctggtacat cagtgtggga gtcgagtagt cagaacttca agtgtcaaaa    52654
catgatagtc tcatttgcga agttacacta tattagagct tgaacctcag agatacttaa    52714
ttataattaa cacttgcaga acatttgata cttacatttt ttttttcacta aagtgtccta   52774 ccaaaattaa atgtgttgca gttgagagtt gtgaggtttt agctatttgg aaactttagg    52834
gatatgttta gtgttctaat tccaatagta ttgatgaaca taaatgtttt actgtagaaa    52894
gagaagtttg agagcaagtt gagcaagaat ctgtcactct aggtcttcta ctctttatta    52954
aagaatgttg gattcattta taacttactg gtcccttaaa tattaaagtt tggtgtttgg    53014
tatcttaaac atgattacat ccttataggg ctctcttcta attgcctgga tactgcacat    53074
ctattaatac agtctcaaag cacacttgct tttttgatag taagagcgta cgatttaatc    53134
acattgaagt tagtccgcaa aggttttgt cttttttttca ggcaagcagc tgatgaatga    53194
atctctacta tccttcactt tgtgactgtg attttctaaa taaatgttgg agattttaac    53254
ttacaattta ttaatttcca tcttgtttct tcaagtccct cctttaagga aatttatgga    53314 aatcttttc cataccatca agtggcttat ttcttttttaa cttttttcct taagttcagg    53374
agtacacgtg caggtttgtt gcataggcaa ccttgggtca tgggagtttg ttgtacaggt    53434
tatttcatca cccaggtatt aagcctagta cccattagtt attttttcctg atcctctccc   53494 tcctcccacc ctccaccctc tgataggccc cggtgtgtgt tgttccctc tgtgtccata     53554 tgtcctcatc atttagctcc cacttataag tgagaacatg cagtatttgg ttttctgttc    53614
ctatgttagt ttgctatgga taatggcctc cagctccatc catgtccatg caaaaaacat    53674
```

```
gatcttattc tcttatatgg ctgcatgtta ttccatggtg tatatataac acagtttttt   53734
tttatccagt ctattattgg tgggcattta ggttgattcc atgtctttgc tattgtgaat   53794
aggactgcag tgaaaatatg tgtgcatgtg tctttataat agaataattt tttttttcctt  53854 tggtatatac ccagtagtgg ggttgctggg ttgaatagta tttctgtctt gaggtctttg   53914
aggaatcgct acactgtctt ccacaatggt tgaactaatt tacattccca ccaatagcat   53974
ataagtgttc cttttctcc gcaacctcac taacgtgtta ttttttgact ttttaataat    54034
agccgtcctg actggtgtga gatggtatct cattgtggtt ttgatttgca tttctctaat   54094
gatcagtgat gttgagcttt atttcatatg tttgttggcc gcatgtatgt cttcttttgt   54154
aaagtgtctg ttcatgtcct ttgcccactt tttcaatggg gatgtttgtt tgtttgtttg   54214
tttttcctgt aaatttaaga tcctataga tgctggatac tattgtcaga tacataaatt    54274
gcaaaatttt tctcccattc tgtaggttgt ctgttttctc tgttgatagt ttattttgct   54334
atgaagaatg tctttagttt aattagatcc catttgtgaa tttttgctat gaactggatc   54394
tgatataagc atatgtttaa ttttaactcc caggtcacac tgtttttttt tgtttgtttt   54454 gttttttgttt ttgttttttgt ttttgttttt ttggagatgg agtctcacgc tgtcaccagt  54514
ctggagtgtg gtgatacaat cttggctcat tgcaacctcc acattccggg ttcaagcaat   54574
tcttctgcct cagcctcctg agtagctggg actacaggca cacaccacca tgcccagcta   54634
atttttgtat ttttagtaaa gatggggttt caccatgttg gccaggatgg tctctatctc   54694
ttgacttcat gatctgcccg cctcagcctc ccaaagtgct gggattacag gcttgagcca   54754
ccacacctgg ccccaggtca tactttttaat caaaatgaga aaaagattg acttcactgg   54814 agtgcttatg tcttgttttta tattcaagtt ttaaatttat gttcttgaga ttattacatc   54874
ttgagttact tgataatacc acggttgaaa tccatgttgt tgaatccttc aacccttga    54934 ggactgagaa ttcccttaa ttatctgtct gaatcattaa atacttgtaa atcaagagtt    54994
caatttagaa atgttatact tgatacattt tttaaagctg gataaattaa cctattaaac   55054
aaaattatct cttcttcaaa aaaaaggcat cacttccccc acaaatgtgt aatttaggaa   55114
ttgttttcta ttggagtggt tcacgcttat atattttagt tgctctaatg caaggtgttt   55174
cctaaaaagt ttaaggaaag tataacttta ttttcatgta tgatagtaaa taatacaata   55234
gggggtgcat ttgtgctatg cttgttttg ttcccatttc agtgctcaat tactgtagct    55294
tctaataaat aaaattatca gttgctaaca tttaaatcaa acagttccac aagtggaagt   55354 attgctatt tgtgagagtt gtgttttttt aaacttaacc ttactgaggg gtttaaggga   55414
ctgctaatta tagattgtac taagcaaagt ataaagtaat agaaggttac caagttgagg   55474
ctagaattca attagtgcca atacagttaa aatggtatca ttaacagaac atcttcatcc   55534
aggacctttt tttttttttt tttttttttt ttcagacagg gtttcactcc tgttgcccag   55594
actgcggtgc agtggcctga ttgaggctca ctgcagcctc aacttcccag gctcaggtga   55654
tcctcccacc tcagcttcca gagtagctga gaccacaggg gcatgccacc accctggct    55714 aattttttgt atttttgta gagacagggt tttgccatgt tgcccaggct gttcgcaaac    55774
tcctggcctc aagcaatcca cctgcctcgg cttcccaaag tgctggaatt atgggaatga   55834
gctgccacac ccagcccctc cggaatcttt agattaccaa cttctgtctt ccaggttttt   55894
atgtccttgg aaatttatgc atatttttag aggtaagacc catcctcatc ttcttcctaa   55954
tccttgacat attgtgaaca cagatatata tacaattaag tagttccctg agttacaaat   56014
```

```
atacttaaat atactttaac ttattataga aggcttacaa aaactgtgga taaataacat    56074
atatttatct tagttaatga ataactgatg ctgaaaataa tgtgaatgtc aaattagttc    56134
tcttttttc  tagccctcac cttgaaaag  cctgagcctc tgagatgtga gatgactgct    56194
gtaaagtgaa gcagcgaatt tctagaggct gggttcacgc ttcaggtcct ctaaatccta    56254
ggtcgcttcc cactactaca tactacccta aaaaatctgt aattcgcaaa tttatttttt    56314
gatcttttc  ataacttatt aaattttat  tgaacaaata caggaaacag ttttaaatta    56374
ctcattgctc ttgaatacat tggtgattat ttttcttctc tgaaattctg ttttccttaa    56434
aggcagtcat ttttggtct  cttctaaatg acacttagta tttttagtaa catcataact    56494
tcagtggcca cagtgagccc tcattttgca acatatgcct acttttcata tctggcttgc    56554
ctttattat  ttataattta atgaaaagaa agtaccactc tttccatagt tttgtaatag    56614
aattgctgtc aacaaagtag tggatgcact atgttataaa gatttcattg tgaaaacatg    56674
aaatggctgt taactataca tcaggcaaaa taaaaacagg aaatataaac atttcctgga    56734
acagggcaga gtatgagtaa taaggtatca aatataattg gatacctgac caaatatttt    56794
taaatgtctt aagaaatgtc actggaaaga ctggagtact tggatttgtc tcttattctt    56854
attttgattc ctaacactgt gcttggcaca tggtaggtaa ttaataaatg tgtgatggat    56914
gaataatgat tgtcattcaa ttagtgacta agagagttgg aaagggctat caatttcaaa    56974
ttggttcctt taagacattt ttacgtaaga tttgggagaa agtaaaaga  gcaccatatg    57034
attatgcttt actaagagct gcttccattc ctacattgac catgtggact catatttggc    57094
ctatataatt acattagaat aaacaaagca ccaaagttg  gaaaggaag  tagtagtagg    57154
agagggtttt aagctatgta tttactggga aaaaaagtca tgttttcttt tttaaaaatg    57214
ttctaaacag tactgtaatc acttgggaat tgaatgtgct ttgtgtcaga caaggtctt    57274
tgtatacaat acattacatt ttgtatacca atacattaca ttacacagaa gggagtgcct    57334
ggctttgtat acaatacatt acattttgta taccaataca ttacattaca cagaaggag   57394
tgcctggctt tgtatacaat acattacgtt ttgtataccaa atacattaca ttacacagaa    57454
gggagtgcct ggctttggga aacacatcta cctaaactct taacatagca caatgctgcc    57514
atacggtagg taataccaag acaaatcagg gccgttatta acaaccttga ggaaatgtct    57574
tgggaaatat ttaaataatt tttgtttaat tataataagg aatctacagc ctctgtgaag    57634
tcatcccaaa ctcttcgagg caaatttagt ctcctcccac ccctgttttt taatgtttct    57694
aaaggatgtt atgtataatc tattagaaaa ctggccaagt gcagtggctc atgcctgtaa    57754
tcgcagcact ttgggaggcc aaggcgggta gattacctga ggtcaggagt ttgagaccag    57814
cctagccaat atggcgaaac cctctctact aaaaatacaa aaattagcca ggcgtagtgg    57874
caagtgcctg taatcccagc tactcaggag gctgaggcag gagaatctct tgaacccggg    57934
aggcgaggtt gcagtgagtt gagttcgcgt cactgcattc cagcctgggc gacgagtga    57994
gactccgtct caaaaacaa  aaacaaacca aaaaaaaaa  aaatatatac acacacacac    58054
acacacacac acacacacac acatacatac atacattaga aaactaatta cattgttttc    58114
ttaaaatgtt ttaagcatct ctcttcctca aggacaagaa tcttgaatcc ttagtgcata    58174
tgaggtactt aatagatatt taaatgaata gtgagctact attgcctaaa aatattagac    58234
atcatgtaat atcaggccta cagttgatag aaaaagtatt ctcaactaag aataatttac    58294
caatggagaa aactgttagt tttcccttct ttttctttgc tttataaaat ttaaatgaca    58354
ttaagagtta cgtttcttgg aaaattgaaa agaatatctg tggcacaatg ggctctgggt    58414
```

-continued

```
ataattgcag gataatttga aaagtttaaa gaatattttc aataggtata agtttattta    58474
ggctctgtgt ctcctcttga gatgacttta gcagtatata tttccctgga acaccatgca    58534
ctctaggttt tctaatttat tggtttaaaa tacatggcat tttactacgt aaatattctc    58594
tgtatctgta ggtacagcac ctctgtgtac actaagttag tgtatgtatt tttttaaaat    58654
tgccttagtt ttgctattca ctagattatt ttccaaggaa cctactctta gatttattaa    58714
gcctactata tatattttgt tattaactaa ttctcttatt tttaaaaatt acttttcctt    58774
tctttgctta aatttgcttt gttttcctaa attagtgatt tggaatactt aattgttttt    58834
attttgtttt gttttgtcaa taaaagagtt ttaagactct agttatacta tagctatagc    58894
caatgcattt tgagaggtgc ttacatatta caattatttt cagaaattcc ttatttcaaa    58954
gctttgcttt ctttgaacaa agagttattt aggaaaagaa aggaataaaa atctcaactt    59014
attctccact tgactagctt tattatttgc agtattctgt tttttacttg ttctaatact    59074
tctttatatt ttgttgtgga attatgtcac ctaacaatat tttccttaac ttcttaattt    59134
tagcctgttt tccaagttaa tcatttatct gttgtttcaa tgaataccta agaaaatttt    59194
ctttgtcagg ataaggcaca tgaggtctaa gatttatttc tagaacagta agcaaatcat    59254
ttctgaaagt gtgttcttct actattaagt aacatgttta tttttgtctt ttagttgaag    59314
tccccccaa cccaataggt actattctga tttgttctcc tattcacaca ttcttgaagg     59374
agagctgatt tatctgtacc cacaaaatta taatataatt ttctcagagt attcaaaaca    59434
ttgtcttttt tattttcttt tttttgagt ttttcactct tgttgcctag gctggagtgc     59494
aatggcagga tctcagctca ctgcaacctc cgcctcccgg tttcaagaga ttctcctgcc    59554
tcagcctccc gagtagctgg gattataggc atgcaccacc actcctggct aattttttc     59614
tattttagt agagacggag tttctccatg ttggtcaggc cggtctcaaa ctcccaacct     59674
caggtgatcc acctgcttca gcctcctaaa gtgctaggat tacaggcgtg agccaccaca    59734
cccagccgaa aacattatct taatggagca tttagaacgt tatcactgac aaacttttt     59794
ctattgaaaa tactgcttaa aagatcaggt catgcccacc ccacaaccca caccctttgt    59854
atttctcttt tacttgtctt ggcctctagt tcagatttat agtttggtaa tgtctgattt    59914
tctttgttag tgcttcagcc catctggttg gggaacagct ctatcccact gggacctctc    59974
cctttcctca tgagtgacgc cagggtcctg ctgcccataa gcattctgtt tgctgagttt    60034
gtatatattt cctttcccca gcttcgctgc ctttggctgc tttgtgatta agtaagacat    60094
acccatgttt cctaaagcct ccttcgcctt tagtccttga tgctggggac cttttggttg    60154
ggaagacagc ttccttatgt cagggtgagc ctgctacaca ggtatgtaac tcagacagtg    60214
acctactgtt gagtttctgt ttagtgtttc tttgtctccc tcaaatggta caaacgtgga    60274
gggcttcaac tgcagtctac ctttgtcctg ttagttttgt ctatcacagc ccatgccctc    60334
caaataagag atgatggagc agtctgctta ttttctgtag cactccacaa ctgactttaa    60394
aagagggact gggattgggc tcttagtgat gacttttaat gtggattcat ctgcattttc    60454
tctagaaatt ctttaaactc tctgcctctc agctggcact attccatggt attttagtgc    60514
taatggggga tcttttctaa ttttttgtttt tctttgactg tttaaatcat ttactggaaa   60574
gagggcttag atatctgctc atatgctcct gctagtctac aagtcctcca gcctgatttt    60634
gttcatgaac atgatggaaa taagcttctt aaatgccttt aatattggat actgctttca    60694
aggaaattta aaatagcaag caggctttca agaagagaga ataaattatc agccagtctc    60754
```

```
gcaagaacaa aaataagcca agtcatataa aacaagtttg gagtaaactt gttttttacat    60814 ttcaaattcg agttgaactc ttcaagtgaa gcttcagaga tataaaaaac tttaactgat    60874
aaagattcca acattaata tatggaaatg tatgagctca ctgaaaattt tacataaatt    60934
ttactagaag aggtgactga ccagttgctt ttataagatt ctcaaaaaga tctcaaatct    60994
tagggactaa tattgtaagt atacggggaa attaagacaa agatttacta tcttgtgagt    61054
ttttagtttg gataatgaac ttaatttcac aagaaattgc tttagcacaa acatgaaaac    61114
cttaagcatg agaactctcc ttttgaagta caaagggaga ctaaagtgaa taactcaaac    61174
tggaaatgta gaaaattgaa tttgctatga tttgaagtcc tttcagaata gccaacagat    61234
tttaaacaag agttttattg catagtttct ttgggatata cattgaagga gaaggagga    61294 gggagtttta aaagacaagt ggaaagcct ttctgcttgt tttggctatg gcttccattt    61354
cagtgtctgt atttaaggga tcataaaagg aactggaaag actggtcaca atggcagctc    61414
tgtacctgta tgatttcgga tgtgaaaaga gtttagcgat ttccttgtta acctatactg    61474
ctgtggaagt cattcattat gcagttaggc attagcagaa caaataaagt tcacagctct    61534
aggaaccaaa tttaactta tcactcttct gatttagaat attttcatat gctttcatat    61594
gtcctacaga cgataagaag atagaatcaa tacttggtga ttgataggtt atttttaaa    61654 agggaagaaa gaattaaaca tccatggttt cttcttaagt aactgggggg atgatagtat    61714
ccctcacacc aatggggagt atagatgaca ggtttggagt gaaagacagt gaattccatt    61774
ttggataagt tgaatttgaa gtgcctatgg gacatacagg tacagatgac taggagacaa    61834
ttgaaaatcc aaattgtgaa ctctgctgaa gattagaagt acagatctga gattaaattg    61894
ctacttgagt tcatgggaat aaaataggtc attctgcaaa tggttatctc aatatcttcc    61954
tggccatctc ttgggtcacc ttgccaactt ttcattctct ttacaatctc taaattctca    62014
tgtttttaag gctctcatct taggccaact tatcttgggt caccttgcta acttttcatt    62074
ctctttacag tctctaaatt tgtgctttta aggcccccatt ctcaagctgg cttctctgtt    62134
ttggtgggaa ctggtagcaa acattcattt gtaaacaacc caaatggcta gcattgagca    62194
ggactcccca acatactcct ctgaattaca ttttgagtta tctgaaggat caatatctca    62254
aactaggaaa ctgtagcttt tcatttatt ttcatcatct aattattttt cttgccttta    62314
agtataaggg atagagactt gattgatttt tatgtacaac aagttaaaaa atttaattag    62374
gcgtctttgc catttaatca gtttatactt cttgaatctt ttccagtcat caaaaagttg    62434
ctgagcatgc gcagctttac ttactagctt atagcatgaa gaagagtaaa ataggagtgg    62494
ataaaggcac agtggtgagt agtcagtgtt tccaattaat ctcaaagttt aggattaatt    62554
tagcgtgaat tctgttcttt tgtgtcttcc tgcttttga cgtggtaacc tgccataaca    62614
aaaggaaaca gcaggaaact tggtaccaat taaaacagtc ttcttccccc aaagaacgaa    62674
ctgtcagcaa acaatctcaa attcaaagtg ataagtgttt tagagtgaaa caaggataaa    62734
gagacaaggc tattaaattt taacatctgc tggaacacaa agcgcatgcc agtagaatta    62794
agtttggcat ttaataagat acaatttgca catcagaaat gaaatagatg cctcaaggca    62854
tggtatatat atatatatat atatatatat atatatatat atatatatat atgtttgagc    62914
gaggggcact tctagcaaaa ctgaatacac tggtataaat gtctgcgtga aaattttttt    62974
atccattcac ttttggtgtg tattccagct gtgagttatt caaccaggct cactaagttt    63034
gagtctgatt aataacgttt aaggtcacat ctgattaaca gtatttgaag tttgaatttg    63094
ttctaagatg actcaagcgc aataacattt tctatatcaa aatgaatttc catccaaata    63154
```

```
gggaggaaat ctgaaatttc agttccagtg ttgactgaga tgctctggat gagcctggac   63214
tcagagctca ccaactttgg atctttatgt taagtagtca gtggggttga cttctagact   63274
agagatcaaa atgttctaca cctcttgata taggtcagtg gctgatgtaa tgtgcttcca   63334
acaactttct tttaactaaa acagtacata taccaagttg gtttgtcaca atgggaacaa   63394
aacagaaatc tgacaacaga tttctctaat ttttgtgtg tatgtttctg aatgggctaa    63454
aatacataat tttactcttc cttggtgaag atgcttttat aagaggacgt gtttaagaaa   63514
attaagaaat gttgtaggta gccatgaaag aattatttta aacagaatta gtatagaggt   63574
gtgaagatct actgaagggt gataagtaag tgtggaagag atggtgttca gcattgggct   63634
tcagtatgaa taggtagaag atgagcaagg cttagagaca agaagttcat tcaataggct   63694
gttgcggtta tccagcaatg agatggtgac agcatgagcc atggtagtaa agtaaggac    63754 atggataatt tgtgggttct acagacaata agaacataga accgataggt tatttttaa    63814 acgggaagaa agaattaaac atccatggtt tcttcttaag taactgcgtg gatgatagta   63874
cccctcacac tgatggggaa tgtagatgac aggtttggag tgaaagaatg aattccattt   63934
tggataagta gagtttgaag tgcctatggg acatacaggt acagatgact aggagacgat   63994
tgaaaatcca aattgtgaac tctgctgaag gttagaagta tagatctgag attgaattgc   64054
tacttgagtt catgggaata aaataggtca ttcagtaaat tgttatctca atatcttcct   64114
ggccatctct tgggtcacct tgttgacttt tcattctctt tacaatgtca aaattctggt   64174
gtttttaagg ccccaatctc aggctggctt ctccaactgt actcttactt gggatgatct   64234
tatctagtca tggggcatta ataccattg gtaggttaac acagttcaca attttctcca    64294
gcttagaccc cttgctgatt tcctgacttg tacactcaac tgcctgccta atatacccac   64354
tttaatgata atgtacatct caaactgagc ttattcgaaa tagaagcctt aattttctg    64414 tcagtcatat tgttcccatt tacccatcct aacaaatagc accatcatca accttttagc   64474
tcaagacaaa actctaggca ttatcttgct ttcattcctt tcatgtactt tctcacatct   64534
aatccattac caagttgttc tgtttctgcc ttcaaaatgt gtcctaaatt tatccatttc   64594
tctgccactg ctattctcta gttcaggaca ttctatcctt tctcttgtat tactgcggtc   64654
tctaaacttc atgtatctat gttttatact tttaattcat tgtctataca gctaccagag   64714
tgatctttta aaggtctaaa tcagttcatg tcactgcttt atatataatg cacctatggc   64774
ttcccactgg atttaaataa taatcttaac actttactcc tccatggcct ttacatactt   64834
ctagccgcac ctcaaaacac tcctcttgtt cactgagaac taactagacc agtttctctt   64894
ctcctcagct atatcatgct aatttatgct tcagtgcctt ttgtacttt gttccctcta    64954 gctgaatcat tcttccaggt cattctatca ttggcttttt cattcagttc agatagatat   65014
cagcaaatca agagagtctt tccttacctg ctctatctaa atagtcctgt tttagtcctc   65074
tttatctcat cactcagatt tatttccctc atagcactca tcagtctgaa attgtttgtt   65134
tatttggcta cttgtttgtc tagataaact tcactggtga aggaatccag actatcttgt   65194
tcatccctac atccctagaa cctagaacaa tatgttaaag ataaataaat aaatagatga   65254
aagaatgttg aagagaagag ggtccagtcc agcccctga ggtgaccagc atttagggaa    65314
taagccgagg cagaggaggg ccattaagaa ggagcaatga gagatagagg aaaactaaga   65374
acaaggtgtc cctaaagtga gagtgtccta acacaggtct aaatgaaagg atagttcaga   65434
agagggcact gcagctggct gaaagagaac aagaaaggct gtaaggtgga ggtgaatttt   65494
```

```
taattgagcc gtgaaagata gggaaattct gtatgaagga gtaaatggag gcatagaggc   65554
atagaggcag aagatgcatg cctgtttggg gaatagtcat cccatttgtc tttcacatat   65614
ctcatttaat acttctcatt taatccttttt agtgttaatg ttgtcactag attaaaaaac   65674
aaaggctcca tcaggatcac acagtaaaca gaagaatatg gatttaaatg gagatctatc   65734
tgactgcaaa gactacttac tgtaacttaa gtcattgaga ttccttatgg ccacctcata   65794
ttcaccctgc atataacagt atgccaatgt aggaatgagg cgtgaataag cagggtaaca   65854
atagaaacat attctcacct tgattattcc tttggtagct tcaagggaaa ttgagtttga   65914
ggataaagta actcttccca tgtcagcact ttatctgtcc tgaaacatga gaaattccaa   65974
atgttcaagc catgcagttt ttatctagtc agatggttga gaagtccagg ttacccatag   66034
ttgtaatgaa tacctcctct ttatcttctt aatgttctgc tttgccaaat gatctataaa   66094
gattactcag tgtacctttc agattgaggt ccagcagact ttcagaacac tacatttaat   66154
tacagaaacc caactaataa aataataagc tcatgttagt ttcaggtgtt gatttgtttt   66214
taatgtagtc aataatattt acatataatg actggcaact taacagagtt ataatagatt   66274
attcacctgt atttgccttt atttgtgggt atacacacat atacatgc cttaaactag    66334 agtaaaatca tttatgcata ctaaatcaaa tttgagagtc ccaaaatttt caaattgtgt   66394
atggctggtc tatattttct aggactgtcc tttctggttt aaatgaaatt aaaaattgaa   66454
ttaatgatat tagtctcttt taattttcta ttttttcat gattaaaaaa tattaatttc     66514
cagccaggtg cggtagctca cgcctgtaat cccagcactt tgggaggctg aggcgggtgg   66574
atcacctgaa gtcaggagtt caaaccagc ctggccaaca tggtgaaacc ctgtctctac     66634
taaaaataca aaaactagcc aggcatggtg gcacgtgcct gtagtcccag atacttggat   66694
ggctgaggca ggagaatcac ttgaacccag gaggcggagg ttgcagtgag ctgagattgt   66754
gccactgcac tctagcctgg tcgacagagt gagaatctgt ctcagaggaa aaaaaaaat    66814 taatttttccc cattccccca cccacccacc aaaagactcc attggagttt tattttacaa   66874
atgcatctgc tcatctactt cttttttaagt gcataaacta gttttacaag cttgagttta   66934
aatcttaact cctcaattct ttttctgaca tagaaatata caggtgcatt atgaaatagc    66994
taatagtgac tattttctag ggctgtaact caatatttat aagcataatg atataaacctg   67054 ctgaagtttg acacgtcagt atagttcttt tgttattcta agtcataaag gcagaatttg    67114
gaaaaattca cagcttttca aatatgcaga agaggaaaaa ttgagaggaa gcatactaaa   67174
atttctttag ccaattttaa tcaaattgag tttgaaactt acaggattat gcttcaaagc   67234
ttgtaatgat cgtcaaaagt agccttattc aaaatgacac actaatttct accacatctg   67294
tattcttctc attgtaagat gttacatata cctatgcttg accaaatgga cttcctgcta    67354
ttttaagata ttttttctgtg ttttaagtct ttctacaaat tttctcaagc atttccctt   67414 acctaggatg ttcttctttc actgcaagtg aagacattct aaaaattcct aaagcacact   67474
accaaaagcc cttcatttgg atgacccacc ttcctatgag tctccatagt tgcatgtctg   67534
atggcattta ttttaactct atgatctgct tctaaattag ataaaagctc tcagagagaa   67594
ctatgaccaa ttgtcattct gtttcccatg gcacctagta cagtactctg ctcacaggct   67654
caataagtaa tgagttgagc tacgttttt taaggcagag tctccctctg tcgcccaggg    67714
tggagtacag tggtgcaatc tctgctcact gcaacctctg ctgctgggtt caagtgattc   67774
tcctgtctca gactcccgag tagctgggac tataccacca tgccaccatg cctggctaac   67834
ttttagtaga aacaaggttt caccatgttg gccaggctgg tctccaactc ctggcctcaa   67894
```

```
gtgatccacc tgccttggcc tcataaagtg ctaggacaaa agtttgccat tgtcatgtta    67954
cgatatatat tggtttttgt ccatggtttc tggttcatag ctccaatatc ccttttttaca   68014 gtcttttgtt agaatgtggg gtgtgttgga cctcggggca ggccttagaa aacagaatct    68074
ctcctgcctt cctttcactt gtcccccgag ggagattttt tttttttttt ttttttttga    68134
gacaagactt ccctgtgtca cccaggctgg agtgcagtgg tgtgatcata gctcaccgca    68194
gcctcagcct cctaggttca agcaatcctc ccatctcagc ctcccaagta cctgggacta    68254
caggcacatg ccaccacacc tggcattttt tttttttttt ttttttttgt agagaggttt    68314
cgccatgttg cccagtctgg cctccagctc ctgggctcaa gtgatccacc caccttggct    68374
caaaccacca cacccaaccc tgagggagat tctaatcttc cccacccttc tgattttgag    68434
tcttaaaacc ccagagaagg tcccacccct tgcactgggg aaaggaatgc tgatgatcat    68494
gaagcctcca taaaaactca ggaggattga gtctggggag cttctggata gctgaaccag    68554
tggaggttcc tggaaggtgg ctcatccagg gaggacttag aagctccgtg cactttcctt    68614
atacttcacc ctaagcatct cttcatctgt atcctttgat aaaccagcaa atataagtaa    68674
gtgtttcttg agttatgtga gctgcttgac caaacgtatt gaacccaaag agggtgttgt    68734
gggaacccca actcgaagct ggttggtcag aagttctgga ggcctggatt tgtgacttgt    68794
gtctgtggca ggagcatctt gggaactgag cgtttaatct acggggtctg acactgtctc    68854
cgggaattaa attggaggac acccagctag tgtctgctgc ttgttattgg ggagaaaccc    68914
tcacacattt ggtcacaaga gagaagtttt ctgttttgaa tattgttgtg atgtgagagc    68974
agaggaaaaa tgcattttgg agaggttttt tcctacacag ccataggcag tgataagaat    69034
atgatgcttt tttccagaaa atgctacatg agacctttt ataaaatcta attttcttca    69094
actgagtagc atttaaacta aaaagaatag gttattcag tgtctctctg taataacatc     69154
ttacaatcac ttgtcagacc atgaaataat gttctagaaa atcagtgaaa gagcttttta    69214
aactttgtga catttgactt atatttatta ccaaaaagcc tgaattatta ttcagcacat    69274
tataatttta tttaaaattt aaattagaga tgaaatactt gtaaatgttt ataagattgg    69334
tagctgtgtg ggcttccaga gttagaaatg cctctgagaa aagatttaga gttttgaaag    69394
tattttgaaa aaagaaacag aaaggaatac aacatttttc ccagcactgc ttcaataatg    69454
cagtcttcag catcatctca aagcaataac tgcagtacag atgagatcag ccagtttttt    69514
tttccccctt atctgcagtg attttaccat ctcttcatgc tacatcttac cacaaagaga    69574
acattgaaac atgggaaaga gtttgctttg atttcaacca gaatgccaac tcatttctgg    69634
ggttctaaac cataaccttt tttagcagag cagtgtagaa ttttatacg ataccataaa     69694 tggtcggcct gagtaacatt ttaactgtaa gtcaatacct ttgaagagac atgtctgaca    69754
actcagagtt ctattttctc catgtgtgac taaagtacct tttctattaa gagatcaacc    69814
accatttcct tctactcttt gttctcccct taaataaagt taattcagct tcaaaatatt    69874
ttatgatctt gattactaac tgtgggtctt tagaagacaa tgtaaaacat tccatgctg     69934 tgaatattag agctagtata cttggagttt ggctagtatt tctgggggag gtagaagagg    69994
agacatagag tacaaatgag tattttaaa gccacgctga ctaaaacaaa aggaatgttt     70054
tatacatgtt tatttcatag tacttctttg aaacaggtcg gggggaggag agttaaaata    70114
ttgctttgaa ttttaatcaa agttctttca tggaattgtt ggtgcttctg gtaataacag    70174
ttctataatc tttgtgagtt aatctgaaat gctcttttc ttcatcgtaa ttcagtgctt     70234
```

```
gtcttaactg gtggacttat tttatggtat tatgtttata agatggcaac taaaatcaga   70294
ttttttatac tcctaaaaga tggatacgat agagggggaaa gggggtaagc tacaactttt   70354
aggttgttgg tgatatttga agtgtttatt gcttctgatt tacatttata tattatattc   70414
aaatataaac tttaaaagta atgatttgcc acaggttaaa gcagaacatt tatatgatat   70474
ttcctagatg ttttcctcta caatcctgtt tttgttctat gaaaaatgcc ataaacttgg   70534
atcattcact aattaatttg aagctgtttt caaacaaaaa gctaattcat cttttagcgg   70594
atttagttat aatcgtgata acagatgtat agctaagtct gttggacaaa ctgttggtca   70654
catcaatctt aaatgcatca tacagcgtga tgtgaattta tgatatttcc taggtaatgt   70714
taaggttata tggaaatttc tttgcaggta gttaagtctt attttgaatt caaatgttat   70774
tttcaataca tacgtggaag tgtattttt gtttgtccta aatgtttaga tttttttgagt   70834 ttacaatttt tttgtgtgtt ctttctttgt tcttgcccct ccctgcattc tctatgaaga   70894
tacatgtcag cactatgcaa cactaaaata acaatcaacc aaattatatc ctatgaacag   70954
accttctctc tcatttcaaa ggcataactt ggatggtctg tttagctcat ggtgaaaaaa   71014
aaaagttatg attttgtatt tgggcaaagt acaggtgaag agcgtgaatc attagaacag   71074
caatataact ggaagaagat agtttagttt ttacaagtta aatttgaagc taaagcaaaa   71134
cttgcatagg tatgtgtcct ttgctcttga aaatgaactc agaactctac atctgagtgg   71194
ttttatgaat ttatactctc ctagtccaca ggttctcatc agtgcctcaa gatctatgca   71254
cagattaaaa ttacataaga tatcatatac tacatctgaa ttagggtttt ccaaagtatg   71314
ctattccatg gaaatactgt ttattcaggg tgctccataa acaatgatcc tgtgtttcat   71374
tatgtccagg aaatgccaca cagcaccttt ccagacatcc tatcatcata ttaaagactt   71434
tgaggccatg cattaaagaa agttttaaat tagaaaaaaa ataagttttc ttgcttgagc   71494
acagaacttt attttttctc aggctggttc tcctttttta aaattacacg ttaatatccc   71554
aaagaaccag tcccatagat agatatcaca tatgataaga atctgtttca atggtgttgg   71614
tgtacatgtg tgttcaggta cctacacatt aggacacatc tctagtttat taatactgca   71674
cttataaaga gacatggtag agacatcaag aagacatcat tttagggtgg acaccattgc   71734
ctaggacctg cttcttaatg tcaaaaattc agaaacccaa ttttatctct cccgcagagt   71794
tgactcgagt gaaggaaatt gagttgtttt aattaaactc acatgagatt gatgtttaaa   71854
caaaattgta agtttatcaa ttaataatca agaattctga ttttttaattt tcaaaatatt   71914 atttatgtcc actgtccagg gtacttgctt taagggcacc cagtgattct tgaagatgaa   71974
gagtcttagg aatatttatt ttctagacct caatgaagaa agcttttaa tcatcctgcc   72034 ccatagaaga atttatgttc ctagtgatgt gatcatattg gccaatccag tgtttctttt   72094
ccaaggacag tactgataag gagcaccaaa tctacctctt tgtcctgaac agatcatctc   72154
catctattca tagtttggct cagaagttgg acaaggctgc attttatatc tacttcttcc   72214
tcatgtcggc tatgccatgc cgtttcgttc ttttagcttg tttacttatg tgtaaaatga   72274
ggtaaaaatt acacccttca aaccgaaagt ggtcttcgtg atgagttatt taattgaagc   72334
cccagtagat atttatcatt gccagttta gagaatcata gcattttaga acacaagatg   72394
accttagatg taatcatgtt cattcccctc gtattataaa ttttttaaaaa ttgagatgtg   72454 gggtggttgt gacttgctca caaacccaca tttagaacca aaactcagca ttcttgttct   72514
gactgtgtct atgtcctgta ggtatatgtc ttgtcttctc agttaaataa ttaaagattc   72574
ttaaagatag agaccatatt ttatgcaact tctggatccc ataaattatg tttccagaag   72634
```

```
aacctttttgt aatgaaaaaa tatatataat gtctatatta tatatatagt ctattactat    72694
tttgataatc taaaacatgc tatataattt taggcgatct taacctattt atcagagctt    72754
ttcagatcaa agaaaattag agtaatcttc atcatgtatg ggaacattga tgtatttttc    72814
tgatgaacac atggttatat gatactcttt taaagcatct gtattactct ttcttctgat    72874
agactggtta ttttgtttat gttatgaaat aatgttggca gcttttcatt agaactgata    72934
catattgaaa tttcttaaat tgatagctca tggatgtgca gttggtttaa tggcatctcc    72994
attattaatc tttaagaaga tcttcatctt actctcaaaa ataaccgtaa tatcctacaa    73054
attaactaaa acatgatcat tgctagttgt tccaaaatag gaagaataaa aatgaccaga    73114
ttgttatggt aaccagttga ttaagactag atcaatagga aaacgaattt attcaagtct    73174
gtacaaaact tctccaaaac atagatggca tgccttttga ggcaatggta gggaacaaaa    73234
tattttttgag aaggagcaga ttttagggat acagtacagt acataattgc caaaatgctt    73294
gtgttacaag gattcctggt acagagtttt taaataaaat gctaggtatg tcatgtttgt    73354
ttcacattaa tattgtagag tcccctgggg atgtgacaat ttagttgacc aactctaata    73414
tagttaattt ctacctttttg atagctttgt ggggttttgt ttgtttgttt tttgttttgc    73474
cattcttgat tttagggctg aagatatgag acaatgtatc aaacagtaaa gaattatgca    73534
ttgattaaga tcatcttggt gaattagatg tttattatat aactcgactt taagactttg    73594
ttcagatctc actatcttaa tgagatttac cctcattata tagtatttaa tagggcaacc    73654
actccccgat actcttgatt cctcgttagc tgccctatta tttctttgtt tttcccttag    73714
cactcaacat tttcttacca caccacataa tttactttct tattgtgttt attgttttttc    73774
tcctcattag aatatcaggt ccaagaagac aggagtattt atctcttttg ttcagtggtg    73834
tgttactggt gactactaga gtgcctgaca catagaatat gttcaataaa tattcgttgc    73894
atgaaagaat gaataccttg acagattatt tttataactc taccagtgtc attatataac    73954
tacactgaat gattatgagc cctcctagaa attacataaa gttcttatat attattagaa    74014
cccatttgtt ggccttatgt aatggttcta ttggaaaaat catacctccg tatataaaaa    74074
tgaaagtatt ttttttctac aattgcccct catatatact attatagtct ccttcaccccc    74134
attcagccat taatgtcttc ttgaccaggt aacataattt ttacagcacc ttttggttat    74194
tagaacaatt ttatttgtct ttcaaactca gtcctattca ttttaaaact cccaactcaa    74254
gcctgagtca gtgttcttct cccagcacaa acttaaacac tggctccaac ccttggagtt    74314
gaaagtaggg gagcctcact cctgatacct ccccctcccc tctaccgtga gcaccagtgc    74374
ctaggagatt gggcaggact gaggaaggat gaaaaggagc tcagggctcc ttaagcacct    74434
gaacaagact ggaggacttt ggatgttgct atttttctgc ctggcattga ctggctattg    74494
gacgccctct gtgaggcagg catccgaata ctggctttct tgacatatat ggagcgttct    74554
ttagagaggc ctacaagggc tctcactgca cagtaccctg ataggagaga tctgtccttta    74614
tttcttctat caccatagct acttcagctt tgcctgctga gtccaccccca cagtctcttt    74674
ctgctgggggc atccttgccc tggacagatt cttagagcat gaccaagcct aaacaacttc    74734
tgcaattttt ctaagtacac ttttatttaa ttgaaagttt caagcattgg ataatataaa    74794
tgtatcctag acagtgttcc agtaaggaca accagctcac aattatccat tctaataatg    74854
gggagtcaact gaaatagaaa aatatagatt tttaaaataa tttatgagaa acaaatattt    74914
gtgacacagt acatttctaa ttatgtttat ctttattatt attattatcg tttccttcag    74974
```

```
tacacactag tttggtgaga cttggagaaa ggccaggaat aagcccaaat tcaaaaaaca   75034
attccaggat taacagataa gtggataata gagaattgac aaaagatcat gctcatttta   75094
ccaataagaa actggttggt taacttgggt tgcaaactga aagcagattt atactaaact   75154
ggcaggtgtc tccagatctt aaatgcagat ctctatctct gagttaatct gcctctcatc   75214
ttcaatggca ttcctctgaa ttttttctccc tcaaataatc tatatattat taaattttgt   75274
ttatactgcc attttaagaa acagatttta aaactttaaa catgggaatt aaataggccc   75334
tactgaggat tatgaaaaac ctgacaaaac ctcctatgca catgatttag attaggagca   75394
gtgcacacgc tgtatgtgta tgtgcagcta cttgtccaat taacacccttt tcagaaatgg   75454 aggaactttc tctgaggact ttgacatatt tgtgtgttca gcagtccttt ttctttttttt   75514 ttatttttta ttttttttatt attatacttt aagttttagg gtacatgggc acaatgtgca   75574
ggttagttac atatgtatac atgtgccatg ctggtgcgct gcacccacta actcgtcatc   75634
tagcattagg tgtatctccc aatgctatcc ctccccccgtc cccccacccc acaacagtcc   75694
ccagagtgtg atgttcccct tcctgtgtcc atgtgttctc attgttcaat tcccacctat   75754
gagtgagaat atgcggtgtt tggttttttg ttcttgtgat agtttactga gaatgatgat   75814
ttccaatttc atccatgtcc ctacaaagga catgaactca tcattttta tggctgcata   75874 gtattccatg gtgtatatgt gccacatttt cttaatccag tctatcattg ttggacatta   75934
gggttggttc caagtctttg ctattgtgaa tagtgccgca ataaacatac gtgtgcatgt   75994
gtctttatag cagcatgatt tatagtcctt tgggtataaa cccagtaatg ggatggctca   76054
gtcaaatggt atttctagtt ctagatccct gaggaatcgc cacactgact tccacaatgg   76114
ttgaactagt ttacagtccc accaacagcg taaaagtgtt cctatttctc cacatcctct   76174
ccagcacttg ttgtgtcctc acttttaat gatcgccatt ctaactggtg tgagatgata   76234
tctcattgtg gttttgattt tcatttctct gatggccagt gatggtgagc attttttcat   76294 gtgtctttg gctgcataaa tgtcttcttt tgagaagtgt ctgttcatgt gcttcgccca   76354 cttttgatg ggattgtttg ttttttttctt gtaaatttgt ttgagttctt tgtagattct   76414
ggatattagc cctttgtcag atgagtaggt tgcgaaaatt ttctgccatt ttgtgggttg   76474
cctgttcact ctgatggtag ttccttttgc tgtgcagaag ctctttagtt taattagatc   76534
ccatttgtca atttttggctt ttgttgccat tgcttttggt gttttagaca tgaagtcctt   76594
gcccgtgcct atgtcgtgaa tggtgttgcc taggttttct tctagggttt ttatggtttt   76654
aggtctaacg tttaagtctt taatccatct tgaattgatt tttgtataag gtgtaaggaa   76714
gggatccagt ttcagctttc cacatatggc tagccagttt tcccagcacc atttattaaa   76774
tagggaatcc tttcccattt tcttgttttt ctcaggtttg tcaaagatca gatagttgta   76834
gatatgtggc cttatttctg agggctctgt tctgttccat tgatctatat ctctgttttg   76894
gtaccagcac caggaccatg ctcagcagtc cttttcaag agatgtgaag tacatcttca   76954 cagatttta aatatttaga tagaaagttc ttacagaatg agaaataaaa agttagcttt   77014
gccttaaaaa tattaattca ccttatattc tccatactta atccatatag gaaacattat   77074
attccaggtc taacatgtgg cttgcttaca ttaattttgc tgttgaaaaa tatatgtttt   77134
ggattatgtt tttaaaattt tagctttaat atttaaatat taaataatgt taactttaaa   77194
ttaacgaaga atagttttta attttataag aaatgcccta taaaaaacac tttctttacc   77254
tcaagagtga gacttggcaa ccataccaat attacatagt aatttaaag tcaaacgaaa   77314 tggagagaac ttaatagata cagaagataa gaatttaaac taacatttg ctcgggattt   77374
```

```
tagaacacta tacagaggga aatttagtag acaataatga agtccatagc attgcacaca   77434
tcttgaaata agtgtataat tgacacaagc tatgtcccat gttgatagga agaatccaaa   77494
atagttttgg agaataatgc catctatgca ggaggtgtgg ccatatacat catctttact   77554
cagtgttttt catgtcaata aatatttaat tcctaacact ctgaattact aatagaggtg   77614
aagcctgtca gtggaagtga cagagagata cacagtgatt cccgtaagtt tgatcctgaa   77674
acacagtgcc tttagcagat atagttccca taagcaagca gtctgaagta tttaccctca   77734
gtaatctgaa tgtataaata aacaggattc atgatggtag agtaatttat atatacttgt   77794
agtattagga catgcaaaac ttattttatg gaaaaaaata atttactacc ttatagtatg   77854
gcaactatac aaatctataa attgactctt ttgtcccctt gaaaaaaagc tgacataaaa   77914
tttaaatgat gtgtatttt tcttagagca ataaagata tacccccacc tagaaaagca   77974
ataaaccaaa aataaaaca aaacaaaat caagccctct tcacaaattt gagcatatct   78034
acagctttat gtggtgagag atacagctac cattcttgag taatccgaag agtcaaatgg   78094
tatggagcaa aattacagtc ctaaatgcat attggtgaaa tgagatgctg atccatttgc   78154
acactaatgt gctatttta agtcatgcat catagcatct tcaaagaggc ctgtcataat   78214
tatgatggat tagactgcag agtcagtcct agatgcagta attgtttcac agatgctgcc   78274
aatgcgacta gaattataa taaattattt tcagagaggc gggagaagga acaaaatcaa   78334
aggaaaactg ctgtggctaa aacctgtttt ggtcttagga aaccaaaatg ttagctagta   78394
gtcaaaaggc cagtattttc aactgagata aacatgcttc attaatacat gcctctgaca   78454
tagaagataa aggttaacat aattgacata tcagccagtc tctctctctc tctctctctc   78514
tctctctctc tctctctctc tgtctcgtag cttatgaaaa tttattctgg ggcattagct   78574
gaaattattg agtggccata taattgttgc atgtttctat ttatgttaaa ttgcctggtt   78634
ataatttgac ctttagaatt tctgaaaaaa atggtggtat ttatagtaaa tagaaatatt   78694 cttttttggtt ccttggaagc ccatgcatta caaagaacat tagattattg gaataaaagg   78754
atagacatac ataatatgac tagtgggatc taaattataa cctttttaaaa ttgtaattta   78814 attagtctgt catttaggca aatgataatt tctaaaactg ccttttttaga cttaaaaaaa   78874 taccaaagtt cttataactt tagcattatg ttttgttcat tcttaaagtt taattcactt   78934
tgttgccttt ttggtaaacc tatgaagaaa tctcatgctg caccatatag taaaaaatcg   78994
tgtgtgtgtg tgtgtgtgtg tgtgatttga ataatgagct atgtgttata ttttgataag   79054
caaagataag tttatagtga agcagataaa catgccatgt attttcctag gttaagggtt   79114
caataatcag aagagcttct acaactcatt tgccttctca ctagttttt tgaaattgcg   79174 ctctatgagt ttttatgtg gtgttctctg tacttgctga ctactgatgc acatttctcc   79234
ttaggtcact ggttctcctc cctcagcaat gttgtaggta gctttgatga acattcgttg   79294
tcagcctttt acctttgact tagtgttttt ctctcatact acggcaagaa gaaatgaagt   79354
taaattttac aagagtgact tgggtggctg atatgcccac attgacaggg acaagagctc   79414
tagtcttccc ctctcctgta ttcccatggc acttcagtag tctcattgcc tcaacataac   79474
cacagttcag ggcagtagag gatgtttgca tctttgtgtt agctccatgc catggcaact   79534
gcactgagtg aggattcaac tcagtgcagc aggactgaaa aataaatga actaatgtgt   79594 cttgagctcc aattctctga gtgacattat caggggagat tcataaatca tcctcaaata   79654
ttctagagaa aaatcatcag cagtccagca ttgcaaagat aatctgggaa ggtggcaaag   79714
```

```
aagggatcag aataactctg tggcagcttc aaattccatg tcctaaaagt ttacgttttc    79774 tttttattc  tatcccaaac cacataaaga aatgatttgt tggcaaaaga catgcaaaat    79834
gcccttaatc atcttaataa ttacagacct acagatacgt agccaaaata cttgttttt    79894 aatcctaaac cttaaaaaaa aagcttaaat tgttggctaa atgtgaattt aataacaaaa    79954
cttactcctt taattatgca cttgtcttag tattgtgtgg tgggaagagc tttagagagc    80014
tgccagagtg cttaggccta gtccctgtgg gagcctctgt tttggtgctt caccatgggc    80074
agattcctca gttttcacat ctttaaaatg agaaaatggt actagatcct tgctgctact    80134
ctgaaatgtt tatacattgt taggaccatt gttacatatt attacttata tttgagtgtc    80194
accttagaat ttcttagccg tgtgatatgg tttggttgtt ggctcctcta aatctcctgt    80254
tgaaatataa tccccagtgt tggaggtggg ggcctggtgg gaagtgtttg gattattggg    80314
gcagatccct catggcatgg tgctgtcctc ctgatagtga gttctcaaga gatctggtta    80374
agggtgtgtg gcacgtcccc ctccctgtct ccttccctcc ctctctcctt ccctccctct    80434 gtccttcct  ccctcttcct ccctcttcct ctctcttttt ctcccactcc agccatgtta    80494
gatgcctgct ccccttttgc tttctgccat gattataagt tttgtaaggc ctcacccaaa    80554
gcagatgcca gtgctttgcc tcctatacag cctgcagaac catgagccaa ttaaacctat    80614
tttcttataa attacccaga cagctatttc tttatagcaa ctcaaaaaca gcctaacata    80674
cctttcaaaa ggttaaaatg ctatttagtc attccagaag caagatctct ttgtccagaa    80734
ttctggaaat aaagatgcca aaataatatg gcatgtattt gatctcaggg aatttttcatt   80794 ttttcaaaag gaggaaaaaa gagtaatata attttttaat attttggtag ctctaacagt    80854
gcttagaacc agttctcaag agcacattgt gaaactttca ggaattgcat gagctgtagg    80914
ttgataacat gatgccagct ataacccata agagcatctc ctgaggaata tgttaaaaac    80974
tgtattcatt cttaaatttt aactaaatgc aatgagtgaa gtattgacat catgaaaatc    81034
atccctgggt aaacaattag tcactccagg ttttcccaaa ggttcttctg tctctgttct    81094
tgtatataaa cttcgtaacc agtttaacaa ccccaaaaaa ggccttaatt ttgattggcc    81154
agcatcctct taggaaagac attgccatcc tcttgtaaag ttgcttctca ttctaaaata    81214
agaattgttt ccatctaggg aatgattttt ataggtagaa tcttatttgg catggactct    81274
tttgcataca gtgaattaca atgtgtagac cttcaatagc aaggtgtttg aatatttagt    81334
tgcacaatag agcagtatct taatattgta taccatatta attttgtgtt ctctggtgta    81394
agaaaaaata gaaggatgtt taatttcaac taaaaaatca atcatgataa ttcaaaatat    81454
ttctgatgag tcatttataa gagcagatat gaattaaaat tatatttttg ttcttagtct    81514
ctgagaagca aaaatcacac aaataatctc catagcaaaa atttatattt atctgaaaaa    81574
cagtttaact ttgaaaaact tttctttgca atcatttaaa ttcataaaaa aaattcatta    81634
actctacttt cactgaatag caggtgaata gcaggtcaat atctacaaaa attcatcttt    81694
gaagattttt ttatcttacg caaaaattat tgacttcatg tagactttt  atgcaagctt    81754 gaaaacactg tgtaaatgac cccataaaaa ctacagcatg aaagcttttt cagtatttct    81814
acaatgagca aaatgcatag gtctcatttc cttctctttt attaagcaaa ataatacttt    81874
atcaacatca gtatgcaagc actaagagct tgaaagagta ctgtgcaagt gggttactgg    81934
atcataatat tccagggtat gtatataaaa agtgtgattt agcacatatt aaagtaaaag    81994
aaaatattgc atttttctcc ttctaaaatg gcagttattt agtttaaatt tcctgaaata    82054
agatttaaag accaataaca aattttcctc attctaacat ataactttcc tgcccttctt    82114
```

```
gtgaaaaagt taaccattaa acttttcaca caaatggttg tataaaggac ttgctgtcac    82174
agacaaaata gttctgtata atgtttaaaa atggccattg tgtttaaaac tccatattga    82234
aatacatttc ttttttagtc accttcattt cttagtagct attattatac tcaaaggatt    82294
tgcccttgac actttaaaga atgtccaaaa ttatgtggaa tggattataa taaaagataa    82354
tatattaaat gcttaaaata ttttatacct tagaaagtag aaaaacatgt attatgtaca    82414
gatcctacaa attttatata atttatcata aatgtcacac tgtatataca tgtaaatacc    82474
ttttgattgc tctgtatatg aattggtgtt ttacagttac caaaagaaaa gtgccttttt    82534
ttggtagtat ctggacaggt aattgacttt cttcctgcag gatttattta gatttatgtc    82594
tatgctcctt aattttgtgaa aagtgatagt gtcctgattt tggagaagcc tctcatatca    82654
aagactacaa atcaattttc atgattttaa aacctaaagt ttctttatta ggtgttattg    82714
atgattaaaa gccattgtct cacccaaatt ttctacttgt tcaatagaaa cataatgtaa    82774
gccacatgga attttacatt ttctagtact cacattaaaa caagtgaaaa agaaacaaat    82834
tgatgatacg tttgatttaa cccaatacat ttaaaatagt tcaacatgta ttaaatatt     82894 tttgagtatt tttgtgtttt tttaacacta aatctttgaa atccaaacta aatgttttca    82954
tagataccac atctcaattt ggactagaca cattttaagg gctcaatagc tatatgtgac    83014
tagtcactgt tggatgatgt atatctagac catctcttaa tgtatggaag gaagtaaatc    83074
tagcagaaat aaaaacatca cttttgttttc tttgtccaat atgagttata actttatttt    83134
tttgagacag agtctcgctc tgttgccagg ctggagtgca gtggcgcgat ctcggctcac    83194
tgcaacctcc gcctcctggg ttcaaatgat tctcctgcct cagcctccca gtaactggg    83254 actacaggca tgcgccacca tgcccagcta cttttttgtat ttttagtagt ggcggtgttt    83314
gaccacgttg gccaagatgg tctcgatctc ttgacctcgt gatctgcctg cctcagcctc    83374
ccaaagtgct gggactacag gcgtgagcca ccgtgcctgg cctttttattt tatttattaa    83434 gtaatacaca tgcttggaag ttatttaaaa aaaaaaaaaa ggaatagtta aaagtaatcc    83494
ccctcccagt gcttttctcc agctgcccca ttcctttttcc tggaggcaaa ttattatggc    83554
cagttcatta tatattctcc agagatgatt ttttttttatt ttacaaaggt ataggttgta    83614
gcattcttat ataaactgtt gtgtagcttc ctttattcca tttaattact gggagatact    83674
tccatctgaa aatatagaga tactaatttt aatagctaca tggtattata ttgtgtggct    83734
gtaccataaa ttatttaaca taacccttat tgatgtaggt tgtttctaac cttttattac    83794
tgcaaaagat tgtgcctaca tcatttaatg tatatatgag catatttgtc agatatatat    83854
atatatattt tttgagacag tgtctcactc tgtcacccag gctggagtgc agcatcacaa    83914
tctcacctca ctgcagtgtc cacctcctgg gttcaggtga ttcttcttcc tcagcctccc    83974
aagtaactgg gattacaggt gcctaccacc atgccctgct aattttttgta tcttttttagg    84034 agagacggga tttcaccatg ttggccaggt tggtctagaa ctcctggcct caggtgatcc    84094
actggcctta gcttcccaaa gtgctgggat tataggcgtg agctaccaca cccagcctgt    84154
cagataaatt cttaaaaggg tcaaggaaag tgtttctgaa attttataca tattgccaaa    84214
ttgtcatcct acatgatatt tgtggcagtt ttgactctca aaagccacat gagagagtat    84274
ctgttttccc acatgcttgc caaacatagt atagtatcaa gcttactgat cttcactaat    84334
tggagaagag aaaaaaactg taccttgttg cagttttaat ttgcatttct ttttatgagc    84394
aatagtagat atcttcttaa atacttaaga gccattcaca tttcattttc tatgaactgt    84454
```

```
ccatgtccct tgtccatttt ttagtatgtg gttattcatt tatttgtagg cgtcctatat    84514
gttaagaaaa gttttataca acttttaact cttttttacat gtttattttg gcacatataa    84574
attttagcaa actttcccat cttttatgac ttctagattt tgtttcacaa aaaaagagct    84634
tagccagtca ttagattttt ttaagttttc tcagattgtt tttaactttt ggggggttt    84694 tatttcctgt attcaaatat taaattcatc tagaatttat cttaaagtgt aagggaatga    84754
tcccacttta tcattttttc aggagattac ccagttgttc taatatcaag tatgtctttg    84814
aaatcccatc cttatcttgt agcatatttc tgtggtttgg gtctattttt gaacattctg    84874
ttttattcca ttgatcatat taatattata tgtgcaaaca caaactattt taagtatagt    84934
agctttgttg cttttaaata tcttttaatt tggctactag gccccataca attcttttc    84994 agaatattcc tggctaccca atttgtttat ttttccaaat gaactttgga gtcaacttcc    85054
ttaattcctc aaaatattct gcaagtactt ttagtaagag tatattaagt gaataatttg    85114
acaactatct aagaacatat tatagctttt cccttgtttt gtttttgtac ttatatatta    85174
gtatagtttt aaagttatat taaaataggt cttccacatt ttaaaaactt attcctagtg    85234
tattaatttc ttctattata actacagtat tttattccag taaaacttct gactggttga    85294
tgctcttata aatcaaggct ataaattttt cttcagctac tttgctgaat tctcacaaac    85354
tgtaaccatt ttttacttga ttctctaggt tgaccagtat ataatctttt tatctgtaaa    85414
caataacttt agcgttgctt tcaacatcta tattcttatt ctatttcatt tttcttgttt    85474
atcaagaaat agctgtttta atagagttgt ttttcgccca aaaagaaaat agtctttctt    85534
tttctactta tatctttaaa ataaatgtaa tgagaaagac tgtgggaaaa taaagcagac    85594
accttataca atggattaat ttttttagtg ccatttcttc tggctttctc tattattggg    85654
actctgaaat cttcgttagt actactctca aaaatgttcg aatgaatgca atcagattca    85714
agggtacaag tgcaggttat ataggtgaat tgcatgcctt ggggtttgg tgtacagact    85774 attttgtcac ccaggtaata agcgtagtac ttaataggta gtttttttgat cctctccctt    85834 ctcccatcct caaagtatcc ctgctgtctg ttgttccccc tctttgtgtc catgtgttct    85894
tgctgtttag ctgccactta agagaacatg tggtatttt ctgttccttt gttagtttgt    85954
ttaggataat ggcctccagc tccatccatg ttgctgcaca gaacacgatt ttgtgtttct    86014
ttatggctgt gtagtattcc atggtgtata tgtaacactt tctttatcca gtctactact    86074
tacggacatt taggttgatt ccatgtcttc gctatcatta atagtgctgt gatgaacata    86134
cgtgtgcaat atgcctttat ggtagaatga tttatatccc tttgggtaat atgccgaata    86194
atgggattgc tcggtcagat ggcaattcta agtcctctga aattaccgca ctgctttcca    86254
caacagctga actagtttac attcccacaa gcaataaggg gataagtgtt ccctttctc    86314 tgcaggaatg attaattctt ttagagagtc aaagatggaa tcctagggaa gatgatatct    86374
gaggcaggtt tagagtcatt gggcaaataa ggggattaag aaggcattct aggcagacag    86434
aaaaccaaag gcatgaagct ctgaaacagc ttactatgtt tggatattta taagctgttg    86494
ttattgttgg agtataaact gtaagagaga gtaggaggac agaaaaaaca gcctgtatgc    86554
ggggggaaga aaacatttaa acagaaattc tcaaaagatt tgggcagcca gcccctctag    86614
agaaaaacat agaatcacct agaagggtt tttcataaag tacacttttc atcaccccta    86674
ttctgtcacc tggaatattg ataacactga agggagtgtg ccttatctct caggtgtatt    86734
tggatgaaat agtttgagaa ccatgcaggc aagtttaagc cagtgtgtta agagaatat    86794 gacatcagat ttgcatttta caatcttcct tttgataaca aagggaacct taaagggctg    86854
```

-continued

```
gaggggaagg gcagacgggg ctaggggagg agaacccttt taaaaagcta ctgcaggtgg  86914
ggtgcggtgg ctcacacctg taatcccagc actttgggag gccaaggcag gcagatcacc  86974
tgaggtcagg agttcaagac cagcctggcc aacatagtaa aaccccatct ctactaaaaa  87034
tacaaaaatt agctaggcat ggtagcaggc acctgtaatc tcagctactt gggaggctga  87094
ggcaggagaa ttgcttgaac ctgggaggca gaggttgcag tgagccaaga ttgtgccgct  87154
gcactccagc ctgggcaaga gagtgagact ccatctcaaa aaaaaaaaaa aaaaagctac  87214
tgcagtagat caggaggagg cacagtgata aagagaagat ctgagctatg aagtggcagt  87274
caagatgatt aaaggaatat ataggaagta cagttgatag aacttagcaa gtgattaggt  87334
aaatgaagtg ctagagaaaa taaaggggat atttttcaat tgtttttagc attttggcaa  87394
aaaattattt aggaatgaaa ttgatgctag taactaagag tatgaacttc ccacattagc  87454
tggtaatttt gatcaccctt gttctccatg accataaata ttttagagtt gctatgaaga  87514
caagaatgtt tatttcctga gtagctgtca gttgtcacta tgaaacatga aaataaatat  87574
cagtttgcta tgtctaggta ttccgatatt tatccacaat tattccttaa gatatattag  87634
tatttttata gatagataga tagatagata gaaataaaca cattttaatt tttgtttcca  87694
tgctctttag aa  ttc aac tag agg gca gcc ttg tgg atg gcc ccg aag     87742
           Lys Phe Asn     Arg Ala Ala Leu Trp Met Ala Pro Lys
                               270                 275
caa gcc tga tgg aac agg ata gaa cca acc atg ttg agg gca aca gac    87790
Gln Ala     Trp Asn Arg Ile Glu Pro Thr Met Leu Arg Ala Thr Asp
            280                 285                 290
taa gtc cat tcc tga tac cat cac ctc cca ttt gcc aga cag aac ctc    87838
    Val His Ser     Tyr His His Leu Pro Phe Ala Arg Gln Asn Leu
            295                     300                 305
tgg cta caa agc tcc aga atg gaa gcc cac tgc ctg aga gag ctc atc    87886
Trp Leu Gln Ser Ser Arg Met Glu Ala His Cys Leu Arg Glu Leu Ile
            310                 315                 320
cag aag taa atg gag aca cca agt ggc act ctt tca aaa gtt att atg    87934
Gln Lys     Met Glu Thr Pro Ser Gly Thr Leu Ser Lys Val Ile Met
            325                 330                 335
gaa tac cct gta tga agg gaa gcc aga ata gtc gtg tga gtc ctg act    87982
Glu Tyr Pro Val     Arg Glu Ala Arg Ile Val Val     Val Leu Thr
        340                     345                     350
tta cac aag aaa gta gag ggt att cca agt gtt tgc aaa atg gag gaa    88030
Leu His Lys Lys Val Glu Gly Ile Pro Ser Val Cys Lys Met Glu Glu
            355                 360                 365
taa aac gca cag tta gtg aac ctt ctc tct ctg ggc tcc ttc aga tca    88078
    Asn Ala Gln Leu Val Asn Leu Leu Ser Leu Gly Ser Phe Arg Ser
            370                 375                 380
aga aat tga aac aag acc aaa agg cta atg gag aaa gac gta act tcg    88126
Arg Asn     Asn Lys Thr Lys Arg Leu Met Glu Lys Asp Val Thr Ser
            385                 390                 395
ggg taa gcc aag aaa gaa atc cag gtg aaa gca gtc aac caa atg tct    88174
Gly     Ala Lys Lys Glu Ile Gln Val Lys Ala Val Asn Gln Met Ser
            400                 405                 410
ccg att tga gtg ata aga aag aat ctg tga gtt ctg tag ccc aag aaa    88222
Pro Ile     Val Ile Arg Lys Asn Leu     Val Leu     Pro Lys Lys
            415                 420                         425
atg cag tta aag att tca cca gtt ttt caa cac ata act gca gtg ggc    88270
Met Gln Leu Lys Ile Ser Pro Val Phe Gln His Ile Thr Ala Val Gly
                430                 435                 440
ctg aaa atc cag agc ttc aga ttc tga atg agc agg agg gga aaa gtg    88318
Leu Lys Ile Gln Ser Phe Arg Phe     Met Ser Arg Arg Gly Lys Val
```

-continued

|  |  |  |  |  |  |  |  |  |  |  |  | |
|---|---|---|---|---|---|---|---|---|---|---|---|---|
| | | 445 | | | | 450 | | | | 455 | | |
| cta | att | acc | atg | aca | aga | aca | ttg | tat | tac | tta | aaa | aca | agg | cag | tgc | 88366 |
| Leu | Ile | Thr | Met | Thr | Arg | Thr | Leu | Tyr | Tyr | Leu | Lys | Thr | Arg | Gln | Cys | |
| | | 460 | | | | | 465 | | | | 470 | | | | | |
| taa | tgc | cta | atg | gtg | cta | cag | ttt | ctg | cct | ctt | ccg | tgg | aac | aca | cac | 88414 |
| | Cys | Leu | Met | Val | Leu | Gln | Phe | Leu | Pro | Leu | Pro | Trp | Asn | Thr | His | |
| | | | 475 | | | | | 480 | | | | 485 | | | | |
| atg | gtg | aac | tcc | tgg | aaa | aaa | cac | tgt | ctc | aat | att | atc | cag | att | gtg | 88462 |
| Met | Val | Asn | Ser | Trp | Lys | Lys | His | Cys | Leu | Asn | Ile | Ile | Gln | Ile | Val | |
| | | 490 | | | | | 495 | | | | 500 | | | | | |
| ttt | cca | ttg | cgg | tgc | aga | aaa | cca | cat | ctc | aca | taa | atg | cca | tta | aca | 88510 |
| Phe | Pro | Leu | Arg | Cys | Arg | Lys | Pro | His | Leu | Thr | | Met | Pro | Leu | Thr | |
| | 505 | | | | | 510 | | | | | | 515 | | | | |
| gtc | agg | cta | cta | atg | agt | tgt | cct | gtg | aga | tca | ctc | acc | cat | cgc | ata | 88558 |
| Val | Arg | Leu | Leu | Met | Ser | Cys | Pro | Val | Arg | Ser | Leu | Thr | His | Arg | Ile | |
| | | 520 | | | | | 525 | | | | | 530 | | | | |
| cct | cag | ggc | aga | tca | att | ccg | cac | aga | cct | cta | act | ctg | agc | tgc | ctc | 88606 |
| Pro | Gln | Gly | Arg | Ser | Ile | Pro | His | Arg | Pro | Leu | Thr | Leu | Ser | Cys | Leu | |
| 535 | | | | 540 | | | | | 545 | | | | | 550 | | |
| caa | agc | cag | ctg | cag | tgg | tga | gtg | agg | cct | gtg | atg | ctg | atg | atg | ctg | 88654 |
| Gln | Ser | Gln | Leu | Gln | Trp | | Val | Arg | Pro | Val | Met | Leu | Met | Met | Leu | |
| | | | | 555 | | | | | | 560 | | | | | 565 | |
| ata | atg | cca | gta | aac | tag | ctg | caa | tgc | taa | ata | cct | gtt | cct | ttc | aga | 88702 |
| Ile | Met | Pro | Val | Asn | | Leu | Gln | Cys | | Ile | Pro | Val | Pro | Phe | Arg | |
| | | | 570 | | | | | | | 575 | | | | | | |
| aac | cag | aac | aac | tac | aac | aac | aaa | aat | cag | ttt | ttg | aga | tat | gcc | cat | 88750 |
| Asn | Gln | Asn | Asn | Tyr | Asn | Asn | Lys | Asn | Gln | Phe | Leu | Arg | Tyr | Ala | His | |
| 580 | | | | | 585 | | | | | 590 | | | | | 595 | |
| ctc | ctg | cag | aaa | ata | aca | tcc | agg | gaa | cca | caa | agc | tag | cgt | ctg | gtg | 88798 |
| Leu | Leu | Gln | Lys | Ile | Thr | Ser | Arg | Glu | Pro | Gln | Ser | | Arg | Leu | Val | |
| | | | | 600 | | | | | 605 | | | | | | 610 | |
| aag | aat | tct | gtt | cag | gtt | cca | gca | gca | att | tgc | aag | ctc | ctg | gtg | gca | 88846 |
| Lys | Asn | Ser | Val | Gln | Val | Pro | Ala | Ala | Ile | Cys | Lys | Leu | Leu | Val | Ala | |
| | | | | 615 | | | | 620 | | | | | 625 | | | |
| gct | ctg | aac | ggt | att | taa | aac | aaa | atg | aaa | tga | atg | gtg | ctt | act | tca | 88894 |
| Ala | Leu | Asn | Gly | Ile | | Asn | Lys | Met | Lys | | Met | Val | Leu | Thr | Ser | |
| | | | 630 | | | | | | 635 | | | | | | 640 | |
| agc | aaa | gct | cag | tgt | tca | cta | agg | att | cct | ttt | ctg | cca | cta | cca | cac | 88942 |
| Ser | Lys | Ala | Gln | Cys | Ser | Leu | Arg | Ile | Pro | Phe | Leu | Pro | Leu | Pro | His | |
| | | | | 645 | | | | | 650 | | | | | 655 | | |
| cac | cac | cac | cat | cac | aat | tgc | ttc | ttt | ctc | ccc | ctc | ctc | ctc | ttc | cac | 88990 |
| His | His | His | His | His | Asn | Cys | Phe | Phe | Leu | Pro | Leu | Leu | Leu | Phe | His | |
| | | | | 660 | | | | | 665 | | | | 670 | | | |
| agg | ttc | ctc | agc | ttc | ctt | cag | aag | gaa | aaa | gca | ctc | tga | atg | gtg | gag | 89038 |
| Arg | Phe | Leu | Ser | Phe | Leu | Gln | Lys | Glu | Lys | Ala | Leu | | Met | Val | Glu | |
| | | | 675 | | | | | 680 | | | | | 685 | | | |
| ttt | tag | aag | aac | acc | acc | act | acc | cca | acc | aaa | gta | aca | caa | cac | ttt | 89086 |
| Phe | | Lys | Asn | Thr | Thr | Thr | Thr | Pro | Thr | Lys | Val | Thr | Gln | His | Phe | |
| | | | | 690 | | | | | 695 | | | | 700 | | | |
| taa | ggg | aag | tga | aaa | tag | agg | gta | aac | ctg | agg | cac | cac | ctt | ccc | aga | 89134 |
| | Gly | Lys | | Lys | | Arg | Val | Asn | Leu | Arg | His | His | Leu | Pro | Arg | |
| | | | | | 705 | | | | | 710 | | | | | 715 | |
| gtc | cta | atc | cat | cta | cac | atg | tat | gca | gcc | ctt | ctc | cga | tgc | ttt | ctg | 89182 |
| Val | Leu | Ile | His | Leu | His | Met | Tyr | Ala | Ala | Leu | Leu | Arg | Cys | Phe | Leu | |
| | | | | 720 | | | | | 725 | | | | | 730 | | |
| aaa | ggc | ctc | aga | ata | att | gtg | tga | aca | gga | atg | aca | tac | aga | ctg | cag | 89230 |
| Lys | Gly | Leu | Arg | Ile | Ile | Val | | Thr | Gly | Met | Thr | Tyr | Arg | Leu | Gln | |
| | | | 735 | | | | | | 740 | | | | | 745 | | |
| gga | caa | tga | ctg | ttc | cat | tgt | gtt | ctg | aga | aaa | caa | gac | caa | tgt | cag | 89278 |

```
                                                                -continued

Gly Gln      Leu Phe His Cys Val Leu Arg Lys Gln Asp Gln Cys Gln
                 750             755             760 aac acc tca agc ata acc cac caa ttt ttg gta gca gtg gag agc tac         89326
Asn Thr Ser Ser Ile Thr His Gln Phe Leu Val Ala Val Glu Ser Tyr
             765             770             775 agg aca act gcc agc agt tga tga gaa aca aag agc aag aga ttc tga         89374
Arg Thr Thr Ala Ser Ser         Glu Thr Lys Ser Lys Arg Phe
             780                         785             790 agg gtc gag aca agg agc aaa cac gag atc ttg tgc ccc caa cac agc         89422
Arg Val Glu Thr Arg Ser Lys His Glu Ile Leu Cys Pro Gln His Ser
                 795             800             805 act atc tga aac cag gat gga ttg aat tga agg ccc ctc gtt ttc acc         89470
Thr Ile     Asn Gln Asp Gly Leu Asn     Arg Pro Leu Val Phe Thr
                     810                     815             820 aag cgg aat ccc atc taa aac gta atg agg cat cac tgc cat caa ttc         89518
Lys Arg Asn Pro Ile     Asn Val Met Arg His His Cys His Gln Phe
                 825             830             835 ttc agt atc aac cca atc tct cca atc aaa tga cct cca aac aat aca         89566
Phe Ser Ile Asn Pro Ile Ser Pro Ile Lys     Pro Pro Asn Asn Thr
             840             845                         850 ctg gaa att cca aca tgc ctg ggg ggc tcc caa ggc aag ctt aca ccc         89614
Leu Glu Ile Pro Thr Cys Leu Gly Gly Ser Gln Gly Lys Leu Thr Pro
             855             860             865 aga aaa caa cac agc tgg agc aca agt cac aaa tgt acc aag ttg aaa         89662
Arg Lys Gln His Ser Trp Ser Thr Ser His Lys Cys Thr Lys Leu Lys
             870             875             880 tga atc aag ggc agt ccc aag gta cag tgg acc aac atc tcc agt tcc         89710
    Ile Lys Gly Ser Pro Lys Val Gln Trp Thr Asn Ile Ser Ser Ser
             885             890             895 aaa aac cct cac acc agg tgc act tct cca aaa cag acc att tac caa         89758
Lys Asn Pro His Thr Arg Cys Thr Ser Pro Lys Gln Thr Ile Tyr Gln
             900             905             910 aag ctc atg tgc agt cac tgt gtg gca cta gat ttc att ttc aac aaa         89806
Lys Leu Met Cys Ser His Cys Val Ala Leu Asp Phe Ile Phe Asn Lys
             915             920             925 gag cag att ccc aaa ctg aaa aac tta tgt ccc cag tgt tga aac agc         89854
Glu Gln Ile Pro Lys Leu Lys Asn Leu Cys Pro Gln Cys     Asn Ser
930             935             940 act tga atc aac agg ctt cag aga ctg agc cat ttt caa act cac acc         89902
Thr     Ile Asn Arg Leu Gln Arg Leu Ser His Phe Gln Thr His Thr
945             950             955 ttt tgc aac ata agc ctc ata aac agg cag cac aaa cac aac cat ccc         89950
Phe Cys Asn Ile Ser Leu Ile Asn Arg Gln His Lys His Asn His Pro
960             965             970             975 aga gtt cac atc tcc ctc aaa acc agc aac agc agc aaa aat tac aaa         89998
Arg Val His Ile Ser Leu Lys Thr Ser Asn Ser Ser Lys Asn Tyr Lys
             980             985             990 taa aga ata aag agg aaa tac tcc aga ctt ttc ctc acc ccc aaa gca         90046
    Arg Ile Lys Arg Lys Tyr Ser Arg Leu Phe Leu Thr Pro Lys Ala
             995             1000            1005 aca atg atc agc aaa gag aag gat cat tct ttg gcc aga cta aag             90091
Thr Met Ile Ser Lys Glu Lys Asp His Ser Leu Ala Arg Leu Lys
             1010            1015            1020 tgg aag aat gtt ttc atg gtg aaa atc agt att caa aat caa gcg             90136
Trp Lys Asn Val Phe Met Val Lys Ile Ser Ile Gln Asn Gln Ala
             1025            1030            1035 agt tcg aga ctc ata atg tcc aaa tgg gac tgg agg aag tac aga             90181
Ser Ser Arg Leu Ile Met Ser Lys Trp Asp Trp Arg Lys Tyr Arg
             1040            1045            1050
```

| | | | | | | | | | | | | |
|---|---|---|---|---|---|---|---|---|---|---|---|---|
| ata | taa | atc | gta | gaa | att | ccc | ctt | ata | gtc | aga | cca | tga aat caa | 90226 |
| Ile | | Ile | Val | Glu | Ile | Pro | Leu | Ile | Val | Arg | Pro | Asn Gln |
| | | | | 1055 | | | | 1060 | | | | |

| gtg | cat | gca | aaa | tac | agg | ttt | ctt | gtt | caa | aca | ata | cac | acc | tag | 90271 |
|---|---|---|---|---|---|---|---|---|---|---|---|---|---|---|---|
| Val | His | Ala | Lys | Tyr | Arg | Phe | Leu | Val | Gln | Thr | Ile | His | Thr | |
| 1065 | | | | 1070 | | | | | 1075 | | | | | |

| ttt | cag | aga | ata | aag | aac | aga | cta | cac | atc | ctg | aac | ttt | ttg | cag | 90316 |
|---|---|---|---|---|---|---|---|---|---|---|---|---|---|---|---|
| Phe | Gln | Arg | Ile | Lys | Asn | Arg | Leu | His | Ile | Leu | Asn | Phe | Leu | Gln | |
| | 1080 | | | | | 1085 | | | | | 1090 | | | | |

| gaa | aca | aga | ccc | aaa | act | tgc | atc | aca | tgc | aat | att | ttc | caa | ata | 90361 |
|---|---|---|---|---|---|---|---|---|---|---|---|---|---|---|---|
| Glu | Thr | Arg | Pro | Lys | Thr | Cys | Ile | Thr | Cys | Asn | Ile | Phe | Gln | Ile | |
| | 1095 | | | | | 1100 | | | | | 1105 | | | | |

| atg | tga | tcc | caa | agc | aag | atc | ttc | ttc | aca | ggt | gct | ttc | aag | aac | 90406 |
|---|---|---|---|---|---|---|---|---|---|---|---|---|---|---|---|
| Met | | Ser | Gln | Ser | Lys | Ile | Phe | Phe | Thr | Gly | Ala | Phe | Lys | Asn | |
| | | 1110 | | | | | 1115 | | | | | 1120 | | | |

| agg | agc | aga | agt | cac | aac | aag | ctt | cag | ttc | tac | agg | gat | ata | aaa | 90451 |
|---|---|---|---|---|---|---|---|---|---|---|---|---|---|---|---|
| Arg | Ser | Arg | Ser | His | Asn | Lys | Leu | Gln | Phe | Tyr | Arg | Asp | Ile | Lys | |
| | 1125 | | | | | 1130 | | | | | 1135 | | | | |

| ata | gaa | acc | aag | ata | tgt | ctg | gtc | aac | aag | ctg | cgc | aac | ttg | ctc | 90496 |
|---|---|---|---|---|---|---|---|---|---|---|---|---|---|---|---|
| Ile | Glu | Thr | Lys | Ile | Cys | Leu | Val | Asn | Lys | Leu | Arg | Asn | Leu | Leu | |
| | 1140 | | | | | 1145 | | | | | 1150 | | | | |

| agc | aaa | ggt | act | tga | tac | ata | acc | atg | caa | atg | ttt | ttc | ctg | tgc | 90541 |
|---|---|---|---|---|---|---|---|---|---|---|---|---|---|---|---|
| Ser | Lys | Gly | Thr | | Tyr | Ile | Thr | Met | Gln | Met | Phe | Phe | Leu | Cys | |
| | 1155 | | | | | 1160 | | | | | 1165 | | | | |

| ctg | acc | agg | gag | gaa | gtc | aca | ctc | aga | ccc | ctc | ccc | aga | agg | aca | 90586 |
|---|---|---|---|---|---|---|---|---|---|---|---|---|---|---|---|
| Leu | Thr | Arg | Glu | Glu | Val | Thr | Leu | Arg | Pro | Leu | Pro | Arg | Arg | Thr | |
| | | 1170 | | | | | 1175 | | | | | 1180 | | | |

| ctc | aaa | agc | atg | ctg | ctc | taa | ggt | ggc | atc | tct | tac | aga | agc | aag | 90631 |
|---|---|---|---|---|---|---|---|---|---|---|---|---|---|---|---|
| Leu | Lys | Ser | Met | Leu | Leu | | Gly | Gly | Ile | Ser | Tyr | Arg | Ser | Lys | |
| | 1185 | | | | | | 1190 | | | | | 1195 | | | |

| aac | agc | agc | aaa | cac | agc | aac | ccc | aaa | ctg | agt | ctt | gcc | ata | gtc | 90676 |
|---|---|---|---|---|---|---|---|---|---|---|---|---|---|---|---|
| Asn | Ser | Ser | Lys | His | Ser | Asn | Pro | Lys | Leu | Ser | Leu | Ala | Ile | Val | |
| | | | 1200 | | | | | 1205 | | | | | 1210 | | |

| aga | tgc | aca | ggc | caa | tta | agg | tgg | aac | ctg | gat | gca | agc | cac | atg | 90721 |
|---|---|---|---|---|---|---|---|---|---|---|---|---|---|---|---|
| Arg | Cys | Thr | Gly | Gln | Leu | Arg | Trp | Asn | Leu | Asp | Ala | Ser | His | Met | |
| | | | 1215 | | | | | 1220 | | | | | 1225 | | |

| cct | gta | tgc | aca | cag | cac | cac | cag | aaa | aca | aaa | cat | gga | aaa | agg | 90766 |
|---|---|---|---|---|---|---|---|---|---|---|---|---|---|---|---|
| Pro | Val | Cys | Thr | Gln | His | His | Gln | Lys | Thr | Lys | His | Gly | Lys | Arg | |
| | | | | 1230 | | | | | 1235 | | | | | 1240 | |

| taa | cta | agc | aag | aga | atc | cac | ctg | caa | gct | gtg | ata | atg | tgc | agc | 90811 |
|---|---|---|---|---|---|---|---|---|---|---|---|---|---|---|---|
| | Leu | Ser | Lys | Arg | Ile | His | Leu | Gln | Ala | Val | Ile | Met | Cys | Ser | |
| | | | | 1245 | | | | | 1250 | | | | | | |

| aaa | aga | gca | tca | ttg | aga | cca | tgg | agc | agc | atc | tga | agc | agt | ttc | 90856 |
|---|---|---|---|---|---|---|---|---|---|---|---|---|---|---|---|
| Lys | Arg | Ala | Ser | Leu | Arg | Pro | Trp | Ser | Ser | Ile | | Ser | Ser | Phe | |
| 1255 | | | | | 1260 | | | | | 1265 | | | | | |

| acg | cca | agt | cgt | tat | ttg | acc | ata | agg | ctc | tta | ctc | tca | aat | cac | 90901 |
|---|---|---|---|---|---|---|---|---|---|---|---|---|---|---|---|
| Thr | Pro | Ser | Arg | Tyr | Leu | Thr | Ile | Arg | Leu | Leu | Leu | Ser | Asn | His | |
| 1270 | | | | | 1275 | | | | | 1280 | | | | | |

| aga | agc | aag | taa | aag | ttg | aaa | tgt | cag | ggc | cag | tca | cag | ttt | tga | 90946 |
|---|---|---|---|---|---|---|---|---|---|---|---|---|---|---|---|
| Arg | Ser | Lys | | Lys | Leu | Lys | Cys | Gln | Gly | Gln | Ser | Gln | Phe | | |
| | 1285 | | | | | 1290 | | | | | 1295 | | | | |

| cta | gac | aaa | cca | ctg | ctg | cag | aac | ttg | ata | gcc | aca | ccc | cag | ctt | 90991 |
|---|---|---|---|---|---|---|---|---|---|---|---|---|---|---|---|
| Leu | Asp | Lys | Pro | Leu | Leu | Gln | Asn | Leu | Ile | Ala | Thr | Pro | Gln | Leu | |
| | | | 1300 | | | | | 1305 | | | | | 1310 | | |

| tag | agc | agc | aaa | caa | ctt | ctt | cag | aaa | aga | cac | caa | cca | aaa | gaa | 91036 |
|---|---|---|---|---|---|---|---|---|---|---|---|---|---|---|---|
| | Ser | Ser | Lys | Gln | Leu | Leu | Gln | Lys | Arg | His | Gln | Pro | Lys | Glu | |
| | | | | 1315 | | | | | 1320 | | | | | 1325 | |

| cag | ctg | ctt | ctg | ttc | tca | ata | att | tta | tag | agt | cac | ctt | cca | aat | 91081 |
|---|---|---|---|---|---|---|---|---|---|---|---|---|---|---|---|
| Gln | Leu | Leu | Leu | Phe | Ser | Ile | Ile | Leu | | Ser | His | Leu | Pro | Asn | |
| | 1330 | | | | | 1335 | | | | | | | | | |

```
tac tag ata ctc cta taa aaa att tat tgg ata cac ctg tca aga        91126
Tyr     Ile Leu Leu     Lys Ile Tyr Trp Ile His Leu Ser Arg
1340                        1345                1350 ctc aat atg att tcc cat ctt gca gat gtg tag gtaagtgcca             91169
Leu Asn Met Ile Ser His Leu Ala Asp Val
        1355            1360 gaaatgtact gagacacatg gcgtttatcc agaattagca aatttatctt cagatatggg  91229
attttccttc ttttttaaaa tcttgagtct ggcagcaatt tgtaaaggct cataaaaatc  91289
tgaagcttac attttttgtc aagttaccga tgcttgtgtc ttgtgaaaga gaacttcact  91349
tacatgcagt ttttccaaaa gaattaaata atcgtgcatg tttattttc cctctcttca   91409 gatcctgtaa aatttgaatg tatctgtttt agatcaattc gcctatttag ctctttgtat  91469
attatctcct ggagagacag ctaggcagca aaaaacaat ctattaaaat gagaaaataa   91529
cgaccatagg cagtctaatg tacgaacttt aaatatttt taattcaagg taaaatatat   91589
tagtttcaca agatttctgg ctaataggga aattattatc ttcagtcttc atgagttggg  91649
ggaaatgata atgctgacac tcttagtgct cctaaagttt cctttctcc atttatacat   91709 ttggaatgtt gtgatttata ttcattttga ttcccttttc tctaaaattt catcttttg   91769 attaaaaaat atgatacagg catacctcag agatattgtg ggtttggctc ataccacaa   91829 taaaatgaat attacaataa agcaagttgt aaggactttt tggtttctca ctgtatgtaa  91889
aagttattta tatactatac tgtaacatac taagtgtgca atagcattgt gtctaaaaaa  91949
tatatacttt aaaaataatt tattgttaaa aaaatgccaa caattatctg ggcctttagt  92009
gagtgctaat cttttgctg gtggagggtc gtgcttcagt attgatcgct gtggactgat   92069
catggtggta gttgctgaag gttgctggga tggctgtgtg tgtggcaatt tcttaaaata  92129
agacaacagt gaagtgctgt atcaattgat ttttccattc acaaaagatt tctctgtagc  92189
atgcaatgct gtttgatagc atttaaccca cagcagaatt tctttgaaaa ttggactcag  92249
tcctctcaaa ctgtgctgct gctttatcaa ctaagttttt gtaattttct gaatcctttg  92309
ttgtcatttc agcagtttac agcatcttca ttggaagtat attccatctc aaacattctt  92369
tgttcatcca taagaagcaa cttcttatca agttttttca tgacattgca gtaactcagc  92429
cccatcttca ggctctactt ctaattctgg ttctcttgct acatctccct catctgcagt  92489
gacctctcca cggaagtctt gaactcctca aagtaatcca tgagggttgg aatcaacttc  92549
taaactcctg ttaatgttga tatattgacc ccctcccatg aattatgaat gttcttaata  92609
acttctaaat ggtgatacct ttccagaagg cttcaatgt actttgcccg gatccatcag   92669
aagactatct tggcagctgt agactaacaa tatatttctt aaatgataag acttgaaagt  92729
caaaagtact ccttaatcca taggctgcag aatcaatgtt gtattaacag gcacgaaaac  92789
agcattaatc ttgtgcatct ccatcggagc tcttgggtga ctaggtgcct tgagcagtaa  92849
tattttgaaa ggaggttttg gttttgtttt ttgtttttt ttttgtttt ttagcagtaa    92909 gtctcaacac tgggcttaaa atattcagta aactatgttg taaaaagatg tgttatcatc  92969
cagactttgt tgttccatta ctctacacaa gcagggtaca cttagcataa ttcttaaggg  93029
ccttggaatt ttcagaatgg taaatgagta tgggcttcaa cttaaaatca tcaactgcat  93089
tagcctgtaa caagagagtc agcctgtcct ttgaagcaag gcattgactt ctatctatga  93149
aagtcttaga tggcaccttg tttcaatagt aggctgttta gtacagccac cttcatcagt  93209
gatcttagct agatcttctg cataacttgc tgcagcttct acatcagcac ttgctgcctc  93269
```

```
accttgtcct tttatgttat agagacagct gcgcttctta aactttataa accaacttct   93329
gctagcttcc aacttctctt ctgcagcttc ctcattctct tcatagaact gaagggagtc   93389
aaggccttgc tctggattaa gctttggctt aaggaatgtt gtggctgacg tgatcttcta   93449
tccagaccac taaagcgctc tccatatcag caataaggcc gttttgcttt cttacctttc   93509
atgtgttcac tggagtaatt tccttcaaga atttttcctt tacattcaca acttggctaa   93569
ctggcatgca aggcctagct ttcagcctgt cttggctttt gacatgcctt cctcacttag   93629
ctcgtcatat ctagctttg atttaaagtg gcaggcatac aactcttcct ttcacttgaa   93689
cacttagagg ccactgtagg gttattaatt ggcctaattt caatattgtt gtgttttagg   93749
gaatagagag gcccagggag agggagagag cccaaacggc tggttgatag agcaggcaga   93809
atgcacacaa catttatcag attatgtttg caccatttac cagattatgg gtacggtttg   93869
tggcaccccc caaaaattag aatagtaaca tcaaagatca ctgatcacag atcgccataa   93929
cataaataat aataaacttt aaaatactgt gagaattacc aaaatgtgat acagagacat   93989
gaagtgagca catgctgttg aaaaaaatga cactgataga catacttaac acgtgggatt   94049
gccacaaacc ttcagtttgt aaagtcaca gtaactgtga ctcacaaaag aacaaagcac    94109
aataaaacga ggtatgcctg tattttaaa aaaagctttt tgttaaaatt caggatatgt    94169
aataggtctg taggaatagt gaaatatttt tgctgatgga tgtagatata tacgtggata   94229
gagatgaaga tcttaattat agctatgcag catagattta gtcaaagaca tttgaaaaga   94289
caaatgttaa attagtgtgg ctaatgacct acccgtgcca tgttttccct cttgcaatga   94349 gatacccac actgtgtaga aggatggagg gaggactcct actgtccctc tttgcgtgtg    94409
gttattaagt tgcctcactg ggctaaaaca ccacacatct catagataat atttggtaag   94469
ttgtaatcgt cttcactctt ctcttatcac ccaccccctat cttcccactt ttccatcttt   94529
gttggtttgc aacagcccct tcttttgcc tgactctcca ggattttctc tcatcataaa    94589
ttgttctaaa gtacatacta atatgggtct ggattgacta ttcttattg caaaacagca    94649 attaaatgtt atagggaagt aggaagaaaa aggggtatcc ttgacaataa accaagcaat   94709
attctggggg tgggatagag caggaaattt tattttttaat cttttaaaat ccaagtaata   94769
ggtaggcttc cagttagctt taaatgtttt tttttttccag ctcaaaaaat tggattgtag  94829
ttgatactac atataataca ttctaattcc ctcactgtat tctttgttta gtttcattta   94889
tttggtttaa ataatttttt tatcccatat ctgaaatgta atatatttt atccaacaac   94949 cagcatgtac atatacttaa ttatgtggca catttttctaa tagatcagtc catcaatcta  95009
ctcattttaa agaaaaaaaa attttaaagt cactttttaga gcccttaatg tgtagttggg  95069
ggttaagctt tgtggatgta gcctttatat ttagtataat tgaggtctaa aataataatc   95129
ttctattatc tcaacag agc aaa tta   ttg aaa aag atg aag   gtc ctt ttt   95179
                   Ser Lys Leu   Leu Lys Lys Met Lys   Val Leu Phe
                       1365                1370 ata ccc atc tag gag cag gtc cta  atg tgg cag cta tta  gag aaa      95224
Ile Pro Ile     Glu Gln Val Leu  Met Trp Gln Leu Leu  Glu Lys
    1375                1380                1385 tca tgg aag  aaa g gtaattaacg caaaggcaca gggcagatta acgtttatcc       95277
Ser Trp Lys  Lys
             1390 ttttgtatat gtcagaattt ttccagcctt cacacacaaa gcagtaaaca attgtaaatt    95337 gagtaattat tagtaggctt agctattcta gggttgccaa cactacacac tgtgctattc    95397 accagagagt cacaatattt gacaggacta atagtctgct agctggcaca ggctgcccac    95457
```

```
tttgcgatgg atgccagaaa acccaggcat gaacaggaat cggccagcca ggctgccagc    95517
cacaaggtac tggcacaggc tccaacgaga ggtcccactc tggctttccc acctgataat    95577
aaagtgtcaa agcagaaaga ctggtaaagt gtggtataag aaaagaacca ctgaattaaa    95637
ttcacctagt gttgcaaatg agtacttatc tctaagtttt cttttaccat aaaaagagag    95697
caagtgtgat atgttgaata gaaagagaaa catactattt acagctgcct ttttttttt     95757 ttttcgctat caatcacagg tatacaagta cttgccttta ctcctgcatg tagaagactc    95817
ttatgagcga gataatgcag agaaggcctt tcatataaat ttatacagct ctgagctgtt    95877
cttcttctag ggtgccttt  cattaagagg taggcagtat tattattaaa gtacttagga    95937
tacattgggg cagctaggac atattcagta tcattcttgc tccatttcca aattattcat    95997
ttctaaatta gcatgtagaa gttcactaaa taatcatcta gtggcctggc agaaatagtg    96057
aatttcccta agtgcctttt ttttgttgtt tttttgtttt gtttttaaa  caagcagtag    96117 gtggtgcttt ggtcataagg gaagatatag tctatttcta ggactattcc atattttcca    96177
tgtggctgga tactaactat ttgccagcct ccttttctaa attgtgagac attcttggag    96237
gaacagttct aactaaaatc tattatgact ccccaagttt taaaatagct aaatttagta    96297
agggaaaaaa tagtttatgt tttagaagac tgaacttagc aaactaacct gaattttgtg    96357
ctttgtgaaa tttatatcg  aaatgagctt tcccattttc acccacatgt aatttacaaa    96417
atagttcatt acaattatct gtacattttg atattgagga aaacaaggc  ttaaaaacca    96477 ttatccagtt tgcttggcgt agacctgttt aaaaaataat aaaccgttca tttctcagga    96537
tgtggtcata gaataaagtt atgctcaaat gttcaaatat tttgattgcc tcttgaattc    96597
atttgctaat tgtatgtgtg tgtgtttctg tgggtttctt taag gt  ttg gac aga    96652
                                                     Gly Leu Asp Arg
                                                              1395 agg gta aag cta tta  gga ttg aaa gag tca  tct ata ctg gta aag        96697
Arg Val Lys Leu Leu  Gly Leu Lys Glu Ser  Ser Ile Leu Val Lys
              1400                  1405                  1410 aag gca aaa gtt ctc  agg gat gtc cta ttg  cta agt gg  gtaagtgtga     96745
Lys Ala Lys Val Leu  Arg Asp Val Leu Leu  Leu Ser Gly
              1415                  1420 cttgataaag cctttggtct taaatcttgg gcattttgat ttgtaaatct gaccctgaga    96805
attgggttac ccagatcaaa gactcatgcc agttaaaaag aacattacct gtatttttta    96865
tcatgtgtta tctcttaaga agaggcagat tagttctaaa atcaacaaat tgtatttaat    96925
tgaaataatt tagtgatgag gaagaggtcc attctagtgc ctgctaaatg tataatcctt    96985
cttagaatgt gaagttgtcc ttaaactttt aaataccttc agttaatctt tatattgtca    97045
tttatgaaaa ccttgaacta agacttatgt atctttcatc tagctctggt tttaatgcag    97105
gtagcattta attgtcccca ctgtactggg tatagtctgc taaacattaa ggagtagttt    97165
tgcatctctc cttgttctga tactagggtc aaagcccact ttttatagat gggcagcaaa    97225
aggcacattg gacatgctga taaatgttgc cctaattgtg atctaaacat gataaaatat    97285
acatacataa gtgcccttat ctgctgcaag tgacccttgt tttgttttgg ttggggtggg    97345
gggtgtttgg gatggaatgg tgatccacgc ag g tgg ttc  gca gaa gca gca       97396
                                    Trp Phe  Ala Glu Ala Ala
                                                 1425 gtg aag aga agc tac tgt  gtt tgg tgc ggg agc  gag ctg gcc aca        97441
Val Lys Arg Ser Tyr Cys  Val Trp Cys Gly Ser  Glu Leu Ala Thr
1430                1435                                 1440
```

| | | |
|---|---|---|
| cct gtg agg ctg cag tga ttg tga ttc tca tcc tgg tgt ggg aag<br>Pro Val Arg Leu Gln      Leu      Phe Ser Ser Trp Cys Gly Lys<br>1445                 1450                       1455 | | 97486 |
| gaa tcc cgc tgt ctc tgg ctg aca aac tct act cgg agc tta ccg<br>Glu Ser Arg Cys Leu Trp Leu Thr Asn Ser Thr Arg Ser Leu Pro<br>       1460                     1465                     1470 | | 97531 |
| aga cgc tga gga aat acg gca cgc tca cca atc gcc ggt gtg cct<br>Arg Arg      Gly Asn Thr Ala Arg Ser Pro Ile Ala Gly Val Pro<br>               1475                       1480                     1485 | | 97576 |
| tga atg aag a gtaagtgaag cccagggcct ctccctctt tgcggccact<br>     Met Lys | | 97626 |
| gataggaaag cccaatcttt ggttgaaagg aagagagttc agcgtgcact tttacattta | | 97686 |
| taaaatgggc atcaaaatgc ctgtttggca gtcatgcgat aagaagttgt atttgctaat | | 97746 |
| gtgaataact tgagatgatt tcattatctg aattgtacag tttagccatt aattaggagc | | 97806 |
| agtcagagtg tctgtaacca catggcctca gttataccat aaacttgaaa ttgtttatgt | | 97866 |
| gctcacatgc tacaagtgac ggctcctgtg tgcctggcca ctatattagt atgtattgac | | 97926 |
| tccacttcca tgttgcagta tctgaaacag aaagtaagtc taatgagaaa ctttgggatt | | 97986 |
| cccaggtcaa ataccttcca tatgtatgta gcaaaaacaa aatacaaagc ctagaagttc | | 98046 |
| tgtagaaata gaactgattt ttactttcat tcaaactatt cattatttcc acaatagtaa | | 98106 |
| tcaaaactgc ttctactttt actgctgcta aatgatcagc aaattactgg atatggatat | | 98166 |
| atattatttt ccaggaatat aagaatttag aatagaactg caagagtatg cacttaaata | | 98226 |
| tatttagtgc atccagttgc taatgttttg ttttaaacac catccacttt gcatgaagtc | | 98286 |
| taaaccttca gttggaaaaa gcctcatttt taatattcct ctactgtgct gataatcctg | | 98346 |
| tataacacta aaagaataga tgaatgttca cggtgctaca cagaaatgtt ttttttttt | | 98406 |
| tttttttttt ttttgagatg gagtttcgct cttgttgccc aggctggagt gcaatggcgc | | 98466 |
| gatcttggtt caccgcgacc tccacctccc aggttcaaga gattctcctg cctcagcctc | | 98526 |
| cctagtagct gggattacag gcatgtgcca ccacacccgg ctaattttgt attttagta | | 98586 |
| gagacagggt ttctccatgt tggtcaggct ggtctgaac tcccgacctc aggtgattgc | | 98646 |
| ccacctcggc ctcccaaagt gccttacagg catgagccgc cgcgcctggc cagaaatctt | | 98706 |
| acaagttatt tgcccacga ttggttttaa aataatttta attttgcact atttcctta | | 98766 |
| gtgtctttt ctctgcatcc accaaactat agaatcattt gctgagctta taagaaatgc | | 98826 |
| tcatactgct cattgcaaca gctagccaaa tttgtccttt gctgtttaaa actctaacta | | 98886 |
| gcatggtttt actaaattta tgttaacaca gtttctctct ctgggttgtg gggagacaaa | | 98946 |
| tcaattataa ataatctctt tagaaaagtt actctttcta tatgaaagtg tgacttgact | | 99006 |
| ttctatgata attatgatcc aaaaatttta tggtgtgtac ctgaccactt ttacaaatga | | 99066 |
| ttaattggaa ggtagaaatt gctgattcat aacatgtaac ttataaactt atgatggact | | 99126 |
| actttaagca taaattttt tttttttttt aagacagagt ttcactctgt cacccaggct | | 99186 |
| ggagtgcaat ggtgcgatct cggctcactg caacctccat ctcctgggtt caagcaattc | | 99246 |
| tcctgcctca gcctcccgaa tagctgggat tacaggcatg cactaccaca cccagctaat | | 99306 |
| tttgtatttt tagtagagac agggtttctc catgttgatc aggctggtct ggaactcctg | | 99366 |
| acctcgggtg atccgcccgc ctcggcctcc cagagtgctg ggattacagg catgagccac | | 99426 |
| tgtgcccagc ctgaaatatt ttttaatctc accctgactc ctcttgctct ttctgaagaa | | 99486 |
| aaattttaa aaatgtatgt aggtgccttt aattagaaaa aaaattaaaa attaaggcaa | | 99546 |

```
cttgtgctca tattggtaat agcatttctt tcaagaactc agtaatactg cattgtcttt    99606
aaagcataat atctcttaga cttgacggtt tgagattcta aatcactgaa gaacctcttg    99666
tgaaaatgat agttttaaaa tttcttttca aaatagtcc tattgcaaaa tgtttgattt     99726
tcttgaagtt tcctggaaac tatatttcat tcattgtaat gaatttaatt ttcattaaca    99786
tagatctcta atatttttct cagctcacca caacctccac ctcccgggtt caagtgattc    99846
tcatgccaca gcctcccgag tagctagaat tacaggcacc cacccggctc attttttgtat  99906 ttttagtaga gacagggttt caccatgttg gccagattga tctcgaactc ctggcttcag   99966
gtaacccacc caccctggcc tcccaaagtg ctgggattac aggtgtaggc caccatgccc  100026
agccagcttt tccataattc ttataaatgc caatgcctga aatggaatct gacatataaa  100086
aaattacatg aagaactttt attattttgc atttgaaaac catgaaaaat agttggacca  100146
gagtctcaga aagcttgtag tttgttagtt taactgctct aaatgtcagg cagatacaaa  100206
actattaaaa gacatgcttc aaatatgaag acaattaaaa agcacagctg tacactttttg 100266 cttttttgtct agtttcaagg taaagatgaa taatcattta gataatgctt aagctatgct  100326
tatgcatact tagagcaatt ctccaaaata aaaaattta atacttaaat acatgattaa    100386
aatagacacg tatccaatgt caatacagac tttactcaga aatagctttt gaagtttctt   100446
ctaccccata aatagatttt attttatggc tggcagaaat gaaaattaca acttttttgcc  100506 aagaacagag aatagaataa tctcaaattg gggctgcgga ctcagttta tgttcaaagc    100566 tgtgtgaacc tcatcactga gttcttacaa atccctgtgt ccacatgctc caaaccaccc  100626
actgtgagtt cagaaaagaa ctctgagtgc atctttcagt aggaaagtaa aaactgattt   100686
ttacatttcc tttgagccaa accagctgtt tcttctttaa agatttccct ttgagatttc   100746 catttttatga ctaagtctaa ccagtatttt tttggcaagt aagagttgtg ggagtgtatc  100806
tgtcatcata aggaaatcaa agccagaaat gccttctgcc atggtgggtg atgttaaaca   100866
tttcaaggaa cttatatta taaaaattgt caaacataaa aggaaagtg caatataatg      100926 aattccatgg acccatcaca cagcatcaat atttatcaac attttatcaa tatttttttca  100986 tatattttttc ccacatccac tcccactagt gtttgaaagc agaagacaga taacttacca  101046
tcttacctgt taacatttca ggatgtattt ctaacaggta aagactttat catttaatat   101106
ttagactgtg tttgttcaaa ttatctgatt agattctatt tcagaaaaca cacacataaa   101166
caaaaatgat aatgagaaaa agaaagccct tccacatgat tgacacttct gagtagtgtg   101226
atcccagttc atgtccattg tctgggatag ctattaaata aaacttcctc tcataaaatt   101286
ctctccattt agaagataaa ttctgtgatt cacaagcctc ttttttattta taatagccct  101346 tcccctttct ttatgaattt gaatttgttt tttaaagaaa ctgtgatttt ctctgtaaaa   101406
ttccccacat tctggatttg gccgatttca tcttggttct tttgtttact ttaacctatt   101466
cctctatccc cagtatcttc tgtggactgg tagtttgact ggttctttt cttttctttt    101526 tttttttttt ttttttttt tgagacaggc tctcgctctg tcgcttaggc tggagtgcag    101586
tggcccaatc tcagctcact gcaacctcca cctcccaggt tcaagctatt ctcatgcctc   101646
agcctcctga gtaactggga ctgcaagcat gtgccacctc atcctgctga tttttgtact   101706
tttagtagag acggggtttc gccatgttgg ccaggctggt ctggaactcc tggcctcaag   101766
tgatccgccc accttggcct cccaaagtgc tgggattaca ggcatgagct atcacgccca   101826
gctgattttt aagtaatata agtatgtgtg catgtatagt atacattggc aaaaacactt   101886
cataagtagt gctaaaatca tcttatttat atacatcagg agacacataa tgtctgtttg   101946
```

```
tttcccattt tagtgatatt aagagtgttt agcatgttta gttgtcagcc tgatccatca 102006 ttatgttctt catcaaactt tcaccagata gtttcacatc aattgatgat cattgcctgt 102066 ttctattatt ttgttttcaa gttgacagtt ttctctcact tgatgttgtg taaatttagt 102126 tatataaagt taaattattt tgctattttt tctatgctgt atacatttga ataactgacc 102186 taatttttac tttaaaaata ttttacaatt agaagtccaa atagtaaatc aaaggttaag 102246 aatttttgca gaaatctgtt atatagatga cattttaata tttgcccttt atatcattta 102306 ccatgagcca aatttcaagt catattaaaa tgactgtcat gtgctaattc taacaatatt 102366 tgaaagaccc ctatcaaaat aaatatacct tttagtagcc actttattag aaaatcaact 102426 ttaagttatt cccccatgtt tttttctaat tgagatataa ttcacatacc ataaaattta 102486 ccctttttaaa gtatacaatt cagttgtttc agtacattca caaagctatg caaatgtcac 102546 ctctacctag tttcagaacg ttttcatcat tcccagaagg aaaccctgta tttattaggc 102606 agtcacttcc ccttctcccc ttcttccttc ctctaagtgg caaccacaaa taaacattca 102666 gtttctctgg atttacctat tctgggcatt ttgtattagt gaaatcatgt atttggcctt 102726 tctctctggc ttctttcatg tacctcaatg ttttcaagtc tcattcattt tattaaaaaa 102786 aaaaagtacc ttttttcttt ttcttttttt ttttttttgtc cacgtatata ttcacaccac 102846 attttttgag acagagtctc gctctgttgc ccaggctagg gtgcaatggt gcaacctcag 102906 ctcactgcaa cctctgtctc ccgggttcaa gtgattctca tgcctcagcc cccaagtagt 102966 tgggattaca gttgtgcacc accacaccca gctaattttt gtattttag tagagacagg 103026 gtttcaccat gttggctagg ctggtctcaa actcagcctc aagtgatcct tctaccttag 103086 cctcctaaag tgctgggatt acaagcatga gccactgtgc ccagccacat tttctttttc 103146 catttattag ttaattgaca tttggatcgt ttctactttt tggcgattat aaattatgct 103206 gcaatgaaca tcggtgtaca agttttttgtg tgaacatgtt ttcagttacc ttgggatata 103266 cacctaggag tgacattgtt agtaatatgg taactttatg tttaactttt tgaagaactg 103326 ccaaactgtt ttccaaagta gctttatgct tttacatttc tgccaacaat gtatgaaggt 103386 tccagtgtat ctccacatcc tcaagaaaat gttattgtct ttttaattgt aaccatccaa 103446 gtgggtatga agtttatctc gtgattttga tttgcatttt cctaatggct gatattgggc 103506 atcttttcac gtgtgtattg accatgtatt ttttttgagaa aagtctactt atatgttttt 103566 aattgtatta ttttttagagt tgtaagaata tgttatgttg atacttgaac tttgtcaaat 103626 gcctggtttg cagatatttt ctcctatccc acaggttgtc gcttcacttt gataatgtcc 103686 ttaaagtaca aaagtttttaa attgattttg atgaaactca atttctttttt aattggcagc 103746 ttgtgcattt ggggtcatat ttaagaaatc attgcctcat tcaagatctg aaagatttac 103806 acctatgctt tcttctcaga gtattataac tttagttctt acatttagat ttttaattaa 103866 tgttgagtta atttgatggt gagagataag agtccaactt cattcctttg caagtagctg 103926 tccagttttc tcagcaccat ttgttaaaag actgtttttt ttcaattaac tgaccaagat 103986 gtatgggttt atttctggac tcttaattct gttaatctgc atgactttttc ttatgccagt 104046 accacactgt gctgattcct gtagttttgt agtaaatttc gaaatcaaga caggtaagtc 104106 ttccaacttt gtacttttgc ctaccatgtt tcttgggttt ccatatgcat tttaagatca 104166 gcttctccgt ttccttctg gatttttttt tttttttttt tttttttttt tttggtggag 104226 ctggagtctt actatattac ccaagctggt tttgaactcc tggctaaaga gatcctccct 104286
```

```
cctaggcttc ccagagagct gggggttacag gcatgagcca ccacatccaa cccccttctg 104346 ggactttgac tggggttctg ttgaatctgt tggtcaattt ggagagtatt gatatcttaa 104406 cattaaagct tccaatttat gaacacaggc tattttttcca tttattctta aatttctttc 104466 agtaatgttt tggatgaaac atgtacaaag tcctgcactt tttatttttt ttaagacaga 104526 gtcttgctct gctgcccagt ccagagtgca gtgctgccat ctcagctcac tgcaacctcc 104586 acctccgggt tcaagtgatt ctcctgcctc agctggaact acaggtgcgc gccaccatgc 104646 ctggctaatt gttttgtgtt tttggtggag acagggtttc accatgttgg ccaggctggt 104706 ctcaaacacc tggcctcaag tgacctgact gccttggcct cccaaagtac tgggattaca 104766 ggcatgagcc accacgcctg gcctgtactt ctgttaaaat ttttctatg tattttttt 104826 atcctattgc aaaatcaaat ttttgttga taatatatgg tcataaattt catttttata 104886 tattggtctc atatcctacc aacttgctga actagcttat tagcactaac tttttttggt 104946 agattcctta ggatttgctg catacaagat tatgtcatct acaagtagag atagttttgt 105006 ttcttcactt ccaatctggg tggctttatg ttttttttctt gcctgattac ccagttagaa 105066 cttccagaaa atgtcaggta caattaacaa ctgcaaacat ccttgtctta ttcattttag 105126 aaagaaattt ttagtttttc accattaagt atgatactag ttgtaggttt tgtttaaaaa 105186 aagactgtgt caagttcaga agttcccttc tgttgctagt ttgttgaata attttatcac 105246 gaaagggtgt tgaactttc tcaaatgctg tggctacatc taatgaaatg atcatgcgtt 105306 cttctccttt attctattaa tatggtatat tatattgatt catttttata cattagatta 105366 acattatatt tctggaataa atcccacttg gcctcagtgt gtattacttt ttatatattg 105426 ctggagtctg tttgcaggta tttcattgag gactttcgca tctctgttga taaggtatac 105486 tgatctttag ttctccttgtg atatctttgg ttttggtgtc agagtaattc tgagttcaca 105546 aaatgcattg ggaaatgttc ccttctctat cttttggaag agtttacaaa ggattggttt 105606 aactctttttt taaatgtttg aggaaaattct ctaccctgg gctttccttt gtgggaattt 105666 ttaaacattt ttaaaataga ttattttttaa agcaatttta gggtaaaagc acattgaatg 105726 aaaggcacag agcttcctta agtacatgct gcccctgtat gtgcatagcc tccctcatta 105786 tcaacatcct ttaccagaat ggtacatttg ttgcagtcaa tgaacctgca ttgacaattg 105846 tcgatgaaag ttcatagttt agagttcacc tttggtgtta tgtattctgt gagtctggat 105906 ccatgtttaa tgatactcat tcaccattac agtatcattc agagtaattt cactgcctta 105966 aaagtcctct gtaccctacc tatttttctc tcctacccca ctaacccta gcaaccaatg 106026 atctttttat ctcaataatt ttgcctattc cagaatgtca tatagttgga atgatacagt 106086 atatggagcc ttttcagact ggttttttgtc acttagtaat aagcttttaa attttccacc 106146 atgtcatgat cgttcatttc ttttcagcat tgaataatat tccattgtct ggtttatcac 106206 agttgattta tccattcaca tagtgaaaga catcttagtt gcttccaagt tttgacaatt 106266 atgaataaag ctgttataaa agtatgtagg tttttgtgtg gacaaaagtt ttcagctcct 106326 ttgagtaaat aacacagagc acagtagctt gattgacagt aagagtaaga aatatttttt 106386 ctcagtctgt gtcttatttt ttcattcact tgacagtgcc atttgcagaa caacagaaa 106446 gttttaatttt taatgaagtc taggttatca gttaattcat gaataatgtt tttggtattg 106506 tatctaaaaa gtcaacacca aggtcatcta tatgttctgt gttatcttcc agaaatttta 106566 tagttctgca ttttacattt agggctgtga cccatttttgc attaattttg caaaagctat 106626 aaagactatg tatagattca cttgtttgca tgtggagttg tccagttgtt cccgtaccat 106686
```

```
ttcttaaaga ctatctttgc tttattgtat tacctttgct actttgtcaa agatcagttg  106746
attataatta agtggtctgt ttctggactc tttattctgt tccattgata tatttgtcta  106806
gactttcacc aataccacac tatcttgtta acttaggctt tagagtaagt cttgcaatca  106866
tgtagtgtca gtcctctgac attgtttttc tccttcagta ttgagttggc tattcttttg  106926
cctattacta agtaaaaaaa gcagtctgaa aaggctatat atacagtcat ttattggtct  106986
tttgcctctt gatataaact ttaaaattac tttgtcagta tcctcaaaat cttgcaggaa  107046
ttttgataga ttgcactgca tttctagatt gagttagaaa tactgccatc ttgacaatac  107106
acatcttcct atccatgaac atggaacatc tctttcttgg atatccttca ttagaatttt  107166
gcattttccc catatagacc atgtacatat tagatttata cataaatatt tcatttgggg  107226
gggtgctaat ggtaatgtat ttttatctca gattctgctt gtacattgct ggtatgcaga  107286
aaagtgatca acttttgtat attaaacttg tttcctgcaa ccatgttata taatcacttt  107346
agatccagtt tttttttttt tggtcattct ttcatatttt ctaggtgatc atgtcatcta  107406
gcaaagacaa cttctttcta atctgtatac cttttatttt cttgtcttaa tgtattagct  107466
agcatttcca gtatgatgtt gaaaggcatt ggtgagaggc aacatacttg ccttgttcct  107526
gatctcagca ggaaatcttc aatttatgt tagctctatg gttttgtaga tattctttat  107586
ttacattaaa tatgttagct gtatggtttt gtatatattc tttatcaggt tcaggtagtt  107646
cccctctttt cctagtttac tgagaggctt ttgaaaatca ttaatcagtg ttggattttg  107706
taaatacttt ttttccacct attgatatta ccatatgatt tttctttagc ttattaacga  107766
aatggattac attaattgat tttcaaattt tgaactagac tggcatacct ggagcaaatc  107826
ccacatggtt gtgatacatt atttatgaat gcattcatgg tcatggttgc tattagtctg  107886
tagttatctt ttattgtaaa gactttggtg ttggtattaa ggtaatgctg ccctcataga  107946
ataagttatg aagtattttc tctgcttctg tcttaattga gattgtagag aattcatata  108006
atttcttcct taaaactttg gtagaaatca gaatgaacca tctgtgtctg gtactttgtt  108066
ttgaaaagtt attgctgatt caatttcttt catagatata ggcctattta gattattatt  108126
ttgcataaat attggtagtt gtgtccttca aggaattggt ccatttcacc ttgattatta  108186
aatgtgtggg cacatttgtt cataatattt ctttattatc ctttgttttt gagacagggt  108246
ctcactctgg ttgcccaggc tggagtgcag tagtatgatc tcagctcact gcagccttga  108306
cttcctgggc tcaagtgatt tacccacctc agcctcccaa gtagctcgga ctacaggcac  108366
atgccaccat gcctggctaa ttttttttatt attattagag atggagtttt cctatgttgc  108426
ccagtgtggt cttgaactcc tggactcaag caatctgcct gcctcagcct ccaaagagtg  108486
atgggattgc aggcatgagc catcacacct agcctgatgg cagaacttt taggaacaat  108546
agaatggtat atggcatttt caaaaattgt ttcccctcc tcctatggaa gcatgaaggg  108606
attttctct agtattcatt gtgagaacct catctggctc ctgaatgtag aaaactcaca  108666
aaactgtgag gaacctatta tgactggatg cctttggagt tgttcacact gaacctccag  108726
caattcatca attatatttc agattttcct atcccaacac tggttcctac agaggtttct  108786
gctccagtaa gctgtaattc ttttttatcca tctgcttcct tggttgtgag ggcagtgatt  108846
ttccctgtga cctcatttct ctgacagatc taagtagtct tgattacatc ttttaacctg  108906
ttgtaggtat attcagattt tctatttctt cttcagtcaa ttttagtagt ttgtgttttt  108966
ctagaagttt gttctctagc tctgctttag ctccatccaa taaaatatga gtatgtcgag  109026
```

```
ttttcattta caacaaggta ttttctaatt tctatcatgt ttttttgatt cctgactgta    109086
taggagtata ttttacccta ttcccaaat ttgcttgtta ttcatgtata attttatcag    109146
aaaacacact ttgcacaatt tttgcagtgt tacatttatt tagacttgtt ttataacttg    109206
acatacagtc catcctggag aatgtttcac gtgtgcttga gaagaatgtg tatattcagc    109266
tgttggtggg tggcatgttt tatagatgtc tgttagacct agttggttta tagtgttttt    109326
tacaacttct gttttctttt taatcttcta tctacttta gccattattg aaagtggatt    109386
agtaaattat ctatttattc ctttaattct gccattttt gcttcatgta ttttggtgct    109446
ctgttgctta ttacatgtat gtttacattt gttacatcat tttaatggct tgaacttttt    109506
attataaaat gtgtatatct tgtagatatc gtatagttaa atcttttaa aaattgatat    109566
tgctagtctt tgccttttaa ttttcaatt tatatacatt taacataatt attgataagg    109626
taggatttgt ctgccatttt gtctgtatct tgtcttttt tgtgttcaat agatattttc    109686
tagtgtactg ttttaattcc cttgtctttt actaaatttt ttgatgttct taatggtttc    109746
cctggggatt acaactaact tataacagct agtctgaagt aataccaatt tcattacaat    109806
ataaggaaac tttgttccca tatagctaca ttccctcttt ttactctgtg ctattataca    109866
aattacattt tattttatgc ccattaacac agattatgtt ttttctttta aatcagattg    109926
atattgtcat ttaaatcaaa tatgagaaaa atagttacaa aaaatacat atatgatttc    109986
atatttacct atgtaattat ctttactggt gctctttaag ttcttaggtg tatttgaggt    110046
actgtctagt gtcctttcct ttcagcctga agtatacatt tagtatttt tgtaggacat    110106
gcctgaaaac aataaactct tatttatcag agaatgtcct aatttattat ataatacatt    110166
tctgaaagat agttttgcaa aatacagaat tcttggttgg cagtcttttt cttgtggttc    110226
tatgtcattc tactgccttc tggtcttcat tgtttctgat cagagatcag ctattaatct    110286
tattgggaat cctgcataca tgataatcat acagttttca tgattttctt gtgttggctt    110346
tcagcagttt ggttatgatg tttatatgta tgcatatctt tgggtttatg ttacatggag    110406
ttagttgagc ttcttggaca tgtagattga tgttgttcat caaatttgag aagttttcgg    110466
ccattatttt tcaaatattc ttcctattct ttattcttca tcctctactt tggggacctg    110526
cattatgtct atgttggtat gctttatggt cttccacaga tctctgaggt tctgtttatg    110586
ttttcatttt tcagactgaa taatctcaat tgacttatct tcaagtccct ttttcccctc    110646
cttttcaact ctgctattga acccctctaa tttttactgc agttattaca ctttcagctt    110706
tagaattcta tttaataata tctttttctt gagtttatct catgtattta ataaatgct    110766
gtagtcttac tttagttatt taaatacagt tttctttcat tatttgggca tacatgaaat    110826
agctgactta aagtctttgt ccagtggcct aacatctgga cttttcagg aatagcctct    110886
attgactact ttataggggc catactttgt ttctgtttct cttaattgtt tagacatttt    110946
aaactaatgt aatggctgag agcagtggct cgtgcctgta atcccagcac gttgagaggc    111006
caaagcagga gcatcactta agcccaggag ttcaagacta gcctgggcag catagtgaga    111066
ccctgtctct acaaaaataa aaataaataa aataatataa tctggtaaat ctgaaaatca    111126
gattctaccc cctgcccaga atatgttact gtttctggtg gttgttgttt atttcttttt    111186
aactactcct ataaagtttg tattgtttct catagatagc catcgaagtc tttgcttggt    111246
taacttagag gtcagctaag gattagacag aattccttag gtgcctgaga tcaataagtc    111306
agtctttgac aaaggggtct gtatgtgtgt tggggcatgc attcaacact cagccaggct    111366
atttgcagct ctggattagc ctttattccc tgcttgtgca gagtctcaag gttagactgt    111426
```

```
ggtgagagtt tagggctttc tgaggtcttt tgtgggccct acagttgcat gtggctttct    111486
aaattcccag gaatatattt tcaaagcctc ctgtggatca tctcatttcc caggtaattt    111546
acttttaagc ttttttagtt atcttatgtt ttgctccagt tattagctac acctgagtca    111606
gtgacaatat tcaacagctg cctatgatta tttgacaaat gcctctgtgg aaaaggtggt    111666
tcacactagg tgaactccaa gttagataaa gtaaagataa ccttactagt gggatcttcc    111726
aggaaactac caaacaggtc aaataatgta aggtctctgt gaatgggact ttagagtata    111786
tccaaccagt ctagagtata tccaaccaat ctggcctcct ctagtggcag cctggctgct    111846
gcttttcata ataaatgtgg gctgttttga tttgaaggct accatagagc tgtgggaaaa    111906
gttaaaatac cacagagctc actcttctca ctgaaatcct gtcttttttt cccttgaaca    111966
aattctccct atattgctgc aagcttttg ctaattccca gatctgaaaa agctgattcc     112026
gacaatattt atcagtactt ttattgcttt tatggaggat aaaattttca gagatcctta    112086
ttctgccatt tttgctgaca tgtgtaaagt gatcatttct aattgtaaaa ttccttttgc    112146
atttattagc tggaatactt tacaggactt ttcctcatca accgttagtt accatttaat    112206
atagtttgta agaatgatag aataaatgca tggcaagaat ctttacttct caaatttcag    112266 agatttgat gggaaattat atttagagat cacaatcagt gtctagatgt gctccctgct     112326
atggaggtgt cattactttt aggcttttt aatgggcaaa tacatgaagt aattatttt     112386 tagaaagaaa atctgagatt aactcaaatc attaattcat actgatttt cctattcata    112446 gttgacagag tattattatc ttttgttctg cttctcttgt acactgaaat tcttggtttt    112506
tgatattaac aattatttac ttatatcaca atatacatac attaatttaa aaataattta    112566
cagtgctacc tgaatatttt ttcttgtaag ttgttttatc tctctttgct tacttgtatg    112626
tttgtttatt gtcattagaa tgtatcaaac tagggctata aagctgtaat actatatttt    112686
agccagaaac taggacctag cactcaaatg cccatcaatg gtagaataat tcatcacatt    112746
tttataagat ggaatatggt actcaatgaa aatgaataaa gtacaactac atgcagtgat    112806
ttggatggat atcccaaaca taatggaaaa agcacacaca aataagctta tattatataa    112866
ttccatatac ctatgtatat atcaagtata aaagtaggca aaacaagcta ctgatggtgg    112926
cacacaccta tagttccagc tatttgggag gctgaggcgg gaagatcact tgagcccaga    112986
agttcaggtt caacctgagc aacatagcaa gaccccatct gtaaaaaaga agcattatt    113046 aacataaaaa taggcagaac tactatattc ttagagaagt tactgttagg gagacagaca    113106
gtgagtgact gaaaggcaaa atgaggggaa attccagggg atagtaaata tttgttct     113166 tagtgtgggt tctacttaac tgggtatttt ccatttgtaa actgtaaaat tatgtgcact    113226
tttctgtatg tgtattacat tgcaataaaa ttgtttaaaa gtcaattgaa atagttctgt    113286
gtgtggttat gccacagctt aatacagagt tagattagac ttcttttcaa actcattttg    113346
catatagaca cctataatat cagctgcaca gcctatataa tgctatccat agcaatgaat    113406
ttggtctttt gattttcag ga  gaa ctt gcg cct gtc agg  ggc tgg atc       113455
                        Arg Glu Leu Ala Pro Val Arg  Gly Trp Ile
                                    1490                 1495 cag aaa  cct gtg gtg cct cct tct ctt ttg gtt gtt  cat gga gca       113500
Gln Lys  Pro Val Val Pro Pro Ser Leu Leu Val Val  His Gly Ala
    1500              1505                  1510 tgt act  aca atg gat gta agt ttg cca gaa gca aga  tcc caa gga       113545
Cys Thr  Thr Met Asp Val Ser Leu Pro Glu Ala Arg  Ser Gln Gly
    1515              1520                  1525
```

| | | | | | | | | |
|---|---|---|---|---|---|---|---|---|
| agt | tta | agc | tgc | ttg | ggg atg | acc caa aag ag | gtttgtttac | 113587 |
| Ser | Leu | Ser | Cys | Leu | Gly Met | Thr Gln Lys Arg | | |
| | 1530 | | | | 1535 | | | | ttcctgatgt ataatcgctt tattttcat agagaattca ttagcttaga tgaagtgaac 113647 aatatgacat atcttggtaa gctcttatta atcaaagttt tcccaaact gtagatacac 113707 actattttt aagttggcat aataatcata ttatgccaaa ataatagata aaatttgagc 113767 aacaaaaact tcctctttgg tcttttatgt taattccaaa gttttaaagg ggtgtcactt 113827 cattgttaaa actaaatgag aattggtgat gttttcata ttttgactct gaattatgga 113887 agttacataa gtactacatt cagaaaagac catttttagt cacatttatg tgcaatgaga 113947 ttcaaataat ttaaagtcac tgtaatgaat gcatttaata aagtcactgt aatgaatgca 114007 tttaagtaac taaaacattt agattttaat ataactctgt aatggaaata aatggacact 114067 aatttctcac tgaagtcatt ggttttgtc ttgtctgtag aatacgtatt tcttataatt 114127 tgcaaattga taaatttaac aacttttggg tggcatgtag tctagagtat agatacttct 114187 tgacttatga ggagactaca ttcctataaa tccgttgtaa aatgaaaatc catttaatac 114247 ccccaataaa cccatcctaa agtaaaaaaa aaacgaagcc attataggtc agggactgtc 114307 tccgtactaa ttgaatgatg agaaaacctc agtatattta gcatttagct atgaccacat 114367 tttcagtcat tctatacact tacaattatc ttttgaattt cgaatacaat taaaatattt 114427 ccatactata gatattataa cattgatgag tcccttttaaa tgaagaattt gttaaccttaa 114487 ttaagctttc acttactatt atagtcacag ttaataaagc aagtgcaaaa actcctgaaa 114547 tcacagtata agtttttaa aggatgtttt caataattaa agtttactta aatgtgcgag 114607 acatcatttc ataagacaag aatatgaata ttaataactt aatgaaaagt actgattttg 114667 cttgctgtca ttttaattt ctacagataa cttttttttt aaccactgtt ttatcaagtg 114727 ataaatgttt atcactttca cgaggtttca tgtaaaccaa atccagagga taccaagtaa 114787 cttattgcct ctgttgggta ggagagctct gttcagaaac ctcctcacct tctaaaattt 114847 acatctctgc caggtggtta tgtctcacaa ctttttttt ttagagaaat atcaatctga 114907 aatgaagact tctaagtata aatggagcag ctaaatatga tcacctacca tttttttaaca 114967 gtatattact tggaaaatct gttcttcatg agcagggcag gtgggggtgt aactgagcat 115027 ttccccttc aagtaaattc tgcaaaggtt ttcatgtatc ctgcattcta gttctgaagc 115087 atttttatcca tatttgaagt gtccagtaaa ttttagttgc tctatggaga gatcattcca 115147 aattatttaa atactatctt tataaacata aaatgtaaag attagaaaata gacaaattaa 115207 gctaaagaag ttcttttaat agttcatctt ccttggtagc taaaaaatgt gacctcttta 115267 agaccatacg gcttaattcc cctaaccccta ctccctggcac aggcttgtgt gtataaaatg 115327 caaaatatct gcatgcagtt agaaaatcaa tcttatgaaa aaaacaaata gctagatatt 115387 tactagcaca tatgaaatta aatgatagtc atgttttaaa gatgctttat ttagtaataa 115447 aggcaccata tattgtgttt gggattcaaa atgtaagggg aataatctaa ctgatagtct 115507 cttttacata gagaaaatgg acttagaatt taatatgtag aattattcac tttatacag 115566

| | | | | | | | |
|---|---|---|---|---|---|---|---|
| g aag | aga | aac tgg agt ctc | att tgc aaa acc tgt | cca ctc tta tgg | 115612 |
| Lys | Arg | Asn Trp Ser Leu | Ile Cys Lys Thr Cys | Pro Leu Leu Trp | |
| | 1540 | | 1545 | 1550 | |

| | | | | | |
|---|---|---|---|---|---|
| cac caa cat ata aga aac ttg cac ctg atg cat ata ata atc ag | 115656 |
| His Gln His Ile Arg Asn Leu His Leu Met His Ile Ile Ile Arg | |
| 1555 | 1560 | 1565 | | gtaagtttaa ataatcattg gcagcaattg taacaactta cttgttacta atgacctatg 115716

```
tccaaaaata ttttgaaac aatgatttt aaatattatt ctaactttc ctcttaattg   115776
ttgaaccac tgcagtgttc agtttcgagt atataaaaat tataccatac aaaagtacat   115836
tttttttgtc ttttagctgt aaagacatgc gcttctaaaa gtcacaggct gttctatcta   115896
ctaatcttgt tctcatatga ataattttgt ttctgtaaac agactatgga gattacatca   115956
aaattatgtg gcccaagcta taggttctaa ctacctattt ttactgcaag tctataagta   116016
taaatgagta ttcataagaa tttatagact tacaaatatt cacataaagc tatgcatata   116076
ctaacattgt aagtatatat atttcggtcc agatgtgtca gattttgctg atcttccttt   116136
tttgtttgac cttgacttca tacaccaagc aaaaacattt tttttttcta ttttacatgt   116196
gtattctaaa ctatagctag ttaagacagg tagatgattt ggtcagaaat ctctcatcat   116256
gaaggcaaaa aactaaaatc ttcactgttt cagtaacatc aacaacaaaa gcattaagtg   116316
aaagtctatt acaaactaaa cactgtgttt agtcactggg aacataaagg tgagcagtgc   116376
catctctgtc tgtctttaag aattccgtct ttgctgggta cggtggctca cacctttaat   116436
cccaacactt tgggaggcca aggcaggtgg atcacctgag gtcaggagtt ctagaccagc   116496
ctgatcaaca tggagaaacc ctgtctctac taaaaataca aaattagctg ggtgtggtgg   116556
caggcacctg taatcccagc tactcggaag gctaaggcag gagaatagct tgaacctggg   116616
aggtggaggt tgcagtgagc cgaagtcaaa ccattgcact ccagcctagg caacaagagc   116676
gaaactccat ctcaaaaaaa aaaaaaatt catctttaac tgggtgcggt agtttatgcc   116736
tgtaatccca gctacccagg agaccaggag tctgaggctg cggtgagcca tgattgcatc   116796
actgtgctcc atcctgggtg acaaagatga cccagattct aaaaaaaag caaaaaacaa   116856
aagaattcct tctttagtgg agacagagac atataaaata aatagcaatt ttagaattac   116916
acagttccag ctggaataga agaatgtgca catttctaaa aaatttaaa aacaaaaccc   116976
aaaagtagac tagatgtcac aagcagcctt agacgctaaa taaagatctt tgaactttat   117036
tctgtaggta accattgggc tgtttcaagt gtgtgttggg gatggaaggg taaagtgatg   117096
taattcgtat tttgaaaaat ttacttaaaa gccaagtaag ggaaatataa cttaaatcta   117156
tgtaagatta gagagagaag aaagctattg caatcattgg gcaagagatt ttaaggacct   117216
aaagaaatgg caggaattaa gtatgtacac taactaaggt ggagcttaga gaacttggtg   117276
actagatgta tggatgagaa aagaatttgg agatacaaca aatttccagt ttggacaggt   117336
agttctatta actagtatca gaaattggta agaaatagta agttttggga tggggagaag   117396
atatcaaaat tttggacatg ctaggcttct aggttaatta gatggagaat caggagaaaa   117456
attcaggcta gcactgtaga tttgagagtc agaatgctgg caggacttaa agttgaatac   117516
ataggaatga aaggaggttt tcaaagtaga gattataaag aggacaaagg gctgatgatg   117576
ggattctgga gccatcaatc attttaggca tgagtggagg aagagaagcc aatgaagtaa   117636
gaactggggg agggagtaga agaaatgtag taggaaaagt gaaagaggga gatggatgga   117696
tggaggaaag ctggaatgat gagaagacac ccagagcaga gtatacagga gcaataggta   117756
tggggctctg ggatgggtgc tctgtcattt acttgataat attaaagact ctcgtgggat   117816
tagattagtt tacacagcag acatggacaa gggactaatc ctaaaatgat ttagctactc   117876
ttcttttcca ctgtggactt taacgtccca acatttttt tttttttg gttcgaacaa   117936
tagaggcaaa ttaacgatg gtctatttgt aagttatttt atgtcaaatt atgttttag    117996
aaatgtgtat gaatatctat gaaaagtttt taaacactat taatagttgg attaatactg   118056
```

```
ttattttgtt tagctagtat cacaaagtat aaggagtgct tgatactgt cgtaaaagtt    118116 taattctcag caagaacttc tgaaataaat caagctataa aaataaataa atgaatgagt    118176
ctatgttgct agatttaaag ttgggtcatt ttctattaaa tgaattttta ataggtgctg    118236
ttaatcaaat ggctttactt gaggcagaat aacaaagcat tgatgttctt tttgctccct    118296
tgattcttat tatggaccgt ctcatacttg aaactatttt atacatttcc taaaacttaa    118356
gtacccaaaa tatgaagcca tcaaatatgt tcaagtttta atatttatat atgaaaatgt    118416
gttgatgtaa tgtctagata aattaagtca attaatagtt gtaaatggat gagatgcttc    118476
tgaatggata aaatattttt atattgcatg gtaggtacta ttggtaatat tcatccatgt    118536
atgttaatat gctttagaga tcaaaataat agccatgtga tgtttccaca cagtacacgg    118596
gaagaccatt tgatgttata gatgctgtca taaaacctac tatttgatct ttacctcctt    118656
tccccaactg agtgtcgtat ctctatttct cacatctgaa tattcttcct tgctttattc    118716
cttgatttca tgaagtctta ttgctaaagt ttagttggct ctccacagca tctcttctgt    118776
cagtcccatg gaattagagc ttcagttttc tcaacttaaa tgtcctttct tcgtgtctat    118836
ccagtagaca tatatttggc tctgtctttt ctatgcctgc cttacaattt aacagtagac    118896
ctgaaatagc aggtgtcaat ctcaaaatcg tgtgctattt atcatacatg aagatgacat    118956
tttagacaaa tgcttctaag agagcttttct atgaagatgg aaatattctc tatttatgct    119016
gttcagtgta ataggcacta gccacatgtg gttattattt aacagttgat acgtggctag    119076
tgtaattgag tttaaattaa tgtaaaaatt aacacaaaca gccacatgtg gataatggtt    119136
accatagtga acagcacaac cttagaccat gagaaagtta tgcatttaga attgtcttcc    119196
agacatttag atggatttcc agtaattcat tcacaaaatc ctgcatggta ttttttagga    119256
gatggcataa gtgtaatttc tagctgattg tatatctgtt tttgttcaag aaacagaata    119316
aagctaacta gaccacagca tgaactgaac ggccacaaag cacacatcta tgttaaagag    119376
tagttggtac cttcattttc ctttggccaa agttttatga ggttagatag acaaatacat    119436
atatgaatcc aacagtaaat aatatgaagc caccacaaac ttttatccta atgcaagttc    119496
atcttctagc catgatggag taaacagaga ctacatatgc cgttacacat ttaagaaaaa    119556
actgacaaaa tatatgaaac aatggttttt agacatagaa taagaaattc aagagacagt    119616
ggcaccagag agaaaggaag taaaaaggtg aacctataaa taccccagtt tacttcctga    119676
agagagtatt aggctccagt gtagccagta ggaacccaaa cacacccagc cttatctctg    119736
tattaaggag acaaagttca aaatttggag aggccaaggt gacgagagtt cactattcag    119796
aatatcagag aggagagagt gttattgaga aaagctccag agacctgcag agggttctga    119856
tccagtcttc agctgagtat taaacagcac atgcatgtga aaaaactgcc aaggctaggt    119916
agggaaagaa ccatcagaag aagcaggcag aataatccct tgatctcaca caggacctgg    119976
aatagttctt gatcatacca gccagacgga gaagacttca taatactatt cataattgta    120036
ttgccttggt agtagaagta aatttggcag ttctgacctc atctaaaaat gcttaaaatg    120096
aaaacataga agggccaaac tgattctaag taatttaact gcatcacagt acaaaaatta    120156
aaaaaaaaat ctaccaacaa ggtaaaattt atagtctagc attccatcag aaaatacaag    120216
gcatacaaag aaaaaagaaa atataacctt tactggggaa caggcagaaa tcaatcaata    120276
aaaatagtcc cagaactgac atatgtgata caatatgtaa ataagttcat taaaatggct    120336
atcatatttc atatgttaaa atgccagagg aaagcatgag agtgataagg aaagatcaga    120396
agatattaaa atacccctaca atgaccttct agaagtgaaa aatatatatc tagattaaaa    120456
```

```
atacactagg cggaattaac agattaagga acttgaagac atagtaatag aaattttttca  120516 gtataaagaa aaaactgaaa aaaatgaata tataaaagac ctattagcca atattgttac  120576
actaatatat gtgtaattgg agtaccagaa ggaggtggga gacagaaaaa tatttaaaga  120636
aacaatggcc aaatttttt cagatttgtt caaaactgtg aacccacaga tctcagcagc  120696
tcagcaaacc ccagattaaa aaacaaagac ataaaaaaag actatcaaaa atttataatc  120756
aacttgctta caatctgtga taaagagaaa ctcagaaagg caaatggaga aaaaaggaca  120816
tattacacta ggtgggaaaa aataagacag gagacttcat tcagaaaaag gcaagagaga  120876
agatgtaaga gaaacatctt taacatacta aagaaaaaa gactctccac ccagaaatat  120936
ataaccaatg aaaacaactc tcaaaaaaga cagcaaaata aagaatatt tttcagacat  120996 acatacaaaa gctgaaagaa ttcaccacca acaaactagc acttaaaaa tgttaaacga  121056 aatccttcag gaagaaagaa catgatacca gacagaaatc cagatcaaca taatgaaatg  121116
aacagtatca aaaatagtaa acatggttaa aagacttta aaaaaatgat aacttgctat  121176
cttaaaaata tattaacaat gtattatgag gtttataaca cgtagaagta gcacagaggc  121236
tgaggaattg aaagtatatt attgtaaagt acttatacga tatgtggact gggtatatta  121296
cttggctgta aactgtgaga cgttagagta cactgtgtac cttaaaccac taaaaaaaaa  121356 aaaaaagta tatagctaat cagccagtaa agacagaaaa atgaaatcaa tccaaaaatg  121416
tttttaaaaa tatataggac caaaaaaga taaatataaa aataaaacaa atagcaagat  121476
ggtttattta aacccaactg tatcaacaac cacattaaat gtaaatggtt ttaacacccc  121536
taattataag gcagagcttg tgatattgaa aaaaagcaa aaccaagaa aaccacttta  121596 aatataaaga tacaaataaa ttaaaaagat attttttaaca taaaaaatga tgttgaaaag  121656
acataacagg aaaaaatatg attattgcag taggtacaga aaaaccattt gataatattc  121716
aacattcata aaaggaaact ttctcaacct attaaataca taaatggaaa gccaaaagct  121776
aatgctatac ttagtggtga aagactaata cttgaccct aagataagga acaagacaac  121836
aatgtccatt tttaaccaac tgcttctatt caacatcaaa ctgtaaattt tagaaagtgc  121896
agtaaggcaa taaataaagc agtcaagatt gggtaggaaa aaataaaact gtacttattt  121956
gcagatgaca tgtttgtcta cataagaagt ctcaaaaaat ctaccagaaa atgaaattaa  122016
tatatgaatt tagcaaagtt gtgaaataca aaattcaagt gtattttat atactagcaa  122076 taaataaatc aaaataaacc attaaaatag catcaaaata taaattctt agacatacat  122136 ttgacaaaaa tgtataagat tatatactgg aaactaaaac attgctgaga taaattatag  122196
aaaacttcag taactggaga gatacactat gttaatggat caaaagacta aatattatta  122256
agatgtcagt tctccccaaa ctaatcaata tgttcaatac atgatgtttc aaaacccag  122316 caggttttt gaaagaattg gacaagatgg ctgtaaaata tatatacttg gaaatgcaaa  122376
ggacttggaa tagtcaaata atattttaaa ataagggcag aatttgagac tatatattgc  122436
atggttttca gatttactga aatctataat tgctactgtc tgtcaagaca gtttgatatt  122496
gcccaggcgc agtggctcac gcctgtaatt ccagcacttt cggaggccga ggtgggtgga  122556
tcacttgagg ccaggagttt tgagaccagc ctggccaaca tggcaaaact ctatctctaa  122616
taaaaataca aaaaattact ggggcatggt ggcgcgtgct tatagtccca gctgcttggg  122676
aggttgaggc ctgagaatcg cttgaatcca ggaggcagag gttgcagtga gcccagatcg  122736
tgccactgca ctccagcctg ggtgacagag tgggactctg tctcaataaa taaataaaat  122796
```

-continued

```
ttttaaaaag tttgatattg acatacctac atacacacca ttatacacaa gtggatcaga    122856
atagagaatc cttaagtaga cccaacatat ataatatggt caattgattt ttaacaaaga    122916
tgattcaatt gggaagggat aaccatttta tccagtagta tctgaacagt tggaaagcca    122976
taagggaaaa aaggtaatct tgacccttaa tttcacacca tttataaaaa ttaactccaa    123036
ataaatccat ttatatgaaa ttctagaaaa tgaaaatctg tagtgataga ttagtagttg    123096
tctgagaaca aagcaggaag catgaattat acagggcat gaggaaattt ttaagagtaa     123156
tgaatatgta ctttattttg gttgtgacaa atatatatca aaactcaaat agcatacttt    123216
atggcctcaa taacactata aaataaaaat tttaccatgt caagatattt gctctatttt    123276
gtgtcattcc attttgtttc tggatatata tttaagttca aaacattttt ttaaagttct    123336
aaatggtcta atactagtg agttttcggt gtaagagtaa aactaactac tttcgcattc     123396
acacacactt ttattttca g a ttg  aat atg aac aca gag  cac cag agt         123445
                         Leu Asn Met Asn Thr Glu  His Gln Ser
                         1570            1575 gcc gtc tgg gtc tga agg aag gcc gtc cat tct cag ggg tca ctg            123490
Ala Val Trp Val Arg Lys Ala Val His Ser Gln Gly Ser Leu
1580                1585                1590 cat gtt tgg act tct gtg ctc atg ccc aca gag act tgc aca aca            123535
His Val Trp Thr Ser Val Leu Met Pro Thr Glu Thr Cys Thr Thr
    1595                1600                1605 tgc aga atg gca gca cat tg gtaagttggg ctgaggacag cttagcagct            123585
Cys Arg Met Ala Ala His Trp
            1610 gttgagtctg ttctcacact gctaataaag acatatgcaa gactgggtaa tttataaagg     123645 aaagagattt aattgactca cagttccaca tggctgtgga ggcctcacaa tcatagctga     123705 aggcaaatga ggagcaaagt cacatcttac atggcggcag gcaagagaac atgtgcaggg     123765 gaactcccct ttataaaatc atcagatctc atgagactta ctctcctgag aacagcatgg     123825 gaaagatctg cccccatgat tcaattacct cccactgggt ccttcccaaa acacatggga     123885 attttgggag ctacaattca agatgagatt taggtaggga cacagccaga ccatatcagc     123945 agcatctcat gttgaggagc agaacactgg aatttagtag cattcggtta gagtaatatg     124005 ttgtctgcag gtttcactgg acagcaatat tttcatgaat gaattcctgt tgcaaagtga     124065 cctgctttgg cataactagc actctcatga taggttggca cattagtttc ctgtcaattg     124125 tgttgacaag cacatgagaa tcatggaaat ccttggtgtt aatctaaacc agtgactatg     124185 cattgccagt tacagttaac ttccaggaaa atctcaaaat tcagtgccag ttacctggta     124245 gattgtaatc agttaagcaa aaagccaaat acaagccatt caccttacag agagagaagc     124305 atattcaccct tacagagaga gaagcataaa tgagaaacac atcatcattg tcacagtaac    124365 tgtggtaacc tattgtaaaa gattcacagt gcaaagagc ctgactacat attacagtgg      124425 gtaaaatgga tcggtcttgt aattggaggc agtggtgagg ggaaaataga tacatgttat     124485 atatatatat atatatatat atgttctata ccaacaaagg gttcagggta aattttgca      124545 tgtaaagggg tgacccagag tagagataaa gaacaaaata ttctgttgaa aaaactatga     124605 atcaatcaac ctaatgaatt atcaacatgg atgtaggtgt agttgaagaa gatggtcagt     124665 gagaatatgg aaacagatat caggaattaa agtcatattc tagggcagaa aagcattcat     124725 ggaggtatta gatgatagct gaagtaattt gaagaagctg gtgtgaagtt tttgttgaga     124785 agcagagaag atattaattt aatgttctag atcagagatt ggaaaactct tctctataaa     124845 gggcaagatg gtaaatattt tagggactgc aggccacata ggatttctgt cacattgttt     124905
```

```
ggtggggttt ttttgtttat tttgtttttt aaaaactcct tgaaaatgta aaaaccattc 124965 ttagtttact ggccatacaa acacaagctg tgaggcacat tagccgtagg ttctggtttc 125025 ctaacttctg atccagaaga acaaacacaa ggcctaccaa ccaccccaac atctaaaatc 125085 atcactaatc atgtactcag cacctgctca ttattaggag gctatgctag tttctgaaaa 125145 gcagaagtag taaatgataa ctggggctat agtgcatcct aatataacca tgtttcattc 125205 caggaaggtg acagagagta agatgatgag aaggatgttt agaatcaaga agaatttgcc 125265 tctgatagag catgggttct gtgaagtaaa atggaaagga gcactagata agaactgaat 125325 agggttaaat atgtatggga aaagtaacaa ggtgctcaga gacatgaatt tgaagacttc 125385 tgtgcagaaa gtgacaggct cattaatacc atctcatgtt gaagttattt ctaaagtcag 125445 tccattgtga tcacatttct ctcaagaata tcttctaatt ttattttaga tcacattaga 125505 tcacattgtc tccattgatc aaaaacacta aatactaaaa agttagtatt taaaaaccac 125565 aaataatctt ttaccaaagc tagtgtaatt gtagtaacta aagcaaaaag taccatttaa 125625 ttatcaaagc aacagaggta gctttcctcc ctccacccct tacccttttc agagtaccca 125685 cttatatggt catatttcag aaaagaaatg aagaaaagag aaagttaggt ttgacagagt 125745 acaaaggagg agagacaaga gagtgaaaat agtattaagt tgcatattac ctgtatcagc 125805 caaatcttta cctttttcatt ttttatattt ttacttcagt tatcttatgg aaatttctta 125865 aacagagaga gttaggtgtc aggtatgtga aaagacatga aatttgtgtt cagaagtatg 125925 agatgaggca aatgtgatac taccaaaaac agaggaagtc atttcgtaga aaaaactttt 125985 agcctgtttt tgaagaggct tcacatctag cacatctatt tttgaagtgt gaaaagcaag 126045 agagtgcttc attttggggg agtgttgctt cttcccatag acagaaacat atgtgaagaa 126105 caagggtcac cacagctaac tgttcctgat agactcagag aaagggtggg tgggcaatgt 126165 caatttgtct tatctcccctg taccattttg ttgctatttt cattaataac aggtaggatg 126225 gttttatggt aatatatatg tcactgatct ggatcaacta ggccaccaac acaaatctga 126285 atactgagag gagaaagata cacacacaca cacgttttt ctttgggacc tgtagttgag 126345 gctgtaatgt cttacttccc taccag g tat    gca ctc tca cta gag    aag aca   126396
                                 Tyr    Ala Leu Ser Leu Glu    Lys Thr
                                                  1615           1620
```
| atc gag aat ttg gag gaa aac ctg agg atg agc agc ttc acg ttc | 126441 |
|---|---|
| Ile Glu Asn Leu Glu Glu Asn Leu Arg Met Ser Ser Phe Thr Phe | |
| 1625              1630              1635 | |

| tgc ctt tat aca aag tct ctg acg tgg atg agt ttg gga gtg tgg | 126486 |
|---|---|
| Cys Leu Tyr Thr Lys Ser Leu Thr Trp Met Ser Leu Gly Val Trp | |
|   1640             1645             1650 | |

| aag ctc agg agg aga aaa aac gga gtg gtg cca ttc agg tac tga | 126531 |
|---|---|
| Lys Leu Arg Arg Arg Lys Asn Gly Val Val Pro Phe Arg Tyr | |
| 1655                1660                1665 | |

| gtt ctt ttc ggc gaa aag tca gga tgt tag cag agc cag tca aga | 126576 |
|---|---|
| Val Leu Phe Gly Glu Lys Ser Gly Cys     Gln Ser Gln Ser Arg | |
|   1670              1675                1680 | |

| ctt gcc gac aaa gga aac tag aag cca aga aag ctg cag ctg aaa | 126621 |
|---|---|
| Leu Ala Asp Lys Gly Asn     Lys Pro Arg Lys Leu Gln Leu Lys | |
|          1685              1690 | |

| agc ttt cct ccc tgg aga aca gct caa ata aaa atg aaa agg aaa | 126666 |
|---|---|
| Ser Phe Pro Pro Trp Arg Thr Ala Gln Ile Lys Met Lys Arg Lys | |
| 1695           1700              1705 | |

| agt cag ccc cat cac gta caa aac aaa ctg aaa acg caa gcc agg | 126711 |
|---|---|
| Ser Gln Pro His His Val Gln Asn Lys Leu Lys Thr Gln Ala Arg | |

```
                1710               1715               1720
cta  aac agt tgg cag  gtaaatttaa tgtaaagcat ttgtagataa atgtgttgtg   126766
Leu  Asn Ser Trp Gln
1725 tggtatatta aaaatgaaaa ttattttggt tttgccccca tcaacttgta agttctgggg   126826
tacacatgca ggatgtgcag gtttgttata caggtaaaca tgtgccatgg tgatttgctg   126886
cacagatcaa cccattacct aggtattaag cccagcatct tcctgatgca ccctaccaa    126946
taggcgccag tgtgtgttgt ccccactccc ccaccatgtg tccatgtgct cttattgtaa   127006
aatgaacatt gttaattttg gaaagttata tcaatcatgg tcttagttct gtgccagagt   127066
cttctctaaa gtagcaaggg ccaggctttg ttctcagaga tggtaatgag atattgcacc   127126
atcaacatgg aaaacatgga aaagtctgga ttttattcta taataaacag caactttttt   127186
taacaggtaa gtgatacgat gaaattcatt gtaatttggc agtaggccaa attagtagag   127246
gagctaatag tttggagata aacacagtaa accagaactg aggtaacaag accttgaatt   127306
ttgttggtta gtagcaaaga tatagcaaaa tgatgcaaat gagctcttcc aaaatgggaa   127366
aaagaaaata cattggtgac aaaacactgg aatgaaagag aagaaaagtt taaagatgac   127426
cccaaagttt taaacctaaa cttaacctac tgttttaggt ttctaaaaca gtactattta   127486
ttgaaataag taagtttgaa aatatgattg agagagagag aggggagaat gaaacatttt   127546
tccttagaca tgttgagtct gtggtttagg aggggttcta catgtagatt atgctacaaa   127606
acttttaccc atcaaaatag attacagctg tagtaataac aatagaacat tattcatgaa   127666
tactaagtta ttgtctttcc atagcctcct gctttatgtc tgcagtttgt aaaagaaaa    127726
aaaatccaaa atttgggatg gtattggcct ggccattaac aaaagcaaac cagtttgctt   127786
aaaactagcc atctttgctg cttcatgaag tcaaatttct ctactgattc atttccaagc   127846
tcagaggaac taagttaaat aatttagaat atgctaaaga tgcttgataa gtgtttattg   127906
actggttgac ttaacactaa gtaaatactg ttcacttagg ttagctgtga aatataatta   127966
gatagaacct tgtctctgct ccctttttaac tggcttctgc aggtaataat cccttctgtt   128026
ctcagaactg ccattgcagt ttcatctatt tgttcttaac tcatatgact tttttaaagtg   128086
aggtcaaaac agaagtatga cttttaaaag tttcatttac aaagctgaaa gtttctttaa   128146
agtgttatct acaactgtgt taacttcctt tctggaaagc ctgcttataa agtagcactt   128206
gttgattata taagatgctt tttgtgttta aatacgtgtc attctttttt ttcacaacat   128266
tcccgaatct tacataataa atcttatttt aattatttag caaattccat tgcatgccag   128326
gcaatgaaga agtaagtaaa ataaaacatt ttccttccca tttaggaatt tacttaccag   128386
tggggggtgaa gagagggcta aaaacataac tataatacat tgtgagtatt gctttatcag   128446
atctatcttt gcagttgagt attacaaaag cactagaaga tgaggtcaaa gcggtccctt   128506
gaggaaggga tgactacacc aaggaaggat agggagagag ggaggaaaag ggaggcactt   128566
caagcagagg catgttcaga agttccaaag aacattttgc tctcaatgga atggctttgg   128626
atgtttatta catttttttt ttcactaagt tttgtatttc taatgcctta gacaaaaaat   128686
tgtgctggac aatgatcaga accctgactt tgctcttatc tttgcttaat gggtgtcgta   128746
tatcactagt ggagtttctt acctacattt aagtatcctc actagccttc ataaaataat   128806
catcaacatc aaagatacct gtttctgttc tctcttaccc tgtccacag aac  ttt      128861
                                                        Asn  Phe
                                                             1730 tgc gac ttt cag  gac cag tca tgc agc  agt ccc agc agc ccc  agc       128906
```

|  |  |  |  |  |  |  |  |  |  |  |  |  |
|---|---|---|---|---|---|---|---|---|---|---|---|---|
| Cys | Asp | Phe | Gln | Asp | Gln | Ser | Cys | Ser | Ser | Pro | Ser | |
|  |  |  | 1735 |  |  | 1740 |  |  |  | 1745 |  | |

| ctc | tac | aga | agc | agc | cac | cac | agc | ccc | agc | agc | agc | aga | gac | ccc | 128951 |
|---|---|---|---|---|---|---|---|---|---|---|---|---|---|---|---|
| Leu | Tyr | Arg | Ser | Ser | His | His | Ser | Pro | Ser | Ser | Ser | Arg | Asp | Pro | |
|  |  | 1750 |  |  |  |  | 1755 |  |  |  |  | 1760 |  |  | |

| agc | agc | agc | agc | cac | atc | acc | ctc | aga | cag | agt | ctg | tca | act | ctt | 128996 |
|---|---|---|---|---|---|---|---|---|---|---|---|---|---|---|---|
| Ser | Ser | Ser | Ser | His | Ile | Thr | Leu | Arg | Gln | Ser | Leu | Ser | Thr | Leu | |
|  | 1765 |  |  |  |  | 1770 |  |  |  |  | 1775 |  |  |  | |

| att | ctg | ctt | ctg | gat | cca | cca | atc | cat | aca | tga | gac | ggc | cca | atc | 129041 |
|---|---|---|---|---|---|---|---|---|---|---|---|---|---|---|---|
| Ile | Leu | Leu | Leu | Asp | Pro | Pro | Ile | His | Thr |  | Asp | Gly | Pro | Ile | |
|  |  |  | 1780 |  |  |  |  | 1785 |  |  |  |  | 1790 |  | |

| cag | tta | gtc | ctt | atc | caa | act | ctt | cac | aca | ctt | cag | ata | tct | atg | 129086 |
|---|---|---|---|---|---|---|---|---|---|---|---|---|---|---|---|
| Gln | Leu | Val | Leu | Ile | Gln | Thr | Leu | His | Thr | Leu | Gln | Ile | Ser | Met | |
|  |  |  | 1795 |  |  |  |  | 1800 |  |  |  |  | 1805 |  | |

| gaa | gca | cca | gcc | cta | tga | act | tct | att | cca | cct | cat | ctc | aag | ctg | 129131 |
|---|---|---|---|---|---|---|---|---|---|---|---|---|---|---|---|
| Glu | Ala | Pro | Ala | Leu |  | Thr | Ser | Ile | Pro | Pro | His | Leu | Lys | Leu | |
|  |  |  | 1810 |  |  |  |  |  | 1815 |  |  |  |  |  | |

| cag | gtt | cat | att | tga | att | ctt | cta | atc | cca | tga | acc | ctt | acc | ctg | 129176 |
|---|---|---|---|---|---|---|---|---|---|---|---|---|---|---|---|
| Gln | Val | His | Ile |  | Ile | Leu | Leu | Ile | Pro |  | Thr | Leu | Thr | Leu | |
| 1820 |  |  |  |  | 1825 |  |  |  |  |  | 1830 |  |  |  | |

| ggc | ttt | tga | atc | aga | ata | ccc | aat | atc | cat | cat | atc | aat | gca | atg | 129221 |
|---|---|---|---|---|---|---|---|---|---|---|---|---|---|---|---|
| Gly | Phe |  | Ile | Arg | Ile | Pro | Asn | Ile | His | His | Ile | Asn | Ala | Met | |
|  |  | 1835 |  |  |  |  | 1840 |  |  |  |  | 1845 |  |  | |

| gaa | acc | tat | cag | tgg | aca | act | gct | ccc | cat | atc | tgg | gtt | cct | att | 129266 |
|---|---|---|---|---|---|---|---|---|---|---|---|---|---|---|---|
| Glu | Thr | Tyr | Gln | Trp | Thr | Thr | Ala | Pro | His | Ile | Trp | Val | Pro | Ile | |
|  |  |  | 1850 |  |  |  |  | 1855 |  |  |  |  | 1860 |  | |

| ctc | ccc | agt | ctc | agc | cga | tgg | atc | tgt | ata | ggt | atc | caa | gcc | aag | 129311 |
|---|---|---|---|---|---|---|---|---|---|---|---|---|---|---|---|
| Leu | Pro | Ser | Leu | Ser | Arg | Trp | Ile | Cys | Ile | Gly | Ile | Gln | Ala | Lys | |
|  |  |  | 1865 |  |  |  |  | 1870 |  |  |  |  | 1875 |  | |

| acc | ctc | tgt | cta | agc | tca | gtc | tac | cac | cca | tcc | ata | cac | ttt | acc | 129356 |
|---|---|---|---|---|---|---|---|---|---|---|---|---|---|---|---|
| Thr | Leu | Cys | Leu | Ser | Ser | Val | Tyr | His | Pro | Ser | Ile | His | Phe | Thr | |
|  |  |  | 1880 |  |  |  |  | 1885 |  |  |  |  | 1890 |  | |

| agc | caa | ggt | ttg | gaa | ata | gcc | aga | gtt | tta | cat | cta | aat | act | tag | 129401 |
|---|---|---|---|---|---|---|---|---|---|---|---|---|---|---|---|
| Ser | Gln | Gly | Leu | Glu | Ile | Ala | Arg | Val | Leu | His | Leu | Asn | Thr |  | |
|  |  |  | 1895 |  |  |  |  | 1900 |  |  |  |  | 1905 |  | |

| gtt | atg | gaa | acc | aaa | ata | tgc | agg | gag | atg | gtt | tca | gca | gtt | gta | 129446 |
|---|---|---|---|---|---|---|---|---|---|---|---|---|---|---|---|
| Val | Met | Glu | Thr | Lys | Ile | Cys | Arg | Glu | Met | Val | Ser | Ala | Val | Val | |
|  |  |  | 1910 |  |  |  |  | 1915 |  |  |  |  | 1920 |  | |

| cca | tta | gac | caa | atg | tac | atc | atg | tag | gga | aat | tgc | ctc | ctt | atc | 129491 |
|---|---|---|---|---|---|---|---|---|---|---|---|---|---|---|---|
| Pro | Leu | Asp | Gln | Met | Tyr | Ile | Met |  | Gly | Asn | Cys | Leu | Leu | Ile | |
|  |  |  | 1925 |  |  |  |  |  | 1930 |  |  |  |  |  | |

| cca | ctc | atg | aga | tgg | atg | gcc | act | tca | tgg | gag | cca | cct | cta | gat | 129536 |
|---|---|---|---|---|---|---|---|---|---|---|---|---|---|---|---|
| Pro | Leu | Met | Arg | Trp | Met | Ala | Thr | Ser | Trp | Glu | Pro | Pro | Leu | Asp | |
| 1935 |  |  |  | 1940 |  |  |  |  | 1945 |  |  |  |  |  | |

| tac | cac | cca | atc | tga | gca | atc | caa | aca | tgg | act | ata | aaa | atg | gtg | 129581 |
|---|---|---|---|---|---|---|---|---|---|---|---|---|---|---|---|
| Tyr | His | Pro | Ile |  | Ala | Ile | Gln | Thr | Trp | Thr | Ile | Lys | Met | Val | |
| 1950 |  |  |  |  | 1955 |  |  |  |  | 1960 |  |  |  |  | |

| aac | atc | att | cac | ctt | ctc | aca | taa | tcc | ata | act | aca | gtg | cag | ctc | 129626 |
|---|---|---|---|---|---|---|---|---|---|---|---|---|---|---|---|
| Asn | Ile | Ile | His | Leu | Leu | Thr |  | Ser | Ile | Thr | Thr | Val | Gln | Leu | |
|  | 1965 |  |  |  |  | 1970 |  |  |  |  | 1975 |  |  |  | |

| cgg | gca | tgt | tca | aca | gct | ctc | ttc | atg | ccc | tgc | atc | tcc | aaa | aca | 129671 |
|---|---|---|---|---|---|---|---|---|---|---|---|---|---|---|---|
| Arg | Ala | Cys | Ser | Thr | Ala | Leu | Phe | Met | Pro | Cys | Ile | Ser | Lys | Thr | |
|  |  | 1980 |  |  |  |  | 1985 |  |  |  |  | 1990 |  |  | |

| agg | aga | atg | aca | tgc | ttt | ccc | aca | cag | cta | atg | ggt | tat | caa | aga | 129716 |
|---|---|---|---|---|---|---|---|---|---|---|---|---|---|---|---|
| Arg | Arg | Met | Thr | Cys | Phe | Pro | Thr | Gln | Leu | Met | Gly | Tyr | Gln | Arg | |
|  |  | 1995 |  |  |  |  | 2000 |  |  |  |  | 2005 |  |  | |

| tgc | ttc | cag | ctc | tta | acc | atg | ata | gaa | ctg | ctt | gtg | tcc | aag | gag | 129761 |
|---|---|---|---|---|---|---|---|---|---|---|---|---|---|---|---|
| Cys | Phe | Gln | Leu | Leu | Thr | Met | Ile | Glu | Leu | Leu | Val | Ser | Lys | Glu | |
|  |  | 2010 |  |  |  |  | 2015 |  |  |  |  | 2020 |  |  | |

```
gct tac aca aat taa gtg atg cta atg gtc agg aaa agc agc cat       129806
Ala Tyr Thr Asn     Val Met Leu Met Val Arg Lys Ser Ser His
            2025                2030                2035 tgg cac tag tcc agg gtg tgg ctt ctg gtg cag agg aca acg atg       129851
Trp His     Ser Arg Val Trp Leu Leu Val Gln Arg Thr Thr Met
                2040                2045                2050 agg tct ggt cag aca gcg agc aga gct ttc tgg atc ctg aca ttg       129896
Arg Ser Gly Gln Thr Ala Ser Arg Ala Phe Trp Ile Leu Thr Leu
                2055                2060                2065 ggg gag tgg ccg tgg ctc caa ctc atg ggt caa ttc tca ttg agt       129941
Gly Glu Trp Pro Trp Leu Gln Leu Met Gly Gln Phe Ser Leu Ser
                2070                2075                2080 gtg caa agc gtg agc tgc atg cca caa ccc ctt taa aga atc cca       129986
Val Gln Ser Val Ser Cys Met Pro Gln Pro Leu     Arg Ile Pro
                2085                2090 ata gga atc acc cca cca gga tct ccc tcg tct ttt acc agc ata       130031
Ile Gly Ile Thr Pro Pro Gly Ser Pro Ser Ser Phe Thr Ser Ile
2095            2100                2105 aga gca tga atg agc caa aac atg gct tgg ctc ttt ggg aag cca       130076
Arg Ala     Met Ser Gln Asn Met Ala Trp Leu Phe Gly Lys Pro
2110                2115                2120 aaa tgg ctg aaa aag ccc gtg aga aag agg aag agt gtg aaa agt       130121
Lys Trp Leu Lys Lys Pro Val Arg Lys Arg Lys Ser Val Lys Ser
    2125                2130                2135 atg gcc cag act atg tgc ctc aga aat ccc atg gca aaa aag tga       130166
Met Ala Gln Thr Met Cys Leu Arg Asn Pro Met Ala Lys Lys
2140                2145                2150 aac ggg agc ctg ctg agc cac atg aaa ctt cag agc cca ctt acc       130211
Asn Gly Ser Leu Leu Ser His Met Lys Leu Gln Ser Pro Leu Thr
            2155                2160                2165 tgc gtt tca tca agt ctc ttg ccg aaa gga cca tgt ccg tga cca       130256
Cys Val Ser Ser Ser Leu Leu Pro Lys Gly Pro Cys Pro     Pro
            2170                2175                2180 cag act cca cag taa cta cat ctc cat atg cct tca ctc ggg tca       130301
Gln Thr Pro Gln     Leu His Leu His Met Pro Ser Leu Gly Ser
                2185                2190                2195 cag ggc ctt aca aca gat ata tat gat atc acc ccc ttt tgt tgg       130346
Gln Gly Leu Thr Thr Asp Ile Tyr Asp Ile Thr Pro Phe Cys Trp
                2200                2205                2210 tta cct cac ttg aaa aga cca caa cca acc tgt cag tag tat agt       130391
Leu Pro His Leu Lys Arg Pro Gln Pro Thr Cys Gln     Tyr Ser
                2215                2220 tct cat gac gtg ggc agt ggg gaa agg tca cag tat tca tga caa       130436
Ser His Asp Val Gly Ser Gly Glu Arg Ser Gln Tyr Ser     Gln
2225                2230                2235 atg tgg tgg gaa aaa cct cag ctc acc agc aac aaa aga ggt tat       130481
Met Trp Trp Glu Lys Pro Gln Leu Thr Ser Asn Lys Arg Gly Tyr
    2240                2245                2250 ctt acc ata gca ctt aat ttt cac tgg ctc cca agt ggt cac aga       130526
Leu Thr Ile Ala Leu Asn Phe His Trp Leu Pro Ser Gly His Arg
    2255                2260                2265 tgg cat cta gga aaa gac caa agc att cta tgc aaa aag aag gtg       130571
Trp His Leu Gly Lys Asp Gln Ser Ile Leu Cys Lys Lys Lys Val
    2270                2275                2280 ggg aag aaa gtg ttc cgc aat tta cat ttt taa aca ctg gtt cta       130616
Gly Lys Lys Val Phe Arg Asn Leu His Phe     Thr Leu Val Leu
    2285                2290                2295 tta ttg gac gag atg ata tgt aaa tgt gat ccc ccc ccg ctt           130661
Leu Leu Asp Glu Met Ile Cys Lys Cys Asp Pro Pro Pro Leu
        2300                2305                2310
```

-continued

```
aca act cta cac atc tgt gac cac ttt taa taa tat caa gtt tgc       130706
Thr Thr Leu His Ile Cys Asp His Phe         Tyr Gln Val Cys
            2315            2320                    2325 ata gtc atg gaa cac aaa tca aac aag tac tgt agt att aca gtg       130751
Ile Val Met Glu His Lys Ser Asn Lys Tyr Cys Ser Ile Thr Val
            2330            2335                    2340 aca gga atc tta aaa tac cat ctg gtg ctg aat ata tga tgt act       130796
Thr Gly Ile Leu Lys Tyr His Leu Val Leu Asn Ile     Cys Thr
            2345            2350 gaa ata ctg gaa tta tgg ctt ttt gaa atg cag ttt tta ctg taa       130841
Glu Ile Leu Glu Leu Trp Leu Phe Glu Met Gln Phe Leu Leu
2355            2360                    2365 tct taa ctt tta ttt atc aaa ata gct aca gga aac atg aat agc       130886
Ser     Leu Leu Phe Ile Lys Ile Ala Thr Gly Asn Met Asn Ser
            2370            2375                    2380 agg aaa aca ctg aat ttg ttt gga tgt tct aag aaa tgg tgc taa       130931
Arg Lys Thr Leu Asn Leu Phe Gly Cys Ser Lys Lys Trp Cys
            2385            2390                    2395 gaa aat ggt gtc ttt aat agc taa aaa ttt aat gcc ttt ata tca       130976
Glu Asn Gly Val Phe Asn Ser     Lys Phe Asn Ala Phe Ile Ser
            2400            2405                    2410 tca aga tgc tat cag tgt act cca gtg ccc ttg aat aat agg ggt       131021
Ser Arg Cys Tyr Gln Cys Thr Pro Val Pro Leu Asn Asn Arg Gly
            2415            2420                    2425 acc ttt tca ttc aag ttt tta tca taa tta cct att ctt aca caa       131066
Thr Phe Ser Phe Lys Phe Leu Ser     Leu Pro Ile Leu Thr Gln
            2430            2435 gct tag ttt tta aaa tgt gga cat ttt aaa ggc ctc tgg att ttg       131111
Ala     Phe Leu Lys Cys Gly His Phe Lys Gly Leu Trp Ile Leu
2440            2445                    2450 ctc atc cag tga agt cct tgt agg aca ata aac gta tat atg tac       131156
Leu Ile Gln     Ser Pro Cys Arg Thr Ile Asn Val Tyr Met Tyr
            2455            2460                    2465 ata tat aca caa aca tgt ata tgt gca cac aca tgt ata tgt ata       131201
Ile Tyr Thr Gln Thr Cys Ile Cys Ala His Thr Cys Ile Cys Ile
            2470            2475                    2480 aat att tta aat ggt gtt tta gaa gca ctt tgt cta cct aag ctt       131246
Asn Ile Leu Asn Gly Val Leu Glu Ala Leu Cys Leu Pro Lys Leu
            2485            2490                    2495 tga caa ctt gaa caa tgc taa ggt act gag atg ttt aaa aaa caa       131291
    Gln Leu Glu Gln Cys     Gly Thr Glu Met Phe Lys Lys Gln
            2500                    2505                    2510 gtt tac ttt cat ttt aga atg caa agt tga ttt ttt taa gga aac aaa   131339
Val Tyr Phe His Phe Arg Met Gln Ser     Phe Phe     Gly Asn Lys
            2515                    2520 gaa agc ttt taa aat att ttt gct ttt agc cat gca tct gct gat       131384
Glu Ser Phe     Asn Ile Phe Ala Phe Ser His Ala Ser Ala Asp
2525            2530                    2535 gag caa ttg tgt cca ttt tta aca cag cca gtt aaa tcc acc atg       131429
Glu Gln Leu Cys Pro Phe Leu Thr Gln Pro Val Lys Ser Thr Met
            2540            2545                    2550 ggg ctt act gga ttc aag gga ata cgt tag tcc aca aaa cat gtt       131474
Gly Leu Thr Gly Phe Lys Gly Ile Arg     Ser Thr Lys His Val
            2555            2560                    2565 ttc tgg tgc tca tct cac atg cta tac tgt aaa aca gtt tta tac       131519
Phe Trp Cys Ser Ser His Met Leu Tyr Cys Lys Thr Val Leu Tyr
            2570            2575                    2580 aaa att gta tga caa gtt cat tgc tca aaa atg tac agt ttt aag       131564
Lys Ile Val     Gln Val His Cys Ser Lys Met Tyr Ser Phe Lys
```

```
                    2585                2590                2595
aat ttt cta tta   act gca ggt aat  aat tag ctg cat  gct gca gac       131609
Asn Phe Leu Leu   Thr Ala Gly Asn  Asn     Leu His  Ala Ala Asp
            2600                2605                2610 tca aca aag cta  gtt cac tga agc  cta tgc tat ttt  atg gat cat        131654
Ser Thr Lys Leu  Val His     Ser  Leu Cys Tyr Phe  Met Asp His
            2615                2620 agg  ctc ttc aga gaa  ctg aat ggc agt  ctg cct ttg tgt  tga taa       131699
Arg  Leu Phe Arg Glu  Leu Asn Gly Ser  Leu Pro Leu Cys
2625                 2630                2635 tta tgt aca ttg  tga cgt tgt cat  ttc tta gct taa  gtg tcc tct        131744
Leu Cys Thr Leu      Arg Cys His  Phe Leu Ala      Val Ser Ser
            2640                2645                2650 tta aca aga gga ttg  agc aga ctg atg cct  gca taa gat gaa taa aca     131792
Leu Thr Arg Gly Leu  Ser Arg Leu Met Pro  Ala     Asp Glu     Thr
                2655                2660 ggg  tta gtt cca tgt  gaa tct gtc agt  taa aaa gaa aca  aaa aca       131837
Gly  Leu Val Pro Cys  Glu Ser Val Ser       Lys Glu Thr  Lys Thr
2665                 2670                 2675 ggc agc tgg ttt  gct gtg gtg gtt  tta aat cat taa  ttt gta taa        131882
Gly Ser Trp Phe  Ala Val Val Val  Leu Asn His      Phe Val
            2680                2685                2690 aga agt gaa aga  gtt gta tag taa  att aaa ttg taa  aca aaa ctt ttt    131930
Arg Ser Glu Arg  Val Val         Ile Lys Leu       Thr Lys Leu Phe
            2695                2700 taa tgc aat gct tta  gta ttt tag tac  tgt aaa aaa att  aaa tat        131975
    Cys Asn Ala Leu  Val Phe     Tyr  Cys Lys Lys Ile  Lys Tyr
        2705                 2710                 2715 ata cat ata tat  ata tat ata tat  ata tat ata tat  gag ttt gaa        132020
Ile His Ile Tyr  Ile Tyr Ile Tyr  Ile Tyr Ile Tyr  Glu Phe Glu
            2720                2725                2730 gca gaa ttc aca  tca tga tgg tgc  tac tca gcc tgc  tac aaa tat        132065
Ala Glu Phe Thr  Ser     Trp Cys  Tyr Ser Ala Cys  Tyr Lys Tyr
            2735                2740                2745 atc ata atg tga  gct aag aat tca  tta aat gtt tga  gtg atg ttc        132110
Ile Ile Met      Ala Lys Asn Ser  Leu Asn Val      Val Met Phe
            2750                2755 cta  ctt gtc ata tac  ctc aac act agt ttg  gca ata gga tat tga        132155
Leu  Leu Val Ile Tyr  Leu Asn Thr Ser Leu  Ala Ile Gly Tyr
2760                 2765                 2770 act gag agt gaa  agc att gtg tac  cat cat ttt ttt  cca agt cct        132200
Thr Glu Ser Glu  Ser Ile Val Tyr  His His Phe Phe  Pro Ser Pro
            2775                2780                2785 ttt ttt tat tgt  taa aaa aaa aag  cat acc ttt ttt  caa tac ttg        132245
Phe Phe Tyr Cys      Lys Lys Lys  His Thr Phe Phe  Gln Tyr Leu
            2790                2795                2800 att tct tag caa  gta taa ctt gaa  ctt caa cct ttt  tgt tct aaa        132290
Ile Ser     Gln  Val     Leu Glu  Leu Gln Pro Phe  Cys Ser Lys
            2805                2810                2815 aat tca ggg ata ttt  cag ctc atg ctc tcc  cta tgc ca acatgtcacc       132338
Asn Ser Gly Ile Phe  Gln Leu Met Leu Ser  Leu Cys
                2820                2825 tgtgtttatg taaaattgtt gtaggttaat aaatatattc tttgtcaggg atttaaccct     132398
tttattttga atcccttcta ttttacttgt                                      132428

<210> SEQ ID NO 2
<211> LENGTH: 2002
<212> TYPE: PRT
<213> ORGANISM: Homo sapiens
```

<400> SEQUENCE: 2

```
Met Glu Gln Asp Arg Thr Asn His Val Glu Gly Asn Arg Leu Ser Pro
 1               5                  10                  15

Phe Leu Ile Pro Ser Pro Ile Cys Gln Thr Glu Pro Leu Ala Thr
             20                  25                  30

Lys Leu Gln Asn Gly Ser Pro Leu Pro Glu Arg Ala His Pro Glu Val
             35                  40                  45

Asn Gly Asp Thr Lys Trp His Ser Phe Lys Ser Tyr Tyr Gly Ile Pro
 50                  55                  60

Cys Met Lys Gly Ser Gln Asn Ser Arg Val Ser Pro Asp Phe Thr Gln
 65                  70                  75                  80

Glu Ser Arg Gly Tyr Ser Lys Cys Leu Gln Asn Gly Gly Ile Lys Arg
                 85                  90                  95

Thr Val Ser Glu Pro Ser Leu Ser Gly Leu Leu Gln Ile Lys Lys Leu
                100                 105                 110

Lys Gln Asp Gln Lys Ala Asn Gly Glu Arg Arg Asn Phe Gly Val Ser
                115                 120                 125

Gln Glu Arg Asn Pro Gly Glu Ser Ser Gln Pro Asn Val Ser Asp Leu
130                 135                 140

Ser Asp Lys Lys Glu Ser Val Ser Ser Val Ala Gln Glu Asn Ala Val
145                 150                 155                 160

Lys Asp Phe Thr Ser Phe Ser Thr His Asn Cys Ser Gly Pro Glu Asn
                165                 170                 175

Pro Glu Leu Gln Ile Leu Asn Glu Gln Glu Gly Lys Ser Ala Asn Tyr
                180                 185                 190

His Asp Lys Asn Ile Val Leu Leu Lys Asn Lys Ala Val Leu Met Pro
                195                 200                 205

Asn Gly Ala Thr Val Ser Ala Ser Ser Val Glu His Thr His Gly Glu
                210                 215                 220

Leu Leu Glu Lys Thr Leu Ser Gln Tyr Tyr Pro Asp Cys Val Ser Ile
225                 230                 235                 240

Ala Val Gln Lys Thr Thr Ser His Ile Asn Ala Ile Asn Ser Gln Ala
                245                 250                 255

Thr Asn Glu Leu Ser Cys Glu Ile Thr His Pro Ser His Thr Ser Gly
                260                 265                 270

Gln Ile Asn Ser Ala Gln Thr Ser Asn Ser Glu Leu Pro Pro Lys Pro
                275                 280                 285

Ala Ala Val Val Ser Glu Ala Cys Asp Ala Asp Asp Ala Asp Asn Ala
                290                 295                 300

Ser Lys Leu Ala Ala Met Leu Asn Thr Cys Ser Phe Gln Lys Pro Glu
305                 310                 315                 320

Gln Leu Gln Gln Gln Lys Ser Val Phe Glu Ile Cys Pro Ser Pro Ala
                325                 330                 335

Glu Asn Asn Ile Gln Gly Thr Thr Lys Leu Ala Ser Gly Glu Glu Phe
                340                 345                 350

Cys Ser Gly Ser Ser Ser Asn Leu Gln Ala Pro Gly Gly Ser Ser Glu
                355                 360                 365

Arg Tyr Leu Lys Gln Asn Glu Met Asn Gly Ala Tyr Phe Lys Gln Ser
                370                 375                 380

Ser Val Phe Thr Lys Asp Ser Phe Ser Ala Thr Thr Thr Pro Pro Pro
385                 390                 395                 400

Pro Ser Gln Leu Leu Leu Ser Pro Pro Pro Leu Pro Gln Val Pro
```

```
                    405                 410                 415
Gln Leu Pro Ser Glu Gly Lys Ser Thr Leu Asn Gly Gly Val Leu Glu
                420                 425                 430

Glu His His His Tyr Pro Asn Gln Ser Asn Thr Thr Leu Leu Arg Glu
                435                 440                 445

Val Lys Ile Glu Gly Lys Pro Glu Ala Pro Ser Gln Ser Pro Asn
        450                 455                 460

Pro Ser Thr His Val Cys Ser Pro Ser Pro Met Leu Ser Glu Arg Pro
465                 470                 475                 480

Gln Asn Asn Cys Val Asn Arg Asn Asp Ile Gln Thr Ala Gly Thr Met
                485                 490                 495

Thr Val Pro Leu Cys Ser Glu Lys Thr Arg Pro Met Ser Glu His Leu
                500                 505                 510

Lys His Asn Pro Pro Ile Phe Gly Ser Ser Gly Glu Leu Gln Asp Asn
                515                 520                 525

Cys Gln Gln Leu Met Arg Asn Lys Glu Gln Glu Ile Leu Lys Gly Arg
                530                 535                 540

Asp Lys Glu Gln Thr Arg Asp Leu Val Pro Pro Thr Gln His Tyr Leu
545                 550                 555                 560

Lys Pro Gly Trp Ile Glu Leu Lys Ala Pro Arg Phe His Gln Ala Glu
                        565                 570                 575

Ser His Leu Lys Arg Asn Glu Ala Ser Leu Pro Ser Ile Leu Gln Tyr
                580                 585                 590

Gln Pro Asn Leu Ser Asn Gln Met Thr Ser Lys Gln Tyr Thr Gly Asn
                595                 600                 605

Ser Asn Met Pro Gly Gly Leu Pro Arg Gln Ala Tyr Thr Gln Lys Thr
        610                 615                 620

Thr Gln Leu Glu His Lys Ser Gln Met Tyr Gln Val Glu Met Asn Gln
625                 630                 635                 640

Gly Gln Ser Gln Gly Thr Val Asp Gln His Leu Gln Phe Gln Lys Pro
                        645                 650                 655

Ser His Gln Val His Phe Ser Lys Thr Asp His Leu Pro Lys Ala His
                660                 665                 670

Val Gln Ser Leu Cys Gly Thr Arg Phe His Phe Gln Gln Arg Ala Asp
                675                 680                 685

Ser Gln Thr Glu Lys Leu Met Ser Pro Val Leu Lys Gln His Leu Asn
                690                 695                 700

Gln Gln Ala Ser Glu Thr Glu Pro Phe Ser Asn Ser His Leu Leu Gln
705                 710                 715                 720

His Lys Pro His Lys Gln Ala Ala Gln Thr Gln Pro Ser Gln Ser Ser
                        725                 730                 735

His Leu Pro Gln Asn Gln Gln Gln Gln Lys Leu Gln Ile Lys Asn
                740                 745                 750

Lys Glu Glu Ile Leu Gln Thr Phe Pro His Pro Gln Ser Asn Asn Asp
                755                 760                 765

Gln Gln Arg Glu Gly Ser Phe Phe Gly Gln Thr Lys Val Glu Glu Cys
                770                 775                 780

Phe His Gly Glu Asn Gln Tyr Ser Lys Ser Ser Glu Phe Glu Thr His
785                 790                 795                 800

Asn Val Gln Met Gly Leu Glu Glu Val Gln Asn Ile Asn Arg Arg Asn
                        805                 810                 815

Ser Pro Tyr Ser Gln Thr Met Lys Ser Ser Ala Cys Lys Ile Gln Val
                820                 825                 830
```

```
Ser Cys Ser Asn Asn Thr His Leu Val Ser Glu Asn Lys Glu Gln Thr
        835                 840                 845

Thr His Pro Glu Leu Phe Ala Gly Asn Lys Thr Gln Asn Leu His His
    850                 855                 860

Met Gln Tyr Phe Pro Asn Asn Val Ile Pro Lys Gln Asp Leu Leu His
865                 870                 875                 880

Arg Cys Phe Gln Glu Gln Glu Gln Lys Ser Gln Gln Ala Ser Val Leu
                885                 890                 895

Gln Gly Tyr Lys Asn Arg Asn Gln Asp Met Ser Gly Gln Gln Ala Ala
                900                 905                 910

Gln Leu Ala Gln Gln Arg Tyr Leu Ile His Asn His Ala Asn Val Phe
            915                 920                 925

Pro Val Pro Asp Gln Gly Gly Ser His Thr Gln Thr Pro Pro Gln Lys
        930                 935                 940

Asp Thr Gln Lys His Ala Ala Leu Arg Trp His Leu Leu Gln Lys Gln
945                 950                 955                 960

Glu Gln Gln Gln Thr Gln Gln Pro Gln Thr Glu Ser Cys His Ser Gln
                965                 970                 975

Met His Arg Pro Ile Lys Val Glu Pro Gly Cys Lys Pro His Ala Cys
        980                 985                 990

Met His Thr Ala Pro Pro Glu Asn Lys Thr Trp Lys Lys Val Thr Lys
        995                 1000                1005

Gln Glu Asn Pro Pro Ala Ser Cys Asp Asn Val Gln Gln Lys Ser
    1010                1015                1020

Ile Ile Glu Thr Met Glu Gln His Leu Lys Gln Phe His Ala Lys
    1025                1030                1035

Ser Leu Phe Asp His Lys Ala Leu Thr Leu Lys Ser Gln Lys Gln
    1040                1045                1050

Val Lys Val Glu Met Ser Gly Pro Val Thr Val Leu Thr Arg Gln
    1055                1060                1065

Thr Thr Ala Ala Glu Leu Asp Ser His Thr Pro Ala Leu Glu Gln
    1070                1075                1080

Gln Thr Thr Ser Ser Glu Lys Thr Pro Thr Lys Arg Thr Ala Ala
    1085                1090                1095

Ser Val Leu Asn Asn Phe Ile Glu Ser Pro Ser Lys Leu Leu Asp
    1100                1105                1110

Thr Pro Ile Lys Asn Leu Leu Asp Thr Pro Val Lys Thr Gln Tyr
    1115                1120                1125

Asp Phe Pro Ser Cys Arg Cys Val Glu Gln Ile Ile Glu Lys Asp
    1130                1135                1140

Glu Gly Pro Phe Tyr Thr His Leu Gly Ala Gly Pro Asn Val Ala
    1145                1150                1155

Ala Ile Arg Glu Ile Met Glu Glu Arg Phe Gly Gln Lys Gly Lys
    1160                1165                1170

Ala Ile Arg Ile Glu Arg Val Ile Tyr Thr Gly Lys Glu Gly Lys
    1175                1180                1185

Ser Ser Gln Gly Cys Pro Ile Ala Lys Trp Val Val Arg Arg Ser
    1190                1195                1200

Ser Ser Glu Glu Lys Leu Leu Cys Leu Val Arg Glu Arg Ala Gly
    1205                1210                1215

His Thr Cys Glu Ala Ala Val Ile Val Ile Leu Ile Leu Val Trp
    1220                1225                1230
```

```
Glu Gly Ile Pro Leu Ser Leu Ala Asp Lys Leu Tyr Ser Glu Leu
    1235                1240                1245

Thr Glu Thr Leu Arg Lys Tyr Gly Thr Leu Thr Asn Arg Arg Cys
    1250                1255                1260

Ala Leu Asn Glu Glu Arg Thr Cys Ala Cys Gln Gly Leu Asp Pro
    1265                1270                1275

Glu Thr Cys Gly Ala Ser Phe Ser Phe Gly Cys Ser Trp Ser Met
    1280                1285                1290

Tyr Tyr Asn Gly Cys Lys Phe Ala Arg Ser Lys Ile Pro Arg Lys
    1295                1300                1305

Phe Lys Leu Leu Gly Asp Asp Pro Lys Glu Glu Lys Leu Glu
    1310                1315                1320

Ser His Leu Gln Asn Leu Ser Thr Leu Met Ala Pro Thr Tyr Lys
    1325                1330                1335

Lys Leu Ala Pro Asp Ala Tyr Asn Asn Gln Ile Glu Tyr Glu His
    1340                1345                1350

Arg Ala Pro Glu Cys Arg Leu Gly Leu Lys Glu Gly Arg Pro Phe
    1355                1360                1365

Ser Gly Val Thr Ala Cys Leu Asp Phe Cys Ala His Ala His Arg
    1370                1375                1380

Asp Leu His Asn Met Gln Asn Gly Ser Thr Leu Val Cys Thr Leu
    1385                1390                1395

Thr Arg Glu Asp Asn Arg Glu Phe Gly Gly Lys Pro Glu Asp Glu
    1400                1405                1410

Gln Leu His Val Leu Pro Leu Tyr Lys Val Ser Asp Val Asp Glu
    1415                1420                1425

Phe Gly Ser Val Glu Ala Gln Glu Glu Lys Lys Arg Ser Gly Ala
    1430                1435                1440

Ile Gln Val Leu Ser Ser Phe Arg Arg Lys Val Arg Met Leu Ala
    1445                1450                1455

Glu Pro Val Lys Thr Cys Arg Gln Arg Lys Leu Glu Ala Lys Lys
    1460                1465                1470

Ala Ala Ala Glu Lys Leu Ser Ser Leu Glu Asn Ser Ser Asn Lys
    1475                1480                1485

Asn Glu Lys Glu Lys Ser Ala Pro Ser Arg Thr Lys Gln Thr Glu
    1490                1495                1500

Asn Ala Ser Gln Ala Lys Gln Leu Ala Glu Leu Leu Arg Leu Ser
    1505                1510                1515

Gly Pro Val Met Gln Gln Ser Gln Gln Pro Gln Pro Leu Gln Lys
    1520                1525                1530

Gln Pro Pro Gln Pro Gln Gln Gln Arg Pro Gln Gln Gln Gln
    1535                1540                1545

Pro His His Pro Gln Thr Glu Ser Val Asn Ser Tyr Ser Ala Ser
    1550                1555                1560

Gly Ser Thr Asn Pro Tyr Met Arg Arg Pro Asn Pro Val Ser Pro
    1565                1570                1575

Tyr Pro Asn Ser Ser His Thr Ser Asp Ile Tyr Gly Ser Thr Ser
    1580                1585                1590

Pro Met Asn Phe Tyr Ser Thr Ser Ser Gln Ala Ala Gly Ser Tyr
    1595                1600                1605

Leu Asn Ser Ser Asn Pro Met Asn Pro Tyr Pro Gly Leu Leu Asn
    1610                1615                1620

Gln Asn Thr Gln Tyr Pro Ser Tyr Gln Cys Asn Gly Asn Leu Ser
```

```
                1625                1630                1635

Val Asp Asn Cys Ser Pro Tyr Leu Gly Ser Tyr Ser Pro Gln Ser
                1640                1645                1650

Gln Pro Met Asp Leu Tyr Arg Tyr Pro Ser Gln Asp Pro Leu Ser
                1655                1660                1665

Lys Leu Ser Leu Pro Pro Ile His Thr Leu Tyr Gln Pro Arg Phe
                1670                1675                1680

Gly Asn Ser Gln Ser Phe Thr Ser Lys Tyr Leu Gly Tyr Gly Asn
                1685                1690                1695

Gln Asn Met Gln Gly Asp Gly Phe Ser Ser Cys Thr Ile Arg Pro
                1700                1705                1710

Asn Val His His Val Gly Lys Leu Pro Pro Tyr Pro Thr His Glu
                1715                1720                1725

Met Asp Gly His Phe Met Gly Ala Thr Ser Arg Leu Pro Pro Asn
                1730                1735                1740

Leu Ser Asn Pro Asn Met Asp Tyr Lys Asn Gly Glu His His Ser
                1745                1750                1755

Pro Ser His Ile Ile His Asn Tyr Ser Ala Ala Pro Gly Met Phe
                1760                1765                1770

Asn Ser Ser Leu His Ala Leu His Leu Gln Asn Lys Glu Asn Asp
                1775                1780                1785

Met Leu Ser His Thr Ala Asn Gly Leu Ser Lys Met Leu Pro Ala
                1790                1795                1800

Leu Asn His Asp Arg Thr Ala Cys Val Gln Gly Gly Leu His Lys
                1805                1810                1815

Leu Ser Asp Ala Asn Gly Gln Glu Lys Gln Pro Leu Ala Leu Val
                1820                1825                1830

Gln Gly Val Ala Ser Gly Ala Glu Asp Asn Asp Glu Val Trp Ser
                1835                1840                1845

Asp Ser Glu Gln Ser Phe Leu Asp Pro Asp Ile Gly Gly Val Ala
                1850                1855                1860

Val Ala Pro Thr His Gly Ser Ile Leu Ile Glu Cys Ala Lys Arg
                1865                1870                1875

Glu Leu His Ala Thr Thr Pro Leu Lys Asn Pro Asn Arg Asn His
                1880                1885                1890

Pro Thr Arg Ile Ser Leu Val Phe Tyr Gln His Lys Ser Met Asn
                1895                1900                1905

Glu Pro Lys His Gly Leu Ala Leu Trp Glu Ala Lys Met Ala Glu
                1910                1915                1920

Lys Ala Arg Glu Lys Glu Glu Cys Glu Lys Tyr Gly Pro Asp
                1925                1930                1935

Tyr Val Pro Gln Lys Ser His Gly Lys Lys Val Lys Arg Glu Pro
                1940                1945                1950

Ala Glu Pro His Glu Thr Ser Glu Pro Thr Tyr Leu Arg Phe Ile
                1955                1960                1965

Lys Ser Leu Ala Glu Arg Thr Met Ser Val Thr Thr Asp Ser Thr
                1970                1975                1980

Val Thr Thr Ser Pro Tyr Ala Phe Thr Arg Val Thr Gly Pro Tyr
                1985                1990                1995

Asn Arg Tyr Ile
                2000

<210> SEQ ID NO 3
```

```
<211> LENGTH: 311
<212> TYPE: PRT
<213> ORGANISM: Homo sapiens

<400> SEQUENCE: 3

Arg Cys Val Glu Gln Ile Ile Glu Lys Asp Glu Gly Pro Phe Tyr Thr
1               5                   10                  15

His Leu Gly Ala Gly Pro Asn Val Ala Ala Ile Arg Glu Ile Met Glu
            20                  25                  30

Glu Arg Phe Gly Gln Lys Gly Lys Ala Ile Arg Ile Glu Arg Val Ile
        35                  40                  45

Tyr Thr Gly Lys Glu Gly Lys Ser Ser Gln Gly Cys Pro Ile Ala Lys
    50                  55                  60

Trp Val Val Arg Arg Ser Ser Ser Glu Glu Lys Leu Leu Cys Leu Val
65                  70                  75                  80

Arg Glu Arg Ala Gly His Thr Cys Glu Ala Ala Val Ile Val Ile Leu
                85                  90                  95

Ile Leu Val Trp Glu Gly Ile Pro Leu Ser Leu Ala Asp Lys Leu Tyr
            100                 105                 110

Ser Glu Leu Thr Glu Thr Leu Arg Lys Tyr Gly Thr Leu Thr Asn Arg
        115                 120                 125

Arg Cys Ala Leu Asn Glu Glu Arg Thr Cys Ala Cys Gln Gly Leu Asp
    130                 135                 140

Pro Glu Thr Cys Gly Ala Ser Phe Ser Phe Gly Cys Ser Trp Ser Met
145                 150                 155                 160

Tyr Tyr Asn Gly Cys Lys Phe Ala Arg Ser Lys Ile Pro Arg Lys Phe
                165                 170                 175

Lys Leu Leu Gly Asp Asp Pro Lys Glu Glu Lys Leu Glu Ser His
            180                 185                 190

Leu Gln Asn Leu Ser Thr Leu Met Ala Pro Thr Tyr Lys Lys Leu Ala
        195                 200                 205

Pro Asp Ala Tyr Asn Asn Gln Ile Glu Tyr Glu His Arg Ala Pro Glu
    210                 215                 220

Cys Arg Leu Gly Leu Lys Glu Gly Arg Pro Phe Ser Gly Val Thr Ala
225                 230                 235                 240

Cys Leu Asp Phe Cys Ala His Ala His Arg Asp Leu His Asn Met Gln
                245                 250                 255

Asn Gly Ser Thr Leu Val Cys Thr Leu Thr Arg Glu Asp Asn Arg Glu
            260                 265                 270

Phe Gly Gly Lys Pro Glu Asp Glu Gln Leu His Val Leu Pro Leu Tyr
        275                 280                 285

Lys Val Ser Asp Val Asp Glu Phe Gly Ser Val Glu Ala Gln Glu Glu
    290                 295                 300

Lys Lys Arg Ser Gly Ala Ile
305                 310

<210> SEQ ID NO 4
<211> LENGTH: 80
<212> TYPE: PRT
<213> ORGANISM: Homo sapiens

<400> SEQUENCE: 4

Asn Asp Glu Val Trp Ser Asp Ser Glu Gln Ser Phe Leu Asp Pro Asp
1               5                   10                  15

Ile Gly Gly Val Ala Val Ala Pro Thr His Gly Ser Ile Leu Ile Glu
            20                  25                  30
```

```
Cys Ala Lys Arg Glu Leu His Ala Thr Thr Pro Leu Lys Asn Pro Asn
     35                  40                  45

Arg Asn His Pro Thr Arg Ile Ser Leu Val Phe Tyr Gln His Lys Ser
 50                  55                  60

Met Asn Glu Pro Lys His Gly Leu Ala Leu Trp Glu Ala Lys Met Ala
 65                  70                  75                  80

<210> SEQ ID NO 5
<211> LENGTH: 22
<212> TYPE: DNA
<213> ORGANISM: Artificial sequence
<220> FEATURE:
<223> OTHER INFORMATION: Primer

<400> SEQUENCE: 5
tgaacttccc acattagctg gt                                        22

<210> SEQ ID NO 6
<211> LENGTH: 24
<212> TYPE: DNA
<213> ORGANISM: Artificial sequence
<220> FEATURE:
<223> OTHER INFORMATION: Primer

<400> SEQUENCE: 6
gaaactgtag caccattagg catt                                      24

<210> SEQ ID NO 7
<211> LENGTH: 25
<212> TYPE: DNA
<213> ORGANISM: Artificial sequence
<220> FEATURE:
<223> OTHER INFORMATION: Primer

<400> SEQUENCE: 7
caaaaggcta atggagaaag acgta                                     25

<210> SEQ ID NO 8
<211> LENGTH: 25
<212> TYPE: DNA
<213> ORGANISM: Artificial sequence
<220> FEATURE:
<223> OTHER INFORMATION: Primer

<400> SEQUENCE: 8
gcagaaaagg aatccttagt gaaca                                     25

<210> SEQ ID NO 9
<211> LENGTH: 25
<212> TYPE: DNA
<213> ORGANISM: Artificial sequence
<220> FEATURE:
<223> OTHER INFORMATION: Primer

<400> SEQUENCE: 9
gccagtaaac tagctgcaat gctaa                                     25

<210> SEQ ID NO 10
<211> LENGTH: 23
<212> TYPE: DNA
<213> ORGANISM: Artificial sequence
<220> FEATURE:
<223> OTHER INFORMATION: Primer

<400> SEQUENCE: 10
```

-continued

```
tgcctcatta cgttttagat ggg                                              23

<210> SEQ ID NO 11
<211> LENGTH: 22
<212> TYPE: DNA
<213> ORGANISM: Artificial sequence
<220> FEATURE:
<223> OTHER INFORMATION: Primer

<400> SEQUENCE: 11
gaccaatgtc agaacacctc aa                                               22

<210> SEQ ID NO 12
<211> LENGTH: 26
<212> TYPE: DNA
<213> ORGANISM: Artificial sequence
<220> FEATURE:
<223> OTHER INFORMATION: Primer

<400> SEQUENCE: 12
ttgattttga atactgattt tcacca                                           26

<210> SEQ ID NO 13
<211> LENGTH: 24
<212> TYPE: DNA
<213> ORGANISM: Artificial sequence
<220> FEATURE:
<223> OTHER INFORMATION: Primer

<400> SEQUENCE: 13
ttgcaacata agcctcataa acag                                             24

<210> SEQ ID NO 14
<211> LENGTH: 22
<212> TYPE: DNA
<213> ORGANISM: Artificial sequence
<220> FEATURE:
<223> OTHER INFORMATION: Primer

<400> SEQUENCE: 14
attggcctgt gcatctgact at                                               22

<210> SEQ ID NO 15
<211> LENGTH: 23
<212> TYPE: DNA
<213> ORGANISM: Artificial sequence
<220> FEATURE:
<223> OTHER INFORMATION: Primer

<400> SEQUENCE: 15
gcaacttgct cagcaaaggt act                                              23

<210> SEQ ID NO 16
<211> LENGTH: 24
<212> TYPE: DNA
<213> ORGANISM: Artificial sequence
<220> FEATURE:
<223> OTHER INFORMATION: Primer

<400> SEQUENCE: 16
tgctgccaga ctcaagattt aaaa                                             24

<210> SEQ ID NO 17
<211> LENGTH: 34
<212> TYPE: DNA
```

```
<213> ORGANISM: Artificial sequence
<220> FEATURE:
<223> OTHER INFORMATION: Primer

<400> SEQUENCE: 17
atactacata taatacattc taattccctc actg                                    34

<210> SEQ ID NO 18
<211> LENGTH: 24
<212> TYPE: DNA
<213> ORGANISM: Artificial sequence
<220> FEATURE:
<223> OTHER INFORMATION: Primer

<400> SEQUENCE: 18
tgtttactgc tttgtgtgtg aagg                                               24

<210> SEQ ID NO 19
<211> LENGTH: 26
<212> TYPE: DNA
<213> ORGANISM: Artificial sequence
<220> FEATURE:
<223> OTHER INFORMATION: Primer

<400> SEQUENCE: 19
catttctcag gatgtggtca tagaat                                             26

<210> SEQ ID NO 20
<211> LENGTH: 23
<212> TYPE: DNA
<213> ORGANISM: Artificial sequence
<220> FEATURE:
<223> OTHER INFORMATION: Primer

<400> SEQUENCE: 20
cccaattctc agggtcagat tta                                                23

<210> SEQ ID NO 21
<211> LENGTH: 29
<212> TYPE: DNA
<213> ORGANISM: Artificial sequence
<220> FEATURE:
<223> OTHER INFORMATION: Primer

<400> SEQUENCE: 21
agacttatgt atctttcatc tagctctgg                                          29

<210> SEQ ID NO 22
<211> LENGTH: 25
<212> TYPE: DNA
<213> ORGANISM: Artificial sequence
<220> FEATURE:
<223> OTHER INFORMATION: Primer

<400> SEQUENCE: 22
actctcttcc tttcaaccaa agatt                                              25

<210> SEQ ID NO 23
<211> LENGTH: 27
<212> TYPE: DNA
<213> ORGANISM: Artificial sequence
<220> FEATURE:
<223> OTHER INFORMATION: Primer

<400> SEQUENCE: 23
atgccacagc ttaatacaga gttagat                                            27
```

```
<210> SEQ ID NO 24
<211> LENGTH: 30
<212> TYPE: DNA
<213> ORGANISM: Artificial sequence
<220> FEATURE:
<223> OTHER INFORMATION: Primer

<400> SEQUENCE: 24
tgtcatattg ttcacttcat ctaagctaat                                      30

<210> SEQ ID NO 25
<211> LENGTH: 28
<212> TYPE: DNA
<213> ORGANISM: Artificial sequence
<220> FEATURE:
<223> OTHER INFORMATION: Primer

<400> SEQUENCE: 25
gatgctttat ttagtaataa aggcacca                                        28

<210> SEQ ID NO 26
<211> LENGTH: 35
<212> TYPE: DNA
<213> ORGANISM: Artificial sequence
<220> FEATURE:
<223> OTHER INFORMATION: Primer

<400> SEQUENCE: 26
ttcaacaatt aagaggaaaa gttagaataa tattt                                35

<210> SEQ ID NO 27
<211> LENGTH: 25
<212> TYPE: DNA
<213> ORGANISM: Artificial sequence
<220> FEATURE:
<223> OTHER INFORMATION: Primer

<400> SEQUENCE: 27
tgtcattcca ttttgtttct ggata                                           25

<210> SEQ ID NO 28
<211> LENGTH: 26
<212> TYPE: DNA
<213> ORGANISM: Artificial sequence
<220> FEATURE:
<223> OTHER INFORMATION: Primer

<400> SEQUENCE: 28
aaattaccca gtcttgcata tgtctt                                          26

<210> SEQ ID NO 29
<211> LENGTH: 22
<212> TYPE: DNA
<213> ORGANISM: Artificial sequence
<220> FEATURE:
<223> OTHER INFORMATION: Primer

<400> SEQUENCE: 29
ctggatcaac taggccacca ac                                              22

<210> SEQ ID NO 30
<211> LENGTH: 33
<212> TYPE: DNA
<213> ORGANISM: Artificial sequence
<220> FEATURE:
```

```
<223> OTHER INFORMATION: Primer

<400> SEQUENCE: 30
ccaaaattaa caatgttcat tttacaataa gag                                    33

<210> SEQ ID NO 31
<211> LENGTH: 25
<212> TYPE: DNA
<213> ORGANISM: Artificial sequence
<220> FEATURE:
<223> OTHER INFORMATION: Primer

<400> SEQUENCE: 31
gctcttatct ttgcttaatg ggtgt                                             25

<210> SEQ ID NO 32
<211> LENGTH: 27
<212> TYPE: DNA
<213> ORGANISM: Artificial sequence
<220> FEATURE:
<223> OTHER INFORMATION: Primer

<400> SEQUENCE: 32
tgtacatttg gtctaatggt acaactg                                           27

<210> SEQ ID NO 33
<211> LENGTH: 24
<212> TYPE: DNA
<213> ORGANISM: Artificial sequence
<220> FEATURE:
<223> OTHER INFORMATION: Primer

<400> SEQUENCE: 33
aatggaaacc tatcagtgga caac                                              24

<210> SEQ ID NO 34
<211> LENGTH: 26
<212> TYPE: DNA
<213> ORGANISM: Artificial sequence
<220> FEATURE:
<223> OTHER INFORMATION: Primer

<400> SEQUENCE: 34
tatatatctg ttgtaaggcc ctgtga                                            26

<210> SEQ ID NO 35
<211> LENGTH: 23
<212> TYPE: DNA
<213> ORGANISM: Artificial sequence
<220> FEATURE:
<223> OTHER INFORMATION: Primer

<400> SEQUENCE: 35
cagagctttc tggatcctga cat                                               23

<210> SEQ ID NO 36
<211> LENGTH: 25
<212> TYPE: DNA
<213> ORGANISM: Artificial sequence
<220> FEATURE:
<223> OTHER INFORMATION: Primer

<400> SEQUENCE: 36
gcccacgtca tgagaactat actac                                             25
```

```
<210> SEQ ID NO 37
<211> LENGTH: 28
<212> TYPE: DNA
<213> ORGANISM: Artificial sequence
<220> FEATURE:
<223> OTHER INFORMATION: Primer

<400> SEQUENCE: 37
tctaagctca gtctaccacc catccata                                               28

<210> SEQ ID NO 38
<211> LENGTH: 25
<212> TYPE: DNA
<213> ORGANISM: Artificial sequence
<220> FEATURE:
<223> OTHER INFORMATION: Primer

<400> SEQUENCE: 38
tgctcgctgt ctgaccagac ctcat                                                  25

<210> SEQ ID NO 39
<211> LENGTH: 6869
<212> TYPE: DNA
<213> ORGANISM: Homo sapiens

<400> SEQUENCE: 39
ccgtgccatc ccaacctccc acctcgcccc caaccttcgc gcttgctctg cttcttctcc           60
caggggtgga gacccgccga ggtccccggg gttcccgagg gctgcaccct tccccgcgct          120
cgccagccct ggcccctact ccgcgctggt ccgggcgcac cactcccccc gcgccactgc          180
acggcgtgag ggcagcccag gtctccactg cgcgccccgc tgtacggccc caggtgccgc          240
cggcctttgt gctggacgcc cggtgcgggg ggctaattcc ctgggagccg gggctgaggg          300
ccccagggcg gcggcgcagg ccggggcgga gcgggaggag gccggggcgg agcaggagga          360
ggcccgggcg gaggaggaga gccggcggta gcggcagtgg cagcggcgag agcttgggcg          420
gccgccgccg cctcctcgcg agcgccgcgc gcccgggtcc cgctcgcatg caagtcacgt          480
ccgcccccctc ggcgcggccg ccccgagacg ccggccccgc tgagtgatga aacagacgt           540
caaactgcct tatgaatatt gatgcggagg ctaggctgct ttcgtagaga agcagaagga          600
agcaagatgg ctgcccttta ggatttgtta gaaaggagac ccgactgcaa ctgctggatt          660
gctgcaaggc tgagggacga gaacgaggct ggcaaacatt cagcagcaca ccctctcaag          720
attgtttact tgcctttgct cctgttgagt tacaacgctt ggaagcagga gatgggctca          780
gcagcagcca ataggacatg atccaggaag agcaaattca actagagggc agccttgtgg          840
atggccccga agcaagcctg atggaacagg atagaaccaa ccatgttgag ggcaacagac          900
taagtccatt cctgatacca tcacctccca tttgccagac agaacctctg ctacaaagc           960
tccagaatgg aagcccactg cctgagagag ctcatccaga agtaaatgga gacaccaagt         1020
ggcactcttt caaagttat tatggaatac cctgtatgaa gggaagccag aatagtcgtg          1080
tgagtcctga ctttacacaa gaaagtagag ggtattccaa gtgtttgcaa aatggaggaa         1140
taaaacgcac agttagtgaa ccttctctct ctgggctcct tcagatcaag aaattgaaac         1200
aagaccaaaa ggctaatgga gaaagacgta acttcgggggt aagccaagaa agaaatccag         1260
gtgaaagcag tcaaccaaat gtctccgatt tgagtgataa gaaagaatct gtgagttctg         1320
tagcccaaga aaatgcagtt aaagatttca ccagttttttc aacacataac tgcagtgggc         1380
ctgaaaatcc agagcttcag attctgaatg agcaggaggg gaaaagtgct aattaccatg         1440
```

```
acaagaacat tgtattactt aaaaacaagg cagtgctaat gcctaatggt gctacagttt    1500
ctgcctcttc cgtggaacac acacatggtg aactcctgga aaaaacactg tctcaatatt    1560
atccagattg tgtttccatt gcggtgcaga aaaccacatc tcacataaat gccattaaca    1620
gtcaggctac taatgagttg tcctgtgaga tcactcaccc atcgcatacc tcagggcaga    1680
tcaattccgc acagacctct aactctgagc tgcctccaaa gccagctgca gtggtgagtg    1740
aggcctgtga tgctgatgat gctgataatg ccagtaaaact agctgcaatg ctaaatacct    1800
gttcctttca gaaaccagaa caactacaac aacaaaaatc agttttttgag atatgcccat    1860 ctcctgcaga aaataacatc cagggaacca caaagctagc gtctggtgaa gaattctgtt    1920
caggttccag cagcaatttg caagctcctg gtggcagctc tgaacggtat ttaaaacaaa    1980
atgaaatgaa tggtgcttac ttcaagcaaa gctcagtgtt cactaaggat tcctttttctg    2040 ccactaccac accaccacca ccatcacaat tgcttctttc tccccctcct cctcttccac    2100
aggttcctca gcttccttca gaaggaaaaa gcactctgaa tggtggagtt ttagaagaac    2160
accaccacta ccccaaccaa agtaacacaa cacttttaag ggaagtgaaa atagagggta    2220
aacctgaggc accaccttcc cagagtccta atccatctac acatgtatgc agcccttctc    2280
cgatgctttc tgaaaggcct cagaataatt gtgtgaacag gaatgacata cagactgcag    2340
ggacaatgac tgttccattg tgttctgaga aaacaagacc aatgtcagaa cacctcaagc    2400
ataacccacc aattttttggt agcagtggag agctacagga caactgccag cagttgatga    2460
gaaacaaaga gcaagagatt ctgaagggtc gagacaagga gcaaacacga gatcttgtgc    2520
ccccaacaca gcactatctg aaaccaggat ggattgaatt gaaggcccct cgttttcacc    2580
aagcggaatc ccatctaaaa cgtaatgagg catcactgcc atcaattctt cagtatcaac    2640
ccaatctctc caatcaaatg acctccaaac aatacactgg aaattccaac atgcctgggg    2700
ggctcccaag gcaagcttac acccagaaaa caacacagct ggagcacaag tcacaaatgt    2760
accaagttga aatgaatcaa gggcagtccc aaggtacagt ggaccaacat ctccagttcc    2820 aaaaacccctc acaccaggtg cacttctcca aaacagacca tttaccaaaa gctcatgtgc    2880
agtcactgtg tggcactaga tttcattttc aacaaagagc agattcccaa actgaaaaac    2940
ttatgtcccc agtgttgaaa cagcacttga atcaacaggc ttcagagact gagccatttt    3000
caaactcaca ccttttgcaa cataagcctc ataaacaggc agcacaaaca caaccatccc    3060
agagttcaca tctccctcaa aaccagcaac agcagcaaaa attacaaata aagaataaag    3120
aggaaatact ccagactttt cctcacccccc aaagcaacaa tgatcagcaa agagaaggat    3180
cattctttgg ccagactaaa gtggaagaat gttttcatgg tgaaaatcag tattcaaaat    3240
caagcgagtt cgagactcat aatgtccaaa tgggactgga ggaagtacag aatataaatc    3300
gtagaaattc ccccttatagt cagaccatga aatcaagtgc atgcaaaata caggtttctt    3360
gttcaaacaa tacacaccta gtttcagaga ataaagaaca gactacacat cctgaactttt    3420 ttgcaggaaa caagacccaa aacttgcatc acatgcaata ttttccaaat aatgtgatcc    3480
caaagcaaga tcttcttcac aggtgctttc aagaacagga gcagaagtca caacaagctt    3540
cagttctaca gggatataaa aatagaaacc aagatatgtc tggtcaacaa gctgcgcaac    3600
ttgctcagca aaggtacttg atacataacc atgcaaatgt ttttcctgtg cctgaccagg    3660
gaggaagtca cactcagacc cctccccaga aggacactca aaagcatgct gctctaaggt    3720
ggcatctctt acagaagcaa gaacagcagc aaacacagca accccaaaact gagtcttgcc    3780 atagtcagat gcacaggcca attaaggtgg aacctggatg caagccacat gcctgtatgc    3840
```

```
acacagcacc accagaaaac aaaacatgga aaaaggtaac taagcaagag aatccacctg   3900
caagctgtga taatgtgcag caaaagagca tcattgagac catggagcag catctgaagc   3960
agtttcacgc caagtcgtta tttgaccata aggctcttac tctcaaatca cagaagcaag   4020
taaaagttga aatgtcaggg ccagtcacag ttttgactag acaaaccact gctgcagaac   4080
ttgatagcca cacccagct ttagagcagc aaacaacttc ttcagaaaag acaccaacca   4140
aaagaacagc tgcttctgtt ctcaataatt ttatagagtc accttccaaa ttactagata   4200
ctcctataaa aaatttattg gatacacctg tcaagactca atatgatttc ccatcttgca   4260
gatgtgtaga gcaaattatt gaaaagatg aaggtccttt ttatacccat ctaggagcag   4320
gtcctaatgt ggcagctatt agagaaatca tggaagaaag gtttggacag aagggtaaag   4380
ctattaggat tgaaagagtc atctatactg gtaaagaagg caaaagttct cagggatgtc   4440
ctattgctaa gtgggtggtt cgcagaagca gcagtgaaga aagctactg tgtttggtgc   4500 gggagcgagc tggccacacc tgtgaggctg cagtgattgt gattctcatc ctggtgtggg   4560
aaggaatccc gctgtctctg gctgacaaac tctactcgga gcttaccgag acgctgagga   4620
aatacggcac gctcaccaat cgccggtgtg ccttgaatga agagaact tgcgcctgtc   4680 aggggctgga tccagaaacc tgtggtgcct ccttctcttt tggttgttca tggagcatgt   4740
actacaatgg atgtaagttt gccagaagca agatcccaag gaagtttaag ctgcttgggg   4800
atgacccaaa agaggaagag aaactggagt ctcatttgca aaacctgtcc actcttatgg   4860
caccaacata taagaaactt gcacctgatg catataataa tcagattgaa atgaacaca   4920 gagcaccaga gtgccgtctg ggtctgaagg aaggccgtcc attctcaggg gtcactgcat   4980
gtttggactt ctgtgctcat gcccacagag acttgcacaa catgcagaat ggcagcacat   5040
tggtatgcac tctcactaga gaagacaatc gagaatttgg aggaaaacct gaggatgagc   5100
agcttcacgt tctgccttta tacaaagtct ctgacgtgga tgagtttggg agtgtggaag   5160
ctcaggagga gaaaaacgg agtggtgcca ttcaggtact gagttctttt cggcgaaaag   5220
tcaggatgtt agcagagcca gtcaagactt gccgacaaag gaaactagaa gccaagaaag   5280
ctgcagctga aaagctttcc tccctggaga acagctcaaa taaaaatgaa aaggaaaagt   5340
cagccccatc acgtacaaaa caaactgaaa acgcaagcca ggctaaacag ttggcagaac   5400
ttttgcgact ttcaggacca gtcatgcagc agtcccagca gccccagcct ctacagaagc   5460
agccaccaca gccccagcag cagcagagac cccagcagca gcagccacat caccctcaga   5520
cagagtctgt caactcttat tctgcttctg gatccaccaa tccatacatg agacggccca   5580
atccagttag tccttatcca aactcttcac acacttcaga tatctatgga agcaccagcc   5640
ctatgaactt ctattccacc tcatctcaag ctgcaggttc atatttgaat tcttctaatc   5700
ccatgaaccc ttaccctggg cttttgaatc agaatacccca atatccatca tatcaatgca   5760
atggaaacct atcagtggac aactgctccc catatctggg ttcctattct ccccagtctc   5820
agccgatgga tctgtatagg tatccaagcc aagaccctct gtctaagctc agtctaccac   5880
ccatccatac actttaccag ccaaggtttg gaaatagcca gagttttaca tctaaatact   5940
taggttatgg aaaccaaaat atgcagggag atggtttcag cagttgtacc attagaccaa   6000
atgtacatca tgtagggaaa ttgcctcctt atcccactca tgagatggat ggccacttca   6060
tgggagccac ctctagatta ccacccaatc tgagcaatcc aaacatggac tataaaaatg   6120
gtgaacatca ttcaccttct cacataatcc ataactacag tgcagctccg ggcatgttca   6180
```

```
acagctctct tcatgccctg catctccaaa acaaggagaa tgacatgctt tcccacacag    6240
ctaatgggtt atcaaagatg cttccagctc ttaaccatga tagaactgct tgtgtccaag    6300
gaggcttaca caaattaagt gatgctaatg gtcaggaaaa gcagccattg cactagtcc     6360 agggtgtggc ttctggtgca gaggacaacg atgaggtctg gtcagacagc gagcagagct    6420
ttctggatcc tgacattggg ggagtggccg tggctccaac tcatgggtca attctcattg    6480
agtgtgcaaa gcgtgagctg catgccacaa cccctttaaa gaatcccaat aggaatcacc    6540
ccaccaggat ctccctcgtc ttttaccagc ataagagcat gaatgagcca aaacatggct    6600
tggctctttg ggaagccaaa atggctgaaa aagcccgtga gaaagaggaa gagtgtgaaa    6660
agtatggccc agactatgtg cctcagaaat cccatggcaa aaaagtgaaa cgggagcctg    6720
ctgagccaca tgaaacttca gagcccactt acctgcgttt catcaagtct cttgccgaaa    6780
ggaccatgtc cgtgaccaca gactccacag taactacatc tccatatgcc ttcactcggg    6840
tcacagggcc ttacaacaga tatatatga                                      6869
```

<210> SEQ ID NO 40  
<211> LENGTH: 20  
<212> TYPE: DNA  
<213> ORGANISM: artificial sequence  
<220> FEATURE:  
<223> OTHER INFORMATION: Primer

<400> SEQUENCE: 40
cagccaggaa gacacttacc                    20

<210> SEQ ID NO 41  
<211> LENGTH: 20  
<212> TYPE: DNA  
<213> ORGANISM: artificial sequence  
<220> FEATURE:  
<223> OTHER INFORMATION: Primer

<400> SEQUENCE: 41
gacaccgatc ttgctggttg                    20

<210> SEQ ID NO 42  
<211> LENGTH: 18  
<212> TYPE: DNA  
<213> ORGANISM: artificial sequence  
<220> FEATURE:  
<223> OTHER INFORMATION: Primer

<400> SEQUENCE: 42
cgccttgcag cacatccc                      18

<210> SEQ ID NO 43  
<211> LENGTH: 18  
<212> TYPE: DNA  
<213> ORGANISM: artificial sequence  
<220> FEATURE:  
<223> OTHER INFORMATION: Primer

<400> SEQUENCE: 43
ggccttcctg tagccagc                      18

<210> SEQ ID NO 44  
<211> LENGTH: 20  
<212> TYPE: DNA  
<213> ORGANISM: artificial sequence  
<220> FEATURE:  
<223> OTHER INFORMATION: Primer

```
<400> SEQUENCE: 44
ggcagaggca tgttgaatga                                              20

<210> SEQ ID NO 45
<211> LENGTH: 21
<212> TYPE: DNA
<213> ORGANISM: artificial sequence
<220> FEATURE:
<223> OTHER INFORMATION: Primer

<400> SEQUENCE: 45
tagacaagcc ctgcaagcaa a                                            21

<210> SEQ ID NO 46
<211> LENGTH: 20
<212> TYPE: DNA
<213> ORGANISM: artificial sequence
<220> FEATURE:
<223> OTHER INFORMATION: Primer

<400> SEQUENCE: 46
ggcagaggca tgttgaatga                                              20

<210> SEQ ID NO 47
<211> LENGTH: 21
<212> TYPE: DNA
<213> ORGANISM: artificial sequence
<220> FEATURE:
<223> OTHER INFORMATION: Primer

<400> SEQUENCE: 47
tagacaagcc ctgcaagcaa a                                            21

<210> SEQ ID NO 48
<211> LENGTH: 20
<212> TYPE: DNA
<213> ORGANISM: artificial sequence
<220> FEATURE:
<223> OTHER INFORMATION: Primer

<400> SEQUENCE: 48
gtgtcccacg gttacacacg                                              20

<210> SEQ ID NO 49
<211> LENGTH: 26
<212> TYPE: DNA
<213> ORGANISM: artificial sequence
<220> FEATURE:
<223> OTHER INFORMATION: Primer

<400> SEQUENCE: 49
agaatcagat actcctggtg aacaaa                                       26

<210> SEQ ID NO 50
<211> LENGTH: 28
<212> TYPE: DNA
<213> ORGANISM: artificial sequence
<220> FEATURE:
<223> OTHER INFORMATION: Primer

<400> SEQUENCE: 50
cctagatggg tataataagg agcttcat                                     28
```

-continued

```
<210> SEQ ID NO 51
<211> LENGTH: 28
<212> TYPE: DNA
<213> ORGANISM: artificial sequence
<220> FEATURE:
<223> OTHER INFORMATION: Probe
<220> FEATURE:
<221> NAME/KEY: misc_binding
<222> LOCATION: (1)..(1)
<223> OTHER INFORMATION: 5' FAM
<220> FEATURE:
<221> NAME/KEY: misc_binding
<222> LOCATION: (28)..(28)
<223> OTHER INFORMATION: 3' TAM

<400> SEQUENCE: 51
tctggattgc atccttcaca tttgccat                                          28

<210> SEQ ID NO 52
<211> LENGTH: 21
<212> TYPE: DNA
<213> ORGANISM: artificial sequence
<220> FEATURE:
<223> OTHER INFORMATION: Primer

<400> SEQUENCE: 52
cccacagaga ccagcagaac a                                                 21

<210> SEQ ID NO 53
<211> LENGTH: 23
<212> TYPE: DNA
<213> ORGANISM: artificial sequence
<220> FEATURE:
<223> OTHER INFORMATION: Primer

<400> SEQUENCE: 53
tgcgttcttc ttctttggtt ttc                                               23

<210> SEQ ID NO 54
<211> LENGTH: 26
<212> TYPE: DNA
<213> ORGANISM: artificial sequence
<220> FEATURE:
<223> OTHER INFORMATION: Probe
<220> FEATURE:
<221> NAME/KEY: misc_binding
<222> LOCATION: (1)..(1)
<223> OTHER INFORMATION: 5' FAM
<220> FEATURE:
<221> NAME/KEY: misc_binding
<222> LOCATION: (26)..(26)
<223> OTHER INFORMATION: 3' TAM

<400> SEQUENCE: 54
cctgggacca ctgtactgcc atttgg                                            26
```